US008822654B2

(12) United States Patent
Borgel et al.

(10) Patent No.: US 8,822,654 B2
(45) Date of Patent: Sep. 2, 2014

(54) MUTATED ANTITHROMBINS, A PROCESS FOR PREPARING THE SAME AND THEIR USE AS DRUGS

(75) Inventors: Delphine Borgel, Paris (FR); Véronique Ferger, Sceaux (FR); Elsa Bianchini, Villebon sur Yvette (FR); Nicolas Lerolle, Angers (FR); Jean-Luc René Diehl, Clamart (FR)

(73) Assignees: Universite Paris—Sud XI, Orsay (FR); Assistance Publique-Hopitaux de Paris, Paris (FR); Universite Paris Descartes, Paris (FR)

( * ) Notice: Subject to any disclaimer, the term of this patent is extended or adjusted under 35 U.S.C. 154(b) by 134 days.

(21) Appl. No.: 13/144,995

(22) PCT Filed: Jan. 15, 2010

(86) PCT No.: PCT/EP2010/050456
§ 371 (c)(1),
(2), (4) Date: Dec. 12, 2011

(87) PCT Pub. No.: WO2010/081878
PCT Pub. Date: Jul. 22, 2010

(65) Prior Publication Data
US 2012/0088715 A1  Apr. 12, 2012

(30) Foreign Application Priority Data

Jan. 16, 2009  (EP) .................................. 09290037

(51) Int. Cl.
| | | |
|---|---|---|
| *A61K 35/14* | (2006.01) | |
| *C07K 1/00* | (2006.01) | |
| *C07K 14/00* | (2006.01) | |
| *C07K 16/00* | (2006.01) | |
| *C07K 17/00* | (2006.01) | |
| *A61K 38/00* | (2006.01) | |
| *A61P 5/00* | (2006.01) | |
| *A61K 38/26* | (2006.01) | |
| *A61P 7/02* | (2006.01) | |
| *C07K 14/475* | (2006.01) | |
| *A61K 38/57* | (2006.01) | |
| *C07K 14/81* | (2006.01) | |
| *C07K 14/745* | (2006.01) | |
| *A61K 38/16* | (2006.01) | |
| *C07H 21/04* | (2006.01) | |
| *A61K 38/36* | (2006.01) | |

(52) U.S. Cl.
CPC .............. *A61K 38/36* (2013.01); *C07K 14/745* (2013.01)
USPC .......... 530/393; 514/1.4; 514/13.7; 514/14.7; 514/21.2; 536/23.5

(58) Field of Classification Search
None
See application file for complete search history.

(56) References Cited

FOREIGN PATENT DOCUMENTS

| | | | |
|---|---|---|---|
| WO | WO 0069256 A1 | * | 11/2000 |
| WO | 03/101398 A | | 12/2003 |
| WO | WO 03101398 A2 | * | 12/2003 |
| WO | 2009/013251 A | | 1/2009 |
| WO | WO 2009013251 A1 | * | 1/2009 |

OTHER PUBLICATIONS

Stephens et al "Site-directed Mutagenesis of the Reactive Center (Serine 394) of Antithrombin III" J Biol Chem 263:15849-15852. Published Nov. 5, 1998.*
Warren Brian L et al: "High-Dose Antithrombin III in Severe Sepsis: A Randomized Controlled Trial", Jama the Journal of the American Medical Association, vol. 286, No. 15, Oct. 17, 2001, pp. 1869-1878, XP009074599.
Kienast J et al: "Treatment effects of high-dose antithrombin without concomitant heparin in patients with severe spesis with or without disseminated intravascular coagulation." Journal of Thrombosis and Hemastasis, vol. 4, No. 1, Jan. 2006, pp. 90-97, XP002544532.
Erdjument K et al: "Antithrombin Milano, single amino acid substitution at the reactive site, Arg393 to Cys." Thrombosis and Haemostatsis Dec. 22, 1988, vol. 60, No. 3, Dec. 22, 1988, pp. 471-475, XP009122426.
Hayashi Tomohiro et al: "Antithrombin aomori: Identification of a point mutation resulting in Arg-393-His substitution", ACTA Medica ET Biologica, vol. 43, No. 3, 1995, pp. 157-163, XP009122424.
Stephens Awet Al: "Antithrombin-III Denver, a reactive site variant." The Journal of Biological Chemistry, Jan. 25, 1987, vol. 262, No. 3, Jan. 25, 1987, pp. 1044-1048, XP002544535.
Desai U R: "New Antithrombib-Based Anticoagulants", Medicinal Research Reviews, vol. 24, No. 2, Jan. 1, 2004, pp. 151-181, XP008057200.
International Search Report, dated May 25, 2010, in Application PCT/EP2010/050456.
European Search Report, dated Sep. 9, 2009, in Application EP 09 29 0037.

* cited by examiner

*Primary Examiner* — Maury Audet
*Assistant Examiner* — Zachary J Miknis
(74) *Attorney, Agent, or Firm* — Young & Thompson

(57) ABSTRACT

The present invention relates to the use of a composition including of at least a mutated antithrombin
  having an anticoagulant activity substantially reduced with respect to the anticoagulant activity of the non mutated antithrombin, or
  having no anticoagulant activity,
for the preparation of a drug intended for the prevention or the treatment of pathologies associated with cellular injury, such as infection, inflammation or hypoxic injury.

8 Claims, 6 Drawing Sheets

MUTATED ANTITHROMBINS, A PROCESS FOR PREPARING THE SAME AND THEIR USE AS DRUGS

FIELD OF THE INVENTION

The present invention relates to mutated antithrombins and their use as drugs. The present invention also discloses a process for preparing mutated antithrombins.

BACKGROUND OF THE INVENTION

Physiology

Systemic activation of the coagulation system is frequently observed in patients with severe sepsis and/or septic shock. Severe sepsis, as a complication of infection, is characterized by systemic inflammation, activation of proteolytic cascades, coagulation abnormalities (DIC), and various organ dysfunctions. Its more severe form, septic shock, associates in addition altered hemodynamic and impaired organ perfusion, aggravating further organ failure and frequently leading to death in multiorgan failure. Mortality in septic shock is high (40% to 50%), and rises tremendously with the number of failing organs, i.e. patients requiring renal replacement therapy for acute renal failure may have mortality rate above 80%. The initiating event for the development of severe sepsis is the activation of monocytes/macrophages by microbial antigens (i.e. lipopolysaccharide (LPS) liberated from Gram-negative bacteria, lipoteichoic acid from Gram-positive bacteria, fungal antigen) via binding to surface Toll-like receptors (Cohen J. *The immunopathogenesis of sepsis. Nature.* 2002; 420:885-91).

Mechanistic

Monocyte/macrophages activation, potentially followed by endothelial cells activation, results in secretion of cytokine mediators (such as interleukin 6 (IL-6), tumor necrosis factor (TNFα) and chemokines, lipid mediators, adhesion molecules and tissue factor expression at the cell membrane, nitric oxyde and oxygen reactive species formation). This step is followed by the activation of biological cascades including the coagulation and the complement, which contribute to the maintenance of the inflammatory reaction and coagulation activation. These events are fully adapted to eradicate microbial agents at the site of infection, but results in deleterious consequences, i.e. various organ failures, if they become widespread, unregulated and sustained. (Aird W. *The role of the endothelium in severe sepsis and multiple organ dysfunction syndrome. Blood.* 2003; 101:3765-77).

Tissue factor expression leads to uncontrolled generation of thrombin from its precursor molecule prothrombin. Endogenous anticoagulants, namely antithrombin (AT), protein C pathway and Tissue Factor Pathway Inhibitor, as well as the fibrinolytic system are activated and function to regulate thrombin generation and its consequences. However, blood levels of endogenous inhibitor are diminished due to their consumption onto their substrate, inhibited synthesis and cleavage by several proteases. Indeed, AT levels decrease precipitously in the early phases of severe sepsis. Fibrinolysis is rapidly inhibited by the production of plasminogen activator inhibitor-1. Thus, a procoagulant state develops in patients with sepsis potentially leading to overt disseminated intravascular coagulation (DIC), which has deleterious effects. Diffuse thrombus formation throughout microcirculation can compromise tissue perfusion to critical organs, and cellular effects of various coagulation proteins participate in the general inflammatory syndrome (Aird W. *The role of the endothelium in severe sepsis and multiple organ dysfunction syndrome. Blood.* 2003; 101:3765-77). It is demonstrated that coagulation abnormalities in severe sepsis is associated with poor outcome. Notably, depletion of AT in septic shock portends a poor prognosis (Fourrier F. *Septic shock, multiple organ failure, and disseminated intravascular coagulation: compared patterns of antithrombin III, protein C, and protein S deficiencies. Chest.* 1992; 101:816-823).

Antithrombin

Antithrombin plays an essential role in maintaining the fluidity of blood. Blood coagulation is mediated by a series of serine proteases. Antithrombin is a potent inhibitor of coagulation serine proteases, in particular, Factors IIa (thrombin), Xa, IXa and XIa. Interaction of AT with heparin-like glycosaminoglycans (HGAGs) on endothelial cells is important for the acceleration of thrombin inhibition by AT (Rosenberg R D. *Biochemistry of heparin antithrombin interactions, and the physiologic role of this natural anticoagulant mechanism. Am J Med.* 1989; 87:2S-9S). Indeed, thrombotic episodes have been observed in patients with congenital AT deficiency and in those with variant AT that lacks affinity for heparin suggesting that the interaction of AT with the endothelial cell surface heparin-like GAGs is important for regulation of the coagulation cascade by AT (Kuhle S, Lane D A, Jochmanns K, Male C, Quehenberger P, Lechner K, Pabinger I. *Homozygous antithrombin deficiency type II (99 Leu to Phe mutation) and childhood thromboembolism. Thromb Haemost.* 2001; 86:1007-11). The physiological importance of antithrombin in preventing excessive coagulation is revealed by studies of individuals whose antithrombin levels are decreased due to heredity or acquired deficiency. Such persons are prone spontaneous thrombosis and the associated risks of disseminated intravascular coagulation, cardiac infarction, cerebrovascular accident and pulmonary embolism.

In addition, AT has been shown to exert cytoprotective properties, through its binding to the glycosaminoglycans present on endothelial cells surface Indeed, AT inhibits NFkB activation endothelial cells and monocytes, resulting in an increase in prostacyclin synthesis, a decrease in pro-inflammatory cytokines production (IL6 and TNFα), a reduction in tissue factor exposure on endothelial cells or monocytes, a reduction in platelet aggregation and in endothelial cells/neutrophil interactions. This effect is abolished by heparin, through a competition process. These cytoprotective effects were observed for AT concentrations ranging from 2.5 to 40 UI/ml (corresponding to 2.5 to 40 fold normal circulating AT levels).

Models of Sepsis

AT has been shown to be efficacious in several experimental models of sepsis and septic shock, regardless of the species investigated, as shown in baboons, dogs, sheep, rabbits, rats, and chicken embryos. AT in these models proved to be effective after inducing a sepsis or septic shock with different agents including live bacteria (*Escherichia coli, Klebsiella pneumoniae*) and bacterial lipopolysaccharide (LPS).

In a guinea pig model, it has been demonstrated that AT could prevent DIC and organ hemorrhage and improve mortality after infection with the Gram-positive bacterium *Staphylococcus aureus.*

Due to the missregulation of coagulation process during sepsis, some anticoagulants have been assayed in human, such as heparin or antithrombin.

Therapeutic doses of heparin (Corrigan J J. *Heparin therapy in bacterial septicemia. J Pediatr.* 1977; 91:695-700) or antithrombin (Schipper H G, Jenkins C S P, Kahl L H, ten Cate J W. *Antithrombin III transfusion in disseminated intravascular coagulation. Lancet.* 1978; 1:854-856) have been used clinically for more than 20 years for the prevention and treatment of disseminated intravascular coagulation and sepsis, without any clear evidence of efficacy.

In order to treat activation of coagulation system and depletion of anticoagulant during severe sepsis, some studies have been made in patients by using high doses of antithrombin.

Warren et al. (*High dose Antithrombin III in severe sepsis*, 2008, *JAMA*, 286(15), 1869-1878) have tested the effect of administration of 30,000 IU (cumulative dose for a 4-day treatment) AT in patients in a randomized controlled trial study. Patients receiving AT treatment had plasma AT levels around 180% of normal circulating blood levels, these levels being lower than doses required to achieve a cytoprotective effect. This study could not demonstrate the efficiency of AT administration on patient survival. Moreover, the authors have demonstrated that the administration of AT, at this dosage, enhances the hemorrhagic risk in patients, said risk being increased when patient has received a concomitant administration of heparin.

A post-hoc analysis of this study focusing on DIC related to severe sepsis reported that this dosage of AT (30,000 IU over 4 days) increases the hemorrhagic risk in patients without heparinic treatment, compared to control treated with a placebo (*Treatment effects of high-dose antithrombin without concomitant heparin in patients with severe sepsis with or without disseminated intravascular coagulation*, 2006, *J. of Thrombosis and Haemostasis*, 4: 90-97), Another study (Eisele at al. *Antithrombin III in patients with severe sepsis, intensive care Med.*, 1998, 24:663-672) has demonstrated that 18,000 UI (cumulative dose for a 5-day treatment) of AT have some benefits in patient survival, without bleeding problems. However, the panel of patients used in this study is too small to be sure that this dosage of AT has no effect on bleeding, and the dosage of AT remains under the identified efficient dosage of antithrombin necessary to provide a good cytoprotective effect: indeed, in this study, patients receiving AT treatment had AT levels ranging from 70 to 130% of normal circulating AT levels.

So there is a need to provide new medicines for treating severe sepsis, which enhances the anticoagulation system in the patient, but without causing hemorrhagic accidents.

Other anticoagulant has been tested in the treatment of severe sepsis.

Activated protein C (drotrecogin α) has been shown to reduce severe sepsis mortality in patients with the highest severity scores [Bernard G R, Vincent J L, Laterre P F, LaRosa S P, Dhainaut J F, Lopez-Rodriguez A, Steingrub J S, Garber G E, Helterbrand J D, Ely E W, Fisher C J Jr; *Recombinant human protein C Worldwide Evaluation in Severe Sepsis (PROWESS) study group. Efficacy and safety of recombinant human activated protein C for severe sepsis*. N Engl J Med 2001; 344:699-709]. In spite of the results of this study, the use of activated protein C remains controversial, as controversy regarding the efficacy/safety profile of this drug notably regarding bleeding. WO2005/007820 discloses the use of a mutated activated protein C variants, with reduced anticoagulant activity, for the treatment of pathologies requiring a cellular cytoprotection, but these variants have not been tested in clinical practice [Kerschen E J, Fernandez J A, Cooley B C, Yang X V, Sood R, Mosnier L O, Castellino F J, Mackman N, Griffin J H, Weiler H. *Endotoxemia and sepsis mortality reduction by non-anticoagulant activated protein C. J Exp Med.* 2007 Oct. 1; 204(10):2439-48.].

Thus, it is important to provide a new medicine that can cure all the forms of severe sepsis, without causing any, or reduced only, hemorrhagic manifestation in patients.

SUMMARY OF THE INVENTION

So, one aim of the invention is to provide a new drug.

Also, another aim of the invention is to provide a new pharmaceutical composition comprising modified antithrombin as an active substance.

The invention relates to the use of a composition comprising of at least a mutated antithrombin:
  having an anticoagulant activity substantially reduced with respect to the anticoagulant activity of the non mutated antithrombin, or
  having substantially no anticoagulant activity,
  for the preparation of a drug intended for the prevention or the treatment of pathologies associated with cellular injury, such as infection, inflammation or hypoxic injury.

The term <<mutated antithrombin>> designates an antithrombin, preferably a human antithrombin, comprising at least a substitution, insertion and/or deletion of one or more amino acids within its amino acid sequence.

The said mutated antithrombins can be prepared according to the method described in the experimental part I/.

The human antithrombin sequence is described in Olds R. J., Lane D. A., Chowdhury V., De Stefano V., Leone G. and Thein S. L. "Complete nucleotide sequence of the antithrombin gene: evidence for homologous recombination causing thrombophilia" *Biochemistry*. 32 (16), 4216-4224 (1993).

The human antithrombin sequence of the invention is a *Homo sapiens* serpin peptidase inhibitor, clade C (antithrombin), member 1 (SERPINC1), mRNA. Accession NM 000488, Version NM 000488.2, GI:50541941.

There are many references which describe said DNA sequence (with signal peptide) but they are not absolutely identical because of the many natural polymorphisms of antithrombin which generally do not change the properties, i.e. the anticoagulant properties, of the antithrombin.

The human aminosequence of antithrombin presents two forms: a "short form" (SEQ ID NO: 2) which does not comprise a signal peptide and a "long form" (SEQ ID NO: 26) which includes a signal peptide.

The signal peptide comprises 32 amino acids and is necessary for antithrombin secretion. It is removed during antithrombin processing and the plasma antithrombin circulates as the <<short form>>.

Accordingly, in the present invention, the mutated antithrombin amino acid sequences, represented by SEQ ID NO: 2, 4, 6, 8, 10, 12, 14, 16, 18, 20, 22, 24, 62, 64, 66, 68 and 78 do not comprise the signal peptide and the mutated antithrombin amino acid sequences, represented, by SEQ ID NO: 26, 28, 30, 32, 34, 36, 38, 40, 42, 44, 46, 48, 70, 72, 74, 76 and 80 include the signal peptide.

The term <<mutated antithrombin>> as used herein, designates mutated antithrombins which are different from the naturally found mutated antithrombin (also called mutants of antithrombin) known in the art in that said mutated antithrombins of the invention have a reduced or no anticoagulant activity, and are able to compete in vivo with plasma antithrombin for glycosaminoglycan binding.

It has unexpectedly been found that the said mutated antithrombins according to the invention are able to prevent the undesired complications of anticoagulation, in particular hemorrhages, resulting from side effects of said anticoagulant activity of antithrombin.

The expression <<mutated antithrombin having substantially no activity>> designates a mutated antithrombin which has lost its capacity to inhibit coagulation.

The expression <<mutated antithrombin having an anticoagulant activity substantially reduced with respect to the anticoagulant activity of the non-mutated antithrombin>> designates a mutated antithrombin which has a reduced (2 to 20 fold reduced) capacity to inhibit coagulation compared to the wild type antithrombin.

The anticoagulant activity of mutated antithrombin will be evaluated in a purified system: mutated antithrombin anti-Xa and anti-IIa inhibitory activities will be measured as described in Material and methods section.

The mutated antithrombin according to the invention has a cytoprotective activity. This "cytoprotective activity" confers to mutated antithrombin properties to protect cells against damage or cellular injuries, such as damage caused by inflammation, infection or ischemia/hypoxia.

The cytoprotective activity of mutated antithrombin are evaluated as described in Material and methods section: briefly, the pro-inflammatory cytokines levels are compaired (IL6 and TNFα) in whole blood exposed to LPS, in the presence or in the absence of mutated antithrombin.

The expression "cellular injury" refers to a damage caused to the structure or function of the cell caused by an agent which may be physical or chemical. Cellular injury occurs when limits of adaptive response to a stimulus are exceeded.

Cellular injury can be caused by, but not limited to, inflammation, infection, hypoxia and ischemia/reperfusion.

Ischemia occurs when arterial flow is impeded by arteriosclerosis or by thrombi and is the most common cause of hypoxia, occurs during an inadequate oxygenation of the blood due to cardiorespiratory failure, or during a loss of oxygen-carrying capacity of the blood as in anemia or carbon monoxide poisoning.

Cellular injury can be reversible or irreversible. In the case of an irreversible injury, many cells will undergo apoptosis or necrosis. Necrosis, which is the more common type of cell death, is manifested by severe cell swelling or cell rupture, coagulation of cytoplasmic proteins, breakdown of cell organelles such as lysosomes, etc. . . .

Since heparin may compete with the interaction between mutated antithrombin and cellular heparin-like glycosaminoglycans, the mutated antithrombin according to the invention is preferably not administered in patients that have received heparin treatment. Other anticoagulants can be used in association with the mutated antithrombin of the invention, provided that said association does not impair the cytoprotective activity of mutated antithrombin.

More preferably, the present invention relates to the use of a mutated antithrombin having an anticoagulant activity substantially reduced with respect to the anticoagulant activity of the non mutated antithrombin, or having substantially no anticoagulant activity, for the preparation of a drug intended for the prevention or the treatment of pathologies associated with cellular injury, such as infection, inflammation or hypoxic injury, said mutated antithrombin being administered in a patient in a need thereof at a concentration from about 0.5 to about 15 UI/ml, particularly from about 1 to about 7.5 UI/ml to reach about 100% to 750% of AT in plasma (cytoprotective effects were observed for AT concentrations more than to 250%, with plasmatic AT).1 IU of antithrombin is defined as the amount of antithrombin contained in 1 mL of plasma, corresponding to a range from about 0.15 g/L to about 0.3 g/L of plasma.

According to the invention, mutated AT is thus preferably administered with a loading dose from about 3000 to about 22500 IU (40 à 300 IU/kg) followed by a continuous intravenous infusion from about 3000 to about 22500 IU (40 à 300 IU/kg) for a period of time from 2 to 7 days, preferably 4 days.

The invention relates to a method for the prevention or the treatment of pathologies associated with cellular injury, such as infection, inflammation hypoxia or ischemia/reperfusion injury, comprising the administering in a patient in a need thereof of a composition comprising at least one mutated antithrombin:

having an anticoagulant activity substantially reduced with respect to the anticoagulant activity of the non mutated antithrombin, or having substantially no anticoagulant activity, said composition being administered at a dosage from about 20 UI/kg/day to about 600 UI/kg/day, preferably from about 40 UI/kg/day to about 300 UI/kg/day.

In a preferred embodiment, the invention relates to the use of a composition comprising at least a mutated antithrombin defined above, for the preparation of a drug intended for the treatment or prevention of pathologies related to cellular ischemia/reperfusion injury, in particular selected from the group comprising: Inflammatory syndromes, cardiovascular diseases, neural or brain diseases, ischemia/reperfusion injury related to surgery, organ transplantation and ischemia/reperfusion injury related to stroke, or for the treatment or prevention of pathologies related to infections, in particular selected from the group comprising infectious diseases, and inflammation associated diseases.

An advantageous embodiment of the invention relates to the use of a composition comprising at least a mutated antithrombin above-defined, wherein said pathologies are selected from the group comprising: sepsis, severe sepsis or septic shock ischemic stroke, heat stroke, acute myocardial infarction, extremity ischemia, acute neurodegenerative disease, chronic neurodegenerative disease, such as Alzheimer's disease, Down syndrome, Huntington's disease, and Parkinson's disease, organ transplantation, chemotherapy, and radiation injury, such as brain radiation injury.

According to the invention, "hypoxic injury" means hypoxia or ischemia/reperfusion. Definition and classification of severe sepsis is known in the art, and for instance is disclosed in Levy, M. M., et al., (Levy, M. M., et al. Intensive Care Med, 2003. 29(4): p. 530-8.

A stroke (acute cerebrovascular attack) occurs when the blood flow to the brain is decreased or stopped.

In one preferred embodiment, the present invention relates to the use of mutated antithrombin as defined above for the preparation of a drug/medicine intended for the prevention or the treatment of sepsis; i.e. systemic inflammatory response syndrome (SIRS) accompanying an infective disease. Examples of syndromes caused by the aggravation of sepsis include severe sepsis, septic shock, and multiple organ dysfunction syndrome.

In one particular embodiment, the invention relates to the above-mentioned use, wherein said mutated antithrombin has:

a thrombin inhibitory activity substantially reduced, or substantially lost, or a factor Xa inhibitory activity reduced, or substantially lost, or a thrombin inhibitory activity and a factor Xa inhibitory activity substantially reduced, or substantially lost.

The complete anticoagulant activity of antithrombin is achieved by the inhibition of the pro-coagulating activity of thrombin and factor Xa. Therefore, in order to reduce the anticoagulant activity of antithrombin it is possible to reduce, by mutation, its ability to inhibit thrombin, and/or factor Xa. Preferably, in order to completely reduce the anticoagulant activity of antithrombin, both of the thrombin and factor X inhibitory activity of antithrombin should be inactivated.

The thrombin inhibitory or factor Xa activity is "substantially reduced" means that the activity of antithrombin to inhibit thrombin or factor Xa is reduced compared to said activity in wild type antithrombin. Preferably, according to the invention, the thrombin inhibitory or factor Xa activity is considered as reduced when said activity represents from about 50% to about 5% of the thrombin inhibitory or factor Xa activity of the wild type antithrombin.

Anti-Xa and anti-IIa inhibitory activities will be measured in a purified system as described in Material and methods section.

The thrombin inhibitory or factor Xa activity is "substantially lost" means that the activity of antithrombin to inhibit thrombin or factor Xa is absent compared to said activity in wild type antithrombin.

Anti-Xa and anti-IIa inhibitory activities are measured in a purified system as described in "Material and methods" section.

In one other preferred embodiment, the invention relates to the above-mentioned use, wherein said mutated antithrombin comprises at least one mutation within the region from the amino acid at position 380 to the amino acid at position 400, particularly within the region from the amino acid at position 390 to the amino acid at position 397, particularly within the region from the amino acid at position 390 to the amino acid at position 394, in particular at positions 393 or 394, the amino acid numbering referring to the antithrombin amino acid sequence represented by SEQ ID NO: 2, said mutation being a substitution, insertion or deletion.

The region from the amino acid at position 380 to the amino acid at position 400 is generally named "reactive center loop" (RCL). The residues in the RCL are numbered according to their positions relative to the scissile P1-P1' bond (non-primed numbers towards the N-terminus and primed numbers towards the C-terminus of the serpin). In particular, the region stretching from P14 to P4' (residues from 380 to 397) is complementary to the active site of its target protease. In particular, residues from P4 to P1' (residues from 390 to 394) directly interact within protease catalytic groove. In particular, residue P1 (393) is crucial for protease inhibition.

The mutated antithrombins of the invention can comprise others mutations, outside of the region from the amino acid at position 380 to the amino acid at position 400, provided there is no change in the above-mentioned properties of the mutated antithrombins.

In one other particular embodiment, the invention relates to the use as mentioned above, wherein said mutated antithrombin further comprises at least one mutation at the glycosylation sites at the amino acid at position 96, 135, 155 or 192, in particular at position 135, the amino acid numbering referring to the antithrombin amino acid sequence represented by SEQ ID NO: 2.

Glysosylation sites are necessary for antithrombin secretion when antithrombin is expressed in eukaryotic cells. However, removing one site does not impair antithrombin secretion while increases heparin-like glycosaminoglycans binding. Indeed, glycosylation chains are involved in antithrombin-cellular heparin-like glycosaminoglycans binding.

The interaction with cellular heparin-like glycosaminoglycans enhances the cytoprotective effect of anthithrombin, and mutatis mutandis, the cytoprotective activity of mutated antithrombin according to the invention.

An advantageous embodiment of the invention relates to the use of a composition comprising at least a mutated antithrombin having an anticoagulant activity substantially reduced with respect to the anticoagulant activity of the non mutated antithrombin, or having substantially no anticoagulant activity,
said mutated antithrombin having further:
a thrombin inhibitory activity substantially reduced, or substantially lost, or
a factor Xa inhibitory activity reduced, or substantially lost, or a thrombin inhibitory activity and a factor Xa inhibitory activity substantially reduced, or substantially lost,
and said mutated antithrombin comprising at least one mutation:
within the region from the amino acid at position 380 to the amino acid at position 400, in particular at positions 393 or 394, the amino acid numbering referring to the antithrombin amino acid sequence represented by SEQ ID NO: 2, or
within the region from the amino acid at position 412 to the amino acid at position 432, in particular at position 425 or 426, the amino acid numbering referring to the antithrombin amino acid sequence comprising the signal peptide, represented by SEQ ID NO: 26,
said mutation being a substitution, insertion or deletion,
for the preparation of a drug intended for the prevention or the treatment of pathologies associated with infection, inflammation or hypoxic injury, in particular sepsis and ischemia/reperfusion related to stroke, ischemia/reperfusion related to surgery and ischemia/reperfusion related to organ transplantation.

A preferred embodiment of the invention relates to the use above mentioned, wherein said mutated antithrombin is an amino acid sequence selected from the group consisting of:
SEQ ID NO:4, said amino acid sequence comprising, in the sequence of antithrombin represented by SEQ ID NO:2, the substitution of the amino acid at position 393, by an Histidine (His),
SEQ ID NO:6, said amino acid sequence comprising, in the sequence of antithrombin represented by SEQ ID NO:2, the insertion of a Proline (Pro) between the amino acid at position 393 and the amino acid at position 394,
SEQ ID NO:8, said amino acid sequence comprising, in the sequence of antithrombin represented by SEQ ID NO:2, the deletion of the amino acid at position 393,
SEQ ID NO:10, said amino acid sequence comprising, in the sequence of antithrombin represented by SEQ ID NO:2, the deletion of the amino acid at position 394,
SEQ ID NO:62, said amino acid sequence comprising, in the sequence of antithrombin represented by SEQ ID NO:2, and the substitution of the amino acid at position 394 by a Glutamine (Gln), and
SEQ ID NO:64, said amino acid sequence comprising, in the sequence of antithrombin represented by SEQ ID NO:2, and the substitution of the amino acid at position 394 by a Glutamic acid (Glu).

Another preferred embodiment of the invention relates to the above defined use, wherein said mutated antithrombin is an amino acid sequence selected from the group consisting of:
SEQ ID NO:14, said amino acid sequence comprising, in the sequence of antithrombin represented by SEQ ID NO:2, the substitution of the amino acid at position 393, by an Histidine (His), and the substitution of the amino acid at position 135, by a Glutamine (Gln),
SEQ ID NO:16, said amino acid sequence comprising, in the sequence of antithrombin represented by SEQ ID NO:2, the insertion of a Proline (Pro) between the amino acid at position 393 and the amino acid at position 394, and the substitution of the amino acid at position 135, by a Glutamine (Gln),
SEQ ID NO:18, said amino acid sequence comprising, in the sequence of antithrombin represented by SEQ ID NO:2, the deletion of the amino acid at position 393 and at position 394,
SEQ ID NO:20, said amino acid sequence comprising, in the sequence of antithrombin represented by SEQ ID NO:2, the deletion of the amino acid at position 393 and the substitution of the amino acid at position 135, by a Glutamine (Gln), SEQ ID NO:22, said amino acid sequence comprising, in the sequence of antithrombin represented by SEQ ID NO:2, the deletion of the amino acid at position 394 and the substitution of the amino acid at position 135, by a Glutamine (Gln), SEQ ID NO:24, said amino acid sequence comprising, in the sequence of antithrombin represented by SEQ ID NO:2, the deletion of the amino acid at position 393 and at position 394, and the substitution of the amino acid at position 135, by a Glutamine (Gln), SEQ ID NO:66, said amino acid sequence comprising, in the sequence of antithrombin represented by SEQ ID NO:2, the substitution of the amino acid at position 394 by a Glutamine (Gln), and the substitution of the amino acid at position 135, by a Glutamine (Gln), and SEQ ID NO:68, said amino acid sequence comprising, in the sequence of antithrombin represented by SEQ ID NO:2, the substitution of the amino acid at position 394 by a Glutamic acid (Glu) and the substitution of the amino acid at position 135, by a Glutamine (Gln).

Another preferred embodiment of the invention related to the above mentioned use, wherein said mutated antithrombin comprises at least one mutation within the region from the amino acid at position 412 to the amino acid at position 432, particularly within the region from the amino acid at position 412 to the amino acid at position 429, particularly within the region from the amino acid at position 422 to the amino acid at position 426, in particular at position 425 or 426, the amino acid numbering referring to the antithrombin amino acid sequence comprising the signal peptide, represented by SEQ ID NO: 26, said mutation being a substitution, insertion or deletion.

The mutated antithrombins of the invention can comprise others mutations, outside of the region from the amino acid at position 412 to the amino acid at position 432, provided there is no change in the above-mentioned properties of the mutated antithrombins.

In a preferred embodiment, the invention relates to the use as mentioned herein, wherein said mutated antithrombin further comprises at least one mutation at the glycosylation sites at the amino acid at position 128, 167, 187 or 224, in particular at position 167 the amino acid numbering referring to the antithrombin amino acid sequence represented by SEQ ID NO: 26.

A more preferred embodiment of the invention relates to the above mentioned use, wherein said mutated antithrombin is an amino acid sequence selected from the group consisting of:

SEQ ID NO:28, said amino acid sequence comprising, in the sequence of antithrombin represented by SEQ ID NO:26, the substitution of the amino acid at position 425, by an Histidine (His), or SEQ ID NO:30, said amino acid sequence comprising, in the sequence of antithrombin represented by SEQ ID NO:26, the insertion of a Proline (Pro) between the amino acid at position 425 and the amino acid at position 426, or SEQ ID NO:32, said amino acid sequence comprising, in the sequence of antithrombin represented by SEQ ID NO:26, the deletion of the amino acid at position 425, or SEQ ID NO:34, said amino acid sequence comprising, in the sequence of antithrombin represented by SEQ ID NO:26, the deletion of the amino acid at position 426, SEQ ID NO:70, said amino acid sequence comprising, in the sequence of antithrombin represented by SEQ ID NO:26, and the substitution of the amino acid at position 426 by a Glutamine (Gln), and SEQ ID NO:72, said amino acid sequence comprising, in the sequence of antithrombin represented by SEQ ID NO: 26, and the substitution of the amino acid at position 426 by a Glutamic acid (Glu).

Another preferred embodiment of the invention relates to the use mentioned above, wherein said mutated antithrombin is an amino acid sequence selected from the group consisting of:

SEQ ID NO:38, said amino acid sequence comprising in the sequence of antithrombin represented by SEQ ID NO:26, the substitution of the amino acid at position 425, by an Histidine (His), and the substitution of the amino acid at position 167, by a Glutamine (Gln), SEQ ID NO:40, said amino acid sequence comprising, in the sequence of antithrombin represented by SEQ ID NO:26, the insertion of a Proline (Pro) between the amino acid at position 425 and the amino acid at position 426, and the substitution of the amino acid at position 167, by a Glutamine (Gln), SEQ ID NO:42, said amino acid sequence comprising, in the sequence of antithrombin represented by SEQ ID NO:26, the deletion of the amino acid at position 425 and at position 426, SEQ ID NO:44, said amino acid sequence comprising, in the sequence of antithrombin represented by SEQ ID NO:26, the deletion of the amino acid at position 425 and the substitution of the amino acid at position 167, by a Glutamine (Gln), SEQ ID NO:46, said amino acid sequence comprising, in the sequence of antithrombin represented by SEQ ID NO:26, the deletion of the amino acid at position 426 and the substitution of the amino acid at position 167, by a Glutamine (Gln), SEQ ID NO:48, said amino acid sequence comprising, in the sequence of antithrombin represented by SEQ ID NO:26, the deletion of the amino acid at position 425 and at position 426 and the substitution of the amino acid at position 167, by a Glutamine (Gln), SEQ ID NO:74, said amino acid sequence comprising, in the sequence of antithrombin represented by SEQ ID NO:26, the substitution of the amino acid at position 426 by a Glutamine (Gln), and the substitution of the amino acid at position 167, by a Glutamine (Gln), and SEQ ID NO:76, said amino acid sequence comprising, in the sequence of antithrombin represented by SEQ ID NO:26, the substitution of the amino acid at position 426 by a Glutamic acid (Glu) and the substitution of the amino acid at position 167, by a Glutamine (Gln).

The invention also relates to the use of a combination comprising a first antithrombin consisting of at least one mutated antithrombin having a substantially reduced anticoagulant activity, or substantially no anticoagulant activity according herein, and a second antithrombin consisting of at least an antithrombin, having an anticoagulant activity similar to that of the wild type antithrombin as a combination product for the preparation of a drug intended for the prevention or the treatment of pathologies associated with cellular injury, such as infection, inflammation or hypoxic injury, said combination product being possibly used for a simultaneous, sequential or separate administration, said first and said second antithrombins being in a predetermined weight ratio, preferably in a respective weight ratio of about 9:1 to about 1:4, preferably from about 4:1 to about 1:2, more preferably from about 2:1 to about 1:2.

According to the invention, the terms "a first antithrombin consisting of at least one mutated antithrombin" refer to the mutated antithrombin as mentioned above.

According to the invention, the terms "a second antithrombin consisting of at least an antithrombin, having an anticoagulant activity similar to that of the wild type antithrombin" refer to any anthithrombin having no mutation and corresponding to wild type antithrobin, or antithrombin having at least one mutation, said mutation not affecting the anticoagulant activity of said second antithrombin.

Thus, the second antithrombin of the invention may have a mutation in one or more glycosylation site, in particular a mutation in the residue at the position 135 of the sequence SEQ ID NO 2 or in the residue at position 167 of the SEQ ID NO 26. These "mutated antithrombin" (a second antithrombin) retain their anticoagulant activity.

Since heparin may compete with the interaction between mutated antithrombin and cellular heparin-like glycosaminoglycans, the mutated antithrombin according to the invention is preferably not administered in patients that have received heparin treatment. Other anticoagulant can be used in association with the mutated antithrombin of the invention provided that said association does not impair the cytoprotective activity of mutated antithrombin.

The combination of the first antithrombin and the second antithrombin according to the invention is administered at a dosage from about 20 UI/kg/day to about 600 UI/kg/day, preferably from about 40 UI/kg/day to about 300 UI/kg/day.

In a case of a ratio first/second antithrombin corresponding to a ratio 9/1, said first antithrombin is administered at a dosage of from about 36 IU/kg/day to about 270 IU/kg/day and said second antithrombin is administered at a dosage of from about 4 IU/kg/day to about 30 IU/kg/day.

Also, the combination of said first and second antithrombin according to the invention can be administered in a patient in a need thereof at a concentration from about 0.5 to about 15 UI/ml, particularly from about 1 to about 7.5 UI/ml to reach about 100% to 750% of AT in plasma. The invention also relates to a method for the prevention or the treatment of pathologies associated with cellular injury, such as infection, inflammation or hypoxic injury, comprising the administering in a patient in a need thereof of a combination comprising:

a first antithrombin consisting of at least one mutated antithrombin having a substantially reduced anticoagulant activity, or substantially no anticoagulant activity according herein, and a second antithrombin consisting of at least an antithrombin, having an anticoagulant activity similar to that of the wild type antithrombin said combination being administered at a dosage from about 20 UI/kg/day to about 600 UI/kg/day, preferably from about 40 UI/kg/day to about 300 UI/kg/day.

The combination according to the invention confers a cytoprotective activity against cellular injury via both first antithrombin while presence of the second antithrombin reduces the hemorrhagic accident.

In a preferred embodiment, the invention relates to the use of a combination as mentioned above, as a combination product for the for the preparation of a drug intended for the treatment or prevention of pathologies related to cellular ischemia/reperfusion injury, in particular selected from the group comprising: Inflammatory syndromes, Cardiovascular diseases, Neural or Brain diseases, Ischemia/reperfusion injury related to surgery, and Ischemia/reperfusion injury related to organ transplantation, or for the treatment or prevention of pathologies related to infections, in particular selected from the group comprising: Infectious diseases, and Inflammation associated diseases.

A preferred embodiment of the invention relates to the use of a combination above defined, wherein said pathologies are selected from the group comprising sepsis, ischemic stroke, acute myocardial infarction, extremity ischemia acute neurodegenerative disease, chronic neurodegenerative disease, such as Alzheimer's disease, Down syndrome, Huntington's disease, and Parkinson's disease, organ transplantation, chemotherapy, and radiation injury, such as brain radiation injury.

In one preferred embodiment, the present invention relates to the use a composition as defined above for the preparation of a drug/medicine intended for the prevention or the treatment of sepsis; i.e. systemic inflammatory response syndrome (SIRS) accompanying an infective disease. Examples of syndromes caused by the aggravation of sepsis include severe sepsis, septic shock, and multiple organ dysfunction syndromes.

In one particular embodiment, the invention relates to the use of a combination mentioned above, wherein said mutated antithrombin has:

a thrombin inhibitory activity substantially reduced, or substantially lost, or a factor Xa inhibitory activity reduced, or substantially lost, or a thrombin inhibitory activity and a factor Xa inhibitory activity substantially reduced, or substantially lost.

A more particular embodiment of the invention relates to the use of a combination above-mentioned, wherein said first antithrombin comprises at least one mutation within the region from the amino acid at position 380 to the amino acid at position 400, particularly within the region from the amino acid at position 390 to the amino acid at position 397, particularly within the region from the amino acid at position 390 to the amino acid at position 394, in particular at positions 393 or 394, the amino acid numbering referring to the antithrombin amino acid sequence represented by SEQ ID NO: 2, said mutation being a substitution, insertion or deletion, and wherein said second antithrombin is the wild type antithrombin.

In an advantageous embodiment, the present invention relates to the use such as defined above, wherein said first antithrombin is an amino acid sequence selected from the group consisting of:

SEQ ID NO:4, said amino acid sequence comprising, in the sequence of antithrombin represented by SEQ ID NO:2, the substitution of the amino acid at position 393, by an Histidine (His), SEQ ID NO:6, said amino acid sequence comprising, in the sequence of antithrombin represented by SEQ ID NO:2, the insertion of a Proline (Pro) between the amino acid at position 393 and the amino acid at position 394, SEQ ID NO:8, said amino acid sequence comprising, in the sequence of antithrombin represented by SEQ ID NO:2, the deletion of the amino acid at position 393, SEQ ID NO:10, said amino acid sequence comprising, in the sequence of antithrombin represented by SEQ ID NO:2, the deletion of the amino acid at position 394, SEQ ID NO:18, said amino acid sequence comprising, in the sequence of antithrombin represented by SEQ ID NO:2, the deletion of the amino acid at position 393 and at position 394, SEQ ID NO:62, said amino acid sequence comprising, in the sequence of antithrombin represented by SEQ ID NO:2, and the substitution of the amino acid at position 394 by a Glutamine (Gln), and SEQ ID NO:64, said amino acid sequence comprising, in the sequence of antithrombin represented by SEQ ID NO:2, and the substitution of the amino acid at position 394 by a Glutamic acid (Glu), and said second antithrombin consists of SEQ ID NO:2.

The above mentioned combination contains at least one mutated first antithrombin having one or two mutations in the "reactive center loop" of antithrombin, in association with the wild type antithrombin.

In an advantageous embodiment, the present invention relates to the use of a composition In such as defined above, wherein said first antithrombin further comprises at least one mutation at the glycosylation sites at the amino acid at position 96, 135, 155 or 192, in particular at position 135, the amino acid numbering referring to the antithrombin amino acid sequence represented by SEQ ID NO: 2.

Another advantageous embodiment of the present invention relates to the use such as defined above, wherein said first antithrombin is an amino acid sequence selected from the group consisting of:

SEQ ID NO:14, said amino acid sequence comprising, in the sequence of antithrombin represented by SEQ ID NO:2, the substitution of the amino acid at position 393, by an Histidine (His), and the substitution of the amino acid at position 135, by a Glutamine (Gln), SEQ ID NO:16, said amino acid sequence comprising, in the sequence of antithrombin represented by SEQ ID NO:2, the insertion of a Proline (Pro) between the amino acid at position 393 and the amino acid at position 394, and the substitution of the amino acid at position 135, by a Glutamine (Gln), SEQ ID NO:20, said amino acid sequence comprising, in the sequence of antithrombin represented by SEQ ID NO:2, the deletion of the amino acid at position 393 and the substitution of the amino acid at position 135, by a Glutamine (Gln), SEQ ID NO:22, said amino acid sequence comprising, in the sequence of antithrombin represented by SEQ ID NO:2, the deletion of the amino acid at position 394 and the substitution of the amino acid at position 135, by a Glutamine (Gln), SEQ ID NO:24, said amino acid sequence comprising, in the sequence of antithrombin represented by SEQ ID NO:2, the deletion of the amino acid at position 393 and at position 394, and the substitution of the amino acid at position 135, by a Glutamine (Gln), SEQ ID NO:66, said amino acid sequence comprising, in the sequence of antithrombin represented by SEQ ID NO:2, the substitution of the amino acid at position 394 by a Glutamine (Gln), and the substitution of the amino acid at position 135, by a Glutamine (Gln), and SEQ ID NO:68, said amino acid sequence comprising, in the sequence of antithrombin represented by SEQ ID NO:2, the substitution of the amino acid at position 394 by a Glutamic acid (Glu) and the substitution of the amino acid at position 135, by a Glutamine (Gln), and said second antithrombin consists of SEQ ID NO:2.

The above mentioned combination contains at least one mutated first antithrombin having one or two mutations in the "reactive center loop" of antithrombin, and a mutation at a glycosylation site, in association with the wild type antithrombin.

In another preferred embodiment, the invention relates to the use of a composition as defined above, wherein said second antithrombin comprises at least one mutation at the glycosylation sites at the amino acid at position 96, 135, 155 or 192, in particular at position 135, the amino acid numbering referring to the antithrombin amino acid sequence represented by SEQ ID NO: 2.

In another preferred embodiment, the invention relates to the use such as defined above, wherein said first antithrombin is an amino acid sequence selected from the group consisting of:

SEQ ID NO:14, said amino acid sequence comprising, in the sequence of antithrombin represented by SEQ ID NO:2, the substitution of the amino acid at position 393, by an Histidine (His), and the substitution of the amino acid at position 135, by a Glutamine (Gln), SEQ ID NO:16, said amino acid sequence comprising, in the sequence of antithrombin represented by SEQ ID NO:2, the insertion of a Proline (Pro) between the amino acid at position 393 and the amino acid at position 394, and the substitution of the amino acid at position 135, by a Glutamine (Gln), SEQ ID NO:20, said amino acid sequence comprising, in the sequence of antithrombin represented by SEQ ID NO:2, the deletion of the amino acid at position 393 and the substitution of the amino acid at position 135, by a Glutamine (Gln), SEQ ID NO:22, said amino acid sequence comprising, in the sequence of antithrombin represented by SEQ ID NO:2, the deletion of the amino acid at position 394 and the substitution of the amino acid at position 135, by a Glutamine (Gln), SEQ ID NO:24, said amino acid sequence comprising, in the sequence of antithrombin represented by SEQ ID NO:2, the deletion of the amino acid at position 393 and at position 394, and the substitution of the amino acid at position 135, by a Glutamine (Gln), SEQ ID NO:66, said amino acid sequence comprising, in the sequence of antithrombin represented by SEQ ID NO:2, the substitution of the amino acid at position 394 by a Glutamine (Gln), and the substitution of the amino acid at position 135, by a Glutamine (Gln), and SEQ ID NO:68, said amino acid sequence comprising, in the sequence of antithrombin represented by SEQ ID NO:2, the substitution of the amino acid at position 394 by a Glutamic acid (Glu) and the substitution of the amino acid at position 135, by a Glutamine (Gln), and said second antithrombin consists of the amino acid sequence SEQ ID NO:78, said amino acid sequence comprising, in the sequence of antithrombin represented by SEQ ID NO:2, the substitution of the amino acid at position 135, by a Glutamine (Gln).

The above mentioned combination contains at least one mutated first antithrombin having one or two mutations in the "reactive center loop" of antithrombin, and a mutation at a glycosylation site, in association with a second antithrombin having a mutation in a glycosylation site, but retaining its anticoagulant activity.

In one other particular embodiment, the invention discloses the use such as defined above, wherein said first antithrombin comprises at least one mutation within the region from the amino acid at position 412 to the amino acid at position 432, particularly within the region from the amino acid at position 412 to the amino acid at position 429, particularly within the region from the amino acid at position 422 to the amino acid at position 426, in particular at position 425 or 426, the amino acid numbering referring to the antithrombin amino acid sequence comprising the signal peptide, represented by SEQ ID NO: 26, said mutation being a substitution, insertion or deletion, and wherein said second antithrombin is the wild type antithrombin.

Another preferred embodiment of the invention relates to the use such as defined above, wherein said first antithrombin is an amino acid sequence selected from the group consisting of:

SEQ ID NO:28, said amino acid sequence comprising, in the sequence of antithrombin represented by SEQ ID NO:26, the substitution of the amino acid at position 425, by an Histidine (His), or SEQ ID NO:30, said amino acid sequence comprising, in the sequence of antithrombin represented by SEQ ID NO:26, the insertion of a Proline (Pro) between the amino acid at position 425 and the amino acid at position 426, or SEQ ID NO:32, said amino acid sequence comprising, in the sequence of antithrombin represented by SEQ ID NO:26, the deletion of the amino acid at position 425, or SEQ ID NO:34, said amino acid sequence comprising, in the sequence of antithrombin represented by SEQ ID NO:26, the deletion of the amino acid at position 426, SEQ ID NO:42, said amino acid sequence comprising, in the sequence of antithrombin represented by SEQ ID NO:26, the deletion of the amino acid at position 425 and at position 426, SEQ ID NO:70, said amino acid sequence comprising, in the sequence of antithrombin represented by SEQ ID NO:26, and the substitution of the amino acid at position 426 by a Glutamine (Gln), and SEQ ID NO:72, said amino acid sequence comprising, in the sequence of antithrombin represented by SEQ ID NO:26, and the substitution of the amino acid at position 426 by a Glutamic acid (Glu), and second antithrombin consists of SEQ ID NO:26.

The above mentioned combination contains at least one mutated first antithrombin having one or two mutations in the "reactive center loop" of antithrombin, in association with the wild type antithrombin.

Also, in another preferred embodiment, the invention relates to the use such as defined above, wherein said first antithrombin further comprises at least one mutation at the glycosylation sites at the amino acid at position 128, 167, 187 or 224, in particular at position 167, the amino acid numbering referring to the antithrombin amino acid sequence represented by SEQ ID NO: 26.

Another preferred embodiment of the invention relates to the use as previously defined, wherein said first antithrombin is an amino acid sequence selected from the group consisting of:

SEQ ID NO:38, said amino acid sequence comprising in the sequence of antithrombin represented by SEQ ID NO:26, the substitution of the amino acid at position 425, by an Histidine (His), and the substitution of the amino acid at position 167, by a Glutamine (Gln), SEQ ID NO:40, said amino acid sequence comprising, in the sequence of antithrombin represented by SEQ ID NO:26, the insertion of a Proline (Pro) between the amino acid at position 425 and the amino acid at position 426, and the substitution of the amino acid at position 167, by a Glutamine (Gln), SEQ ID NO:44, said amino acid sequence comprising, in the sequence of antithrombin represented by SEQ ID NO:26, the deletion of the amino acid at position 425 and the substitution of the amino acid at position 167, by a Glutamine (Gln), SEQ ID NO:46, said amino acid sequence comprising, in the sequence of antithrombin represented by SEQ ID NO:26, the deletion of the amino acid at position 426 and the substitution of the amino acid at position 167, by a Glutamine (Gln), SEQ ID NO:48, said amino acid sequence comprising, in the sequence of antithrombin represented by SEQ ID NO:26, the deletion of the amino acid at position 425 and at position 426 and the substitution of the amino acid at position 167, by a Glutamine (Gln), SEQ ID NO:74, said amino acid sequence comprising, in the sequence of antithrombin represented by SEQ ID NO:26, the substitution of the amino acid at position 426 by a Glutamine (Gln), and the substitution of the amino acid at position 167, by a Glutamine (Gln), and SEQ ID NO:76, said amino acid sequence comprising, in the sequence of antithrombin represented by SEQ ID NO:26, the substitution of the amino acid at position 426 by a Glutamic acid (Glu) and the substitution of the amino acid at position 167, by a Glutamine (Gln), and second antithrombin consists of SEQ ID NO:26.

The above mentioned combination contains at least one mutated first antithrombin having one or two mutations in the "reactive center loop" of antithrombin, and a mutation at a glycosylation site, in association with the wild type antithrombin.

Another preferred embodiment of the invention relates to the use such as defined above, wherein said second antithrombin comprises at least one mutation at the glycosylation sites at the amino acid at position 128, 167, 187 or 224, in particular at position 167, the amino acid numbering referring to the antithrombin amino acid sequence represented by SEQ ID NO: 26.

Another preferred embodiment of the invention relates to the use such as defined above, wherein said first antithrombin is an amino acid sequence selected from the group consisting of:

SEQ ID NO:38, said amino acid sequence comprising in the sequence of antithrombin represented by SEQ ID NO:26, the substitution of the amino acid at position 425, by an Histidine (His), and the substitution of the amino acid at position 167, by a Glutamine (Gln), SEQ ID NO:40, said amino acid sequence comprising, in the sequence of antithrombin represented by SEQ ID NO:26, the insertion of a Proline (Pro) between the amino acid at position 425 and the amino acid at position 426, and the substitution of the amino acid at position 167, by a Glutamine (Gln), SEQ ID NO:44, said amino acid sequence comprising, in the sequence of antithrombin represented by SEQ ID NO:26, the deletion of the amino acid at position 425 and the substitution of the amino acid at position 167, by a Glutamine (Gln), SEQ ID NO:46, said amino acid sequence comprising, in the sequence of antithrombin represented by SEQ ID NO:26, the deletion of the amino acid at position 426 and the substitution of the amino acid at position 167, by a Glutamine (Gln), SEQ ID NO:48, said amino acid sequence comprising, in the sequence of antithrombin represented by SEQ ID NO:26, the deletion of the amino acid at position 425 and at position 426 and the substitution of the amino acid at position 167, by a Glutamine (Gln), SEQ ID NO:74, said amino acid sequence comprising, in the sequence of antithrombin represented by SEQ ID NO:26, the substitution of the amino acid at position 426 by a Glutamine (Gln), and the substitution of the amino acid at position 167, by a Glutamine (Gln), and SEQ ID NO:76, said amino acid sequence comprising, in the sequence of antithrombin represented by SEQ ID NO:26, the substitution of the amino acid at position 426 by a Glutamic acid (Glu) and the substitution of the amino acid at position 167, by a Glutamine (Gln), and second antithrombin consists of the amino acid sequence SEQ ID NO:80, said amino acid sequence comprising, in the sequence of antithrombin represented by SEQ ID NO:26, the substitution of the amino acid at position 167, by a Glutamine (Gln).

The above mentioned combination contains at least one mutated first antithrombin having one or two mutations in the "reactive center loop" of antithrombin, and a mutation at a glycosylation site, in association with a second antithrombin having a mutation in a glycosylation site, but retaining its anticoagulant activity.

The invention also relates to a composition comprising at least
- a first antithrombin consisting of at least one mutated antithrombin having a substantially reduced anticoagulant activity, or substantially no anticoagulant activity according to any of claim 1 to 5 or 9, and
- a second antithrombin consisting of at least an antithrombin, having an anticoagulant activity similar to that of the wild type antithrombin as a combination product for the preparation of a drug intended for the prevention or the treatment of pathologies associated with cellular injury, such as infection, inflammation or hypoxic injury., said combination product being possibly used for a simultaneous, sequential or separate administration, said first and said second antithrombins being in a predetermined weight ratio being in a predetermined weight ratio, preferably in a respective weight ratio of about 10:1 to about 1:5, preferably from about 5:1 to about 1:2, more preferably from about 2:1 to about 1:2.

In one preferred embodiment, the invention discloses a combination such as defined above, as a combination product for the preparation of a drug intended for the treatment or prevention of pathologies related to cellular ischemia/reperfusion injury, in particular selected from the group comprising: Inflammatory syndromes, Cardiovascular diseases, Neural or Brain diseases. Ischemia/reperfusion injury related to surgery, and Ischemia/reperfusion injury related to organ transplantation, or for the treatment or prevention of pathologies related to infections, in particular selected from the group comprising: infectious diseases, and inflammation associated diseases.

In another preferred embodiment, the invention relates to a combination above defined, wherein said pathologies are selected from the group comprising: sepsis, ischemic stroke, acute myocardial infarction, extremity ischemia, acute neurodegenerative disease, chronic neurodegenerative disease, such as Alzheimer's disease, Down syndrome, Huntington's disease, and Parkinson's disease, organ transplantation, chemotherapy, and radiation injury, such as brain radiation injury.

In other specific embodiment, the invention relates to a combination as defined above, wherein said first antithrombin has:
- a thrombin inhibitory activity substantially reduced, or substantially lost, or
- a factor Xa inhibitory activity reduced, or substantially lost, or
- a thrombin inhibitory activity and a factor Xa inhibitory activity substantially reduced, or substantially lost.

Another preferred embodiment of the invention relates to a combination such as previously defined, wherein said first antithrombin is an amino acid sequence selected from the group consisting of: SEQ ID NO:4, SEQ ID NO:6, SEQ ID NO:8, SEQ ID NO:10, SEQ ID NO:18, SEQ ID NO: 62, and SEQ ID NO: 64, and said second antithrombin consists of SEQ ID NO:2.

In one other particular embodiment the invention relates to a combination such as previously defined, wherein said first antithrombin is an amino acid sequence selected from the group consisting of: SEQ ID NO:14, SEQ ID NO:16, SEQ ID NO:20, SEQ ID NO:22, SEQ ID NO:24, SEQ ID NO:66, and SEQ ID NO:68, and said second antithrombin consists of SEQ ID NO: 2 or SEQ ID NO:78.

Also, in another preferred embodiment, the invention relates to a combination according to the above definition, wherein said first antithrombin is chosen from the group consisting of: SEQ ID NO:28, SEQ ID NO:30, SEQ ID NO:32, SEQ ID NO:34, SEQ ID NO:42, SEQ ID NO:70, and SEQ ID NO:72, and said second antithrombin consists of SEQ ID NO:26.

In one other particular embodiment the invention relates to a combination such as previously defined, wherein said first antithrombin is chosen from the group consisting of: SEQ ID NO:38, SEQ ID NO:40, SEQ ID NO:44, SEQ ID NO:46, SEQ ID NO:48, SEQ ID NO:74, and SEQ ID NO:76, and said second antithrombin consists of SEQ ID NO:26 or SEQ ID NO:80.

The invention also relates to a pharmaceutical composition comprising as active ingredient at least a mutated antithrombin, as defined above, in association with a pharmaceutically acceptable vehicle, in particular a mutated antithrombin of SEQ ID NO: 62, SEQ ID NO: 64, SEQ ID NO: 66, SEQ ID NO: 68, SEQ ID NO: 70, SEQ ID NO: 72, SEQ ID NO: 74 and SEQ ID NO: 76.

By the expression "pharmaceutically acceptable vehicle", one means pharmaceutically acceptable solid or liquid, diluting or encapsulating, filling or carrying agents, which are usually employed in pharmaceutical industry for making pharmaceutical compositions.

The dosage forms of the pharmaceutical composition includes immediate release, extended release, pulse release, variable release, controlled release, timed release, sustained release, delayed release, long acting, and combinations thereof.

Preferably, the pharmaceutical composition according to the invention can be, intravenously, intraperitonealy, subcutaneously or orally delivered.

In one other preferred embodiment, the invention relates to a pharmaceutical composition as mentioned above, said pharmaceutical composition being preferably administered at a dosage from about 80 IU/kg/day to about 300 IU/kg/day, preferably from about 100 IU/kg/day to about 200 IU/kg/day.

The invention also relates to a pharmaceutical composition, comprising as active ingredient a combination of the group comprising:
- of at least a first antithrombine consisting of one mutated antithrombin having a substantially reduced anticoagulant activity, or substantially no anticoagulant activity such as defined above, and
- at least a second antithrombine consisting of at least an antithrombin, having an anticoagulant activity similar to that of the wild type antithrombin of the group consisting of:
SEQ ID NO: 4; SEQ ID NO: 6, SEQ ID NO: 8 or SEQ ID NO: 10, SEQ ID NO: 18 SEQ ID NO: 62 or SEQ ID NO: 64, in association with SEQ ID NO 2,
SEQ ID NO: 14, SEQ ID NO: 16, SEQ ID NO: 20, SEQ ID NO: 22, SEQ ID NO: 24, SEQ ID NO: 66 or SEQ ID NO: 68, in association with SEQ ID NO 2,
SEQ ID NO: 14, SEQ ID NO: 16, SEQ ID NO: 20, SEQ ID NO: 22, SEQ ID NO: 24, SEQ ID NO: 66 or SEQ ID NO: 68, in association with SEQ ID NO 78,
SEQ ID NO: 28, SEQ ID NO: 30, SEQ ID NO: 32, SEQ ID NO: 34, SEQ ID NO: 42; SEQ ID NO: 70 or SEQ ID NO: 72, in association with SEQ ID NO 26,
SEQ ID NO: 38, SEQ ID NO: 40, SEQ ID NO: 44, SEQ ID NO: 46, SEQ ID NO: 48, SEQ ID NO: 74 or SEQ ID NO: 76, in association with SEQ ID NO 26, and
SEQ ID NO: 38, SEQ ID NO: 40, SEQ ID NO: 44, SEQ ID NO: 46, SEQ ID NO: 48, SEQ ID NO: 74 or SEQ ID NO: 76, in association with SEQ ID NO 80,
in association with a pharmaceutically acceptable vehicle.

Preferably, the pharmaceutical composition according to the invention can be, intravenously, intraperitonealy, subcutaneously or orally delivered.

In one other preferred embodiment, the invention relates to a pharmaceutical composition as mentioned above, said pharmaceutical composition being preferably administered at a dosage from about 20 UI/kg/day to about 600 UI/kg/day, preferably from about 40 UI/kg/day to about 300 UI/kg/day.

The invention also relates to a mutated antithrombin, which contains at least an amino acid substitution of the amino acid at position 394 of SEQ ID NO:2 by a glutamic acid (Glu) or a Glutamine (Gln), and in particular mutated antithrombin represented by SEQ ID NO: 62 or SEQ ID NO 64.

The invention also relates to a mutated antithrombin, which contains at least two mutations:
the first mutation being, in the sequence of antithrombin represented by SEQ ID NO:2, the substitution of the amino acid at position 394, by glutamic acid (Glu) or a Glutamine (Gln), and
the second mutation being the substitution of the amino acid at position 135, by a Glutamine (Gln),
said mutated antithrombin being in particular represented by SEQ ID NO: 66 or 68.

The invention also relates to a mutated antithrombin, which contains at least an amino acid substitution of the amino acid at position 426 of SEQ ID NO:26 by a glutamic acid (Glu) or a Glutamine (Gln), and in particular mutated antithrombin represented by SEQ ID NO: 70 or SEQ ID NO:72.

The invention also relates to a mutated antithrombin, which contains at least two mutations:
the first mutation being, in the sequence of antithrombin represented by SEQ ID NO:26, the substitution of the amino acid at position 426, by glutamic acid (Glu) or a Glutamine (Gln), and
the second mutation being the substitution of the amino acid at position 167, by a Glutamine (Gln),
said mutated antithrombin being in particular represented by SEQ ID NO: 74 or 76.

The invention also relates to a nucleotide sequence coding for a mutated antithrombin as defined abovesaid nucleic acid sequence being a DNA or an RNA, in particular nucleotide sequences chosen in the group consisting of SEQ ID NO: 61, SEQ ID NO: 63, SEQ ID NO: 65, SEQ ID NO: 67, SEQ ID NO: 69, SEQ ID NO: 71, SEQ ID NO: 73 and SEQ ID NO: 75, or a complementary sequence of said nucleic acid sequence.

The invention is illustrated, but not limited to, by the following example and the following figures.

2 μg of pENTR vector containing truncated AT cDNA (lane 1 and 2), pCMV6 vector containing full length AT cDNA (lane 3 and 4) or shuttle vector pENTR-AT (lane 5 and 6) are loaded on 1% agarose gel before (lane 1, 3, 5) or after (lane 2, 4, 6) complete digestion by both SacII and StuI. Molecular weight standard sizes are inducated on the left hand of the figure and expressed in base pair (bp). SacII/StuI digestion of pCMV6 vector containing full length AT cDNA releases a 1182 by band corresponding to full length AT cDNA cloned into pENTR vector isolated from SacII/StuI digestion of pENTR vector containing truncated AT cDNA. After ligation of these two fragments the final product is effectively recircularized and shows the expected profile for pENTR-AT after SacII/StuI digestion.

Figure 2:
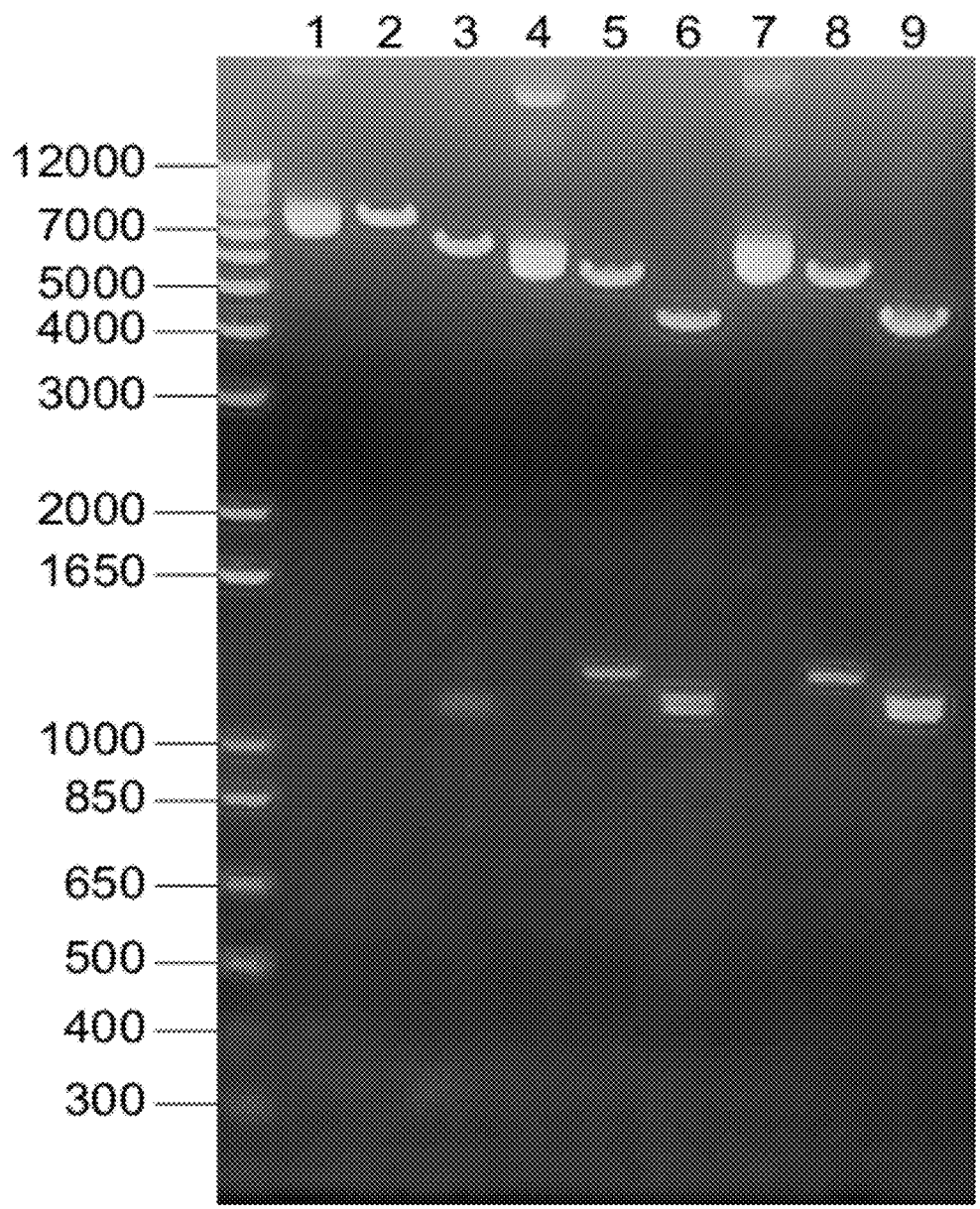

FIG. 2: Characterization of the AT expression vector.

2 μg of pCDNA 3.2 vector (lane 1, 2, 3), pCDNA 3.2 vector containing full length AT cDNA (lane 4, 5, 6) or pCDNA 3.2 vector containing full length AT-N135Q-Pro394 cDNA (lane 7, 8, 9) are loaded on 1% agarose gel before endonucleases treatment (lane 1, 4, 7), after cleavage by StuI (lane 2, 5, 8), or after complete cleavage by both SacII and StuI (lane 3, 6, 9). Molecular weight standard sizes are indicated on the right hand of the figure and expressed in base pair (bp). There is one SacII and one StuI cleavage site in pCDNA 3.2 vector at position 3189 and 4329 respectively. Therefore cleavage of pCDNA 3.2 by StuI only leads to linearization of the vector (7711 bp band) whereas cleavage of pCDNA 3.2 by both StuI and SacII cuts the vector in two fragments (6571 bp and 1140 bp). Substitution of 912-3174 fragment by AT cDNA fragment (1448 bp) into pCDNA 3.2 by recombination introduces one more SacII site at position 1070 and one more StuI site at position 2252 into pcDNA-AT. Then cleavage of pCDNA-AT by StuI gives two fragments (5634 bp and 1263 bp) and cleavage by both endonucleases gives 4 fragments (4452 bp, 1182 bp, 1140 and 123 bp). The same is true for -N135Q-Pro394 cDNA.

Figure 3:
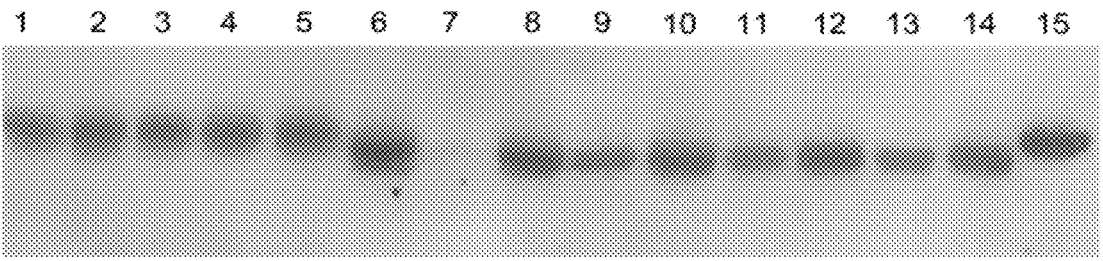

FIG. 3: Clone screening for secretion of recombinant AT in cell culture media.

For each clone isolated after transfection with pCDNA-AT (clone 1 to 5 in lane 1 to 5, respectively), pCDNA-AT-N135Q (clone 1 to 4 in lane 6 to 9, respectively), or with pCDNA-AT-N135Q-Pro394 (clone 1 to 5 in lane 10 to 14, respectively), 30 μl of conditioned media harvested after 24 hours contact with cells are analysed by western-blotting in denaturing condition for their ability to secrete full length recombinant antithrombin. For each clone a single band of variable intensity corresponding to recombinant antithrombin can be seen. Recombinant wild type antithrombin migrate at the same level than control antithrombin purified from plasma (lane 15, 150 ng/lane) and expression level is estimated around 2 mg/L according to band intensity measurement. For wt-AT, clone 4 is chosen for expansion into cell factory, since the level of expression seems to be slightly higher than the others. Mutant AT-N135Q and AT-N135Q-Pro394 migrate just below control antithrombin purified from plasma (lane 15) confirming the loss of a glycosylation site due to substitution N135Q. The stable expression clones selected for large scale protein production are clones 1 for both AT-N135Q and AT-N135Q-Pro394.

Figure 4:
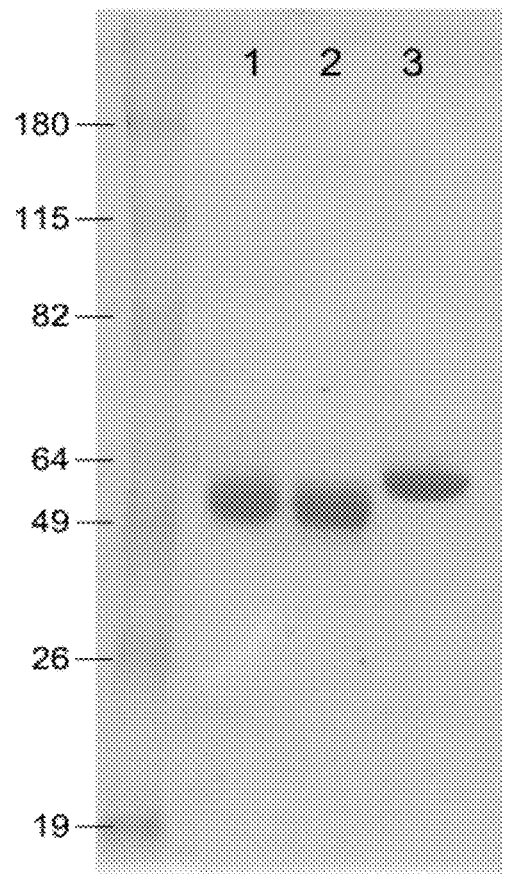

FIG. 4: Integrity and purity of recombinant antithrombin.

To verify integrity and purity of recombinant antithrombin after heparin affinity purification and ion exchange concentration, 2 µg of AT-N135Q-R393H (lane 1), AT-N135Q-Pro394 (lane 2) or control plasma antithrombin (lane 3) are analyzed by SDS-PAGE followed by coomassie staining. As expected, the two mutated antithrombins migrate at molecular weight slightly lower than plasma antithrombin because of loss of a glycosylation site (substitution N135Q) and they show a single band pattern with band intensity corresponding to quantity loaded on the gel (based on absorbance estimation). Then recombinant antithrombin appears pure and can be tested for its anticoagulant properties and affinity for heparin derivatives. Molecular weight standard sizes are presented on the right hand of the figure and expressed in kilo-Dalton (KD).

FIG. 5: Anti-factor Xa activity of plasmatic or mutated antithrombins at saturating pentasaccharide concentration.

Figure 5A:
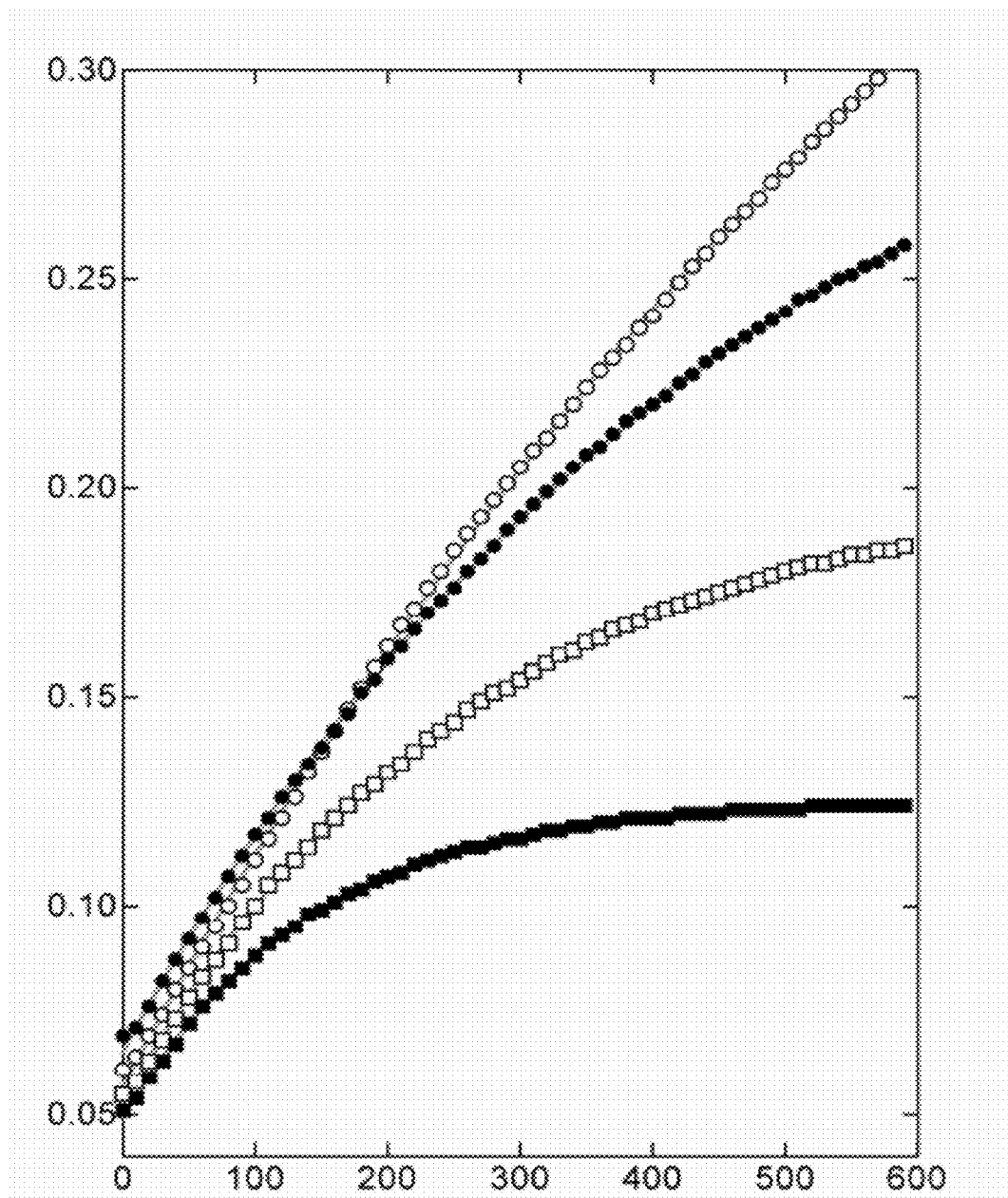

FIG. 5A: Plasma AT (black square: 80 nM, hollow square: 40 nM, Black circle: 20 nM, hollow circle: 10 nM) is tested for its ability to inhibit chromogenic substrate S2765 (200 µM) hydrolysis by FXa (1 nM) in the presence of pentasaccharide (1 µM or 1.73 mg/L) in continuous assay. Time expressed in second is plotted in abscissa; absorbence at 405 nm is plotted in ordinate. substrate hydrolysis curves are fitted using equation 3 to determine the kinetic rate constant (k), (gray lines)

Figure 5B:
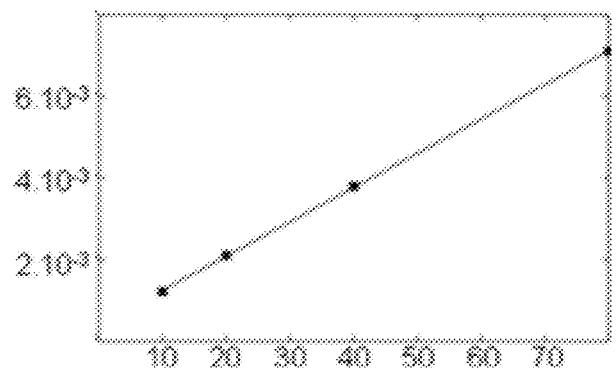

FIG. 5B: Kinetic rate constant (k) determined in FIG. 5 a is thus plotted as the function of AT concentration and fitted using equation 4 to determine inhibition rate constant kon. The plasma antithrombin concentration (nM) is plotted in abscissa; the kinetic rate constante (k) expressed in $s^{-1}$ is plotted in ordinate.

Figure 6:
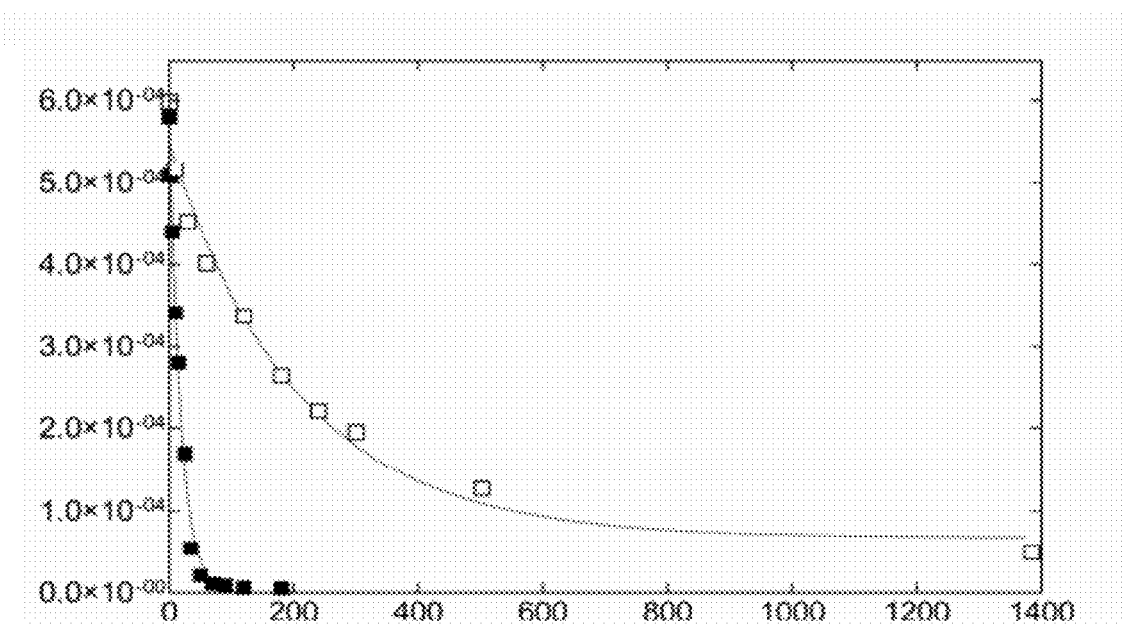

FIG. 6: AT-N135Q-R393H and AT-N135Q-Pro394 are tested for their ability to inhibit FXa activity in discontinuous assay. In a first time AT-N135Q-R393H (black square: 200 nM) or AT-N135Q-Pro394 (hollow square: 2.5 µM) are incubated with FXa (20 nM) in the presence of pentasaccharide (10 µM or 17.3 mg/L) over a period of time from 0 to 120 min (for AT-N135Q-R393H) or from 0 to 1400 min (for AT-N135Q-Pro394). In a second time FXa residual activity is measured by adding 190 µl of 52765 (200 µM) to 10 µl of previous mixture. Initial rate of substrate hydrolysis is then plotted as the function of incubation time with inhibitor and curves are fitted with equation 1 to determine kon (gray lines). Time expressed in minute is plotted in abscissa; substrate hydrolysis rate expressed in $OD/s^{-1}$ is plotted in ordinate.

Figure 7:
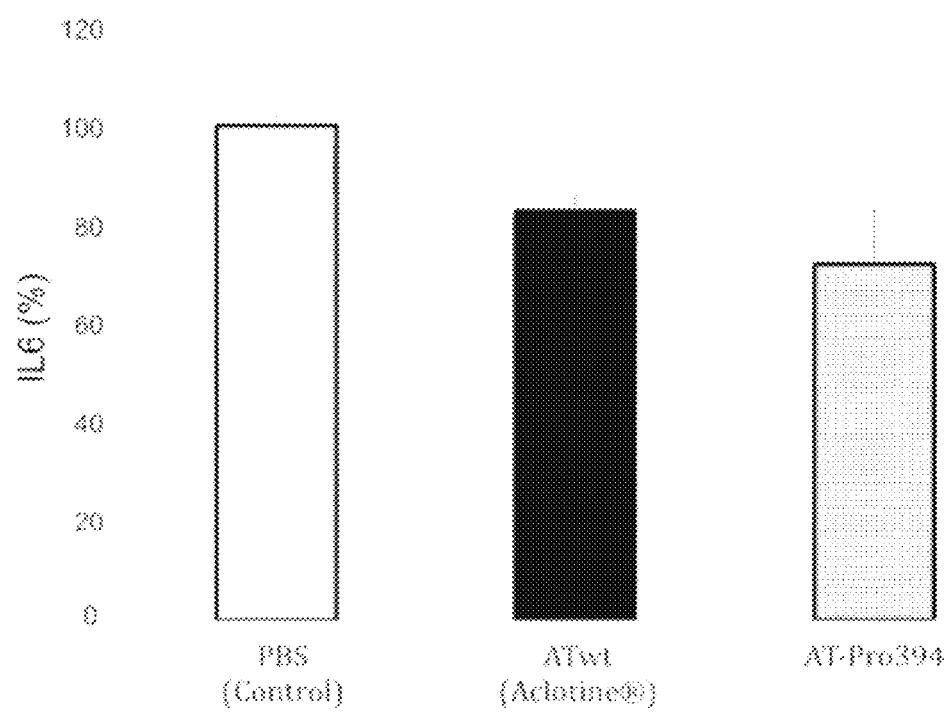

FIG. 7: AT-Pro394 is tested for its ability to inhibit IL6 production by LPS stimulated blood cells.

Blood is pre-treated for 5 minutes at 37° C. with either PBS (white box), either AT-wt (Aclotine®, final concentration of 1.6 IU/ml, black box) or AT-Pro394 (final concentration of 1.6 IU/ml, gray box), and then exposed to 16 hours stimulation with 10 or 100 µg/mL LPS. Blood is then centrifugated at 2300 g for 10 minutes at 12° C. and IL6 protein levels from plasma supernatants are measured quantitatively. Plasma IL6 concentration expressed in percentage is plotted in ordinate (100% corresponds to the IL6 level of the PBS control). The experience was performed with the blood of 2 different healthy subjects.

DETAILED DESCRIPTION OF THE INVENTION

Experimental Part

In order to produce a mutated antithrombin having lost or reduced anticoagulant activity, in particular factor Xa and IIa inhibitory activity, and able to bind to heparin and to the pentasaccharide, differents types of mutations have been contemplated and particularly, mutations within the reactive center loop (region from the amino acid 380 to amino acid 400), mutations within an exosite region remote from the loop accessible for proteinase interaction (Chuang Y J, Swanson R, Raja S M, Olson S T. Heparin enhances the specificity of antithrombin for thrombin and factor Xa independent of the reactive center loop sequence. Evidence for an exosite determinant of factor Xa specificity in heparin-activated antithrombin *J Biol Chem.* 2001; 276:14961-71) and mutations within a consensus sequence of glycosylation (amino acids 135 to 137 and 155 to 157) (Fan B, Crews B C, Turko I V, Choay J, Zettlmeissl G, Gettins P. Heterogeneity of recombinant human antithrombin III expressed in baby hamster kidney cells. Effect of glycosylation differences on heparin binding and structure *J Biol Chem.* 1993; 268:17588-96).

Several mutations have been carried out to obtain mutated antithrombins, and in particular:

deletion within the reactive loop of the antithrombin, in the region P4-P4' (Ala 391-Asn 396) in order to eliminate antithrombin inhibitory activity toward any coagulant proteases such as FXa and FIIa, substitution of amino acids within the region P4-P4' (Ala 391-Asn 396) of the reactive loop, and in particular the substitution of the amino acid at position 393 (Arg) by an Histidine, or the substitution of the amino acid at position 394 (Ser) by a Glutamic acid or by a Glutamine.

insertion of a Proline between the amino acid at position 393 and the amino acid at position 394, and substitution of amino acids within the region of glycosylation of the antithrombin, and in particular the substitution of the amino acid at position 135 (Asp) by a Glutamine, in order to increase the affinity with heparin and pentasaccharide.

Material and Methods

I/ Preparation of Mutated Antithrombins

Figure 1:
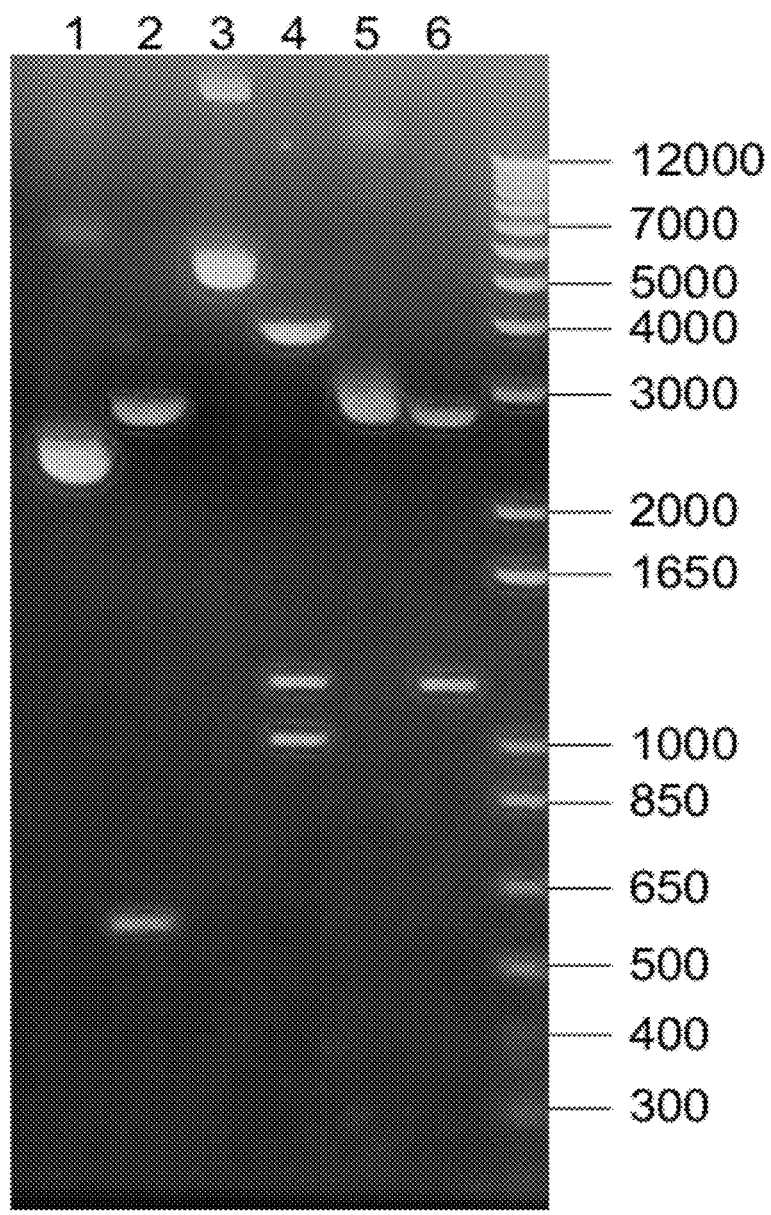
FIG. 1: preparation of shuttle vector carrying full length antithrombin cDNA.

Preparation of Shuttle Vector pENTR Carrying Full Length Antithrombin cDNA (pENTR-AT):

The antithrombin cDNA sequence initially cloned into pENTR vector (Invitrogen, HORF clone reference IOH14497) is found to be truncated and has to be replaced by the full length antithrombin sequence, cloned into pCMV6 (Origene, reference TC110831). The plasmid pCMV6 containing full length antithrombin cDNA is digested by both SacII and StuI endonucleases. The 1182 base pairs fragment is isolated on 1% agarose gel and purified using the QIAquick Gel Extraction Kit. This 1182 base pairs fragment, corresponding to the SacII-StuI fragment of antithrombin cDNA, is ligated into pENTR vector (2760 bp) also linearized by SacII and StuI and recover as described above. Result of this cassette exchange is verified by electrophoresis on 1% agarose gel (FIG. 1) and sequencing.

Mutagenesis on Antithrombin cDNA:

The resulting plasmid pENTR carrying cDNA encoding for wild type antithrombin (pENTR-ATwt) is used as a template for further mutagenesis by PCR using the QuickChange II Site-Directed Mutagenesis Kit according to the manufacturer recommendations (Stratagene). The wild type antithrombin has the same amino acid sequence as the plasma antithrombin but is produced under a recombinant form. Mutagenic primers (table 1) are used to introduce a codon for Glutamine in place of codon for Arginine 135 (N135Q) for production of plasmid pENTR-AT-N135Q. Single amino acid substitution of Arginine 393 by an Histidine (R393H), single amino acid substitution of Serine 394 by a Glutamic acid (S394Q) or by a Glutamine (S394E), insertion of a Proline between Arginine 393 and Serine 394 (Pro394), or deletion of Arginine 393 (ΔR393), Serine 394 (ΔS394) or both Arginine 393 and Serine 394 (ΔR393S394) are introduced by PCR using the QuickChange II Site-Directed Mutagenesis Kit with pENTR-ATwt as template and mutagenic primers as described in table 1. The same couples of mutagenic primers are used in PCR reaction with pENTR-AT-N135Q as template to prepare plasmids carrying cDNA encoding for double-mutant and triple-mutant antithrombin N135Q-R393H, N135Q-S394Q, N135Q-S394E, N135Q-Pro394, N135Q-ΔR393, N135Q-ΔA394, N135Q-ΔR393S394 respectively. Then the integrity of each variant cassette that is to say cDNA encoding for the double-mutant or triple-mutant antithrombin above mentioned is established by DNA sequencing.

Cassette Exchange Between Shuttle Vector and Expression Vector:

All the cDNAs described above encoding for antithrombin, single antithrombin mutants or double antithrombin mutants are transferred from shuttle vector pENTR into eucaryote expression vector pCDNA 3.2 by recombination using Gateway LR Clonase II Enzyme Mix ("Gateway Technology" developed by Invitrogen). The final expression constructs are verified by electrophoresis on 1% agarose gel and sequencing again before transfection (FIG. 2).

Transfection of Eucaryote Cells and Protein Production:

Plasmid constructs resulting of previous recombination named pCDNA-ATwt, pCDNA-AT-N135Q, pCDNA-AT-R393H, pCDNA-AT-S394Q, pCDNA-AT-S394E, pCDNA-AT-Pro394, pCDNA-AT-ΔR393, pCDNA-AT-ΔS394, pCDNA-AT-ΔR393S394, pCDNA-AT-N135Q-R393H, pCDNA-AT-N135Q-S394Q pCDNA-AT-N135Q-S394E pCDNA-AT-N135Q-Pro394, pCDNA-AT-N135Q-ΔR393, pCDNA-AT-N135Q-ΔS394 and pCDNA-AT-N135Q-ΔR393S394, respectively are used for transfection of modified human embryonic kidney cells (HEK-293) or baby hamster kidney cells (BHK-21). Cells are grown in "Dulbeco's Modified Eagle's Medium/F-12" containing 2 mM L-Glutamine, 100 U/ml penicillin, 100 µg/ml Streptomycin and 5% foetal bovine serum (Invitrogen) and approximately $10^6$ cells are transfected with 20 µg of DNA by calcium-phosphate coprecpitation (Sambrook et al. Molecular cloning: A laboratory manual, $2^{nd}$ edition, page 16.33). The stable expression cell lines are selected by G418 (during clones selection, G418 concentration is 0.8 mg/ml in cell culture media and then decreased to 0.4 mg/ml to maintain selection pressure during clones amplification) and screened for anti-thrombin secretion by ELISA, using mouse monoclonal antibody anti antithrombin as capture antibody and Horse Radish Peroxydase conjugate sheep polyclonal antibody anti antithrombin as detecting antibody (Antithrombine BioAssay™ ELISA Kit (EUROMEDEX)). The integrity of secreted antithrombin is established by western blotting using sheep monoclonal antibody anti antithrombin and Horse Radish Peroxydase conjugate donkey polyclonal antibody anti sheep (The Binding Site, UK) (FIG. 3). For each mutated antithrombin, a single stable expression clone is expanded into "cell factories nunclon" (Nunc) and large scale protein production is conducted with 300 µl/cm², (as recommended by manufacturer, the minimum volume suitable for a 6320 cm² culture area cell factory is 2 liters) of <<Dulbeco's Modified Eagle's Medium/F-12" containing 2 mM L-Glutamine, 100 U/ml penicillin, 100 µg/ml Streptomycin and 5 µg/ml Insulin/Transferrin/Selenium (Invitrogen). Conditioned media, harvested daily, are centrifuged for 15 min at 3000 g at 4° C., treated with 5 mM benzamidine, 5 mM EDTA and stored at −20° C.

Protein Purification:

Conditioned media are thawed, pooled, salt concentration adjusted to 0.4 M NaCl and then applied on an heparin immobilized column (Hitrap Heparin 5 ml or Heparin-sepharose CL6B 50 ml, GE Biological) equilibrated with 10 mM Tris, or with 20 mM phosphate buffer, 0.4 M NaCl and 0.1 mM EDTA, pH 7.4. The bound proteins are eluted in the same buffer with a gradient from 0.4 M to 2 M NaCl. The fractions eluted from 0.8 M NaCl and more contained only wild type antithrombin or mutated antithrombins with high heparin affinity. Mutated antithrombins carrying substitution of asparagin 135 by a glutamin (AT-N135, ATN135Q-R393H, AT-N135Q-S394Q, AT-N135Q-S394E, AT-N135Q-Pro394, AT-N135Q-ΔR393, AT-N135Q-ΔS394, AT-N135Q-ΔR393S394) are eluted from affinity column at higher ionic strength than wild type antithrombin, confirming that destruction of glycosylation site at position 135 increases affinity of antithrombin for heparin (about 90% of mutated antithrombin carrying substitution N135Q is eluted between 1 and 1.4 M NaCl compared to wild type antithrombin which 90% is eluted between 0.8 and 1.2 M NaCl). The collected fractions are pooled and the salt concentration is decreased either by over night dialysis against 10 mM Tris, or 20 mM phosphate, and 0.1 M NaCl, pH 7.4 at 4° C. or applied on an HiPrep 26/10 desalting column equilibrated with 10 mM Tris, or 20 mM phosphate, and 0.1 M NaCl, pH 7.4. The antithrombin is then concentrated by ion exchange chromatography using a "Resource Q" 1 ml column (GE, Biological) equilibrated with 10 mM Tris, or 20 mM phosphate, and 0.1 M NaCl, pH 7.4 and eluted in the same buffer with a NaCl gradient from 0.1 mM to 0.5 M or 20 mM to 0.5 M.

The antithrombin concentration in each elution fraction is estimated by absorbance at 280 nM with an absorption coefficient $\epsilon=0.65$ g$^{-1}$·l·cm$^{-1}$ and the integrity of purified wild type antithrombin or mutated antithrombins is tested by western blotting using the same couple of antibodies as described before, and electrophoresis on 10% acrylamide/bisacrylamide gel in native and denaturing conditions followed by coomassie brilliant blue R-250 staining (FIG. 4). Then, the antithrombin preparation is aliquoted and stored at −80° C. before use for functional assay. The same procedure is used to purify plasma antithrombin (used as internal reference) from human plasma. Commercialized AT obtained from human plasma (Aclotine®, LFB, France) was also used as a control in the following experiments.

TABLE 1 oligonucleotides used for the mutated AT constructions

| Sens | Mutation | Sequence | SEQ ID NO |
|---|---|---|---|
| forward | N135Q | GCCGACTCTATCGAAAAGCCCAGAAATCCTCCAAGTTAGTG | 49 |
| reverse | N135Q | CACTAACTTGGAGGATTTCTGGGCTTTTCGATAGAGTCGGC | 50 |

TABLE 1-continued oligonucleotides used for the mutated AT constructions

| Sens | Mutation | Sequence | SEQ ID NO |
|---|---|---|---|
| forward | R393H | GTTGTGATTGCTGGCCATTCGCTAAACCCCAAC | 51 |
| reverse | R393H | GTTGGGGTTTAGCGAATGGCCAGCAATCACAAC | 52 |
| forward | S394Q | GTGATTGCTGGCCGTCAGCTAAACCCCAACAGG | 81 |
| reverse | S394Q | CCTGTTGGGGTTTAGCTGACGGCCAGCAATCAC | 82 |
| forward | S394E | GTGATTGCTGGCCGTGAGCTAAACCCCAACAGG | 83 |
| reverse | S394E | CCTGTTGGGGTTTAGCTCACGGCCAGCAATCAC | 84 |
| forward | Pro394 | GTTGTGATTGCTGGCCGTCCATCGCTAAACCCCAAC | 53 |
| reverse | Pro394 | GTTGGGGTTTAGCGATGGACGGCCAGCAATCACAAC | 54 |
| forward | ΔR393-S394 | GCTGTTGTGATTGCTGGCCTAAACCCCAACAGGGTG | 55 |
| reverse | ΔR393-S394 | CACCCTGTTGGGGTTTAGGCCAGCAATCACAACAGC | 56 |
| forward | ΔR393 | CTGTTGTGATTGCTGGCTCGCTAAACCCCAACAG | 57 |
| reverse | ΔR393 | CTGTTGGGGTTTAGCGAGCCAGCAATCACAACAG | 58 |
| forward | ΔS394 | TGTGATTGCTGGCCGTCTAAACCCCAACAGGG | 59 |
| reverse | ΔS394 | CCCTGTTGGGGTTTAGACGGCCAGCAATCACA | 60 |

II/ In Vitro Characterization of the Mutated Antithrombins

Characterization of the mutated antithrombins aims at a) demonstrating that, in a purified system, the following mutated antithrombins: AT-R393H, S394Q, AT-S394E, AT-Pro394, AT-ΔR393-S394, AT-ΔR393, AT-ΔS394, AT-N135Q-R393H, AT-N135Q-S394Q, AT-N135Q-S394E, AT-N135Q-Pro394, AT-N135Q-ΔR393-S394, AT-N135Q-ΔR393 and AT-N135Q-ΔS394 exhibit a reduced anti FXa and anti FIIa activity compared with that of wild type antithrombin (AT-wt) in the presence or absence of heparin's derivatives.

b) demonstrating that, the following mutated antithrombins AT-R393H, AT-S394Q, AT-S394E, AT-Pro394, AT-ΔR393-S394, AT-ΔR393, AT-ΔS394, AT-N135Q-R393H, AT-N135Q-S394Q, AT-N135Q-S394E AT-N135Q-Pro394, AT-N135Q-ΔR393-S394, AT-N135Q-ΔR393, AT-N135Q-ΔS394, or a composition comprising at least one of these mutated antithrombins and an antithrombin having an anticoagulant activity similar to that of the wild type antithrombin, have, at least, equivalent cytoprotective properties when compared to wild type antithrombin.

a) Anti Factor Xa Inhibitory Activity of the Mutated Antithrombins in a Purified System The kinetic assays for antithrombin inhibition of factor Xa (FXa, Kordia) are performed in 'kinetic' buffer (Hepes, 20 mM phosphate, pH 7.4, 0.15 M NaCl, 0.1% PEG 8000 and 1 mg/ml bovine serum albumin) in pseudo first order conditions. Briefly, factor Xa is incubated with an excess of tested antithrombins (corresponding to plasma antithrombin, or wild type antithrombin or mutated antithrombins and varying in each assay realized) in the presence or absence of pentasaccharide (Fondaparinux sodique, Arixtra®, GlaxoSmithKline) and the factor Xa residual activity is measured as a function of time. The pentasaccharide is added in excess in the reaction media so that every tested antithrombin is bound to the pentasaccharide. In the absence of pentasaccharide, polybrene (100 μg/ml final) is added in order to neutralize any sulfated glycosaminoglycan that may be present in the reaction media. The residual factor Xa activity is measured as the increase in absorbance at 405 nm resulting from cleavage of the chromogenic substrate (S2765 or S2222, Chromogenix) using a microplate reader (Dynatech MR 5000). The analysis of the data is performed using the GraphPad Prism version 3 software. Absorbance recording is continuous or discontinuous according to the expected inhibition rate constant (kon).

The inhibition rate constant (kon) is the second order rate constant given in $M^{-1} \cdot s^{-1}$ which define the velocity of stable complex formation between protease and antithrombin (higher is the kon value, faster will the complex be established).

When the expected kon is lower than $10^4$ $M^{-1} \cdot s^{-1}$ the discontinuous method is used. Factor Xa (2 to 200 nM) is incubated with tested antithrombins (20 nM to 20 μM) in the presence of pentasaccharide or polybrene in a final volume of 10 μl for 10 seconds to 5 hours, or 10 seconds to 24 hours. At the end of this incubation period, 190 μl of kinetic buffer containing 200 μM substrate is added and absorbance at 405 nm is recorded.

The kinetic rate constant (k) is estimated by fitting the substrate hydrolysis initial rate curve to equation (1) using non-linear regression with v0 and v∞ being the substrate hydrolysis rate at time to or t∞ respectively.

$$vt = (v0 + v\infty) \cdot \exp(-k \cdot t) \quad (1)$$

The inhibition rate constant (kon) is calculated from the rate constant (k) using equation (2) where AT is the tested antithrombin concentration.

$$k = AT \cdot kon \quad (2)$$

When the expected kon is higher than $10^4$ $M^{-1} \cdot s^{-1}$, the continuous method is used. The tested antithrombin (1 nM to 1 µM) is incubated with the substrate (200 µM) in the presence of pentasaccharide or polybrene in a final volume of 190 µl and the reaction is started by addition of 10 µL of factor Xa (2 to 200 nM). The rate constant (k) is obtained by fitting the substrate hydrolysis curve to equation (3) or (3') using non-linear regression analysis where A0 is the absorbance at t0, and vi and vs are respectively the initial and final rates of substrate hydrolysis in the absence of tested antithrombin.

$$A405 = A0 + vi \cdot (1 - \exp(-k \cdot t))/k \quad (3)$$

Equation (3') is also used, particularly in presence of plasma.

$$A405 = A0 + vs^* t + (vi - vs)^* (1 - \exp(-kt))/k$$

The inhibition rate constant (kon) is calculated from the kinetic constant (k) using equation (4) that takes into account the competitive effect of the substrate, with S being the initial substrate concentration, Km, the Michaelis constant for factor Xa-substrate interaction, AT the tested antithrombin concentration.

$$k = (kon/(1 + S/Km)) \cdot [AT] \quad (4)$$

Mutated antithrombins and wild type AT inhibitory activity are measured in the same conditions and compared with plasma AT inhibitory activity.

The results with or without pentasaccharide are:

wild type antithrombin and AT-N135Q factor Xa inhibitory activity is similar to plasma antithrombin factor Xa inhibitory activity, factor Xa inhibitory activity of the following mutated antithrombins: AT-R393H, AT-Pro394, AT-ΔR393-S394, AT-ΔR393, AT-ΔS394, AT-N135Q-R393H, AT-N135Q-Pro394, AT-N135Q-ΔR393-S394, AT-N135Q-ΔR393, AT-N135Q-ΔS394, is negligible compared with wild type antithrombin factor Xa inhibitory activity.

factor Xa inhibitory activity of the following mutated antithrombins: AT-S394Q, AT-S394E, AT-N135Q-S394Q and AT-N135Q-S394E, is 2 to 20 fold decreased compared with wild type antithrombin factor Xa inhibitory activity.

A decrease in factor Xa inhibitory activity from 2 to 20 fold compared with wild type antithrombin is reached with a composition containing one of the following mutated antithrombins: AT-R393H, AT-S394Q, AT-S394E, AT-Pro394, AT-ΔR393-S394, AT-ΔR393, AT-ΔS394, AT-N135Q-R393H, AT-N135Q-S394Q, AT-N135Q-S394E, AT-N135Q-Pro394, AT-N135Q-ΔR393-S394, AT-N135Q-ΔR393, or AT-N135Q-ΔS394, and AT-wt or AT-N135Q, in a varying ratio.

For example, inhibition rate constant (kon) of plasma AT for factor Xa in the presence of saturating amount of pentasaccharide is estimated using continuous method (FIGS. 5a and 5b). A value of $2.52 \times 10^5$ $M^{-1} \cdot s^{-1}$ is found which is comparable to published values (Olson S T, Björk I, Sheffer R, Craig P A, Shore J D, Choay J., *J Biol Chem.* 1992 June 25; 267 (18): 12528-38, "Role of the antithrombin-binding pentasaccharide in heparin acceleration of antithrombin-proteinase reactions. Resolution of the antithrombin conformational change contribution to heparin rate enhancement.") Using this method AT-N135Q-R393H and AT-N135Q-Pro394 are found to be slow factor Xa inhibitors, even in the presence of saturating pentasaccharide concentration. Thus, discontinuous method was performed to evaluate kon values for factor Xa inhibition by AT-N135Q-R393H and AT-N135Q-Pro394 in the presence of pentasaccharide (FIG. 6). AT-N135Q-R393H anticoagulant activity is largely reduced whereas AT-N135Q-Pro394 is almost devoided of anti-factor Xa activity. AT-N135Q-R393H and AT-N135Q-Pro394 kon values are estimated at 4415 $M^{-1} \cdot s^{-1}$ and 33 $M^{-1} \cdot s^{-1}$, respectively, which is 95 times and at least 7600 times lower than plasma AT.

b) Anti Factor IIa Inhibitory Activity of the Mutated Antithrombins in a Purified System.

The kinetic assays for antithrombin inhibition of factor IIa (FIIa, Kordia) are performed in 'kinetic' buffer (Hepes, 20 mM phosphate, pH 7.4, 0.15 M NaCl, 0.1% PEG 8000 and 1 mg/ml bovine serum albumin) in pseudo first order conditions. Briefly, factor IIa is incubated with an excess of tested antithrombins (corresponding to plasma antithrombin, or wild type antithrombin or mutated antithrombins and varying in each assay realized) in the presence or absence of heparin (heparin sodium, Choay®) and the factor IIa residual activity is measured as a function of time. Heparin is added in excess in the reaction media so that every tested antithrombin is bound to heparin. In the absence of heparin, polybrene (100 µg/ml final) is added in order to neutralize any sulfated glycosaminoglycan that may be present in the reaction media. The residual factor IIa activity is measured as the increase in absorbance at 405 nm resulting from cleavage of the chromogenic substrate (S2238, Chromogenix) using a microplate reader (Dynatech MR 5000). The analysis of the data is performed using the GraphPad Prism version 3 software. Absorbance recording is continuous or discontinuous according to the expected inhibition rate constant (kon).

The inhibition rate constant (kon) is the second order rate constante given in $M^{-1} \cdot s^{-1}$ which define the velocity of stable complex formation between protease and antithrombin (higher is the kon value, faster will the complex be established).

When the expected kon is lower than $10^4$ $M^{-1} \cdot s^{-1}$ the discontinuous method is used. Factor IIa (2 to 200 nM) is incubated with tested antithrombins (20 nM to 20 µM) in the presence of heparin or polybrene in a final volume of 10 µl for 10 seconds to 5 hours, or 10 seconds to 24 hours. At the end of this incubation period, 190 µl of kinetic buffer containing 200 µM substrate is added and absorbance at 405 nm is recorded.

The kinetic rate constant (k) is estimated by fitting the substrate hydrolysis initial rate curve to equation (1) using non-linear regression with v0 and v∞ being the substrate hydrolysis rate at time to or t∞ respectively.

$$vt = (v0 + v\infty) \cdot \exp(-k \cdot t) \quad (1)$$

The inhibition rate constant (kon) is calculated from the rate constant (k) using equation (2) where AT is the tested antithrombin concentration.

$$k = AT \cdot kon \quad (2)$$

When the expected kon is higher than $10^4$ $M^{-1} \cdot s^{-1}$, the continuous method is used. The tested antithrombin (1 nM to 1 µM) is incubated with the substrate (200 µM) in the presence of heparin or polybrene in a final volume of 190 µl and the reaction is started by addition of 10 µL of factor IIa (2 to 200 nM). The rate constant (k) is obtained by fitting the substrate hydrolysis curve to equation (3) or (3') using non-linear regression analysis where A0 is the absorbance at t0, and vi and vs are respectively the initial and final rates of substrate hydrolysis in the absence of tested antithrombin.

$$A405 = A0 + vi \cdot (1 - \exp(-k \cdot t))/k \quad (3)$$

$$A405 = A0 + vs^* t + (vi - vs)^* (1 - \exp(-kt))/k \quad (3')$$

The inhibition rate constant (kon) is calculated from the kinetic constant (k) using equation (4) that takes into account the competitive effect of the substrate, with S being the initial substrate concentration, Km, the Michaelis constant for factor IIa-substrate interaction, AT the tested antithrombin concentration.

$$k=(kon/(1+S/Km))\cdot[AT] \quad (4)$$

Mutated antithrombins and wild type AT inhibitory activity are measured in the same conditions and compared with plasma AT inhibitory activity.

The results with or without heparin are:

wild type antithrombin and AT-N135Q factor IIa inhibitory activity is similar to plasma antithrombin factor IIa inhibitory activity, factor IIa inhibitory activity of the following mutated antithrombins: AT-R393H, AT-Pro394, AT-ΔR393-S394, AT-ΔR393, AT-ΔS394, AT-N135Q-R393H, AT-N135Q-Pro394, AT-N135Q-ΔR393-S394, AT-N135Q-ΔR393, AT-N135Q-ΔS394, is negligible compared with wild type antithrombin factor IIa inhibitory activity.

factor IIa inhibitory activity of the following mutated antithrombins: AT-S394Q, AT-S394E, AT-N135Q-S394Q and AT-N135Q-S394E, is 2 to 20 fold decreased compared with wild type antithrombin factor IIa inhibitory activity.

A decrease in factor IIa inhibitory activity from 2 to 20 fold compared with wild type antithrombin is reached with a composition containing one of the following mutated antithrombins: AT-R393H, AT-S394Q, AT-S394E, AT-Pro394, AT-ΔR393-S394, AT-ΔR393, AT-ΔS394, AT-N135Q-R393H, AT-N135Q-S394Q, AT-N135Q-S394E, AT-N135Q-Pro394, AT-N135Q-ΔR393-S394, AT-N135Q-ΔR393, or AT-N135Q-ΔS394, and AT-wt or AT-N135Q, in a varying ratio.

c) In vitro Evaluation of Cytoprotective Properties of the Mutated Antithrombins c-1) Evaluation on Human Whole Blood Cytoprotective properties of mutated antithrombins (AT-R393H, AT-S394Q, AT-S394E, AT-Pro394, AT-ΔR393-S394, AT-ΔR393, AT-ΔS394, AT-N135Q-R393H, AT-N135Q-S394Q, AT-N135Q-S394E, AT-N135Q-Pro394, AT-N135Q-ΔR393-S394, AT-N135Q-ΔR393 and AT-N135Q-ΔS394) are evaluated, in vitro, on human whole blood exposed to bacterial lipopolysaccharide (LPS).

Venous blood was collected into tubes containing 0.11 mol/L trisodium citrate (1:10). Blood is either untreated or pre-treated with different concentration ranging from 1 to 10 IU/mL of wild type or mutated AT for 5 or 30 minutes at 37° C., and then exposed to 5 or 16 hours stimulation with 10, 50 or 100 μg/mL LPS. Blood is then centrifuged at 2300 g for 10 minutes at 12° C. and plasma supernatants stored at −80° C. until use. IL6 and TNFα protein levels from plasma supernatants are measured quantitatively using a commercially available enzyme-linked immunosorbent assay (ELISA) (IL-6 duoset and TNFα duoset, R&D System, Minneapolis, Minn., USA)

In the condition of the assay, addition of AT-R393H, AT-S394Q, AT-S394E, AT-Pro394, AT-ΔR393-S394, AT-ΔR393, AT-ΔS394, AT-N135Q-R393H, AT-N135Q-Pro394, AT-N135Q-ΔR393-S394, AT-N135Q-ΔR393, AT-N135Q-ΔS394, or a composition comprising at least one of these AT variants with AT-wt or AT-N135Q, produces a significant decrease in IL6 and TNFα levels in blood samples.

c-2) Evaluation on Murine Mixed Cortical Cultures

Culturing of primary cells is performed as described (Lubetzki, C., Demerens, C., Anglade, P., Villarroya, H., Frankfurter, A., Lee, V. M. Y., Zalc, B., 1993. Proc. Natl. Acad. Sci. U.S.A. 90, 6820-6824. <<Even in culture, oligodendrocytes myelinate solely axons>>) by using brain tissue from embryos isolated from mice at 16 days post-coitum. Cerebral hemispheres are dissected from embryo brains, dissociated via trypsin digestion and the single cell suspension is seeded at $10^5$ cells in 200 μl medium per well onto BioCoat® poly-L-lysine coated 96-well plates (Becton Dickinson, Bedford, Mass. 01730, USA). Cells are cultured in Bottenstein-Sato medium (GIBCO Invitrogen), supplemented with 1% FCS, 1% penicillin—streptomycin solution (Seromed) and recombinant platelet-derived growth factor AA (PDGF-AA, R&D Systems) at 10 ng/mL. Cultures are grown at 37° C. and 10% $CO^2$ for several weeks.

LPS Stimulation

Cells are either untreated or pre-treated with various concentrations ranging from 1 to 10 IU/ml of wild type or mutated AT for 3 hours and are incubated for 48 hours with 10 ng/ml of LPS, at 37° C. and 10% $CO^2$. Cell supernatants are then centrifuged at 2300 g for 10 minutes at 12° C. and stored at −80° C. until use. IL6 and TNFα protein levels from cell supernatants are measured quantitatively using a commercially available enzyme-linked immunosorbent assay (ELISA) (IL-6 duoset and TNFα duoset, R&D System, Minneapolis, Minn., USA)

In the condition of the assay, addition of AT-R393H, AT-S394Q, AT-S394E, AT-Pro394, AT-ΔR393-S394, AT-ΔR393, AT-ΔS394, AT-N135Q-R393H, AT-N135Q-Pro394, AT-N135Q-ΔR393-S394, AT-N135Q-ΔR393, AT-N135Q-ΔS394, or a composition comprising at least one of these AT variants with AT-wt or AT-N135Q, produces a significant decrease in IL6 and TNFα levels in cell culture supernatant.

Oxygen-Glucose Deprivation (OGD)

To induce hypoxia/reoxygenation injury, oxygen-glucose deprivation (OGD) experiments were done by treatment for 1 to 12 hours with 95% $N_2$/5% $CO_2$ in serum-free DMEM without glucose, followed by 12 to 24 hours of exposure to normoxic conditions with 5 mmol/L glucose. Wild type or mutated AT (concentration ranging from 1 to 10 IU/mL) was added throughout the entire time of the study (13 to 36 hours).

Cell damage was evaluated by measuring the amount of lactate dehydrogenase (LDH) released from injured cells into the extracellular fluid 24 hours after exposure to OGD. Background LDH release was determined in control cultures not exposed to OGD and was subtracted from all experimental values In the condition of the assay, addition of AT-R393H, AT-S394Q, AT-S394E, AT-Pro394, AT-ΔR393-S394, AT-ΔR393, AT-ΔS394, AT-N135Q-R393H, AT-N135Q-Pro394, AT-N135Q-ΔR393-S394, AT-N135Q-ΔR393, AT-N135Q-ΔS394, or a composition comprising at least one of these AT variants with AT-wt or AT-N135Q, produces a significant decrease in LDH release from injured cells into the extracellular fluid.

III/ In Vivo Evaluation of Cytoprotective Properties of the Mutated Antithrombins The efficiency of the mutated antithrombins AT-R393H, AT-Pro394, AT-ΔR393-S394, AT-ΔR393, AT-ΔS394, AT-N135Q-R393H, AT-N135Q-S394Q, AT-N135Q-S394E, AT-N135Q-Pro394, AT-N135Q-ΔR393-S394, AT-N135Q-ΔR393, AT-N135Q-ΔS394 as antidotes is evaluated in a murine model.

a) Animals

Wild-type C57BL/6 male mice, at least 12-week-old (JANVIER) are anesthetized using a protocol that does not modify the coagulation parameters, and in accordance with the European guidelines for animal experimentation.

In all experiments, antithrombin variant or placebo is administrated by intra-venous injection in the caudal vein.

The blood is collected by punction in cave vein into tubes containing 0.105 mol/L trisodium citrate (1:10). Platelet— poor plasma is obtained by centrifugation at 2300 g for 10 minutes at 12° C. and stored at −80° C. until use.

b) Experimental Protocol

Mouse experiments are performed to assess each antithrombin variant against placebo in two sepsis models: 1) cecum ligature and puncture (CLP), 2) lipopolysaccharide (LPS) injection. For each antithrombin variant, a first set of experiment compares inflammatory and coagulant response to sepsis with the placebo in both sepsis models. In a second set of experiment, survival after CLP and LPS injection is compared between antithrombin injected-mice and placebo-injected mice. Housing and experiments are in accordance with French regulations and European Community experimental guidelines.

1—Sepsis Models

The CLP procedure is performed as described elsewhere (Wichterman K A, Baue A E, Chaudry I H. Sepsis and septic shock—a review of laboratory models and a proposal. *J Surg Res* 1980; 29: 189-201). Briefly, under isoflurane anesthesia the abdominal wall is opened through a 1-cm midline incision. The cecum is exposed and ligated about 15 mm proximal to the cecal pole with 5/0 Prolene thread (Ethicon, Somerville, N.J., USA), without stricture of the ileocecal valve. The ligated cecum is then punctured once with a 21-gauge needle. The cecum is gently pressed until a small drop of stool appeared; 1 ml of 0.9% normal saline is injected into the peritoneal cavity just before abdominal closure in sham and CLP animals. No further resuscitation is performed and no antibiotics are administered. The abdominal wall are then closed (two layers, muscle and skin; 5/0 Ethilon thread). As a control, sham surgery is performed according to the CLP procedure except that the cecum is neither ligated nor punctured.

In the LPS sepsis model, LPS injection (5 or 10 mg/kg) is realized intraperitoneally. Control animals will be injected with the solvent only.

In both models, AT is administered by intra-venous injection in the caudal vein at a dose from about 40 to about 300 IU/kg/day.

2—Survival Analyses

For each antithrombin variant to be tested 2 groups of 15 mice each are used for CLP sepsis model:

In the first group mice receive antithrombin variant and are subjected to CLP.

In the second group, mice receive placebo and are subjected to CLP.

For each antithrombin variant to be tested 2 groups of 10 mice each are used for LPS sepsis model:

In the first group mice receive antithrombin variant and are injected with LPS.

In the second group, mice receive placebo and are injected with solvent.

All paired mice undergo surgery or injection on the same days. Post-operative or post-LPS injection survival is assessed every 2 hours for 48 hours and then every 8 hours until all mice have died.

In these experimental conditions, a longer survival in antithrombin variants-injected mice in comparison with placebo-injected mice is observed.

3—Evaluation of Inflammatory and Coagulant Response

For each antithrombin variant to be tested, 4 groups of 5 mice each are used for each sepsis model:

CLP model:

In the first group, mice receive antithrombin variant and are subjected to CLP.

In the second group, mice receive placebo and are subjected to CLP.

In the third group, mice receive antithrombin variant and are sham-operated.

In the last group, mice receive placebo and are sham-operated.

LPS model:

In the first group, mice receive antithrombin variant and are injected with LPS.

In the second group, mice receive placebo and are injected with LPS.

In the third group, mice receive antithrombin variant and are injected with solvent.

In the last group, mice receive placebo and are injected with solvent.

Blood is sampled 1 week preoperatively and at 16 hours post surgery.

Influence of mutated AT administration on bleeding tendancy is evaluated by examination of the abdominal cavity in Sham and CLP operated mice after sacrifice following post-operative blood sampling.

Antithrombin antigen levels are measured using an ELISA test (Antithrombin BioAssay™ ELISA Kit (EUROMEDEX), and antithrombin factor Xa inhibitory activity in mice's plasma is determined during the Biophen® AT kit (Hyphen BiMed, France). Inflammatory and procoagulant response to sepsis in mice injected with the antithrombin variants is evaluated by measurement of several parameters. Leukocyte, and platelet counts and hemoglobin level determinations are automated (Sci Vet ABC Animal Blood Counter, ABX Diagnostics, Montpellier, France). Plasma interleukin-6 (IL-6) and TNFα concentrations are assessed with the mouse IL-6 and TNFα Quantikine kits (R&D Systems, Minneapolis, Minn., USA). Coagulation activation is evaluated by F1+2 measurement.

Moreover, intravascular fibrin depositions are also assessed immunohistochemically using polyclonal antibodies to fibrinogen. Fibrinogen/fibrin-bound antibodies are detected with direct immunofluorescence. Sections treated without primary antibodies serve as negative controls.

Using these experimental conditions, we observed a diminished inflammatory and procoagulant response to sepsis in mice injected with the antithrombin variants in comparison with placebo-injected mice. Notably, a lower IL-6 and TNFα concentrations, a reduced decline in platelet and leukocyte count, a lower thrombin generation evidenced by lower F1+2 fragments, reduced fibrin deposition in the kidneys. AT variants administration results in a 1 to 7.5 fold increase in AT circulating antigen levels.

The invention claimed is:

1. A composition comprising a mutated antithrombin; said mutated antithrobmin having an anticoagulant activity substantially reduced with respect to the anticoagulant activity of the non mutated antithrombin, or having substantially no anticoagulant activity; said mutated antithrombin having an inhibitory activity selected from the group consisting of: (i) a thrombin inhibitory activity substantially reduced, or substantially lost, with respect to the non mutated antithrombin (ii) a factor Xa inhibitory activity reduced, or substantially lost, with respect to the non mutated antithrombin and (iii) a thrombin inhibitory activity and a factor Xa inhibitory activity substantially reduced, or substantially lost, with respect to the non mutated antithrombin; said mutated antithrombin comprising at:
one mutation at position 393 or 394, and a substitution at a glycosylation site at the amino acid at position 96, 135, 155 or 192, the amino acid numbering referring to the antithrombin amino acid sequence represented by SEQ ID NO: 2, or
one mutation at position 425 or 426, and a substitution at a glycosylation site at the amino acid at position 128, 167, 187 or 224, the amino acid numbering referring to the antithrombin amino acid sequence comprising the signal peptide, represented by SEQ ID NO: 26, or
a deletion of amino acids at positions 393 and 394, the amino acid numbering referring to the antithrombin amino acid sequence represented by SEQ ID NO: 2, or
a deletion of amino acids at positions 425 and 426, the amino acid numbering referring to the antithrombin amino acid sequence represented by SEQ ID NO: 26;
wherein said composition is for the preparation of a drug intended for the treatment of infection, inflammation or hypoxic injury, in particular sepsis and ischemia/reperfusion related to stroke, ischemia/reperfusion related to surgery and ischemia/reperfusion related to organ transplantation.

2. The composition according to claim 1, wherein said mutated antithrombin is selected from the group consisting of the amino acid sequence of: SEQ ID NO:14, SEQ ID NO:16, SEQ ID NO:18, SEQ ID NO:20, SEQ ID NO:22, SEQ ID NO:24, SEQ ID NO:66, and SEQ ID NO:68.

3. The composition according to claim 2, wherein said mutated antithrombin is selected from the group consisting of the amino acid sequence of: SEQ ID NO:38, SEQ ID NO:40, SEQ ID NO:42, SEQ ID NO:44, SEQ ID NO:46, SEQ ID NO:48, SEQ ID NO:74 and SEQ ID NO:76.

4. A pharmaceutical composition comprising as active ingredient a composition comprising at least one mutated antithrombin according to claim 1 in association with a pharmaceutically acceptable vehicle, said at least one mutated antithrombin being selected from the group consisting of SEQ ID NO: 66, SEQ ID NO: 68, SEQ ID NO: 74 and SEQ ID NO: 76.

5. A mutated antithrombin, comprising:
a substitution of the amino acid at position 394 of the amino acid sequence of SEQ ID NO:2 by a glutamic acid (Glu) or a Glutamine (Gln), and a substitution of the amino acid at position 135, by a Glutamine (Gln).

6. A mutated antithrombin, comprising:

a substitution of the amino acid at position 426 of the amino acid sequence of SEQ ID NO:26 by a glutamic acid (Glu) or a Glutamine (Gln), and a substitution of the amino acid at position 167, by a Glutamine (Gln).

7. The composition according to claim 1, wherein said mutated antithrobmin comprises:

said one mutation at position 393 or 394 and said substitution at a glycosylation site at the amino acid at position 96, 135, 155 or 192, wherein said mutation is selected from the group consisting of a substitution of the amino acid at position 393 by His, a substitution of the amino acid at position 394 by Glu or Gln, an insertion of Pro between the amino acids at positions 393 and 394, a deletion of the amino acid at position 393, a deletion of the amino acid at position 394, and a deletion of the amino acids at positions 393 and 394, or said one mutation at position 425 or 426, and said substitution at a glycosylation site at the amino acid at position 128, 167, 187 or 224, wherein said mutation is selected from the group consisting of a substitution of the amino acid at position 425 by His, a substitution of the amino acid at position 426 by Glu or Gln, an insertion of Pro between the amino acids at positions 425 and 426, a deletion of the amino acid at position 425, a deletion of the amino acid at position 426, and a deletion of the amino acids at positions 426 and 427.

8. The composition according to claim 1, wherein said mutated antithrobmin comprises:

said one mutation at position 393 or 394 and said substitution at a glycosylation site, wherein said substitution is at position 135 by Gln, or said one mutation at position 425 or 426, and said substitution at a glycosylation site, wherein said substitution is at position 167 by Gln.

* * * * *

SEQUENCE LISTING

```
<160> NUMBER OF SEQ ID NOS: 84

<210> SEQ ID NO 1
<211> LENGTH: 1387
<212> TYPE: DNA
<213> ORGANISM: Homo sapiens
<220> FEATURE:
<221> NAME/KEY: CDS
<222> LOCATION: (1)..(1296)
```

<400> SEQUENCE: 1

```
cac ggg agc cct gtg gac atc tgc aca gcc aag ccg cgg gac att ccc        48
His Gly Ser Pro Val Asp Ile Cys Thr Ala Lys Pro Arg Asp Ile Pro
1               5                   10                  15 atg aat ccc atg tgc att tac cgc tcc ccg gag aag aag gca act gag        96
Met Asn Pro Met Cys Ile Tyr Arg Ser Pro Glu Lys Lys Ala Thr Glu
            20                  25                  30 gat gag ggc tca gaa cag aag atc ccg gag gcc acc aac cgg cgt gtc       144
Asp Glu Gly Ser Glu Gln Lys Ile Pro Glu Ala Thr Asn Arg Arg Val
        35                  40                  45 tgg gaa ctg tcc aag gcc aat tcc cgc ttt gct acc act ttc tat cag       192
Trp Glu Leu Ser Lys Ala Asn Ser Arg Phe Ala Thr Thr Phe Tyr Gln
    50                  55                  60 cac ctg gca gat tcc aag aat gac aat gat aac att ttc ctg tca ccc       240
His Leu Ala Asp Ser Lys Asn Asp Asn Asp Asn Ile Phe Leu Ser Pro
65                  70                  75                  80 ctg agt atc tcc acg gct ttt gct atg acc aag ctg ggt gcc tgt aat       288
Leu Ser Ile Ser Thr Ala Phe Ala Met Thr Lys Leu Gly Ala Cys Asn
                85                  90                  95 gac acc ctc cag caa ctg atg gag gta ttt aag ttt gac acc ata tct       336
Asp Thr Leu Gln Gln Leu Met Glu Val Phe Lys Phe Asp Thr Ile Ser
            100                 105                 110 gag aaa aca tct gat cag atc cac ttc ttc ttt gcc aaa ctg aac tgc       384
Glu Lys Thr Ser Asp Gln Ile His Phe Phe Phe Ala Lys Leu Asn Cys
        115                 120                 125 cga ctc tat cga aaa gcc aac aaa tcc tcc aag tta gta tca gcc aat       432
Arg Leu Tyr Arg Lys Ala Asn Lys Ser Ser Lys Leu Val Ser Ala Asn
    130                 135                 140 cgc ctt ttt gga gac aaa tcc ctt acc ttc aat gag acc tac cag gac       480
Arg Leu Phe Gly Asp Lys Ser Leu Thr Phe Asn Glu Thr Tyr Gln Asp
145                 150                 155                 160 atc agt gag ttg gta tat gga gcc aag ctc cag ccc ctg gac ttc aag       528
Ile Ser Glu Leu Val Tyr Gly Ala Lys Leu Gln Pro Leu Asp Phe Lys
                165                 170                 175 gaa aat gca gag caa tcc aga gcg gcc atc aac aaa tgg gtg tcc aat       576
Glu Asn Ala Glu Gln Ser Arg Ala Ala Ile Asn Lys Trp Val Ser Asn
            180                 185                 190 aag acc gaa ggc cga atc acc gat gtc att ccc tcg gaa gcc atc aat       624
Lys Thr Glu Gly Arg Ile Thr Asp Val Ile Pro Ser Glu Ala Ile Asn
        195                 200                 205 gag ctc act gtt ctg gtg ctg gtt aac acc att tac ttc aag ggc ctg       672
Glu Leu Thr Val Leu Val Leu Val Asn Thr Ile Tyr Phe Lys Gly Leu
    210                 215                 220 tgg aag tca aag ttc agc cct gag aac aca agg aag gaa ctg ttc tac       720
Trp Lys Ser Lys Phe Ser Pro Glu Asn Thr Arg Lys Glu Leu Phe Tyr
225                 230                 235                 240 aag gct gat gga gag tcg tgt tca gca tct atg atg tac cag gaa ggc       768
Lys Ala Asp Gly Glu Ser Cys Ser Ala Ser Met Met Tyr Gln Glu Gly
                245                 250                 255 aag ttc cgt tat cgg cgc gtg gct gaa ggc acc cag gtg ctt gag ttg       816
Lys Phe Arg Tyr Arg Arg Val Ala Glu Gly Thr Gln Val Leu Glu Leu
            260                 265                 270 ccc ttc aaa ggt gat gac atc acc atg gtc ctc atc ttg ccc aag cct       864
Pro Phe Lys Gly Asp Asp Ile Thr Met Val Leu Ile Leu Pro Lys Pro
        275                 280                 285 gag aag agc ctg gcc aag gta gag aag gaa ctc acc cca gag gtg ctg       912
Glu Lys Ser Leu Ala Lys Val Glu Lys Glu Leu Thr Pro Glu Val Leu
    290                 295                 300
```

-continued

| | | |
|---|---|---|
| caa gag tgg ctg gat gaa ttg gag gag atg atg ctg gtg gtc cac atg<br>Gln Glu Trp Leu Asp Glu Leu Glu Glu Met Met Leu Val Val His Met<br>305                         310                      315                   320 | 960 |
| ccc cgc ttc cgc att gag gac ggc ttc agt ttg aag gag cag ctg caa<br>Pro Arg Phe Arg Ile Glu Asp Gly Phe Ser Leu Lys Glu Gln Leu Gln<br>                     325                         330                      335 | 1008 |
| gac atg ggc ctt gtc gat ctg ttc agc cct gaa aag tcc aaa ctc cca<br>Asp Met Gly Leu Val Asp Leu Phe Ser Pro Glu Lys Ser Lys Leu Pro<br>                   340                         345                     350 | 1056 |
| ggt att gtt gca gaa ggc cga gat gac ctc tat gtc tca gat gca ttc<br>Gly Ile Val Ala Glu Gly Arg Asp Asp Leu Tyr Val Ser Asp Ala Phe<br>355                         360                      365 | 1104 |
| cat aag gca ttt ctt gag gta aat gaa gaa ggc agt gaa gca gct gca<br>His Lys Ala Phe Leu Glu Val Asn Glu Glu Gly Ser Glu Ala Ala Ala<br>    370                      375                     380 | 1152 |
| agt acc gct gtt gtg att gct ggc cgt tcg cta aac ccc aac agg gtg<br>Ser Thr Ala Val Val Ile Ala Gly Arg Ser Leu Asn Pro Asn Arg Val<br>385                         390                      395                   400 | 1200 |
| act ttc aag gcc aac agg cct ttc ctg gtt ttt ata aga gaa gtt cct<br>Thr Phe Lys Ala Asn Arg Pro Phe Leu Val Phe Ile Arg Glu Val Pro<br>                   405                       410                     415 | 1248 |
| ctg aac act att atc ttc atg ggc aga gta gcc aac cct tgt gtt aag<br>Leu Asn Thr Ile Ile Phe Met Gly Arg Val Ala Asn Pro Cys Val Lys<br>            420                     425                     430 | 1296 |
| taaaatgttc ttattctttg cacctcttcc tattttggt tgtgaacag aagtaaaaat | 1356 |
| aaatacaaac tacttccatc tcacattaaa a | 1387 |

<210> SEQ ID NO 2
<211> LENGTH: 432
<212> TYPE: PRT
<213> ORGANISM: Homo sapiens

<400> SEQUENCE: 2

His Gly Ser Pro Val Asp Ile Cys Thr Ala Lys Pro Arg Asp Ile Pro
1               5                   10                  15

Met Asn Pro Met Cys Ile Tyr Arg Ser Pro Glu Lys Lys Ala Thr Glu
            20                  25                  30

Asp Glu Gly Ser Glu Gln Lys Ile Pro Glu Ala Thr Asn Arg Arg Val
        35                  40                  45

Trp Glu Leu Ser Lys Ala Asn Ser Arg Phe Ala Thr Thr Phe Tyr Gln
    50                  55                  60

His Leu Ala Asp Ser Lys Asn Asp Asn Asp Asn Ile Phe Leu Ser Pro
65                  70                  75                  80

Leu Ser Ile Ser Thr Ala Phe Ala Met Thr Lys Leu Gly Ala Cys Asn
                85                  90                  95

Asp Thr Leu Gln Gln Leu Met Glu Val Phe Lys Phe Asp Thr Ile Ser
            100                 105                 110

Glu Lys Thr Ser Asp Gln Ile His Phe Phe Phe Ala Lys Leu Asn Cys
        115                 120                 125

Arg Leu Tyr Arg Lys Ala Asn Lys Ser Ser Lys Leu Val Ser Ala Asn
    130                 135                 140

Arg Leu Phe Gly Asp Lys Ser Leu Thr Phe Asn Glu Thr Tyr Gln Asp
145                 150                 155                 160

Ile Ser Glu Leu Val Tyr Gly Ala Lys Leu Gln Pro Leu Asp Phe Lys
                165                 170                 175

Glu Asn Ala Glu Gln Ser Arg Ala Ala Ile Asn Lys Trp Val Ser Asn
            180                 185                 190

```
Lys Thr Glu Gly Arg Ile Thr Asp Val Ile Pro Ser Glu Ala Ile Asn
            195                 200                 205

Glu Leu Thr Val Leu Val Leu Val Asn Thr Ile Tyr Phe Lys Gly Leu
        210                 215                 220

Trp Lys Ser Lys Phe Ser Pro Glu Asn Thr Arg Lys Glu Leu Phe Tyr
225                 230                 235                 240

Lys Ala Asp Gly Glu Ser Cys Ser Ala Ser Met Met Tyr Gln Glu Gly
                245                 250                 255

Lys Phe Arg Tyr Arg Arg Val Ala Glu Gly Thr Gln Val Leu Glu Leu
            260                 265                 270

Pro Phe Lys Gly Asp Asp Ile Thr Met Val Leu Ile Leu Pro Lys Pro
        275                 280                 285

Glu Lys Ser Leu Ala Lys Val Glu Lys Glu Leu Thr Pro Glu Val Leu
290                 295                 300

Gln Glu Trp Leu Asp Glu Leu Glu Glu Met Met Leu Val Val His Met
305                 310                 315                 320

Pro Arg Phe Arg Ile Glu Asp Gly Phe Ser Leu Lys Glu Gln Leu Gln
                325                 330                 335

Asp Met Gly Leu Val Asp Leu Phe Ser Pro Glu Lys Ser Lys Leu Pro
            340                 345                 350

Gly Ile Val Ala Glu Gly Arg Asp Asp Leu Tyr Val Ser Asp Ala Phe
        355                 360                 365

His Lys Ala Phe Leu Glu Val Asn Glu Glu Gly Ser Glu Ala Ala Ala
    370                 375                 380

Ser Thr Ala Val Val Ile Ala Gly Arg Ser Leu Asn Pro Asn Arg Val
385                 390                 395                 400

Thr Phe Lys Ala Asn Arg Pro Phe Leu Val Phe Ile Arg Glu Val Pro
                405                 410                 415

Leu Asn Thr Ile Ile Phe Met Gly Arg Val Ala Asn Pro Cys Val Lys
            420                 425                 430

<210> SEQ ID NO 3
<211> LENGTH: 1387
<212> TYPE: DNA
<213> ORGANISM: Homo sapiens
<220> FEATURE:
<221> NAME/KEY: CDS
<222> LOCATION: (1)..(1296)

<400> SEQUENCE: 3 cac ggg agc cct gtg gac atc tgc aca gcc aag ccg cgg gac att ccc     48
His Gly Ser Pro Val Asp Ile Cys Thr Ala Lys Pro Arg Asp Ile Pro
1               5                   10                  15 atg aat ccc atg tgc att tac cgc tcc ccg gag aag aag gca act gag     96
Met Asn Pro Met Cys Ile Tyr Arg Ser Pro Glu Lys Lys Ala Thr Glu
            20                  25                  30 gat gag ggc tca gaa cag aag atc ccg gag gcc acc aac cgg cgt gtc    144
Asp Glu Gly Ser Glu Gln Lys Ile Pro Glu Ala Thr Asn Arg Arg Val
        35                  40                  45 tgg gaa ctg tcc aag gcc aat tcc cgc ttt gct acc act ttc tat cag    192
Trp Glu Leu Ser Lys Ala Asn Ser Arg Phe Ala Thr Thr Phe Tyr Gln
    50                  55                  60 cac ctg gca gat tcc aag aat gac aat gat aac att ttc ctg tca ccc    240
His Leu Ala Asp Ser Lys Asn Asp Asn Asp Asn Ile Phe Leu Ser Pro
65                  70                  75                  80 ctg agt atc tcc acg gct ttt gct atg acc aag ctg ggt gcc tgt aat    288
Leu Ser Ile Ser Thr Ala Phe Ala Met Thr Lys Leu Gly Ala Cys Asn
```

```
                        85              90              95
gac acc ctc cag caa ctg atg gag gta ttt aag ttt gac acc ata tct     336
Asp Thr Leu Gln Gln Leu Met Glu Val Phe Lys Phe Asp Thr Ile Ser
        100             105             110 gag aaa aca tct gat cag atc cac ttc ttc ttt gcc aaa ctg aac tgc     384
Glu Lys Thr Ser Asp Gln Ile His Phe Phe Phe Ala Lys Leu Asn Cys
            115             120             125 cga ctc tat cga aaa gcc aac aaa tcc tcc aag tta gta tca gcc aat     432
Arg Leu Tyr Arg Lys Ala Asn Lys Ser Ser Lys Leu Val Ser Ala Asn
130             135             140 cgc ctt ttt gga gac aaa tcc ctt acc ttc aat gag acc tac cag gac     480
Arg Leu Phe Gly Asp Lys Ser Leu Thr Phe Asn Glu Thr Tyr Gln Asp
145             150             155             160 atc agt gag ttg gta tat gga gcc aag ctc cag ccc ctg gac ttc aag     528
Ile Ser Glu Leu Val Tyr Gly Ala Lys Leu Gln Pro Leu Asp Phe Lys
                165             170             175 gaa aat gca gag caa tcc aga gcg gcc atc aac aaa tgg gtg tcc aat     576
Glu Asn Ala Glu Gln Ser Arg Ala Ala Ile Asn Lys Trp Val Ser Asn
            180             185             190 aag acc gaa ggc cga atc acc gat gtc att ccc tcg gaa gcc atc aat     624
Lys Thr Glu Gly Arg Ile Thr Asp Val Ile Pro Ser Glu Ala Ile Asn
        195             200             205 gag ctc act gtt ctg gtg ctg gtt aac acc att tac ttc aag ggc ctg     672
Glu Leu Thr Val Leu Val Leu Val Asn Thr Ile Tyr Phe Lys Gly Leu
    210             215             220 tgg aag tca aag ttc agc cct gag aac aca agg aag gaa ctg ttc tac     720
Trp Lys Ser Lys Phe Ser Pro Glu Asn Thr Arg Lys Glu Leu Phe Tyr
225             230             235             240 aag gct gat gga gag tcg tgt tca gca tct atg atg tac cag gaa ggc     768
Lys Ala Asp Gly Glu Ser Cys Ser Ala Ser Met Met Tyr Gln Glu Gly
                245             250             255 aag ttc cgt tat cgg cgc gtg gct gaa ggc acc cag gtg ctt gag ttg     816
Lys Phe Arg Tyr Arg Arg Val Ala Glu Gly Thr Gln Val Leu Glu Leu
            260             265             270 ccc ttc aaa ggt gat gac atc acc atg gtc ctc atc ttg ccc aag cct     864
Pro Phe Lys Gly Asp Asp Ile Thr Met Val Leu Ile Leu Pro Lys Pro
        275             280             285 gag aag agc ctg gcc aag gta gag aag gaa ctc acc cca gag gtg ctg     912
Glu Lys Ser Leu Ala Lys Val Glu Lys Glu Leu Thr Pro Glu Val Leu
    290             295             300 caa gag tgg ctg gat gaa ttg gag gag atg atg ctg gtg gtc cac atg     960
Gln Glu Trp Leu Asp Glu Leu Glu Glu Met Met Leu Val Val His Met
305             310             315             320 ccc cgc ttc cgc att gag gac ggc ttc agt ttg aag gag cag ctg caa     1008
Pro Arg Phe Arg Ile Glu Asp Gly Phe Ser Leu Lys Glu Gln Leu Gln
                325             330             335 gac atg ggc ctt gtc gat ctg ttc agc cct gaa aag tcc aaa ctc cca     1056
Asp Met Gly Leu Val Asp Leu Phe Ser Pro Glu Lys Ser Lys Leu Pro
            340             345             350 ggt att gtt gca gaa ggc cga gat gac ctc tat gtc tca gat gca ttc     1104
Gly Ile Val Ala Glu Gly Arg Asp Asp Leu Tyr Val Ser Asp Ala Phe
        355             360             365 cat aag gca ttt ctt gag gta aat gaa gaa ggc agt gaa gca gct gca     1152
His Lys Ala Phe Leu Glu Val Asn Glu Glu Gly Ser Glu Ala Ala Ala
    370             375             380 agt acc gct gtt gtg att gct ggc cat tcg cta aac ccc aac agg gtg     1200
Ser Thr Ala Val Val Ile Ala Gly His Ser Leu Asn Pro Asn Arg Val
385             390             395             400 act ttc aag gcc aac agg cct ttc ctg gtt ttt ata aga gaa gtt cct     1248
```

```
                    Thr Phe Lys Ala Asn Arg Pro Phe Leu Val Phe Ile Arg Glu Val Pro
                                    405                 410                 415 ctg aac act att atc ttc atg ggc aga gta gcc aac cct tgt gtt aag             1296
Leu Asn Thr Ile Ile Phe Met Gly Arg Val Ala Asn Pro Cys Val Lys
            420                 425                 430 taaaatgttc ttattctttg cacctcttcc tattttggt ttgtgaacag aagtaaaaat             1356
aaatacaaac tacttccatc tcacattaaa a                                          1387

<210> SEQ ID NO 4
<211> LENGTH: 432
<212> TYPE: PRT
<213> ORGANISM: Homo sapiens

<400> SEQUENCE: 4

His Gly Ser Pro Val Asp Ile Cys Thr Ala Lys Pro Arg Asp Ile Pro
1               5                   10                  15

Met Asn Pro Met Cys Ile Tyr Arg Ser Pro Glu Lys Lys Ala Thr Glu
            20                  25                  30

Asp Glu Gly Ser Glu Gln Lys Ile Pro Glu Ala Thr Asn Arg Arg Val
        35                  40                  45

Trp Glu Leu Ser Lys Ala Asn Ser Arg Phe Ala Thr Thr Phe Tyr Gln
50                  55                  60

His Leu Ala Asp Ser Lys Asn Asp Asn Asp Asn Ile Phe Leu Ser Pro
65                  70                  75                  80

Leu Ser Ile Ser Thr Ala Phe Ala Met Thr Lys Leu Gly Ala Cys Asn
                85                  90                  95

Asp Thr Leu Gln Gln Leu Met Glu Val Phe Lys Phe Asp Thr Ile Ser
            100                 105                 110

Glu Lys Thr Ser Asp Gln Ile His Phe Phe Phe Ala Lys Leu Asn Cys
        115                 120                 125

Arg Leu Tyr Arg Lys Ala Asn Lys Ser Ser Lys Leu Val Ser Ala Asn
130                 135                 140

Arg Leu Phe Gly Asp Lys Ser Leu Thr Phe Asn Glu Thr Tyr Gln Asp
145                 150                 155                 160

Ile Ser Glu Leu Val Tyr Gly Ala Lys Leu Gln Pro Leu Asp Phe Lys
                165                 170                 175

Glu Asn Ala Glu Gln Ser Arg Ala Ala Ile Asn Lys Trp Val Ser Asn
            180                 185                 190

Lys Thr Glu Gly Arg Ile Thr Asp Val Ile Pro Ser Glu Ala Ile Asn
        195                 200                 205

Glu Leu Thr Val Leu Val Leu Val Asn Thr Ile Tyr Phe Lys Gly Leu
210                 215                 220

Trp Lys Ser Lys Phe Ser Pro Glu Asn Thr Arg Lys Glu Leu Phe Tyr
225                 230                 235                 240

Lys Ala Asp Gly Glu Ser Cys Ser Ala Ser Met Met Tyr Gln Glu Gly
                245                 250                 255

Lys Phe Arg Tyr Arg Arg Val Ala Glu Gly Thr Gln Val Leu Glu Leu
            260                 265                 270

Pro Phe Lys Gly Asp Asp Ile Thr Met Val Leu Ile Leu Pro Lys Pro
        275                 280                 285

Glu Lys Ser Leu Ala Lys Val Glu Lys Glu Leu Thr Pro Glu Val Leu
290                 295                 300

Gln Glu Trp Leu Asp Glu Leu Glu Glu Met Met Leu Val Val His Met
305                 310                 315                 320
```

```
Pro Arg Phe Arg Ile Glu Asp Gly Phe Ser Leu Lys Glu Gln Leu Gln
            325                 330                 335

Asp Met Gly Leu Val Asp Leu Phe Ser Pro Glu Lys Ser Lys Leu Pro
        340                 345                 350

Gly Ile Val Ala Glu Gly Arg Asp Asp Leu Tyr Val Ser Asp Ala Phe
                355                 360                 365

His Lys Ala Phe Leu Glu Val Asn Glu Glu Gly Ser Glu Ala Ala Ala
        370                 375                 380

Ser Thr Ala Val Val Ile Ala Gly His Ser Leu Asn Pro Asn Arg Val
385                 390                 395                 400

Thr Phe Lys Ala Asn Arg Pro Phe Leu Val Phe Ile Arg Glu Val Pro
                405                 410                 415

Leu Asn Thr Ile Ile Phe Met Gly Arg Val Ala Asn Pro Cys Val Lys
            420                 425                 430

<210> SEQ ID NO 5
<211> LENGTH: 1390
<212> TYPE: DNA
<213> ORGANISM: Homo sapiens
<220> FEATURE:
<221> NAME/KEY: CDS
<222> LOCATION: (1)..(1299)

<400> SEQUENCE: 5 cac ggg agc cct gtg gac atc tgc aca gcc aag ccg cgg gac att ccc       48
His Gly Ser Pro Val Asp Ile Cys Thr Ala Lys Pro Arg Asp Ile Pro
1               5                   10                  15 atg aat ccc atg tgc att tac cgc tcc ccg gag aag aag gca act gag       96
Met Asn Pro Met Cys Ile Tyr Arg Ser Pro Glu Lys Lys Ala Thr Glu
            20                  25                  30 gat gag ggc tca gaa cag aag atc ccg gag gcc acc aac cgg cgt gtc      144
Asp Glu Gly Ser Glu Gln Lys Ile Pro Glu Ala Thr Asn Arg Arg Val
        35                  40                  45 tgg gaa ctg tcc aag gcc aat tcc cgc ttt gct acc act ttc tat cag      192
Trp Glu Leu Ser Lys Ala Asn Ser Arg Phe Ala Thr Thr Phe Tyr Gln
    50                  55                  60 cac ctg gca gat tcc aag aat gac aat gat aac att ttc ctg tca ccc      240
His Leu Ala Asp Ser Lys Asn Asp Asn Asp Asn Ile Phe Leu Ser Pro
65                  70                  75                  80 ctg agt atc tcc acg gct ttt gct atg acc aag ctg ggt gcc tgt aat      288
Leu Ser Ile Ser Thr Ala Phe Ala Met Thr Lys Leu Gly Ala Cys Asn
                85                  90                  95 gac acc ctc cag caa ctg atg gag gta ttt aag ttt gac acc ata tct      336
Asp Thr Leu Gln Gln Leu Met Glu Val Phe Lys Phe Asp Thr Ile Ser
            100                 105                 110 gag aaa aca tct gat cag atc cac ttc ttc ttt gcc aaa ctg aac tgc      384
Glu Lys Thr Ser Asp Gln Ile His Phe Phe Phe Ala Lys Leu Asn Cys
        115                 120                 125 cga ctc tat cga aaa gcc aac aaa tcc tcc aag tta gta tca gcc aat      432
Arg Leu Tyr Arg Lys Ala Asn Lys Ser Ser Lys Leu Val Ser Ala Asn
    130                 135                 140 cgc ctt ttt gga gac aaa tcc ctt acc ttc aat gag acc tac cag gac      480
Arg Leu Phe Gly Asp Lys Ser Leu Thr Phe Asn Glu Thr Tyr Gln Asp
145                 150                 155                 160 atc agt gag ttg gta tat gga gcc aag ctc cag ccc ctg gac ttc aag      528
Ile Ser Glu Leu Val Tyr Gly Ala Lys Leu Gln Pro Leu Asp Phe Lys
                165                 170                 175 gaa aat gca gag caa tcc aga gcg gcc atc aac aaa tgg gtg tcc aat      576
Glu Asn Ala Glu Gln Ser Arg Ala Ala Ile Asn Lys Trp Val Ser Asn
            180                 185                 190
```

```
aag acc gaa ggc cga atc acc gat gtc att ccc tcg gaa gcc atc aat      624
Lys Thr Glu Gly Arg Ile Thr Asp Val Ile Pro Ser Glu Ala Ile Asn
            195                 200                 205 gag ctc act gtt ctg gtg ctg gtt aac acc att tac ttc aag ggc ctg      672
Glu Leu Thr Val Leu Val Leu Val Asn Thr Ile Tyr Phe Lys Gly Leu
    210                 215                 220 tgg aag tca aag ttc agc cct gag aac aca agg aag gaa ctg ttc tac      720
Trp Lys Ser Lys Phe Ser Pro Glu Asn Thr Arg Lys Glu Leu Phe Tyr
225                 230                 235                 240 aag gct gat gga gag tcg tgt tca gca tct atg atg tac cag gaa ggc      768
Lys Ala Asp Gly Glu Ser Cys Ser Ala Ser Met Met Tyr Gln Glu Gly
                245                 250                 255 aag ttc cgt tat cgg cgc gtg gct gaa ggc acc cag gtg ctt gag ttg      816
Lys Phe Arg Tyr Arg Arg Val Ala Glu Gly Thr Gln Val Leu Glu Leu
            260                 265                 270 ccc ttc aaa ggt gat gac atc acc atg gtc ctc atc ttg ccc aag cct      864
Pro Phe Lys Gly Asp Asp Ile Thr Met Val Leu Ile Leu Pro Lys Pro
    275                 280                 285 gag aag agc ctg gcc aag gta gag aag gaa ctc acc cca gag gtg ctg      912
Glu Lys Ser Leu Ala Lys Val Glu Lys Glu Leu Thr Pro Glu Val Leu
290                 295                 300 caa gag tgg ctg gat gaa ttg gag gag atg atg ctg gtg gtc cac atg      960
Gln Glu Trp Leu Asp Glu Leu Glu Glu Met Met Leu Val Val His Met
305                 310                 315                 320 ccc cgc ttc cgc att gag gac ggc ttc agt ttg aag gag cag ctg caa     1008
Pro Arg Phe Arg Ile Glu Asp Gly Phe Ser Leu Lys Glu Gln Leu Gln
                325                 330                 335 gac atg ggc ctt gtc gat ctg ttc agc cct gaa aag tcc aaa ctc cca     1056
Asp Met Gly Leu Val Asp Leu Phe Ser Pro Glu Lys Ser Lys Leu Pro
            340                 345                 350 ggt att gtt gca gaa ggc cga gat gac ctc tat gtc tca gat gca ttc     1104
Gly Ile Val Ala Glu Gly Arg Asp Asp Leu Tyr Val Ser Asp Ala Phe
    355                 360                 365 cat aag gca ttt ctt gag gta aat gaa gaa ggc agt gaa gca gct gca     1152
His Lys Ala Phe Leu Glu Val Asn Glu Glu Gly Ser Glu Ala Ala Ala
370                 375                 380 agt acc gct gtt gtg att gct ggc cgt cca tcg cta aac ccc aac agg     1200
Ser Thr Ala Val Val Ile Ala Gly Arg Pro Ser Leu Asn Pro Asn Arg
385                 390                 395                 400 gtg act ttc aag gcc aac agg cct ttc ctg gtt ttt ata aga gaa gtt     1248
Val Thr Phe Lys Ala Asn Arg Pro Phe Leu Val Phe Ile Arg Glu Val
                405                 410                 415 cct ctg aac act att atc ttc atg ggc aga gta gcc aac cct tgt gtt     1296
Pro Leu Asn Thr Ile Ile Phe Met Gly Arg Val Ala Asn Pro Cys Val
            420                 425                 430 aag taaaatgttc ttattctttg caccctcttcc tattttggt tgtgaacag           1349
Lys aagtaaaaat aaatacaaac tacttccatc tcacattaaa a                       1390

<210> SEQ ID NO 6
<211> LENGTH: 433
<212> TYPE: PRT
<213> ORGANISM: Homo sapiens

<400> SEQUENCE: 6

His Gly Ser Pro Val Asp Ile Cys Thr Ala Lys Pro Arg Asp Ile Pro
1               5                   10                  15

Met Asn Pro Met Cys Ile Tyr Arg Ser Pro Glu Lys Lys Ala Thr Glu
            20                  25                  30
```

```
Asp Glu Gly Ser Glu Gln Lys Ile Pro Glu Ala Thr Asn Arg Arg Val
         35                  40                  45

Trp Glu Leu Ser Lys Ala Asn Ser Arg Phe Ala Thr Thr Phe Tyr Gln
 50                  55                  60

His Leu Ala Asp Ser Lys Asn Asp Asn Asp Ile Phe Leu Ser Pro
 65                  70                  75                  80

Leu Ser Ile Ser Thr Ala Phe Ala Met Thr Lys Leu Gly Ala Cys Asn
                 85                  90                  95

Asp Thr Leu Gln Gln Leu Met Glu Val Phe Lys Phe Asp Thr Ile Ser
                100                 105                 110

Glu Lys Thr Ser Asp Gln Ile His Phe Phe Ala Lys Leu Asn Cys
         115                 120                 125

Arg Leu Tyr Arg Lys Ala Asn Lys Ser Ser Lys Leu Val Ser Ala Asn
         130                 135                 140

Arg Leu Phe Gly Asp Lys Ser Leu Thr Phe Asn Glu Thr Tyr Gln Asp
145                 150                 155                 160

Ile Ser Glu Leu Val Tyr Gly Ala Lys Leu Gln Pro Leu Asp Phe Lys
                 165                 170                 175

Glu Asn Ala Glu Gln Ser Arg Ala Ala Ile Asn Lys Trp Val Ser Asn
                180                 185                 190

Lys Thr Glu Gly Arg Ile Thr Asp Val Ile Pro Ser Glu Ala Ile Asn
         195                 200                 205

Glu Leu Thr Val Leu Val Leu Val Asn Thr Ile Tyr Phe Lys Gly Leu
 210                 215                 220

Trp Lys Ser Lys Phe Ser Pro Glu Asn Thr Arg Lys Glu Leu Phe Tyr
225                 230                 235                 240

Lys Ala Asp Gly Glu Ser Cys Ser Ala Ser Met Met Tyr Gln Glu Gly
                 245                 250                 255

Lys Phe Arg Tyr Arg Arg Val Ala Glu Gly Thr Gln Val Leu Glu Leu
                 260                 265                 270

Pro Phe Lys Gly Asp Asp Ile Thr Met Val Leu Ile Leu Pro Lys Pro
         275                 280                 285

Glu Lys Ser Leu Ala Lys Val Glu Lys Glu Leu Thr Pro Glu Val Leu
 290                 295                 300

Gln Glu Trp Leu Asp Glu Leu Glu Glu Met Met Leu Val Val His Met
305                 310                 315                 320

Pro Arg Phe Arg Ile Glu Asp Gly Phe Ser Leu Lys Glu Gln Leu Gln
                 325                 330                 335

Asp Met Gly Leu Val Asp Leu Phe Ser Pro Glu Lys Ser Lys Leu Pro
                 340                 345                 350

Gly Ile Val Ala Glu Gly Arg Asp Asp Leu Tyr Val Ser Asp Ala Phe
                 355                 360                 365

His Lys Ala Phe Leu Glu Val Asn Glu Glu Gly Ser Glu Ala Ala Ala
         370                 375                 380

Ser Thr Ala Val Val Ile Ala Gly Arg Pro Ser Leu Asn Pro Asn Arg
385                 390                 395                 400

Val Thr Phe Lys Ala Asn Arg Pro Phe Leu Val Phe Ile Arg Glu Val
                 405                 410                 415

Pro Leu Asn Thr Ile Ile Phe Met Gly Arg Val Ala Asn Pro Cys Val
                 420                 425                 430

Lys
```

<210> SEQ ID NO 7
<211> LENGTH: 1384
<212> TYPE: DNA
<213> ORGANISM: Homo sapiens
<220> FEATURE:
<221> NAME/KEY: CDS
<222> LOCATION: (1)..(1293)

<400> SEQUENCE: 7

| | | | | | | | | | | | | | | | | |
|---|---|---|---|---|---|---|---|---|---|---|---|---|---|---|---|---|
| cac | ggg | agc | cct | gtg | gac | atc | tgc | aca | gcc | aag | ccg | cgg | gac | att | ccc | 48 |
| His | Gly | Ser | Pro | Val | Asp | Ile | Cys | Thr | Ala | Lys | Pro | Arg | Asp | Ile | Pro | |
| 1 | | | | 5 | | | | | 10 | | | | | 15 | | |
| atg | aat | ccc | atg | tgc | att | tac | cgc | tcc | ccg | gag | aag | aag | gca | act | gag | 96 |
| Met | Asn | Pro | Met | Cys | Ile | Tyr | Arg | Ser | Pro | Glu | Lys | Lys | Ala | Thr | Glu | |
| | | | 20 | | | | | 25 | | | | | 30 | | | |
| gat | gag | ggc | tca | gaa | cag | aag | atc | ccg | gag | gcc | acc | aac | cgg | cgt | gtc | 144 |
| Asp | Glu | Gly | Ser | Glu | Gln | Lys | Ile | Pro | Glu | Ala | Thr | Asn | Arg | Arg | Val | |
| | 35 | | | | | 40 | | | | | 45 | | | | | |
| tgg | gaa | ctg | tcc | aag | gcc | aat | tcc | cgc | ttt | gct | acc | act | ttc | tat | cag | 192 |
| Trp | Glu | Leu | Ser | Lys | Ala | Asn | Ser | Arg | Phe | Ala | Thr | Thr | Phe | Tyr | Gln | |
| 50 | | | | | 55 | | | | | 60 | | | | | | |
| cac | ctg | gca | gat | tcc | aag | aat | gac | aat | gat | aac | att | ttc | ctg | tca | ccc | 240 |
| His | Leu | Ala | Asp | Ser | Lys | Asn | Asp | Asn | Asp | Asn | Ile | Phe | Leu | Ser | Pro | |
| 65 | | | | | 70 | | | | | 75 | | | | | 80 | |
| ctg | agt | atc | tcc | acg | gct | ttt | gct | atg | acc | aag | ctg | ggt | gcc | tgt | aat | 288 |
| Leu | Ser | Ile | Ser | Thr | Ala | Phe | Ala | Met | Thr | Lys | Leu | Gly | Ala | Cys | Asn | |
| | | | | 85 | | | | | 90 | | | | | 95 | | |
| gac | acc | ctc | cag | caa | ctg | atg | gag | gta | ttt | aag | ttt | gac | acc | ata | tct | 336 |
| Asp | Thr | Leu | Gln | Gln | Leu | Met | Glu | Val | Phe | Lys | Phe | Asp | Thr | Ile | Ser | |
| | | | 100 | | | | | 105 | | | | | 110 | | | |
| gag | aaa | aca | tct | gat | cag | atc | cac | ttc | ttc | ttt | gcc | aaa | ctg | aac | tgc | 384 |
| Glu | Lys | Thr | Ser | Asp | Gln | Ile | His | Phe | Phe | Phe | Ala | Lys | Leu | Asn | Cys | |
| | | 115 | | | | | 120 | | | | | 125 | | | | |
| cga | ctc | tat | cga | aaa | gcc | aac | aaa | tcc | tcc | aag | tta | gta | tca | gcc | aat | 432 |
| Arg | Leu | Tyr | Arg | Lys | Ala | Asn | Lys | Ser | Ser | Lys | Leu | Val | Ser | Ala | Asn | |
| | 130 | | | | | 135 | | | | | 140 | | | | | |
| cgc | ctt | ttt | gga | gac | aaa | tcc | ctt | acc | ttc | aat | gag | acc | tac | cag | gac | 480 |
| Arg | Leu | Phe | Gly | Asp | Lys | Ser | Leu | Thr | Phe | Asn | Glu | Thr | Tyr | Gln | Asp | |
| 145 | | | | | 150 | | | | | 155 | | | | | 160 | |
| atc | agt | gag | ttg | gta | tat | gga | gcc | aag | ctc | cag | ccc | ctg | gac | ttc | aag | 528 |
| Ile | Ser | Glu | Leu | Val | Tyr | Gly | Ala | Lys | Leu | Gln | Pro | Leu | Asp | Phe | Lys | |
| | | | | 165 | | | | | 170 | | | | | 175 | | |
| gaa | aat | gca | gag | caa | tcc | aga | gcg | gcc | atc | aac | aaa | tgg | gtg | tcc | aat | 576 |
| Glu | Asn | Ala | Glu | Gln | Ser | Arg | Ala | Ala | Ile | Asn | Lys | Trp | Val | Ser | Asn | |
| | | | 180 | | | | | 185 | | | | | 190 | | | |
| aag | acc | gaa | ggc | cga | atc | acc | gat | gtc | att | ccc | tcg | gaa | gcc | atc | aat | 624 |
| Lys | Thr | Glu | Gly | Arg | Ile | Thr | Asp | Val | Ile | Pro | Ser | Glu | Ala | Ile | Asn | |
| | | 195 | | | | | 200 | | | | | 205 | | | | |
| gag | ctc | act | gtt | ctg | gtg | ctg | gtt | aac | acc | att | tac | ttc | aag | ggc | ctg | 672 |
| Glu | Leu | Thr | Val | Leu | Val | Leu | Val | Asn | Thr | Ile | Tyr | Phe | Lys | Gly | Leu | |
| | 210 | | | | | 215 | | | | | 220 | | | | | |
| tgg | aag | tca | aag | ttc | agc | cct | gag | aac | aca | agg | aag | gaa | ctg | ttc | tac | 720 |
| Trp | Lys | Ser | Lys | Phe | Ser | Pro | Glu | Asn | Thr | Arg | Lys | Glu | Leu | Phe | Tyr | |
| 225 | | | | | 230 | | | | | 235 | | | | | 240 | |
| aag | gct | gat | gga | gag | tcg | tgt | tca | gca | tct | atg | atg | tac | cag | gaa | ggc | 768 |
| Lys | Ala | Asp | Gly | Glu | Ser | Cys | Ser | Ala | Ser | Met | Met | Tyr | Gln | Glu | Gly | |
| | | | | 245 | | | | | 250 | | | | | 255 | | |
| aag | ttc | cgt | tat | cgg | cgc | gtg | gct | gaa | ggc | acc | cag | gtg | ctt | gag | ttg | 816 |
| Lys | Phe | Arg | Tyr | Arg | Arg | Val | Ala | Glu | Gly | Thr | Gln | Val | Leu | Glu | Leu | |
| | | | 260 | | | | | 265 | | | | | 270 | | | |
| ccc | ttc | aaa | ggt | gat | gac | atc | acc | atg | gtc | ctc | atc | ttg | ccc | aag | cct | 864 |

-continued

```
                Pro Phe Lys Gly Asp Asp Ile Thr Met Val Leu Ile Leu Pro Lys Pro
                                275                 280                 285 gag aag agc ctg gcc aag gta gag aag gaa ctc acc cca gag gtg ctg        912
Glu Lys Ser Leu Ala Lys Val Glu Lys Glu Leu Thr Pro Glu Val Leu
        290                 295                 300 caa gag tgg ctg gat gaa ttg gag gag atg atg ctg gtg gtc cac atg        960
Gln Glu Trp Leu Asp Glu Leu Glu Glu Met Met Leu Val Val His Met
305                 310                 315                 320 ccc cgc ttc cgc att gag gac ggc ttc agt ttg aag gag cag ctg caa       1008
Pro Arg Phe Arg Ile Glu Asp Gly Phe Ser Leu Lys Glu Gln Leu Gln
                325                 330                 335 gac atg ggc ctt gtc gat ctg ttc agc cct gaa aag tcc aaa ctc cca       1056
Asp Met Gly Leu Val Asp Leu Phe Ser Pro Glu Lys Ser Lys Leu Pro
            340                 345                 350 ggt att gtt gca gaa ggc cga gat gac ctc tat gtc tca gat gca ttc       1104
Gly Ile Val Ala Glu Gly Arg Asp Asp Leu Tyr Val Ser Asp Ala Phe
        355                 360                 365 cat aag gca ttt ctt gag gta aat gaa gaa ggc agt gaa gca gct gca       1152
His Lys Ala Phe Leu Glu Val Asn Glu Glu Gly Ser Glu Ala Ala Ala
370                 375                 380 agt acc gct gtt gtg att gct ggc tcg cta aac ccc aac agg gtg act       1200
Ser Thr Ala Val Val Ile Ala Gly Ser Leu Asn Pro Asn Arg Val Thr
385                 390                 395                 400 ttc aag gcc aac agg cct ttc ctg gtt ttt ata aga gaa gtt cct ctg       1248
Phe Lys Ala Asn Arg Pro Phe Leu Val Phe Ile Arg Glu Val Pro Leu
                405                 410                 415 aac act att atc ttc atg ggc aga gta gcc aac cct tgt gtt aag           1293
Asn Thr Ile Ile Phe Met Gly Arg Val Ala Asn Pro Cys Val Lys
            420                 425                 430 taaaatgttc ttattctttg cacctcttcc tattttggt ttgtgaacag aagtaaaaat      1353
aaatacaaac tacttccatc tcacattaaa a                                    1384

<210> SEQ ID NO 8
<211> LENGTH: 431
<212> TYPE: PRT
<213> ORGANISM: Homo sapiens

<400> SEQUENCE: 8

His Gly Ser Pro Val Asp Ile Cys Thr Ala Lys Pro Arg Asp Ile Pro
1               5                   10                  15

Met Asn Pro Met Cys Ile Tyr Arg Ser Pro Glu Lys Lys Ala Thr Glu
                20                  25                  30

Asp Glu Gly Ser Glu Gln Lys Ile Pro Glu Ala Thr Asn Arg Arg Val
            35                  40                  45

Trp Glu Leu Ser Lys Ala Asn Ser Arg Phe Ala Thr Thr Phe Tyr Gln
        50                  55                  60

His Leu Ala Asp Ser Lys Asn Asp Asn Asp Asn Ile Phe Leu Ser Pro
65                  70                  75                  80

Leu Ser Ile Ser Thr Ala Phe Ala Met Thr Lys Leu Gly Ala Cys Asn
                85                  90                  95

Asp Thr Leu Gln Gln Leu Met Glu Val Phe Lys Phe Asp Thr Ile Ser
            100                 105                 110

Glu Lys Thr Ser Asp Gln Ile His Phe Phe Ala Lys Leu Asn Cys
        115                 120                 125

Arg Leu Tyr Arg Lys Ala Asn Lys Ser Ser Lys Leu Val Ser Ala Asn
130                 135                 140

Arg Leu Phe Gly Asp Lys Ser Leu Thr Phe Asn Glu Thr Tyr Gln Asp
```

-continued

```
            145                 150                 155                 160
        Ile Ser Glu Leu Val Tyr Gly Ala Lys Leu Gln Pro Leu Asp Phe Lys
                        165                 170                 175

Glu Asn Ala Glu Gln Ser Arg Ala Ala Ile Asn Lys Trp Val Ser Asn
                        180                 185                 190

Lys Thr Glu Gly Arg Ile Thr Asp Val Ile Pro Ser Glu Ala Ile Asn
                        195                 200                 205

Glu Leu Thr Val Leu Val Leu Val Asn Thr Ile Tyr Phe Lys Gly Leu
                        210                 215                 220

Trp Lys Ser Lys Phe Ser Pro Glu Asn Thr Arg Lys Glu Leu Phe Tyr
        225                 230                 235                 240

Lys Ala Asp Gly Glu Ser Cys Ser Ala Ser Met Met Tyr Gln Glu Gly
                        245                 250                 255

Lys Phe Arg Tyr Arg Arg Val Ala Glu Gly Thr Gln Val Leu Glu Leu
                        260                 265                 270

Pro Phe Lys Gly Asp Asp Ile Thr Met Val Leu Ile Leu Pro Lys Pro
                        275                 280                 285

Glu Lys Ser Leu Ala Lys Val Glu Lys Glu Leu Thr Pro Glu Val Leu
                        290                 295                 300

Gln Glu Trp Leu Asp Glu Leu Glu Glu Met Met Leu Val Val His Met
        305                 310                 315                 320

Pro Arg Phe Arg Ile Glu Asp Gly Phe Ser Leu Lys Glu Gln Leu Gln
                        325                 330                 335

Asp Met Gly Leu Val Asp Leu Phe Ser Pro Glu Lys Ser Lys Leu Pro
                        340                 345                 350

Gly Ile Val Ala Glu Gly Arg Asp Asp Leu Tyr Val Ser Asp Ala Phe
                        355                 360                 365

His Lys Ala Phe Leu Glu Val Asn Glu Glu Gly Ser Glu Ala Ala Ala
                        370                 375                 380

Ser Thr Ala Val Val Ile Ala Gly Ser Leu Asn Pro Asn Arg Val Thr
        385                 390                 395                 400

Phe Lys Ala Asn Arg Pro Phe Leu Val Phe Ile Arg Glu Val Pro Leu
                        405                 410                 415

Asn Thr Ile Ile Phe Met Gly Arg Val Ala Asn Pro Cys Val Lys
                        420                 425                 430

<210> SEQ ID NO 9
<211> LENGTH: 1384
<212> TYPE: DNA
<213> ORGANISM: Homo sapiens
<220> FEATURE:
<221> NAME/KEY: CDS
<222> LOCATION: (1)..(1293)

<400> SEQUENCE: 9 cac ggg agc cct gtg gac atc tgc aca gcc aag ccg cgg gac att ccc    48
His Gly Ser Pro Val Asp Ile Cys Thr Ala Lys Pro Arg Asp Ile Pro
1               5                   10                  15 atg aat ccc atg tgc att tac cgc tcc ccg gag aag aag gca act gag    96
Met Asn Pro Met Cys Ile Tyr Arg Ser Pro Glu Lys Lys Ala Thr Glu
            20                  25                  30 gat gag ggc tca gaa cag aag atc ccg gag gcc acc aac cgg gtg tc   144
Asp Glu Gly Ser Glu Gln Lys Ile Pro Glu Ala Thr Asn Arg Val
        35                  40                  45 tgg gaa ctg tcc aag gcc aat tcc cgc ttt gct acc act ttc tat cag   192
Trp Glu Leu Ser Lys Ala Asn Ser Arg Phe Ala Thr Thr Phe Tyr Gln
50                  55                  60
```

-continued

```
cac ctg gca gat tcc aag aat gac aat gat aac att ttc ctg tca ccc     240
His Leu Ala Asp Ser Lys Asn Asp Asn Asp Asn Ile Phe Leu Ser Pro
65              70                  75                  80 ctg agt atc tcc acg gct ttt gct atg acc aag ctg ggt gcc tgt aat     288
Leu Ser Ile Ser Thr Ala Phe Ala Met Thr Lys Leu Gly Ala Cys Asn
                85                  90                  95 gac acc ctc cag caa ctg atg gag gta ttt aag ttt gac acc ata tct     336
Asp Thr Leu Gln Gln Leu Met Glu Val Phe Lys Phe Asp Thr Ile Ser
            100                 105                 110 gag aaa aca tct gat cag atc cac ttc ttc ttt gcc aaa ctg aac tgc     384
Glu Lys Thr Ser Asp Gln Ile His Phe Phe Phe Ala Lys Leu Asn Cys
        115                 120                 125 cga ctc tat cga aaa gcc aac aaa tcc tcc aag tta gta tca gcc aat     432
Arg Leu Tyr Arg Lys Ala Asn Lys Ser Ser Lys Leu Val Ser Ala Asn
130                 135                 140 cgc ctt ttt gga gac aaa tcc ctt acc ttc aat gag acc tac cag gac     480
Arg Leu Phe Gly Asp Lys Ser Leu Thr Phe Asn Glu Thr Tyr Gln Asp
145                 150                 155                 160 atc agt gag ttg gta tat gga gcc aag ctc cag ccc ctg gac ttc aag     528
Ile Ser Glu Leu Val Tyr Gly Ala Lys Leu Gln Pro Leu Asp Phe Lys
                165                 170                 175 gaa aat gca gag caa tcc aga gcg gcc atc aac aaa tgg gtg tcc aat     576
Glu Asn Ala Glu Gln Ser Arg Ala Ala Ile Asn Lys Trp Val Ser Asn
            180                 185                 190 aag acc gaa ggc cga atc acc gat gtc att ccc tcg gaa gcc atc aat     624
Lys Thr Glu Gly Arg Ile Thr Asp Val Ile Pro Ser Glu Ala Ile Asn
        195                 200                 205 gag ctc act gtt ctg gtg ctg gtt aac acc att tac ttc aag ggc ctg     672
Glu Leu Thr Val Leu Val Leu Val Asn Thr Ile Tyr Phe Lys Gly Leu
210                 215                 220 tgg aag tca aag ttc agc cct gag aac aca agg aag gaa ctg ttc tac     720
Trp Lys Ser Lys Phe Ser Pro Glu Asn Thr Arg Lys Glu Leu Phe Tyr
225                 230                 235                 240 aag gct gat gga gag tcg tgt tca gca tct atg atg tac cag gaa ggc     768
Lys Ala Asp Gly Glu Ser Cys Ser Ala Ser Met Met Tyr Gln Glu Gly
                245                 250                 255 aag ttc cgt tat cgg cgc gtg gct gaa ggc acc cag gtg ctt gag ttg     816
Lys Phe Arg Tyr Arg Arg Val Ala Glu Gly Thr Gln Val Leu Glu Leu
            260                 265                 270 ccc ttc aaa ggt gat gac atc acc atg gtc ctc atc ttg ccc aag cct     864
Pro Phe Lys Gly Asp Asp Ile Thr Met Val Leu Ile Leu Pro Lys Pro
        275                 280                 285 gag aag agc ctg gcc aag gta gag aag gaa ctc acc cca gag gtg ctg     912
Glu Lys Ser Leu Ala Lys Val Glu Lys Glu Leu Thr Pro Glu Val Leu
290                 295                 300 caa gag tgg ctg gat gaa ttg gag gag atg atg ctg gtg gtc cac atg     960
Gln Glu Trp Leu Asp Glu Leu Glu Glu Met Met Leu Val Val His Met
305                 310                 315                 320 ccc cgc ttc cgc att gag gac ggc ttc agt ttg aag gag cag ctg caa    1008
Pro Arg Phe Arg Ile Glu Asp Gly Phe Ser Leu Lys Glu Gln Leu Gln
                325                 330                 335 gac atg ggc ctt gtc gat ctg ttc agc cct gaa aag tcc aaa ctc cca    1056
Asp Met Gly Leu Val Asp Leu Phe Ser Pro Glu Lys Ser Lys Leu Pro
            340                 345                 350 ggt att gtt gca gaa ggc cga gat gac ctc tat gtc tca gat gca ttc    1104
Gly Ile Val Ala Glu Gly Arg Asp Asp Leu Tyr Val Ser Asp Ala Phe
        355                 360                 365 cat aag gca ttt ctt gag gta aat gaa gaa ggc agt gaa gca gct gca    1152
His Lys Ala Phe Leu Glu Val Asn Glu Glu Gly Ser Glu Ala Ala Ala
```

```
                370                 375                 380
agt acc gct gtt gtg att gct ggc cgt cta aac ccc aac agg gtg act    1200
Ser Thr Ala Val Val Ile Ala Gly Arg Leu Asn Pro Asn Arg Val Thr
385                 390                 395                 400 ttc aag gcc aac agg cct ttc ctg gtt ttt ata aga gaa gtt cct ctg    1248
Phe Lys Ala Asn Arg Pro Phe Leu Val Phe Ile Arg Glu Val Pro Leu
            405                 410                 415 aac act att atc ttc atg ggc aga gta gcc aac cct tgt gtt aag        1293
Asn Thr Ile Ile Phe Met Gly Arg Val Ala Asn Pro Cys Val Lys
420                 425                 430 taaaatgttc ttattctttg cacctcttcc tatttttggt ttgtgaacag aagtaaaaat  1353
aaatacaaac tacttccatc tcacattaaa a                                 1384

<210> SEQ ID NO 10
<211> LENGTH: 431
<212> TYPE: PRT
<213> ORGANISM: Homo sapiens

<400> SEQUENCE: 10

His Gly Ser Pro Val Asp Ile Cys Thr Ala Lys Pro Arg Asp Ile Pro
1               5                   10                  15

Met Asn Pro Met Cys Ile Tyr Arg Ser Pro Glu Lys Lys Ala Thr Glu
            20                  25                  30

Asp Glu Gly Ser Glu Gln Lys Ile Pro Glu Ala Thr Asn Arg Arg Val
        35                  40                  45

Trp Glu Leu Ser Lys Ala Asn Ser Arg Phe Ala Thr Thr Phe Tyr Gln
    50                  55                  60

His Leu Ala Asp Ser Lys Asn Asp Asn Asp Asn Ile Phe Leu Ser Pro
65                  70                  75                  80

Leu Ser Ile Ser Thr Ala Phe Ala Met Thr Lys Leu Gly Ala Cys Asn
                85                  90                  95

Asp Thr Leu Gln Gln Leu Met Glu Val Phe Lys Phe Asp Thr Ile Ser
            100                 105                 110

Glu Lys Thr Ser Asp Gln Ile His Phe Phe Phe Ala Lys Leu Asn Cys
        115                 120                 125

Arg Leu Tyr Arg Lys Ala Asn Lys Ser Ser Lys Leu Val Ser Ala Asn
    130                 135                 140

Arg Leu Phe Gly Asp Lys Ser Leu Thr Phe Asn Glu Thr Tyr Gln Asp
145                 150                 155                 160

Ile Ser Glu Leu Val Tyr Gly Ala Lys Leu Gln Pro Leu Asp Phe Lys
                165                 170                 175

Glu Asn Ala Glu Gln Ser Arg Ala Ala Ile Asn Lys Trp Val Ser Asn
            180                 185                 190

Lys Thr Glu Gly Arg Ile Thr Asp Val Ile Pro Ser Glu Ala Ile Asn
        195                 200                 205

Glu Leu Thr Val Leu Val Leu Val Asn Thr Ile Tyr Phe Lys Gly Leu
    210                 215                 220

Trp Lys Ser Lys Phe Ser Pro Glu Asn Thr Arg Lys Glu Leu Phe Tyr
225                 230                 235                 240

Lys Ala Asp Gly Glu Ser Cys Ser Ala Ser Met Met Tyr Gln Glu Gly
                245                 250                 255

Lys Phe Arg Tyr Arg Arg Val Ala Glu Gly Thr Gln Val Leu Glu Leu
            260                 265                 270

Pro Phe Lys Gly Asp Asp Ile Thr Met Val Leu Ile Leu Pro Lys Pro
        275                 280                 285
```

```
Glu Lys Ser Leu Ala Lys Val Glu Lys Glu Leu Thr Pro Glu Val Leu
    290                 295                 300
Gln Glu Trp Leu Asp Glu Leu Glu Glu Met Met Leu Val Val His Met
305                 310                 315                 320
Pro Arg Phe Arg Ile Glu Asp Gly Phe Ser Leu Lys Glu Gln Leu Gln
                325                 330                 335
Asp Met Gly Leu Val Asp Leu Phe Ser Pro Glu Lys Ser Lys Leu Pro
                340                 345                 350
Gly Ile Val Ala Glu Gly Arg Asp Asp Leu Tyr Val Ser Asp Ala Phe
            355                 360                 365
His Lys Ala Phe Leu Glu Val Asn Glu Glu Gly Ser Glu Ala Ala Ala
    370                 375                 380
Ser Thr Ala Val Val Ile Ala Gly Arg Leu Asn Pro Asn Arg Val Thr
385                 390                 395                 400
Phe Lys Ala Asn Arg Pro Phe Leu Val Phe Ile Arg Glu Val Pro Leu
                405                 410                 415
Asn Thr Ile Ile Phe Met Gly Arg Val Ala Asn Pro Cys Val Lys
                420                 425                 430

<210> SEQ ID NO 11
<211> LENGTH: 1387
<212> TYPE: DNA
<213> ORGANISM: Homo sapiens
<220> FEATURE:
<221> NAME/KEY: CDS
<222> LOCATION: (1)..(1296)

<400> SEQUENCE: 11 cac ggg agc cct gtg gac atc tgc aca gcc aag ccg cgg gac att ccc      48
His Gly Ser Pro Val Asp Ile Cys Thr Ala Lys Pro Arg Asp Ile Pro
1               5                   10                  15 atg aat ccc atg tgc att tac cgc tcc ccg gag aag aag gca act gag      96
Met Asn Pro Met Cys Ile Tyr Arg Ser Pro Glu Lys Lys Ala Thr Glu
            20                  25                  30 gat gag ggc tca gaa cag aag atc ccg gag gcc acc aac cgg cgt gtc     144
Asp Glu Gly Ser Glu Gln Lys Ile Pro Glu Ala Thr Asn Arg Arg Val
        35                  40                  45 tgg gaa ctg tcc aag gcc aat tcc cgc ttt gct acc act ttc tat cag     192
Trp Glu Leu Ser Lys Ala Asn Ser Arg Phe Ala Thr Thr Phe Tyr Gln
    50                  55                  60 cac ctg gca gat tcc aag aat gac aat gat aac att ttc ctg tca ccc     240
His Leu Ala Asp Ser Lys Asn Asp Asn Asp Asn Ile Phe Leu Ser Pro
65                  70                  75                  80 ctg agt atc tcc acg gct ttt gct atg acc aag ctg ggt gcc tgt aat     288
Leu Ser Ile Ser Thr Ala Phe Ala Met Thr Lys Leu Gly Ala Cys Asn
                85                  90                  95 gac acc ctc cag caa ctg atg gag gta ttt aag ttt gac acc ata tct     336
Asp Thr Leu Gln Gln Leu Met Glu Val Phe Lys Phe Asp Thr Ile Ser
            100                 105                 110 gag aaa aca tct gat cag atc cac ttc ttc ttt gcc aaa ctg aac tgc     384
Glu Lys Thr Ser Asp Gln Ile His Phe Phe Phe Ala Lys Leu Asn Cys
        115                 120                 125 cga ctc tat cga aaa gcc cag aaa tcc tcc aag tta gta tca gcc aat     432
Arg Leu Tyr Arg Lys Ala Gln Lys Ser Ser Lys Leu Val Ser Ala Asn
    130                 135                 140 cgc ctt ttt gga gac aaa tcc ctt acc ttc aat gag acc tac cag gac     480
Arg Leu Phe Gly Asp Lys Ser Leu Thr Phe Asn Glu Thr Tyr Gln Asp
145                 150                 155                 160
```

| | | |
|---|---|---|
| atc agt gag ttg gta tat gga gcc aag ctc cag ccc ctg gac ttc aag<br>Ile Ser Glu Leu Val Tyr Gly Ala Lys Leu Gln Pro Leu Asp Phe Lys<br>165 170 175 | | 528 |
| gaa aat gca gag caa tcc aga gcg gcc atc aac aaa tgg gtg tcc aat<br>Glu Asn Ala Glu Gln Ser Arg Ala Ala Ile Asn Lys Trp Val Ser Asn<br>180 185 190 | | 576 |
| aag acc gaa ggc cga atc acc gat gtc att ccc tcg gaa gcc atc aat<br>Lys Thr Glu Gly Arg Ile Thr Asp Val Ile Pro Ser Glu Ala Ile Asn<br>195 200 205 | | 624 |
| gag ctc act gtt ctg gtg ctg gtt aac acc att tac ttc aag ggc ctg<br>Glu Leu Thr Val Leu Val Leu Val Asn Thr Ile Tyr Phe Lys Gly Leu<br>210 215 220 | | 672 |
| tgg aag tca aag ttc agc cct gag aac aca agg aag gaa ctg ttc tac<br>Trp Lys Ser Lys Phe Ser Pro Glu Asn Thr Arg Lys Glu Leu Phe Tyr<br>225 230 235 240 | | 720 |
| aag gct gat gga gag tcg tgt tca gca tct atg atg tac cag gaa ggc<br>Lys Ala Asp Gly Glu Ser Cys Ser Ala Ser Met Met Tyr Gln Glu Gly<br>245 250 255 | | 768 |
| aag ttc cgt tat cgg cgc gtg gct gaa ggc acc cag gtg ctt gag ttg<br>Lys Phe Arg Tyr Arg Arg Val Ala Glu Gly Thr Gln Val Leu Glu Leu<br>260 265 270 | | 816 |
| ccc ttc aaa ggt gat gac atc acc atg gtc ctc atc ttg ccc aag cct<br>Pro Phe Lys Gly Asp Asp Ile Thr Met Val Leu Ile Leu Pro Lys Pro<br>275 280 285 | | 864 |
| gag aag agc ctg gcc aag gta gag aag gaa ctc acc cca gag gtg ctg<br>Glu Lys Ser Leu Ala Lys Val Glu Lys Glu Leu Thr Pro Glu Val Leu<br>290 295 300 | | 912 |
| caa gag tgg ctg gat gaa ttg gag gag atg atg ctg gtg gtc cac atg<br>Gln Glu Trp Leu Asp Glu Leu Glu Glu Met Met Leu Val Val His Met<br>305 310 315 320 | | 960 |
| ccc cgc ttc cgc att gag gac ggc ttc agt ttg aag gag cag ctg caa<br>Pro Arg Phe Arg Ile Glu Asp Gly Phe Ser Leu Lys Glu Gln Leu Gln<br>325 330 335 | | 1008 |
| gac atg ggc ctt gtc gat ctg ttc agc cct gaa aag tcc aaa ctc cca<br>Asp Met Gly Leu Val Asp Leu Phe Ser Pro Glu Lys Ser Lys Leu Pro<br>340 345 350 | | 1056 |
| ggt att gtt gca gaa ggc cga gat gac ctc tat gtc tca gat gca ttc<br>Gly Ile Val Ala Glu Gly Arg Asp Asp Leu Tyr Val Ser Asp Ala Phe<br>355 360 365 | | 1104 |
| cat aag gca ttt ctt gag gta aat gaa gaa ggc agt gaa gca gct gca<br>His Lys Ala Phe Leu Glu Val Asn Glu Glu Gly Ser Glu Ala Ala Ala<br>370 375 380 | | 1152 |
| agt acc gct gtt gtg att gct ggc cgt tcg cta aac ccc aac agg gtg<br>Ser Thr Ala Val Val Ile Ala Gly Arg Ser Leu Asn Pro Asn Arg Val<br>385 390 395 400 | | 1200 |
| act ttc aag gcc aac agg cct ttc ctg gtt ttt ata aga gaa gtt cct<br>Thr Phe Lys Ala Asn Arg Pro Phe Leu Val Phe Ile Arg Glu Val Pro<br>405 410 415 | | 1248 |
| ctg aac act att atc ttc atg ggc aga gta gcc aac cct tgt gtt aag<br>Leu Asn Thr Ile Ile Phe Met Gly Arg Val Ala Asn Pro Cys Val Lys<br>420 425 430 | | 1296 |
| taaaatgttc ttattctttg cacctcttcc tattttggt ttgtgaacag aagtaaaaat | | 1356 |
| aaatacaaac tacttccatc tcacattaaa a | | 1387 |

```
<210> SEQ ID NO 12
<211> LENGTH: 432
<212> TYPE: PRT
<213> ORGANISM: Homo sapiens

<400> SEQUENCE: 12
```

```
His Gly Ser Pro Val Asp Ile Cys Thr Ala Lys Pro Arg Asp Ile Pro
1               5                   10                  15

Met Asn Pro Met Cys Ile Tyr Arg Ser Pro Glu Lys Lys Ala Thr Glu
                20                  25                  30

Asp Glu Gly Ser Glu Gln Lys Ile Pro Glu Ala Thr Asn Arg Arg Val
            35                  40                  45

Trp Glu Leu Ser Lys Ala Asn Ser Arg Phe Ala Thr Thr Phe Tyr Gln
    50                  55                  60

His Leu Ala Asp Ser Lys Asn Asp Asn Asp Asn Ile Phe Leu Ser Pro
65                  70                  75                  80

Leu Ser Ile Ser Thr Ala Phe Ala Met Thr Lys Leu Gly Ala Cys Asn
                85                  90                  95

Asp Thr Leu Gln Gln Leu Met Glu Val Phe Lys Phe Asp Thr Ile Ser
            100                 105                 110

Glu Lys Thr Ser Asp Gln Ile His Phe Phe Phe Ala Lys Leu Asn Cys
        115                 120                 125

Arg Leu Tyr Arg Lys Ala Gln Lys Ser Ser Lys Leu Val Ser Ala Asn
    130                 135                 140

Arg Leu Phe Gly Asp Lys Ser Leu Thr Phe Asn Glu Thr Tyr Gln Asp
145                 150                 155                 160

Ile Ser Glu Leu Val Tyr Gly Ala Lys Leu Gln Pro Leu Asp Phe Lys
                165                 170                 175

Glu Asn Ala Glu Gln Ser Arg Ala Ala Ile Asn Lys Trp Val Ser Asn
            180                 185                 190

Lys Thr Glu Gly Arg Ile Thr Asp Val Ile Pro Ser Glu Ala Ile Asn
        195                 200                 205

Glu Leu Thr Val Leu Val Leu Val Asn Thr Ile Tyr Phe Lys Gly Leu
    210                 215                 220

Trp Lys Ser Lys Phe Ser Pro Glu Asn Thr Arg Lys Glu Leu Phe Tyr
225                 230                 235                 240

Lys Ala Asp Gly Glu Ser Cys Ser Ala Ser Met Met Tyr Gln Glu Gly
                245                 250                 255

Lys Phe Arg Tyr Arg Arg Val Ala Glu Gly Thr Gln Val Leu Glu Leu
            260                 265                 270

Pro Phe Lys Gly Asp Asp Ile Thr Met Val Leu Ile Leu Pro Lys Pro
        275                 280                 285

Glu Lys Ser Leu Ala Lys Val Glu Lys Glu Leu Thr Pro Glu Val Leu
    290                 295                 300

Gln Glu Trp Leu Asp Glu Leu Glu Glu Met Met Leu Val Val His Met
305                 310                 315                 320

Pro Arg Phe Arg Ile Glu Asp Gly Phe Ser Leu Lys Glu Gln Leu Gln
                325                 330                 335

Asp Met Gly Leu Val Asp Leu Phe Ser Pro Glu Lys Ser Lys Leu Pro
            340                 345                 350

Gly Ile Val Ala Glu Gly Arg Asp Asp Leu Tyr Val Ser Asp Ala Phe
        355                 360                 365

His Lys Ala Phe Leu Glu Val Asn Glu Glu Gly Ser Glu Ala Ala Ala
    370                 375                 380

Ser Thr Ala Val Val Ile Ala Gly Arg Ser Leu Asn Pro Asn Arg Val
385                 390                 395                 400

Thr Phe Lys Ala Asn Arg Pro Phe Leu Val Phe Ile Arg Glu Val Pro
                405                 410                 415
```

```
                Leu Asn Thr Ile Ile Phe Met Gly Arg Val Ala Asn Pro Cys Val Lys
                                420                 425                 430

<210> SEQ ID NO 13
<211> LENGTH: 1387
<212> TYPE: DNA
<213> ORGANISM: Homo sapiens
<220> FEATURE:
<221> NAME/KEY: CDS
<222> LOCATION: (1)..(1296)

<400> SEQUENCE: 13 cac ggg agc cct gtg gac atc tgc aca gcc aag ccg cgg gac att ccc        48
His Gly Ser Pro Val Asp Ile Cys Thr Ala Lys Pro Arg Asp Ile Pro
1               5                   10                  15 atg aat ccc atg tgc att tac cgc tcc ccg gag aag aag gca act gag        96
Met Asn Pro Met Cys Ile Tyr Arg Ser Pro Glu Lys Lys Ala Thr Glu
            20                  25                  30 gat gag ggc tca gaa cag aag atc ccg gag gcc acc aac cgg cgt gtc       144
Asp Glu Gly Ser Glu Gln Lys Ile Pro Glu Ala Thr Asn Arg Arg Val
        35                  40                  45 tgg gaa ctg tcc aag gcc aat tcc cgc ttt gct acc act ttc tat cag       192
Trp Glu Leu Ser Lys Ala Asn Ser Arg Phe Ala Thr Thr Phe Tyr Gln
    50                  55                  60 cac ctg gca gat tcc aag aat gac aat gat aac att ttc ctg tca ccc       240
His Leu Ala Asp Ser Lys Asn Asp Asn Asp Asn Ile Phe Leu Ser Pro
65                  70                  75                  80 ctg agt atc tcc acg gct ttt gct atg acc aag ctg ggt gcc tgt aat       288
Leu Ser Ile Ser Thr Ala Phe Ala Met Thr Lys Leu Gly Ala Cys Asn
                85                  90                  95 gac acc ctc cag caa ctg atg gag gta ttt aag ttt gac acc ata tct       336
Asp Thr Leu Gln Gln Leu Met Glu Val Phe Lys Phe Asp Thr Ile Ser
            100                 105                 110 gag aaa aca tct gat cag atc cac ttc ttc ttt gcc aaa ctg aac tgc       384
Glu Lys Thr Ser Asp Gln Ile His Phe Phe Phe Ala Lys Leu Asn Cys
        115                 120                 125 cga ctc tat cga aaa gcc cag aaa tcc tcc aag tta gta tca gcc aat       432
Arg Leu Tyr Arg Lys Ala Gln Lys Ser Ser Lys Leu Val Ser Ala Asn
    130                 135                 140 cgc ctt ttt gga gac aaa tcc ctt acc ttc aat gag acc tac cag gac       480
Arg Leu Phe Gly Asp Lys Ser Leu Thr Phe Asn Glu Thr Tyr Gln Asp
145                 150                 155                 160 atc agt gag ttg gta tat gga gcc aag ctc cag ccc ctg gac ttc aag       528
Ile Ser Glu Leu Val Tyr Gly Ala Lys Leu Gln Pro Leu Asp Phe Lys
                165                 170                 175 gaa aat gca gag caa tcc aga gcg gcc atc aac aaa tgg gtg tcc aat       576
Glu Asn Ala Glu Gln Ser Arg Ala Ala Ile Asn Lys Trp Val Ser Asn
            180                 185                 190 aag acc gaa ggc cga atc acc gat gtc att ccc tcg gaa gcc atc aat       624
Lys Thr Glu Gly Arg Ile Thr Asp Val Ile Pro Ser Glu Ala Ile Asn
        195                 200                 205 gag ctc act gtt ctg gtg ctg gtt aac acc att tac ttc aag ggc ctg       672
Glu Leu Thr Val Leu Val Leu Val Asn Thr Ile Tyr Phe Lys Gly Leu
    210                 215                 220 tgg aag tca aag ttc agc cct gag aac aca agg aag gaa ctg ttc tac       720
Trp Lys Ser Lys Phe Ser Pro Glu Asn Thr Arg Lys Glu Leu Phe Tyr
225                 230                 235                 240 aag gct gat gga gag tcg tgt tca gca tct atg atg tac cag gaa ggc       768
Lys Ala Asp Gly Glu Ser Cys Ser Ala Ser Met Met Tyr Gln Glu Gly
                245                 250                 255 aag ttc cgt tat cgg cgc gtg gct gaa ggc acc cag gtg ctt gag ttg       816
Lys Phe Arg Tyr Arg Arg Val Ala Glu Gly Thr Gln Val Leu Glu Leu
```

```
                                                                        -continued Lys Phe Arg Tyr Arg Arg Val Ala Glu Gly Thr Gln Val Leu Glu Leu
            260                 265                 270 ccc ttc aaa ggt gat gac atc acc atg gtc ctc atc ttg ccc aag cct        864
Pro Phe Lys Gly Asp Asp Ile Thr Met Val Leu Ile Leu Pro Lys Pro
        275                 280                 285 gag aag agc ctg gcc aag gta gag aag gaa ctc acc cca gag gtg ctg        912
Glu Lys Ser Leu Ala Lys Val Glu Lys Glu Leu Thr Pro Glu Val Leu
290                 295                 300 caa gag tgg ctg gat gaa ttg gag gag atg atg ctg gtg gtc cac atg        960
Gln Glu Trp Leu Asp Glu Leu Glu Glu Met Met Leu Val Val His Met
305                 310                 315                 320 ccc cgc ttc cgc att gag gac ggc ttc agt ttg aag gag cag ctg caa       1008
Pro Arg Phe Arg Ile Glu Asp Gly Phe Ser Leu Lys Glu Gln Leu Gln
                325                 330                 335 gac atg ggc ctt gtc gat ctg ttc agc cct gaa aag tcc aaa ctc cca       1056
Asp Met Gly Leu Val Asp Leu Phe Ser Pro Glu Lys Ser Lys Leu Pro
            340                 345                 350 ggt att gtt gca gaa ggc cga gat gac ctc tat gtc tca gat gca ttc       1104
Gly Ile Val Ala Glu Gly Arg Asp Asp Leu Tyr Val Ser Asp Ala Phe
        355                 360                 365 cat aag gca ttt ctt gag gta aat gaa gaa ggc agt gaa gca gct gca       1152
His Lys Ala Phe Leu Glu Val Asn Glu Glu Gly Ser Glu Ala Ala Ala
    370                 375                 380 agt acc gct gtt gtg att gct ggc cat tcg cta aac ccc aac agg gtg       1200
Ser Thr Ala Val Val Ile Ala Gly His Ser Leu Asn Pro Asn Arg Val
385                 390                 395                 400 act ttc aag gcc aac agg cct ttc ctg gtt ttt ata aga gaa gtt cct       1248
Thr Phe Lys Ala Asn Arg Pro Phe Leu Val Phe Ile Arg Glu Val Pro
                405                 410                 415 ctg aac act att atc ttc atg ggc aga gta gcc aac cct tgt gtt aag       1296
Leu Asn Thr Ile Ile Phe Met Gly Arg Val Ala Asn Pro Cys Val Lys
            420                 425                 430 taaaatgttc ttattctttg cacctcttcc tattttggt ttgtgaacag aagtaaaaat       1356
aaatacaaac tacttccatc tcacattaaa a                                     1387

<210> SEQ ID NO 14
<211> LENGTH: 432
<212> TYPE: PRT
<213> ORGANISM: Homo sapiens

<400> SEQUENCE: 14

His Gly Ser Pro Val Asp Ile Cys Thr Ala Lys Pro Arg Asp Ile Pro
1               5                   10                  15

Met Asn Pro Met Cys Ile Tyr Arg Ser Pro Glu Lys Lys Ala Thr Glu
            20                  25                  30

Asp Glu Gly Ser Glu Gln Lys Ile Pro Glu Ala Thr Asn Arg Arg Val
        35                  40                  45

Trp Glu Leu Ser Lys Ala Asn Ser Arg Phe Ala Thr Thr Phe Tyr Gln
    50                  55                  60

His Leu Ala Asp Ser Lys Asn Asp Asn Asp Asn Ile Phe Leu Ser Pro
65                  70                  75                  80

Leu Ser Ile Ser Thr Ala Phe Ala Met Thr Lys Leu Gly Ala Cys Asn
                85                  90                  95

Asp Thr Leu Gln Gln Leu Met Glu Val Phe Lys Phe Asp Thr Ile Ser
            100                 105                 110

Glu Lys Thr Ser Asp Gln Ile His Phe Phe Phe Ala Lys Leu Asn Cys
        115                 120                 125
```

-continued

```
Arg Leu Tyr Arg Lys Ala Gln Lys Ser Ser Lys Leu Val Ser Ala Asn
130                 135                 140

Arg Leu Phe Gly Asp Lys Ser Leu Thr Phe Asn Glu Thr Tyr Gln Asp
145                 150                 155                 160

Ile Ser Glu Leu Val Tyr Gly Ala Lys Leu Gln Pro Leu Asp Phe Lys
            165                 170                 175

Glu Asn Ala Glu Gln Ser Arg Ala Ala Ile Asn Lys Trp Val Ser Asn
        180                 185                 190

Lys Thr Glu Gly Arg Ile Thr Asp Val Ile Pro Ser Glu Ala Ile Asn
    195                 200                 205

Glu Leu Thr Val Leu Val Leu Val Asn Thr Ile Tyr Phe Lys Gly Leu
210                 215                 220

Trp Lys Ser Lys Phe Ser Pro Glu Asn Thr Arg Lys Glu Leu Phe Tyr
225                 230                 235                 240

Lys Ala Asp Gly Glu Ser Cys Ser Ala Ser Met Met Tyr Gln Glu Gly
            245                 250                 255

Lys Phe Arg Tyr Arg Arg Val Ala Glu Gly Thr Gln Val Leu Glu Leu
        260                 265                 270

Pro Phe Lys Gly Asp Asp Ile Thr Met Val Leu Ile Leu Pro Lys Pro
    275                 280                 285

Glu Lys Ser Leu Ala Lys Val Glu Lys Glu Leu Thr Pro Glu Val Leu
290                 295                 300

Gln Glu Trp Leu Asp Glu Leu Glu Glu Met Met Leu Val Val His Met
305                 310                 315                 320

Pro Arg Phe Arg Ile Glu Asp Gly Phe Ser Leu Lys Glu Gln Leu Gln
            325                 330                 335

Asp Met Gly Leu Val Asp Leu Phe Ser Pro Glu Lys Ser Lys Leu Pro
        340                 345                 350

Gly Ile Val Ala Glu Gly Arg Asp Asp Leu Tyr Val Ser Asp Ala Phe
    355                 360                 365

His Lys Ala Phe Leu Glu Val Asn Glu Glu Gly Ser Glu Ala Ala Ala
370                 375                 380

Ser Thr Ala Val Val Ile Ala Gly His Ser Leu Asn Pro Asn Arg Val
385                 390                 395                 400

Thr Phe Lys Ala Asn Arg Pro Phe Leu Val Phe Ile Arg Glu Val Pro
            405                 410                 415

Leu Asn Thr Ile Ile Phe Met Gly Arg Val Ala Asn Pro Cys Val Lys
        420                 425                 430

<210> SEQ ID NO 15
<211> LENGTH: 1390
<212> TYPE: DNA
<213> ORGANISM: Homo sapiens
<220> FEATURE:
<221> NAME/KEY: CDS
<222> LOCATION: (1)..(1299)

<400> SEQUENCE: 15 cac ggg agc cct gtg gac atc tgc aca gcc aag ccg cgg gac att ccc      48
His Gly Ser Pro Val Asp Ile Cys Thr Ala Lys Pro Arg Asp Ile Pro
1               5                   10                  15 atg aat ccc atg tgc att tac cgc tcc ccg gag aag aag gca act gag      96
Met Asn Pro Met Cys Ile Tyr Arg Ser Pro Glu Lys Lys Ala Thr Glu
            20                  25                  30 gat gag ggc tca gaa cag aag atc ccg gag gcc acc aac cgg cgt gtc     144
Asp Glu Gly Ser Glu Gln Lys Ile Pro Glu Ala Thr Asn Arg Arg Val
        35                  40                  45
```

```
tgg gaa ctg tcc aag gcc aat tcc cgc ttt gct acc act ttc tat cag        192
Trp Glu Leu Ser Lys Ala Asn Ser Arg Phe Ala Thr Thr Phe Tyr Gln
     50              55                  60 cac ctg gca gat tcc aag aat gac aat gat aac att ttc ctg tca ccc        240
His Leu Ala Asp Ser Lys Asn Asp Asn Asp Asn Ile Phe Leu Ser Pro
 65              70                  75                  80 ctg agt atc tcc acg gct ttt gct atg acc aag ctg ggt gcc tgt aat        288
Leu Ser Ile Ser Thr Ala Phe Ala Met Thr Lys Leu Gly Ala Cys Asn
                 85                  90                  95 gac acc ctc cag caa ctg atg gag gta ttt aag ttt gac acc ata tct        336
Asp Thr Leu Gln Gln Leu Met Glu Val Phe Lys Phe Asp Thr Ile Ser
                100                 105                 110 gag aaa aca tct gat cag atc cac ttc ttc ttt gcc aaa ctg aac tgc        384
Glu Lys Thr Ser Asp Gln Ile His Phe Phe Phe Ala Lys Leu Asn Cys
            115                 120                 125 cga ctc tat cga aaa gcc cag aaa tcc tcc aag tta gta tca gcc aat        432
Arg Leu Tyr Arg Lys Ala Gln Lys Ser Ser Lys Leu Val Ser Ala Asn
        130                 135                 140 cgc ctt ttt gga gac aaa tcc ctt acc ttc aat gag acc tac cag gac        480
Arg Leu Phe Gly Asp Lys Ser Leu Thr Phe Asn Glu Thr Tyr Gln Asp
145                 150                 155                 160 atc agt gag ttg gta tat gga gcc aag ctc cag ccc ctg gac ttc aag        528
Ile Ser Glu Leu Val Tyr Gly Ala Lys Leu Gln Pro Leu Asp Phe Lys
                165                 170                 175 gaa aat gca gag caa tcc aga gcg gcc atc aac aaa tgg gtg tcc aat        576
Glu Asn Ala Glu Gln Ser Arg Ala Ala Ile Asn Lys Trp Val Ser Asn
            180                 185                 190 aag acc gaa ggc cga atc acc gat gtc att ccc tcg gaa gcc atc aat        624
Lys Thr Glu Gly Arg Ile Thr Asp Val Ile Pro Ser Glu Ala Ile Asn
        195                 200                 205 gag ctc act gtt ctg gtg ctg gtt aac acc att tac ttc aag ggc ctg        672
Glu Leu Thr Val Leu Val Leu Val Asn Thr Ile Tyr Phe Lys Gly Leu
    210                 215                 220 tgg aag tca aag ttc agc cct gag aac aca agg aag gaa ctg ttc tac        720
Trp Lys Ser Lys Phe Ser Pro Glu Asn Thr Arg Lys Glu Leu Phe Tyr
225                 230                 235                 240 aag gct gat gga gag tcg tgt tca gca tct atg atg tac cag gaa ggc        768
Lys Ala Asp Gly Glu Ser Cys Ser Ala Ser Met Met Tyr Gln Glu Gly
                245                 250                 255 aag ttc cgt tat cgg cgc gtg gct gaa ggc acc cag gtg ctt gag ttg        816
Lys Phe Arg Tyr Arg Arg Val Ala Glu Gly Thr Gln Val Leu Glu Leu
            260                 265                 270 ccc ttc aaa ggt gat gac atc acc atg gtc ctc atc ttg ccc aag cct        864
Pro Phe Lys Gly Asp Asp Ile Thr Met Val Leu Ile Leu Pro Lys Pro
        275                 280                 285 gag aag agc ctg gcc aag gta gag aag gaa ctc acc cca gag gtg ctg        912
Glu Lys Ser Leu Ala Lys Val Glu Lys Glu Leu Thr Pro Glu Val Leu
    290                 295                 300 caa gag tgg ctg gat gaa ttg gag gag atg atg ctg gtg gtc cac atg        960
Gln Glu Trp Leu Asp Glu Leu Glu Glu Met Met Leu Val Val His Met
305                 310                 315                 320 ccc cgc ttc cgc att gag gac ggc ttc agt ttg aag gag cag ctg caa       1008
Pro Arg Phe Arg Ile Glu Asp Gly Phe Ser Leu Lys Glu Gln Leu Gln
                325                 330                 335 gac atg ggc ctt gtc gat ctg ttc agc cct gaa aag tcc aaa ctc cca       1056
Asp Met Gly Leu Val Asp Leu Phe Ser Pro Glu Lys Ser Lys Leu Pro
            340                 345                 350 ggt att gtt gca gaa ggc cga gat gac ctc tat gtc tca gat gca ttc       1104
Gly Ile Val Ala Glu Gly Arg Asp Asp Leu Tyr Val Ser Asp Ala Phe
```

```
                     355                 360                 365
cat aag gca ttt ctt gag gta aat gaa gaa ggc agt gaa gca gct gca     1152
His Lys Ala Phe Leu Glu Val Asn Glu Glu Gly Ser Glu Ala Ala Ala
    370                 375                 380 agt acc gct gtt gtg att gct ggc cgt cca tcg cta aac ccc aac agg     1200
Ser Thr Ala Val Val Ile Ala Gly Arg Pro Ser Leu Asn Pro Asn Arg
385                 390                 395                 400 gtg act ttc aag gcc aac agg cct ttc ctg gtt ttt ata aga gaa gtt     1248
Val Thr Phe Lys Ala Asn Arg Pro Phe Leu Val Phe Ile Arg Glu Val
                405                 410                 415 cct ctg aac act att atc ttc atg ggc aga gta gcc aac cct tgt gtt     1296
Pro Leu Asn Thr Ile Ile Phe Met Gly Arg Val Ala Asn Pro Cys Val
            420                 425                 430 aag taaaatgttc ttattctttg cacctcttcc tattttggt ttgtgaacag           1349
Lys aagtaaaaat aaatacaaac tacttccatc tcacattaaa a                       1390

<210> SEQ ID NO 16
<211> LENGTH: 433
<212> TYPE: PRT
<213> ORGANISM: Homo sapiens

<400> SEQUENCE: 16

His Gly Ser Pro Val Asp Ile Cys Thr Ala Lys Pro Arg Asp Ile Pro
1               5                   10                  15

Met Asn Pro Met Cys Ile Tyr Arg Ser Pro Glu Lys Lys Ala Thr Glu
            20                  25                  30

Asp Glu Gly Ser Glu Gln Lys Ile Pro Glu Ala Thr Asn Arg Arg Val
        35                  40                  45

Trp Glu Leu Ser Lys Ala Asn Ser Arg Phe Ala Thr Thr Phe Tyr Gln
    50                  55                  60

His Leu Ala Asp Ser Lys Asn Asp Asn Asp Asn Ile Phe Leu Ser Pro
65                  70                  75                  80

Leu Ser Ile Ser Thr Ala Phe Ala Met Thr Lys Leu Gly Ala Cys Asn
                85                  90                  95

Asp Thr Leu Gln Gln Leu Met Glu Val Phe Lys Phe Asp Thr Ile Ser
            100                 105                 110

Glu Lys Thr Ser Asp Gln Ile His Phe Phe Phe Ala Lys Leu Asn Cys
        115                 120                 125

Arg Leu Tyr Arg Lys Ala Gln Lys Ser Ser Lys Leu Val Ser Ala Asn
130                 135                 140

Arg Leu Phe Gly Asp Lys Ser Leu Thr Phe Asn Glu Thr Tyr Gln Asp
145                 150                 155                 160

Ile Ser Glu Leu Val Tyr Gly Ala Lys Leu Gln Pro Leu Asp Phe Lys
                165                 170                 175

Glu Asn Ala Glu Gln Ser Arg Ala Ala Ile Asn Lys Trp Val Ser Asn
            180                 185                 190

Lys Thr Glu Gly Arg Ile Thr Asp Val Ile Pro Ser Glu Ala Ile Asn
        195                 200                 205

Glu Leu Thr Val Leu Val Leu Val Asn Thr Ile Tyr Phe Lys Gly Leu
    210                 215                 220

Trp Lys Ser Lys Phe Ser Pro Glu Asn Thr Arg Lys Glu Leu Phe Tyr
225                 230                 235                 240

Lys Ala Asp Gly Glu Ser Cys Ser Ala Ser Met Met Tyr Gln Glu Gly
                245                 250                 255
```

```
Lys Phe Arg Tyr Arg Arg Val Ala Glu Gly Thr Gln Val Leu Glu Leu
            260                 265                 270

Pro Phe Lys Gly Asp Asp Ile Thr Met Val Leu Ile Leu Pro Lys Pro
        275                 280                 285

Glu Lys Ser Leu Ala Lys Val Glu Lys Glu Leu Thr Pro Glu Val Leu
    290                 295                 300

Gln Glu Trp Leu Asp Glu Leu Glu Glu Met Met Leu Val Val His Met
305                 310                 315                 320

Pro Arg Phe Arg Ile Glu Asp Gly Phe Ser Leu Lys Glu Gln Leu Gln
                325                 330                 335

Asp Met Gly Leu Val Asp Leu Phe Ser Pro Glu Lys Ser Lys Leu Pro
            340                 345                 350

Gly Ile Val Ala Glu Gly Arg Asp Asp Leu Tyr Val Ser Asp Ala Phe
        355                 360                 365

His Lys Ala Phe Leu Glu Val Asn Glu Glu Gly Ser Glu Ala Ala Ala
    370                 375                 380

Ser Thr Ala Val Val Ile Ala Gly Arg Pro Ser Leu Asn Pro Asn Arg
385                 390                 395                 400

Val Thr Phe Lys Ala Asn Arg Pro Phe Leu Val Phe Ile Arg Glu Val
                405                 410                 415

Pro Leu Asn Thr Ile Ile Phe Met Gly Arg Val Ala Asn Pro Cys Val
            420                 425                 430

Lys

<210> SEQ ID NO 17
<211> LENGTH: 1381
<212> TYPE: DNA
<213> ORGANISM: Homo sapiens
<220> FEATURE:
<221> NAME/KEY: CDS
<222> LOCATION: (1)..(1290)

<400> SEQUENCE: 17 cac ggg agc cct gtg gac atc tgc aca gcc aag ccg cgg gac att ccc     48
His Gly Ser Pro Val Asp Ile Cys Thr Ala Lys Pro Arg Asp Ile Pro
1               5                   10                  15 atg aat ccc atg tgc att tac cgc tcc ccg gag aag aag gca act gag     96
Met Asn Pro Met Cys Ile Tyr Arg Ser Pro Glu Lys Lys Ala Thr Glu
            20                  25                  30 gat gag ggc tca gaa cag aag atc ccg gag gcc acc aac cgg cgt gtc    144
Asp Glu Gly Ser Glu Gln Lys Ile Pro Glu Ala Thr Asn Arg Arg Val
        35                  40                  45 tgg gaa ctg tcc aag gcc aat tcc cgc ttt gct acc act ttc tat cag    192
Trp Glu Leu Ser Lys Ala Asn Ser Arg Phe Ala Thr Thr Phe Tyr Gln
    50                  55                  60 cac ctg gca gat tcc aag aat gac aat gat aac att ttc ctg tca ccc    240
His Leu Ala Asp Ser Lys Asn Asp Asn Asp Asn Ile Phe Leu Ser Pro
65                  70                  75                  80 ctg agt atc tcc acg gct ttt gct atg acc aag ctg ggt gcc tgt aat    288
Leu Ser Ile Ser Thr Ala Phe Ala Met Thr Lys Leu Gly Ala Cys Asn
                85                  90                  95 gac acc ctc cag caa ctg atg gag gta ttt aag ttt gac acc ata tct    336
Asp Thr Leu Gln Gln Leu Met Glu Val Phe Lys Phe Asp Thr Ile Ser
            100                 105                 110 gag aaa aca tct gat cag atc cac ttc ttc ttt gcc aaa ctg aac tgc    384
Glu Lys Thr Ser Asp Gln Ile His Phe Phe Phe Ala Lys Leu Asn Cys
        115                 120                 125 cga ctc tat cga aaa gcc aac aaa tcc tcc aag tta gta tca gcc aat    432
```

```
           Arg Leu Tyr Arg Lys Ala Asn Lys Ser Ser Lys Leu Val Ser Ala Asn
           130                 135                 140 cgc ctt ttt gga gac aaa tcc ctt acc ttc aat gag acc tac cag gac        480
Arg Leu Phe Gly Asp Lys Ser Leu Thr Phe Asn Glu Thr Tyr Gln Asp
145                 150                 155                 160 atc agt gag ttg gta tat gga gcc aag ctc cag ccc ctg gac ttc aag        528
Ile Ser Glu Leu Val Tyr Gly Ala Lys Leu Gln Pro Leu Asp Phe Lys
                165                 170                 175 gaa aat gca gag caa tcc aga gcg gcc atc aac aaa tgg gtg tcc aat        576
Glu Asn Ala Glu Gln Ser Arg Ala Ala Ile Asn Lys Trp Val Ser Asn
            180                 185                 190 aag acc gaa ggc cga atc acc gat gtc att ccc tcg gaa gcc atc aat        624
Lys Thr Glu Gly Arg Ile Thr Asp Val Ile Pro Ser Glu Ala Ile Asn
        195                 200                 205 gag ctc act gtt ctg gtg ctg gtt aac acc att tac ttc aag ggc ctg        672
Glu Leu Thr Val Leu Val Leu Val Asn Thr Ile Tyr Phe Lys Gly Leu
    210                 215                 220 tgg aag tca aag ttc agc cct gag aac aca agg aag gaa ctg ttc tac        720
Trp Lys Ser Lys Phe Ser Pro Glu Asn Thr Arg Lys Glu Leu Phe Tyr
225                 230                 235                 240 aag gct gat gga gag tcg tgt tca gca tct atg atg tac cag gaa ggc        768
Lys Ala Asp Gly Glu Ser Cys Ser Ala Ser Met Met Tyr Gln Glu Gly
                245                 250                 255 aag ttc cgt tat cgg cgc gtg gct gaa ggc acc cag gtg ctt gag ttg        816
Lys Phe Arg Tyr Arg Arg Val Ala Glu Gly Thr Gln Val Leu Glu Leu
            260                 265                 270 ccc ttc aaa ggt gat gac atc acc atg gtc ctc atc ttg ccc aag cct        864
Pro Phe Lys Gly Asp Asp Ile Thr Met Val Leu Ile Leu Pro Lys Pro
        275                 280                 285 gag aag agc ctg gcc aag gta gag aag gaa ctc acc cca gag gtg ctg        912
Glu Lys Ser Leu Ala Lys Val Glu Lys Glu Leu Thr Pro Glu Val Leu
    290                 295                 300 caa gag tgg ctg gat gaa ttg gag gag atg atg ctg gtg gtc cac atg        960
Gln Glu Trp Leu Asp Glu Leu Glu Glu Met Met Leu Val Val His Met
305                 310                 315                 320 ccc cgc ttc cgc att gag gac ggc ttc agt ttg aag gag cag ctg caa       1008
Pro Arg Phe Arg Ile Glu Asp Gly Phe Ser Leu Lys Glu Gln Leu Gln
                325                 330                 335 gac atg ggc ctt gtc gat ctg ttc agc cct gaa aag tcc aaa ctc cca       1056
Asp Met Gly Leu Val Asp Leu Phe Ser Pro Glu Lys Ser Lys Leu Pro
            340                 345                 350 ggt att gtt gca gaa ggc cga gat gac ctc tat gtc tca gat gca ttc       1104
Gly Ile Val Ala Glu Gly Arg Asp Asp Leu Tyr Val Ser Asp Ala Phe
        355                 360                 365 cat aag gca ttt ctt gag gta aat gaa gaa ggc agt gaa gca gct gca       1152
His Lys Ala Phe Leu Glu Val Asn Glu Glu Gly Ser Glu Ala Ala Ala
    370                 375                 380 agt acc gct gtt gtg att gct ggc cta aac ccc aac agg gtg act ttc       1200
Ser Thr Ala Val Val Ile Ala Gly Leu Asn Pro Asn Arg Val Thr Phe
385                 390                 395                 400 aag gcc aac agg cct ttc ctg gtt ttt ata aga gaa gtt cct ctg aac       1248
Lys Ala Asn Arg Pro Phe Leu Val Phe Ile Arg Glu Val Pro Leu Asn
                405                 410                 415 act att atc ttc atg ggc aga gta gcc aac cct tgt gtt aag                1290
Thr Ile Ile Phe Met Gly Arg Val Ala Asn Pro Cys Val Lys
            420                 425                 430 taaaatgttc ttattctttg cacctcttcc tattttggt tgtgaacag aagtaaaaat       1350 aaatacaaac tacttccatc tcacattaaa a                                    1381
```

<210> SEQ ID NO 18
<211> LENGTH: 430
<212> TYPE: PRT
<213> ORGANISM: Homo sapiens

<400> SEQUENCE: 18

```
His Gly Ser Pro Val Asp Ile Cys Thr Ala Lys Pro Arg Asp Ile Pro
  1               5                  10                  15

Met Asn Pro Met Cys Ile Tyr Arg Ser Pro Glu Lys Lys Ala Thr Glu
             20                  25                  30

Asp Glu Gly Ser Glu Gln Lys Ile Pro Glu Ala Thr Asn Arg Arg Val
         35                  40                  45

Trp Glu Leu Ser Lys Ala Asn Ser Arg Phe Ala Thr Thr Phe Tyr Gln
 50                  55                  60

His Leu Ala Asp Ser Lys Asn Asp Asn Asp Asn Ile Phe Leu Ser Pro
 65                  70                  75                  80

Leu Ser Ile Ser Thr Ala Phe Ala Met Thr Lys Leu Gly Ala Cys Asn
             85                  90                  95

Asp Thr Leu Gln Gln Leu Met Glu Val Phe Lys Phe Asp Thr Ile Ser
            100                 105                 110

Glu Lys Thr Ser Asp Gln Ile His Phe Phe Phe Ala Lys Leu Asn Cys
        115                 120                 125

Arg Leu Tyr Arg Lys Ala Asn Lys Ser Ser Lys Leu Val Ser Ala Asn
130                 135                 140

Arg Leu Phe Gly Asp Lys Ser Leu Thr Phe Asn Glu Thr Tyr Gln Asp
145                 150                 155                 160

Ile Ser Glu Leu Val Tyr Gly Ala Lys Leu Gln Pro Leu Asp Phe Lys
                165                 170                 175

Glu Asn Ala Glu Gln Ser Arg Ala Ala Ile Asn Lys Trp Val Ser Asn
            180                 185                 190

Lys Thr Glu Gly Arg Ile Thr Asp Val Ile Pro Ser Glu Ala Ile Asn
        195                 200                 205

Glu Leu Thr Val Leu Val Leu Val Asn Thr Ile Tyr Phe Lys Gly Leu
    210                 215                 220

Trp Lys Ser Lys Phe Ser Pro Glu Asn Thr Arg Lys Glu Leu Phe Tyr
225                 230                 235                 240

Lys Ala Asp Gly Glu Ser Cys Ser Ala Ser Met Met Tyr Gln Glu Gly
                245                 250                 255

Lys Phe Arg Tyr Arg Arg Val Ala Glu Gly Thr Gln Val Leu Glu Leu
            260                 265                 270

Pro Phe Lys Gly Asp Asp Ile Thr Met Val Leu Ile Leu Pro Lys Pro
        275                 280                 285

Glu Lys Ser Leu Ala Lys Val Glu Lys Glu Leu Thr Pro Glu Val Leu
    290                 295                 300

Gln Glu Trp Leu Asp Glu Leu Glu Glu Met Met Leu Val Val His Met
305                 310                 315                 320

Pro Arg Phe Arg Ile Glu Asp Gly Phe Ser Leu Lys Glu Gln Leu Gln
                325                 330                 335

Asp Met Gly Leu Val Asp Leu Phe Ser Pro Lys Ser Lys Leu Pro
            340                 345                 350

Gly Ile Val Ala Glu Gly Arg Asp Asp Leu Tyr Val Ser Asp Ala Phe
        355                 360                 365

His Lys Ala Phe Leu Glu Val Asn Glu Glu Gly Ser Glu Ala Ala Ala
    370                 375                 380
```

```
Ser Thr Ala Val Val Ile Ala Gly Leu Asn Pro Asn Arg Val Thr Phe
385                 390                 395                 400

Lys Ala Asn Arg Pro Phe Leu Val Phe Ile Arg Glu Val Pro Leu Asn
                405                 410                 415

Thr Ile Ile Phe Met Gly Arg Val Ala Asn Pro Cys Val Lys
            420                 425                 430

<210> SEQ ID NO 19
<211> LENGTH: 1384
<212> TYPE: DNA
<213> ORGANISM: Homo sapiens
<220> FEATURE:
<221> NAME/KEY: CDS
<222> LOCATION: (1)..(1293)

<400> SEQUENCE: 19 cac ggg agc cct gtg gac atc tgc aca gcc aag ccg cgg gac att ccc    48
His Gly Ser Pro Val Asp Ile Cys Thr Ala Lys Pro Arg Asp Ile Pro
1               5                   10                  15 atg aat ccc atg tgc att tac cgc tcc ccg gag aag aag gca act gag    96
Met Asn Pro Met Cys Ile Tyr Arg Ser Pro Glu Lys Lys Ala Thr Glu
            20                  25                  30 gat gag ggc tca gaa cag aag atc ccg gag gcc acc aac cgg cgt gtc   144
Asp Glu Gly Ser Glu Gln Lys Ile Pro Glu Ala Thr Asn Arg Arg Val
        35                  40                  45 tgg gaa ctg tcc aag gcc aat tcc cgc ttt gct acc act ttc tat cag   192
Trp Glu Leu Ser Lys Ala Asn Ser Arg Phe Ala Thr Thr Phe Tyr Gln
50                  55                  60 cac ctg gca gat tcc aag aat gac aat gat aac att ttc ctg tca ccc   240
His Leu Ala Asp Ser Lys Asn Asp Asn Asp Asn Ile Phe Leu Ser Pro
65                  70                  75                  80 ctg agt atc tcc acg gct ttt gct atg acc aag ctg ggt gcc tgt aat   288
Leu Ser Ile Ser Thr Ala Phe Ala Met Thr Lys Leu Gly Ala Cys Asn
                85                  90                  95 gac acc ctc cag caa ctg atg gag gta ttt aag ttt gac acc ata tct   336
Asp Thr Leu Gln Gln Leu Met Glu Val Phe Lys Phe Asp Thr Ile Ser
            100                 105                 110 gag aaa aca tct gat cag atc cac ttc ttc ttt gcc aaa ctg aac tgc   384
Glu Lys Thr Ser Asp Gln Ile His Phe Phe Phe Ala Lys Leu Asn Cys
        115                 120                 125 cga ctc tat cga aaa gcc cag aaa tcc tcc aag tta gta tca gcc aat   432
Arg Leu Tyr Arg Lys Ala Gln Lys Ser Ser Lys Leu Val Ser Ala Asn
130                 135                 140 cgc ctt ttt gga gac aaa tcc ctt acc ttc aat gag acc tac cag gac   480
Arg Leu Phe Gly Asp Lys Ser Leu Thr Phe Asn Glu Thr Tyr Gln Asp
145                 150                 155                 160 atc agt gag ttg gta tat gga gcc aag ctc cag ccc ctg gac ttc aag   528
Ile Ser Glu Leu Val Tyr Gly Ala Lys Leu Gln Pro Leu Asp Phe Lys
                165                 170                 175 gaa aat gca gag caa tcc aga gcg gcc atc aac aaa tgg gtg tcc aat   576
Glu Asn Ala Glu Gln Ser Arg Ala Ala Ile Asn Lys Trp Val Ser Asn
            180                 185                 190 aag acc gaa ggc cga atc acc gat gtc att ccc tcg gaa gcc atc aat   624
Lys Thr Glu Gly Arg Ile Thr Asp Val Ile Pro Ser Glu Ala Ile Asn
        195                 200                 205 gag ctc act gtt ctg gtg ctg gtt aac acc att tac ttc aag ggc ctg   672
Glu Leu Thr Val Leu Val Leu Val Asn Thr Ile Tyr Phe Lys Gly Leu
    210                 215                 220 tgg aag tca aag ttc agc cct gag aac aca agg aag gaa ctg ttc tac   720
Trp Lys Ser Lys Phe Ser Pro Glu Asn Thr Arg Lys Glu Leu Phe Tyr
```

```
aag gct gat gga gag tcg tgt tca gca tct atg atg tac cag gaa ggc    768
Lys Ala Asp Gly Glu Ser Cys Ser Ala Ser Met Met Tyr Gln Glu Gly
                245                 250                 255 aag ttc cgt tat cgg cgc gtg gct gaa ggc acc cag gtg ctt gag ttg    816
Lys Phe Arg Tyr Arg Arg Val Ala Glu Gly Thr Gln Val Leu Glu Leu
            260                 265                 270 ccc ttc aaa ggt gat gac atc acc atg gtc ctc atc ttg ccc aag cct    864
Pro Phe Lys Gly Asp Asp Ile Thr Met Val Leu Ile Leu Pro Lys Pro
        275                 280                 285 gag aag agc ctg gcc aag gta gag aag gaa ctc acc cca gag gtg ctg    912
Glu Lys Ser Leu Ala Lys Val Glu Lys Glu Leu Thr Pro Glu Val Leu
    290                 295                 300 caa gag tgg ctg gat gaa ttg gag gag atg atg ctg gtg gtc cac atg    960
Gln Glu Trp Leu Asp Glu Leu Glu Glu Met Met Leu Val Val His Met
305                 310                 315                 320 ccc cgc ttc cgc att gag gac ggc ttc agt ttg aag gag cag ctg caa   1008
Pro Arg Phe Arg Ile Glu Asp Gly Phe Ser Leu Lys Glu Gln Leu Gln
                325                 330                 335 gac atg ggc ctt gtc gat ctg ttc agc cct gaa aag tcc aaa ctc cca   1056
Asp Met Gly Leu Val Asp Leu Phe Ser Pro Glu Lys Ser Lys Leu Pro
            340                 345                 350 ggt att gtt gca gaa ggc cga gat gac ctc tat gtc tca gat gca ttc   1104
Gly Ile Val Ala Glu Gly Arg Asp Asp Leu Tyr Val Ser Asp Ala Phe
        355                 360                 365 cat aag gca ttt ctt gag gta aat gaa gaa ggc agt gaa gca gct gca   1152
His Lys Ala Phe Leu Glu Val Asn Glu Glu Gly Ser Glu Ala Ala Ala
    370                 375                 380 agt acc gct gtt gtg att gct ggc tcg cta aac ccc aac agg gtg act   1200
Ser Thr Ala Val Val Ile Ala Gly Ser Leu Asn Pro Asn Arg Val Thr
385                 390                 395                 400 ttc aag gcc aac agg cct ttc ctg gtt ttt ata aga gaa gtt cct ctg   1248
Phe Lys Ala Asn Arg Pro Phe Leu Val Phe Ile Arg Glu Val Pro Leu
                405                 410                 415 aac act att atc ttc atg ggc aga gta gcc aac cct tgt gtt aag       1293
Asn Thr Ile Ile Phe Met Gly Arg Val Ala Asn Pro Cys Val Lys
                420                 425                 430 taaaatgttc ttattctttg cacctcttcc tattttggt ttgtgaacag aagtaaaaat   1353
aaatacaaac tacttccatc tcacattaaa a                                 1384

<210> SEQ ID NO 20
<211> LENGTH: 431
<212> TYPE: PRT
<213> ORGANISM: Homo sapiens

<400> SEQUENCE: 20

His Gly Ser Pro Val Asp Ile Cys Thr Ala Lys Pro Arg Asp Ile Pro
1               5                   10                  15

Met Asn Pro Met Cys Ile Tyr Arg Ser Pro Glu Lys Lys Ala Thr Glu
            20                  25                  30

Asp Glu Gly Ser Glu Gln Lys Ile Pro Glu Ala Thr Asn Arg Arg Val
        35                  40                  45

Trp Glu Leu Ser Lys Ala Asn Ser Arg Phe Ala Thr Thr Phe Tyr Gln
    50                  55                  60

His Leu Ala Asp Ser Lys Asn Asp Asn Asp Asn Ile Phe Leu Ser Pro
65                  70                  75                  80

Leu Ser Ile Ser Thr Ala Phe Ala Met Thr Lys Leu Gly Ala Cys Asn
                85                  90                  95
```

```
Asp Thr Leu Gln Gln Leu Met Glu Val Phe Lys Phe Asp Thr Ile Ser
                100                 105                 110

Glu Lys Thr Ser Asp Gln Ile His Phe Phe Ala Lys Leu Asn Cys
            115                 120                 125

Arg Leu Tyr Arg Lys Ala Gln Lys Ser Ser Lys Leu Val Ser Ala Asn
130                 135                 140

Arg Leu Phe Gly Asp Lys Ser Leu Thr Phe Asn Glu Thr Tyr Gln Asp
145                 150                 155                 160

Ile Ser Glu Leu Val Tyr Gly Ala Lys Leu Gln Pro Leu Asp Phe Lys
                165                 170                 175

Glu Asn Ala Glu Gln Ser Arg Ala Ala Ile Asn Lys Trp Val Ser Asn
            180                 185                 190

Lys Thr Glu Gly Arg Ile Thr Asp Val Ile Pro Ser Glu Ala Ile Asn
        195                 200                 205

Glu Leu Thr Val Leu Val Leu Val Asn Thr Ile Tyr Phe Lys Gly Leu
    210                 215                 220

Trp Lys Ser Lys Phe Ser Pro Glu Asn Thr Arg Lys Glu Leu Phe Tyr
225                 230                 235                 240

Lys Ala Asp Gly Glu Ser Cys Ser Ala Ser Met Met Tyr Gln Glu Gly
                245                 250                 255

Lys Phe Arg Tyr Arg Arg Val Ala Glu Gly Thr Gln Val Leu Glu Leu
            260                 265                 270

Pro Phe Lys Gly Asp Asp Ile Thr Met Val Leu Ile Leu Pro Lys Pro
        275                 280                 285

Glu Lys Ser Leu Ala Lys Val Glu Lys Glu Leu Thr Pro Glu Val Leu
    290                 295                 300

Gln Glu Trp Leu Asp Glu Leu Glu Glu Met Met Leu Val Val His Met
305                 310                 315                 320

Pro Arg Phe Arg Ile Glu Asp Gly Phe Ser Leu Lys Glu Gln Leu Gln
                325                 330                 335

Asp Met Gly Leu Val Asp Leu Phe Ser Pro Glu Lys Ser Lys Leu Pro
            340                 345                 350

Gly Ile Val Ala Glu Gly Arg Asp Asp Leu Tyr Val Ser Asp Ala Phe
        355                 360                 365

His Lys Ala Phe Leu Glu Val Asn Glu Glu Gly Ser Glu Ala Ala Ala
    370                 375                 380

Ser Thr Ala Val Val Ile Ala Gly Ser Leu Asn Pro Asn Arg Val Thr
385                 390                 395                 400

Phe Lys Ala Asn Arg Pro Phe Leu Val Phe Ile Arg Glu Val Pro Leu
                405                 410                 415

Asn Thr Ile Ile Phe Met Gly Arg Val Ala Asn Pro Cys Val Lys
            420                 425                 430

<210> SEQ ID NO 21
<211> LENGTH: 1384
<212> TYPE: DNA
<213> ORGANISM: Homo sapiens
<220> FEATURE:
<221> NAME/KEY: CDS
<222> LOCATION: (1)..(1293)

<400> SEQUENCE: 21 cac ggg agc cct gtg gac atc tgc aca gcc aag ccg cgg gac att ccc      48
His Gly Ser Pro Val Asp Ile Cys Thr Ala Lys Pro Arg Asp Ile Pro
1               5                   10                  15
```

| | | |
|---|---|---|
| atg aat ccc atg tgc att tac cgc tcc ccg gag aag aag gca act gag<br>Met Asn Pro Met Cys Ile Tyr Arg Ser Pro Glu Lys Lys Ala Thr Glu<br>20 25 30 | | 96 |
| gat gag ggc tca gaa cag aag atc ccg gag gcc acc aac cgg cgt gtc<br>Asp Glu Gly Ser Glu Gln Lys Ile Pro Glu Ala Thr Asn Arg Arg Val<br>35 40 45 | | 144 |
| tgg gaa ctg tcc aag gcc aat tcc cgc ttt gct acc act ttc tat cag<br>Trp Glu Leu Ser Lys Ala Asn Ser Arg Phe Ala Thr Thr Phe Tyr Gln<br>50 55 60 | | 192 |
| cac ctg gca gat tcc aag aat gac aat gat aac att ttc ctg tca ccc<br>His Leu Ala Asp Ser Lys Asn Asp Asn Asp Asn Ile Phe Leu Ser Pro<br>65 70 75 80 | | 240 |
| ctg agt atc tcc acg gct ttt gct atg acc aag ctg ggt gcc tgt aat<br>Leu Ser Ile Ser Thr Ala Phe Ala Met Thr Lys Leu Gly Ala Cys Asn<br>85 90 95 | | 288 |
| gac acc ctc cag caa ctg atg gag gta ttt aag ttt gac acc ata tct<br>Asp Thr Leu Gln Gln Leu Met Glu Val Phe Lys Phe Asp Thr Ile Ser<br>100 105 110 | | 336 |
| gag aaa aca tct gat cag atc cac ttc ttc ttt gcc aaa ctg aac tgc<br>Glu Lys Thr Ser Asp Gln Ile His Phe Phe Phe Ala Lys Leu Asn Cys<br>115 120 125 | | 384 |
| cga ctc tat cga aaa gcc cag aaa tcc tcc aag tta gta tca gcc aat<br>Arg Leu Tyr Arg Lys Ala Gln Lys Ser Ser Lys Leu Val Ser Ala Asn<br>130 135 140 | | 432 |
| cgc ctt ttt gga gac aaa tcc ctt acc ttc aat gag acc tac cag gac<br>Arg Leu Phe Gly Asp Lys Ser Leu Thr Phe Asn Glu Thr Tyr Gln Asp<br>145 150 155 160 | | 480 |
| atc agt gag ttg gta tat gga gcc aag ctc cag ccc ctg gac ttc aag<br>Ile Ser Glu Leu Val Tyr Gly Ala Lys Leu Gln Pro Leu Asp Phe Lys<br>165 170 175 | | 528 |
| gaa aat gca gag caa tcc aga gcg gcc atc aac aaa tgg gtg tcc aat<br>Glu Asn Ala Glu Gln Ser Arg Ala Ala Ile Asn Lys Trp Val Ser Asn<br>180 185 190 | | 576 |
| aag acc gaa ggc cga atc acc gat gtc att ccc tcg gaa gcc atc aat<br>Lys Thr Glu Gly Arg Ile Thr Asp Val Ile Pro Ser Glu Ala Ile Asn<br>195 200 205 | | 624 |
| gag ctc act gtt ctg gtg ctg gtt aac acc att tac ttc aag ggc ctg<br>Glu Leu Thr Val Leu Val Leu Val Asn Thr Ile Tyr Phe Lys Gly Leu<br>210 215 220 | | 672 |
| tgg aag tca aag ttc agc cct gag aac aca agg aag gaa ctg ttc tac<br>Trp Lys Ser Lys Phe Ser Pro Glu Asn Thr Arg Lys Glu Leu Phe Tyr<br>225 230 235 240 | | 720 |
| aag gct gat gga gag tcg tgt tca gca tct atg atg tac cag gaa ggc<br>Lys Ala Asp Gly Glu Ser Cys Ser Ala Ser Met Met Tyr Gln Glu Gly<br>245 250 255 | | 768 |
| aag ttc cgt tat cgg cgc gtg gct gaa ggc acc cag gtg ctt gag ttg<br>Lys Phe Arg Tyr Arg Arg Val Ala Glu Gly Thr Gln Val Leu Glu Leu<br>260 265 270 | | 816 |
| ccc ttc aaa ggt gat gac atc acc atg gtc ctc atc ttg ccc aag cct<br>Pro Phe Lys Gly Asp Asp Ile Thr Met Val Leu Ile Leu Pro Lys Pro<br>275 280 285 | | 864 |
| gag aag agc ctg gcc aag gta gag aag gaa ctc acc cca gag gtg ctg<br>Glu Lys Ser Leu Ala Lys Val Glu Lys Glu Leu Thr Pro Glu Val Leu<br>290 295 300 | | 912 |
| caa gag tgg ctg gat gaa ttg gag gag atg atg ctg gtg gtc cac atg<br>Gln Glu Trp Leu Asp Glu Leu Glu Glu Met Met Leu Val Val His Met<br>305 310 315 320 | | 960 |
| ccc cgc ttc cgc att gag gac ggc ttc agt ttg aag gag cag ctg caa<br>Pro Arg Phe Arg Ile Glu Asp Gly Phe Ser Leu Lys Glu Gln Leu Gln<br>325 330 335 | | 1008 |

```
gac atg ggc ctt gtc gat ctg ttc agc cct gaa aag tcc aaa ctc cca      1056
Asp Met Gly Leu Val Asp Leu Phe Ser Pro Glu Lys Ser Lys Leu Pro
        340                 345                 350 ggt att gtt gca gaa ggc cga gat gac ctc tat gtc tca gat gca ttc      1104
Gly Ile Val Ala Glu Gly Arg Asp Asp Leu Tyr Val Ser Asp Ala Phe
        355                 360                 365 cat aag gca ttt ctt gag gta aat gaa gaa ggc agt gaa gca gct gca      1152
His Lys Ala Phe Leu Glu Val Asn Glu Glu Gly Ser Glu Ala Ala Ala
370                 375                 380 agt acc gct gtt gtg att gct ggc cgt cta aac ccc aac agg gtg act      1200
Ser Thr Ala Val Val Ile Ala Gly Arg Leu Asn Pro Asn Arg Val Thr
385                 390                 395                 400 ttc aag gcc aac agg cct ttc ctg gtt ttt ata aga gaa gtt cct ctg      1248
Phe Lys Ala Asn Arg Pro Phe Leu Val Phe Ile Arg Glu Val Pro Leu
                405                 410                 415 aac act att atc ttc atg ggc aga gta gcc aac cct tgt gtt aag          1293
Asn Thr Ile Ile Phe Met Gly Arg Val Ala Asn Pro Cys Val Lys
                420                 425                 430 taaaatgttc ttattctttg cacctcttcc tattttggt ttgtgaacag aagtaaaaat     1353
aaatacaaac tacttccatc tcacattaaa a                                   1384

<210> SEQ ID NO 22
<211> LENGTH: 431
<212> TYPE: PRT
<213> ORGANISM: Homo sapiens

<400> SEQUENCE: 22

His Gly Ser Pro Val Asp Ile Cys Thr Ala Lys Pro Arg Asp Ile Pro
1               5                   10                  15

Met Asn Pro Met Cys Ile Tyr Arg Ser Pro Glu Lys Lys Ala Thr Glu
            20                  25                  30

Asp Glu Gly Ser Glu Gln Lys Ile Pro Glu Ala Thr Asn Arg Arg Val
        35                  40                  45

Trp Glu Leu Ser Lys Ala Asn Ser Arg Phe Ala Thr Thr Phe Tyr Gln
    50                  55                  60

His Leu Ala Asp Ser Lys Asn Asp Asn Asp Asn Ile Phe Leu Ser Pro
65                  70                  75                  80

Leu Ser Ile Ser Thr Ala Phe Ala Met Thr Lys Leu Gly Ala Cys Asn
                85                  90                  95

Asp Thr Leu Gln Gln Leu Met Glu Val Phe Lys Phe Asp Thr Ile Ser
            100                 105                 110

Glu Lys Thr Ser Asp Gln Ile His Phe Phe Ala Lys Leu Asn Cys
        115                 120                 125

Arg Leu Tyr Arg Lys Ala Gln Lys Ser Ser Lys Leu Val Ser Ala Asn
130                 135                 140

Arg Leu Phe Gly Asp Lys Ser Leu Thr Phe Asn Glu Thr Tyr Gln Asp
145                 150                 155                 160

Ile Ser Glu Leu Val Tyr Gly Ala Lys Leu Gln Pro Leu Asp Phe Lys
                165                 170                 175

Glu Asn Ala Glu Gln Ser Arg Ala Ala Ile Asn Lys Trp Val Ser Asn
            180                 185                 190

Lys Thr Glu Gly Arg Ile Thr Asp Val Ile Pro Ser Glu Ala Ile Asn
        195                 200                 205

Glu Leu Thr Val Leu Val Leu Val Asn Thr Ile Tyr Phe Lys Gly Leu
    210                 215                 220
```

```
Trp Lys Ser Lys Phe Ser Pro Glu Asn Thr Arg Lys Glu Leu Phe Tyr
225                 230                 235                 240

Lys Ala Asp Gly Glu Ser Cys Ser Ala Ser Met Met Tyr Gln Glu Gly
                245                 250                 255

Lys Phe Arg Tyr Arg Arg Val Ala Glu Gly Thr Gln Val Leu Glu Leu
            260                 265                 270

Pro Phe Lys Gly Asp Asp Ile Thr Met Val Leu Ile Leu Pro Lys Pro
        275                 280                 285

Glu Lys Ser Leu Ala Lys Val Glu Lys Glu Leu Thr Pro Glu Val Leu
    290                 295                 300

Gln Glu Trp Leu Asp Glu Leu Glu Glu Met Met Leu Val Val His Met
305                 310                 315                 320

Pro Arg Phe Arg Ile Glu Asp Gly Phe Ser Leu Lys Glu Gln Leu Gln
                325                 330                 335

Asp Met Gly Leu Val Asp Leu Phe Ser Pro Glu Lys Ser Lys Leu Pro
            340                 345                 350

Gly Ile Val Ala Glu Gly Arg Asp Asp Leu Tyr Val Ser Asp Ala Phe
        355                 360                 365

His Lys Ala Phe Leu Glu Val Asn Glu Glu Gly Ser Glu Ala Ala Ala
    370                 375                 380

Ser Thr Ala Val Val Ile Ala Gly Arg Leu Asn Pro Asn Arg Val Thr
385                 390                 395                 400

Phe Lys Ala Asn Arg Pro Phe Leu Val Phe Ile Arg Glu Val Pro Leu
                405                 410                 415

Asn Thr Ile Ile Phe Met Gly Arg Val Ala Asn Pro Cys Val Lys
            420                 425                 430

<210> SEQ ID NO 23
<211> LENGTH: 1381
<212> TYPE: DNA
<213> ORGANISM: Homo sapiens
<220> FEATURE:
<221> NAME/KEY: CDS
<222> LOCATION: (1)..(1290)

<400> SEQUENCE: 23 cac ggg agc cct gtg gac atc tgc aca gcc aag ccg cgg gac att ccc      48
His Gly Ser Pro Val Asp Ile Cys Thr Ala Lys Pro Arg Asp Ile Pro
1               5                   10                  15 atg aat ccc atg tgc att tac cgc tcc ccg gag aag aag gca act gag      96
Met Asn Pro Met Cys Ile Tyr Arg Ser Pro Glu Lys Lys Ala Thr Glu
            20                  25                  30 gat gag ggc tca gaa cag aag atc ccg gag gcc acc aac cgg gtc gtc     144
Asp Glu Gly Ser Glu Gln Lys Ile Pro Glu Ala Thr Asn Arg Val Val
        35                  40                  45 tgg gaa ctg tcc aag gcc aat tcc cgc ttt gct acc act ttc tat cag     192
Trp Glu Leu Ser Lys Ala Asn Ser Arg Phe Ala Thr Thr Phe Tyr Gln
    50                  55                  60 cac ctg gca gat tcc aag aat gac aat gat aac att ttc ctg tca ccc     240
His Leu Ala Asp Ser Lys Asn Asp Asn Asp Asn Ile Phe Leu Ser Pro
65                  70                  75                  80 ctg agt atc tcc acg gct ttt gct atg acc aag ctg ggt gcc tgt aat     288
Leu Ser Ile Ser Thr Ala Phe Ala Met Thr Lys Leu Gly Ala Cys Asn
                85                  90                  95 gac acc ctc cag caa ctg atg gag gta ttt aag ttt gac acc ata tct     336
Asp Thr Leu Gln Gln Leu Met Glu Val Phe Lys Phe Asp Thr Ile Ser
            100                 105                 110 gag aaa aca tct gat cag atc cac ttc ttc ttt gcc aaa ctg aac tgc     384
```

```
Glu Lys Thr Ser Asp Gln Ile His Phe Phe Ala Lys Leu Asn Cys
        115                 120                 125 cga ctc tat cga aaa gcc cag aaa tcc tcc aag tta gta tca gcc aat    432
Arg Leu Tyr Arg Lys Ala Gln Lys Ser Ser Lys Leu Val Ser Ala Asn
130                 135                 140 cgc ctt ttt gga gac aaa tcc ctt acc ttc aat gag acc tac cag gac    480
Arg Leu Phe Gly Asp Lys Ser Leu Thr Phe Asn Glu Thr Tyr Gln Asp
145                 150                 155                 160 atc agt gag ttg gta tat gga gcc aag ctc cag ccc ctg gac ttc aag    528
Ile Ser Glu Leu Val Tyr Gly Ala Lys Leu Gln Pro Leu Asp Phe Lys
                165                 170                 175 gaa aat gca gag caa tcc aga gcg gcc atc aac aaa tgg gtg tcc aat    576
Glu Asn Ala Glu Gln Ser Arg Ala Ala Ile Asn Lys Trp Val Ser Asn
            180                 185                 190 aag acc gaa ggc cga atc acc gat gtc att ccc tcg gaa gcc atc aat    624
Lys Thr Glu Gly Arg Ile Thr Asp Val Ile Pro Ser Glu Ala Ile Asn
        195                 200                 205 gag ctc act gtt ctg gtg ctg gtt aac acc att tac ttc aag ggc ctg    672
Glu Leu Thr Val Leu Val Leu Val Asn Thr Ile Tyr Phe Lys Gly Leu
210                 215                 220 tgg aag tca aag ttc agc cct gag aac aca agg aag gaa ctg ttc tac    720
Trp Lys Ser Lys Phe Ser Pro Glu Asn Thr Arg Lys Glu Leu Phe Tyr
225                 230                 235                 240 aag gct gat gga gag tcg tgt tca gca tct atg atg tac cag gaa ggc    768
Lys Ala Asp Gly Glu Ser Cys Ser Ala Ser Met Met Tyr Gln Glu Gly
                245                 250                 255 aag ttc cgt tat cgg cgc gtg gct gaa ggc acc cag gtg ctt gag ttg    816
Lys Phe Arg Tyr Arg Arg Val Ala Glu Gly Thr Gln Val Leu Glu Leu
            260                 265                 270 ccc ttc aaa ggt gat gac atc acc atg gtc ctc atc ttg ccc aag cct    864
Pro Phe Lys Gly Asp Asp Ile Thr Met Val Leu Ile Leu Pro Lys Pro
        275                 280                 285 gag aag agc ctg gcc aag gta gag aag gaa ctc acc cca gag gtg ctg    912
Glu Lys Ser Leu Ala Lys Val Glu Lys Glu Leu Thr Pro Glu Val Leu
290                 295                 300 caa gag tgg ctg gat gaa ttg gag gag atg atg ctg gtg gtc cac atg    960
Gln Glu Trp Leu Asp Glu Leu Glu Glu Met Met Leu Val Val His Met
305                 310                 315                 320 ccc cgc ttc cgc att gag gac ggc ttc agt ttg aag gag cag ctg caa   1008
Pro Arg Phe Arg Ile Glu Asp Gly Phe Ser Leu Lys Glu Gln Leu Gln
                325                 330                 335 gac atg ggc ctt gtc gat ctg ttc agc cct gaa aag tcc aaa ctc cca   1056
Asp Met Gly Leu Val Asp Leu Phe Ser Pro Glu Lys Ser Lys Leu Pro
            340                 345                 350 ggt att gtt gca gaa ggc cga gat gac ctc tat gtc tca gat gca ttc   1104
Gly Ile Val Ala Glu Gly Arg Asp Asp Leu Tyr Val Ser Asp Ala Phe
        355                 360                 365 cat aag gca ttt ctt gag gta aat gaa gaa ggc agt gaa gca gct gca   1152
His Lys Ala Phe Leu Glu Val Asn Glu Glu Gly Ser Glu Ala Ala Ala
370                 375                 380 agt acc gct gtt gtg att gct ggc cta aac ccc aac agg gtg act ttc   1200
Ser Thr Ala Val Val Ile Ala Gly Leu Asn Pro Asn Arg Val Thr Phe
385                 390                 395                 400 aag gcc aac agg cct ttc ctg gtt ttt ata aga gaa gtt cct ctg aac   1248
Lys Ala Asn Arg Pro Phe Leu Val Phe Ile Arg Glu Val Pro Leu Asn
                405                 410                 415 act att atc ttc atg ggc aga gta gcc aac cct tgt gtt aag           1290
Thr Ile Ile Phe Met Gly Arg Val Ala Asn Pro Cys Val Lys
            420                 425                 430
```

```
taaaatgttc ttattctttg cacctcttcc tattttggt tgtgaacag aagtaaaaat    1350 aaatacaaac tacttccatc tcacattaaa a                                 1381
```

<210> SEQ ID NO 24
<211> LENGTH: 430
<212> TYPE: PRT
<213> ORGANISM: Homo sapiens

<400> SEQUENCE: 24

```
His Gly Ser Pro Val Asp Ile Cys Thr Ala Lys Pro Arg Asp Ile Pro
1               5                   10                  15

Met Asn Pro Met Cys Ile Tyr Arg Ser Pro Glu Lys Lys Ala Thr Glu
            20                  25                  30

Asp Glu Gly Ser Glu Gln Lys Ile Pro Glu Ala Thr Asn Arg Arg Val
        35                  40                  45

Trp Glu Leu Ser Lys Ala Asn Ser Arg Phe Ala Thr Thr Phe Tyr Gln
    50                  55                  60

His Leu Ala Asp Ser Lys Asn Asp Asn Asp Ile Phe Leu Ser Pro
65                  70                  75                  80

Leu Ser Ile Ser Thr Ala Phe Ala Met Thr Lys Leu Gly Ala Cys Asn
                85                  90                  95

Asp Thr Leu Gln Gln Leu Met Glu Val Phe Lys Phe Asp Thr Ile Ser
            100                 105                 110

Glu Lys Thr Ser Asp Gln Ile His Phe Phe Ala Lys Leu Asn Cys
        115                 120                 125

Arg Leu Tyr Arg Lys Ala Gln Lys Ser Ser Lys Leu Val Ser Ala Asn
    130                 135                 140

Arg Leu Phe Gly Asp Lys Ser Leu Thr Phe Asn Glu Thr Tyr Gln Asp
145                 150                 155                 160

Ile Ser Glu Leu Val Tyr Gly Ala Lys Leu Gln Pro Leu Asp Phe Lys
                165                 170                 175

Glu Asn Ala Glu Gln Ser Arg Ala Ala Ile Asn Lys Trp Val Ser Asn
            180                 185                 190

Lys Thr Glu Gly Arg Ile Thr Asp Val Ile Pro Ser Glu Ala Ile Asn
        195                 200                 205

Glu Leu Thr Val Leu Val Leu Val Asn Thr Ile Tyr Phe Lys Gly Leu
    210                 215                 220

Trp Lys Ser Lys Phe Ser Pro Glu Asn Thr Arg Lys Glu Leu Phe Tyr
225                 230                 235                 240

Lys Ala Asp Gly Glu Ser Cys Ser Ala Ser Met Met Tyr Gln Glu Gly
                245                 250                 255

Lys Phe Arg Tyr Arg Arg Val Ala Glu Gly Thr Gln Val Leu Glu Leu
            260                 265                 270

Pro Phe Lys Gly Asp Asp Ile Thr Met Val Leu Ile Leu Pro Lys Pro
        275                 280                 285

Glu Lys Ser Leu Ala Lys Val Glu Lys Glu Leu Thr Pro Glu Val Leu
    290                 295                 300

Gln Glu Trp Leu Asp Glu Leu Glu Glu Met Met Leu Val Val His Met
305                 310                 315                 320

Pro Arg Phe Arg Ile Glu Asp Gly Phe Ser Leu Lys Glu Gln Leu Gln
                325                 330                 335

Asp Met Gly Leu Val Asp Leu Phe Ser Pro Glu Lys Ser Lys Leu Pro
            340                 345                 350

Gly Ile Val Ala Glu Gly Arg Asp Asp Leu Tyr Val Ser Asp Ala Phe
```

```
                       355                 360                 365
His Lys Ala Phe Leu Glu Val Asn Glu Glu Gly Ser Glu Ala Ala Ala
        370                 375                 380

Ser Thr Ala Val Val Ile Ala Gly Leu Asn Pro Asn Arg Val Thr Phe
385                 390                 395                 400

Lys Ala Asn Arg Pro Phe Leu Val Phe Ile Arg Glu Val Pro Leu Asn
                405                 410                 415

Thr Ile Ile Phe Met Gly Arg Val Ala Asn Pro Cys Val Lys
            420                 425                 430

<210> SEQ ID NO 25
<211> LENGTH: 1483
<212> TYPE: DNA
<213> ORGANISM: Homo sapiens
<220> FEATURE:
<221> NAME/KEY: CDS
<222> LOCATION: (1)..(1392)

<400> SEQUENCE: 25 atg tat tcc aat gtg ata gga act gta acc tct gga aaa agg aag gtt      48
Met Tyr Ser Asn Val Ile Gly Thr Val Thr Ser Gly Lys Arg Lys Val
1               5                   10                  15 tat ctt ttg tcc ttg ctg ctc att ggc ttc tgg gac tgc gtg acc tgt      96
Tyr Leu Leu Ser Leu Leu Leu Ile Gly Phe Trp Asp Cys Val Thr Cys
                20                  25                  30 cac ggg agc cct gtg gac atc tgc aca gcc aag ccg cgg gac att ccc     144
His Gly Ser Pro Val Asp Ile Cys Thr Ala Lys Pro Arg Asp Ile Pro
            35                  40                  45 atg aat ccc atg tgc att tac cgc tcc ccg gag aag aag gca act gag     192
Met Asn Pro Met Cys Ile Tyr Arg Ser Pro Glu Lys Lys Ala Thr Glu
        50                  55                  60 gat gag ggc tca gaa cag aag atc ccg gag gcc acc aac cgg cgt gtc     240
Asp Glu Gly Ser Glu Gln Lys Ile Pro Glu Ala Thr Asn Arg Arg Val
65                  70                  75                  80 tgg gaa ctg tcc aag gcc aat tcc cgc ttt gct acc act ttc tat cag     288
Trp Glu Leu Ser Lys Ala Asn Ser Arg Phe Ala Thr Thr Phe Tyr Gln
                85                  90                  95 cac ctg gca gat tcc aag aat gac aat gat aac att ttc ctg tca ccc     336
His Leu Ala Asp Ser Lys Asn Asp Asn Asp Asn Ile Phe Leu Ser Pro
            100                 105                 110 ctg agt atc tcc acg gct ttt gct atg acc aag ctg ggt gcc tgt aat     384
Leu Ser Ile Ser Thr Ala Phe Ala Met Thr Lys Leu Gly Ala Cys Asn
        115                 120                 125 gac acc ctc cag caa ctg atg gag gta ttt aag ttt gac acc ata tct     432
Asp Thr Leu Gln Gln Leu Met Glu Val Phe Lys Phe Asp Thr Ile Ser
130                 135                 140 gag aaa aca tct gat cag atc cac ttc ttc ttt gcc aaa ctg aac tgc     480
Glu Lys Thr Ser Asp Gln Ile His Phe Phe Phe Ala Lys Leu Asn Cys
145                 150                 155                 160 cga ctc tat cga aaa gcc aac aaa tcc tcc aag tta gta tca gcc aat     528
Arg Leu Tyr Arg Lys Ala Asn Lys Ser Ser Lys Leu Val Ser Ala Asn
                165                 170                 175 cgc ctt ttt gga gac aaa tcc ctt acc ttc aat gag acc tac cag gac     576
Arg Leu Phe Gly Asp Lys Ser Leu Thr Phe Asn Glu Thr Tyr Gln Asp
            180                 185                 190 atc agt gag ttg gta tat gga gcc aag ctc cag ccc ctg gac ttc aag     624
Ile Ser Glu Leu Val Tyr Gly Ala Lys Leu Gln Pro Leu Asp Phe Lys
        195                 200                 205 gaa aat gca gag caa tcc aga gcg gcc atc aac aaa tgg gtg tcc aat     672
Glu Asn Ala Glu Gln Ser Arg Ala Ala Ile Asn Lys Trp Val Ser Asn
```

-continued

```
                 210                 215                 220
aag acc gaa ggc cga atc acc gat gtc att ccc tcg gaa gcc atc aat   720
Lys Thr Glu Gly Arg Ile Thr Asp Val Ile Pro Ser Glu Ala Ile Asn
225                 230                 235                 240 gag ctc act gtt ctg gtg ctg gtt aac acc att tac ttc aag ggc ctg   768
Glu Leu Thr Val Leu Val Leu Val Asn Thr Ile Tyr Phe Lys Gly Leu
            245                 250                 255 tgg aag tca aag ttc agc cct gag aac aca agg aag gaa ctg ttc tac   816
Trp Lys Ser Lys Phe Ser Pro Glu Asn Thr Arg Lys Glu Leu Phe Tyr
        260                 265                 270 aag gct gat gga gag tcg tgt tca gca tct atg atg tac cag gaa ggc   864
Lys Ala Asp Gly Glu Ser Cys Ser Ala Ser Met Met Tyr Gln Glu Gly
    275                 280                 285 aag ttc cgt tat cgg cgc gtg gct gaa ggc acc cag gtg ctt gag ttg   912
Lys Phe Arg Tyr Arg Arg Val Ala Glu Gly Thr Gln Val Leu Glu Leu
290                 295                 300 ccc ttc aaa ggt gat gac atc acc atg gtc ctc atc ttg ccc aag cct   960
Pro Phe Lys Gly Asp Asp Ile Thr Met Val Leu Ile Leu Pro Lys Pro
305                 310                 315                 320 gag aag agc ctg gcc aag gta gag aag gaa ctc acc cca gag gtg ctg  1008
Glu Lys Ser Leu Ala Lys Val Glu Lys Glu Leu Thr Pro Glu Val Leu
            325                 330                 335 caa gag tgg ctg gat gaa ttg gag gag atg atg ctg gtg gtc cac atg  1056
Gln Glu Trp Leu Asp Glu Leu Glu Glu Met Met Leu Val Val His Met
        340                 345                 350 ccc cgc ttc cgc att gag gac ggc ttc agt ttg aag gag cag ctg caa  1104
Pro Arg Phe Arg Ile Glu Asp Gly Phe Ser Leu Lys Glu Gln Leu Gln
    355                 360                 365 gac atg ggc ctt gtc gat ctg ttc agc cct gaa aag tcc aaa ctc cca  1152
Asp Met Gly Leu Val Asp Leu Phe Ser Pro Glu Lys Ser Lys Leu Pro
370                 375                 380 ggt att gtt gca gaa ggc cga gat gac ctc tat gtc tca gat gca ttc  1200
Gly Ile Val Ala Glu Gly Arg Asp Asp Leu Tyr Val Ser Asp Ala Phe
385                 390                 395                 400 cat aag gca ttt ctt gag gta aat gaa gaa ggc agt gaa gca gct gca  1248
His Lys Ala Phe Leu Glu Val Asn Glu Glu Gly Ser Glu Ala Ala Ala
            405                 410                 415 agt acc gct gtt gtg att gct ggc cgt tcg cta aac ccc aac agg gtg  1296
Ser Thr Ala Val Val Ile Ala Gly Arg Ser Leu Asn Pro Asn Arg Val
        420                 425                 430 act ttc aag gcc aac agg cct ttc ctg gtt ttt ata aga gaa gtt cct  1344
Thr Phe Lys Ala Asn Arg Pro Phe Leu Val Phe Ile Arg Glu Val Pro
    435                 440                 445 ctg aac act att atc ttc atg ggc aga gta gcc aac cct tgt gtt aag  1392
Leu Asn Thr Ile Ile Phe Met Gly Arg Val Ala Asn Pro Cys Val Lys
450                 455                 460 taaaatgttc ttattctttg cacctcttcc tattttggt ttgtgaacag aagtaaaaat    1452
aaatacaaac tacttccatc tcacattaaa a                                 1483

<210> SEQ ID NO 26
<211> LENGTH: 464
<212> TYPE: PRT
<213> ORGANISM: Homo sapiens

<400> SEQUENCE: 26

Met Tyr Ser Asn Val Ile Gly Thr Val Thr Ser Gly Lys Arg Lys Val
1               5                   10                  15

Tyr Leu Leu Ser Leu Leu Leu Ile Gly Phe Trp Asp Cys Val Thr Cys
            20                  25                  30
```

-continued

```
His Gly Ser Pro Val Asp Ile Cys Thr Ala Lys Pro Arg Asp Ile Pro
        35                  40                  45
Met Asn Pro Met Cys Ile Tyr Arg Ser Pro Glu Lys Lys Ala Thr Glu
 50                  55                  60
Asp Glu Gly Ser Glu Gln Lys Ile Pro Glu Ala Thr Asn Arg Arg Val
 65                  70                  75                  80
Trp Glu Leu Ser Lys Ala Asn Ser Arg Phe Ala Thr Thr Phe Tyr Gln
                 85                  90                  95
His Leu Ala Asp Ser Lys Asn Asp Asn Asp Asn Ile Phe Leu Ser Pro
                100                 105                 110
Leu Ser Ile Ser Thr Ala Phe Ala Met Thr Lys Leu Gly Ala Cys Asn
                115                 120                 125
Asp Thr Leu Gln Gln Leu Met Glu Val Phe Lys Phe Asp Thr Ile Ser
            130                 135                 140
Glu Lys Thr Ser Asp Gln Ile His Phe Phe Ala Lys Leu Asn Cys
145                 150                 155                 160
Arg Leu Tyr Arg Lys Ala Asn Lys Ser Lys Leu Val Ser Ala Asn
                165                 170                 175
Arg Leu Phe Gly Asp Lys Ser Leu Thr Phe Asn Glu Thr Tyr Gln Asp
                180                 185                 190
Ile Ser Glu Leu Val Tyr Gly Ala Lys Leu Gln Pro Leu Asp Phe Lys
            195                 200                 205
Glu Asn Ala Glu Gln Ser Arg Ala Ala Ile Asn Lys Trp Val Ser Asn
210                 215                 220
Lys Thr Glu Gly Arg Ile Thr Asp Val Ile Pro Ser Glu Ala Ile Asn
225                 230                 235                 240
Glu Leu Thr Val Leu Val Leu Val Asn Thr Ile Tyr Phe Lys Gly Leu
                245                 250                 255
Trp Lys Ser Lys Phe Ser Pro Glu Asn Thr Arg Lys Glu Leu Phe Tyr
                260                 265                 270
Lys Ala Asp Gly Glu Ser Cys Ser Ala Ser Met Met Tyr Gln Glu Gly
            275                 280                 285
Lys Phe Arg Tyr Arg Arg Val Ala Glu Gly Thr Gln Val Leu Glu Leu
            290                 295                 300
Pro Phe Lys Gly Asp Asp Ile Thr Met Val Leu Ile Leu Pro Lys Pro
305                 310                 315                 320
Glu Lys Ser Leu Ala Lys Val Glu Lys Glu Leu Thr Pro Glu Val Leu
                325                 330                 335
Gln Glu Trp Leu Asp Glu Leu Glu Glu Met Met Leu Val Val His Met
            340                 345                 350
Pro Arg Phe Arg Ile Glu Asp Gly Phe Ser Leu Lys Glu Gln Leu Gln
            355                 360                 365
Asp Met Gly Leu Val Asp Leu Phe Ser Pro Glu Lys Ser Lys Leu Pro
370                 375                 380
Gly Ile Val Ala Glu Gly Arg Asp Asp Leu Tyr Val Ser Asp Ala Phe
385                 390                 395                 400
His Lys Ala Phe Leu Glu Val Asn Glu Glu Gly Ser Glu Ala Ala Ala
                405                 410                 415
Ser Thr Ala Val Val Ile Ala Gly Arg Ser Leu Asn Pro Asn Arg Val
            420                 425                 430
Thr Phe Lys Ala Asn Arg Pro Phe Leu Val Phe Ile Arg Glu Val Pro
            435                 440                 445
```

```
Leu Asn Thr Ile Ile Phe Met Gly Arg Val Ala Asn Pro Cys Val Lys
        450                 455                 460

<210> SEQ ID NO 27
<211> LENGTH: 1483
<212> TYPE: DNA
<213> ORGANISM: Homo sapiens
<220> FEATURE:
<221> NAME/KEY: CDS
<222> LOCATION: (1)..(1392)

<400> SEQUENCE: 27 atg tat tcc aat gtg ata gga act gta acc tct gga aaa agg aag gtt      48
Met Tyr Ser Asn Val Ile Gly Thr Val Thr Ser Gly Lys Arg Lys Val
1               5                   10                  15 tat ctt ttg tcc ttg ctc att ggc ttc tgg gac tgc gtg acc tgt          96
Tyr Leu Leu Ser Leu Leu Ile Gly Phe Trp Asp Cys Val Thr Cys
                20                  25                  30 cac ggg agc cct gtg gac atc tgc aca gcc aag ccg cgg gac att ccc     144
His Gly Ser Pro Val Asp Ile Cys Thr Ala Lys Pro Arg Asp Ile Pro
            35                  40                  45 atg aat ccc atg tgc att tac cgc tcc ccg gag aag aag gca act gag     192
Met Asn Pro Met Cys Ile Tyr Arg Ser Pro Glu Lys Lys Ala Thr Glu
50                  55                  60 gat gag ggc tca gaa cag aag atc ccg gag gcc acc aac cgg gtc gtc     240
Asp Glu Gly Ser Glu Gln Lys Ile Pro Glu Ala Thr Asn Arg Val Val
65                  70                  75                  80 tgg gaa ctg tcc aag gcc aat tcc cgc ttt gct acc act ttc tat cag     288
Trp Glu Leu Ser Lys Ala Asn Ser Arg Phe Ala Thr Thr Phe Tyr Gln
                85                  90                  95 cac ctg gca gat tcc aag aat gac aat gat aac att ttc ctg tca ccc     336
His Leu Ala Asp Ser Lys Asn Asp Asn Asp Asn Ile Phe Leu Ser Pro
            100                 105                 110 ctg agt atc tcc acg gct ttt gct atg acc aag ctg ggt gcc tgt aat     384
Leu Ser Ile Ser Thr Ala Phe Ala Met Thr Lys Leu Gly Ala Cys Asn
        115                 120                 125 gac acc ctc cag caa ctg atg gag gta ttt aag ttt gac acc ata tct     432
Asp Thr Leu Gln Gln Leu Met Glu Val Phe Lys Phe Asp Thr Ile Ser
130                 135                 140 gag aaa aca tct gat cag atc cac ttc ttc ttt gcc aaa ctg aac tgc     480
Glu Lys Thr Ser Asp Gln Ile His Phe Phe Phe Ala Lys Leu Asn Cys
145                 150                 155                 160 cga ctc tat cga aaa gcc aac aaa tcc tcc aag tta gta tca gcc aat     528
Arg Leu Tyr Arg Lys Ala Asn Lys Ser Ser Lys Leu Val Ser Ala Asn
                165                 170                 175 cgc ctt ttt gga gac aaa tcc ctt acc ttc aat gag acc tac cag gac     576
Arg Leu Phe Gly Asp Lys Ser Leu Thr Phe Asn Glu Thr Tyr Gln Asp
            180                 185                 190 atc agt gag ttg gta tat gga gcc aag ctc cag ccc ctg gac ttc aag     624
Ile Ser Glu Leu Val Tyr Gly Ala Lys Leu Gln Pro Leu Asp Phe Lys
        195                 200                 205 gaa aat gca gag caa tcc aga gcg gcc atc aac aaa tgg gtg tcc aat     672
Glu Asn Ala Glu Gln Ser Arg Ala Ala Ile Asn Lys Trp Val Ser Asn
210                 215                 220 aag acc gaa ggc cga atc acc gat gtc att ccc tcg gaa gcc atc aat     720
Lys Thr Glu Gly Arg Ile Thr Asp Val Ile Pro Ser Glu Ala Ile Asn
225                 230                 235                 240 gag ctc act gtt ctg gtg ctg gtt aac acc att tac ttc aag ggc ctg     768
Glu Leu Thr Val Leu Val Leu Val Asn Thr Ile Tyr Phe Lys Gly Leu
                245                 250                 255 tgg aag tca aag ttc agc cct gag aac aca agg aag gaa ctg ttc tac     816
```

```
                Trp Lys Ser Lys Phe Ser Pro Glu Asn Thr Arg Lys Glu Leu Phe Tyr
                                260                 265                 270 aag gct gat gga gag tcg tgt tca gca tct atg atg tac cag gaa ggc        864
Lys Ala Asp Gly Glu Ser Cys Ser Ala Ser Met Met Tyr Gln Glu Gly
                275                 280                 285 aag ttc cgt tat cgg cgc gtg gct gaa ggc acc cag gtg ctt gag ttg        912
Lys Phe Arg Tyr Arg Arg Val Ala Glu Gly Thr Gln Val Leu Glu Leu
            290                 295                 300 ccc ttc aaa ggt gat gac atc acc atg gtc ctc atc ttg ccc aag cct        960
Pro Phe Lys Gly Asp Asp Ile Thr Met Val Leu Ile Leu Pro Lys Pro
305                 310                 315                 320 gag aag agc ctg gcc aag gta gag aag gaa ctc acc cca gag gtg ctg       1008
Glu Lys Ser Leu Ala Lys Val Glu Lys Glu Leu Thr Pro Glu Val Leu
                325                 330                 335 caa gag tgg ctg gat gaa ttg gag gag atg atg ctg gtg gtc cac atg       1056
Gln Glu Trp Leu Asp Glu Leu Glu Glu Met Met Leu Val Val His Met
                340                 345                 350 ccc cgc ttc cgc att gag gac ggc ttc agt ttg aag gag cag ctg caa       1104
Pro Arg Phe Arg Ile Glu Asp Gly Phe Ser Leu Lys Glu Gln Leu Gln
            355                 360                 365 gac atg ggc ctt gtc gat ctg ttc agc cct gaa aag tcc aaa ctc cca       1152
Asp Met Gly Leu Val Asp Leu Phe Ser Pro Glu Lys Ser Lys Leu Pro
370                 375                 380 ggt att gtt gca gaa ggc cga gat gac ctc tat gtc tca gat gca ttc       1200
Gly Ile Val Ala Glu Gly Arg Asp Asp Leu Tyr Val Ser Asp Ala Phe
385                 390                 395                 400 cat aag gca ttt ctt gag gta aat gaa gaa ggc agt gaa gca gct gca       1248
His Lys Ala Phe Leu Glu Val Asn Glu Glu Gly Ser Glu Ala Ala Ala
                405                 410                 415 agt acc gct gtt gtg att gct ggc cat tcg cta aac ccc aac agg gtg       1296
Ser Thr Ala Val Val Ile Ala Gly His Ser Leu Asn Pro Asn Arg Val
                420                 425                 430 act ttc aag gcc aac agg cct ttc ctg gtt ttt ata aga gaa gtt cct       1344
Thr Phe Lys Ala Asn Arg Pro Phe Leu Val Phe Ile Arg Glu Val Pro
            435                 440                 445 ctg aac act att atc ttc atg ggc aga gta gcc aac cct tgt gtt aag       1392
Leu Asn Thr Ile Ile Phe Met Gly Arg Val Ala Asn Pro Cys Val Lys
450                 455                 460 taaaatgttc ttattctttg cacctcttcc tattttggt ttgtgaacag aagtaaaaat     1452
aaatacaaac tacttccatc tcacattaaa a                                    1483

<210> SEQ ID NO 28
<211> LENGTH: 464
<212> TYPE: PRT
<213> ORGANISM: Homo sapiens

<400> SEQUENCE: 28

Met Tyr Ser Asn Val Ile Gly Thr Val Thr Ser Gly Lys Arg Lys Val
1               5                   10                  15

Tyr Leu Leu Ser Leu Leu Leu Ile Gly Phe Trp Asp Cys Val Thr Cys
                20                  25                  30

His Gly Ser Pro Val Asp Ile Cys Thr Ala Lys Pro Arg Asp Ile Pro
            35                  40                  45

Met Asn Pro Met Cys Ile Tyr Arg Ser Pro Glu Lys Lys Ala Thr Glu
        50                  55                  60

Asp Glu Gly Ser Glu Gln Lys Ile Pro Glu Ala Thr Asn Arg Arg Val
65                  70                  75                  80

Trp Glu Leu Ser Lys Ala Asn Ser Arg Phe Ala Thr Thr Phe Tyr Gln
```

```
                      85                  90                  95
His Leu Ala Asp Ser Lys Asn Asp Asn Asp Asn Ile Phe Leu Ser Pro
                100                 105                 110

Leu Ser Ile Ser Thr Ala Phe Ala Met Thr Lys Leu Gly Ala Cys Asn
            115                 120                 125

Asp Thr Leu Gln Gln Leu Met Glu Val Phe Lys Phe Asp Thr Ile Ser
        130                 135                 140

Glu Lys Thr Ser Asp Gln Ile His Phe Phe Ala Lys Leu Asn Cys
145                 150                 155                 160

Arg Leu Tyr Arg Lys Ala Asn Lys Ser Ser Lys Leu Val Ser Ala Asn
                165                 170                 175

Arg Leu Phe Gly Asp Lys Ser Leu Thr Phe Asn Glu Thr Tyr Gln Asp
            180                 185                 190

Ile Ser Glu Leu Val Tyr Gly Ala Lys Leu Gln Pro Leu Asp Phe Lys
        195                 200                 205

Glu Asn Ala Glu Gln Ser Arg Ala Ala Ile Asn Lys Trp Val Ser Asn
    210                 215                 220

Lys Thr Glu Gly Arg Ile Thr Asp Val Ile Pro Ser Glu Ala Ile Asn
225                 230                 235                 240

Glu Leu Thr Val Leu Val Leu Val Asn Thr Ile Tyr Phe Lys Gly Leu
                245                 250                 255

Trp Lys Ser Lys Phe Ser Pro Glu Asn Thr Arg Lys Glu Leu Phe Tyr
            260                 265                 270

Lys Ala Asp Gly Glu Ser Cys Ser Ala Ser Met Met Tyr Gln Glu Gly
        275                 280                 285

Lys Phe Arg Tyr Arg Arg Val Ala Glu Gly Thr Gln Val Leu Glu Leu
    290                 295                 300

Pro Phe Lys Gly Asp Asp Ile Thr Met Val Leu Ile Leu Pro Lys Pro
305                 310                 315                 320

Glu Lys Ser Leu Ala Lys Val Glu Lys Glu Leu Thr Pro Glu Val Leu
                325                 330                 335

Gln Glu Trp Leu Asp Glu Leu Glu Glu Met Met Leu Val Val His Met
            340                 345                 350

Pro Arg Phe Arg Ile Glu Asp Gly Phe Ser Leu Lys Glu Gln Leu Gln
        355                 360                 365

Asp Met Gly Leu Val Asp Leu Phe Ser Pro Glu Lys Ser Lys Leu Pro
    370                 375                 380

Gly Ile Val Ala Glu Gly Arg Asp Asp Leu Tyr Val Ser Asp Ala Phe
385                 390                 395                 400

His Lys Ala Phe Leu Glu Val Asn Glu Glu Gly Ser Glu Ala Ala Ala
                405                 410                 415

Ser Thr Ala Val Val Ile Ala Gly His Ser Leu Asn Pro Asn Arg Val
            420                 425                 430

Thr Phe Lys Ala Asn Arg Pro Phe Leu Val Phe Ile Arg Glu Val Pro
        435                 440                 445

Leu Asn Thr Ile Ile Phe Met Gly Arg Val Ala Asn Pro Cys Val Lys
    450                 455                 460

<210> SEQ ID NO 29
<211> LENGTH: 1486
<212> TYPE: DNA
<213> ORGANISM: Homo sapiens
<220> FEATURE:
<221> NAME/KEY: CDS
<222> LOCATION: (1)..(1395)
```

<400> SEQUENCE: 29

| | | | | | | | | | | | | | | | | |
|---|---|---|---|---|---|---|---|---|---|---|---|---|---|---|---|---|
| atg | tat | tcc | aat | gtg | ata | gga | act | gta | acc | tct | gga | aaa | agg | aag | gtt | 48 |
| Met | Tyr | Ser | Asn | Val | Ile | Gly | Thr | Val | Thr | Ser | Gly | Lys | Arg | Lys | Val | |
| 1 | | | | 5 | | | | | 10 | | | | | 15 | | |
| tat | ctt | ttg | tcc | ttg | ctg | ctc | att | ggc | ttc | tgg | gac | tgc | gtg | acc | tgt | 96 |
| Tyr | Leu | Leu | Ser | Leu | Leu | Leu | Ile | Gly | Phe | Trp | Asp | Cys | Val | Thr | Cys | |
| | | | 20 | | | | | 25 | | | | | 30 | | | |
| cac | ggg | agc | cct | gtg | gac | atc | tgc | aca | gcc | aag | ccg | cgg | gac | att | ccc | 144 |
| His | Gly | Ser | Pro | Val | Asp | Ile | Cys | Thr | Ala | Lys | Pro | Arg | Asp | Ile | Pro | |
| | | 35 | | | | | 40 | | | | | 45 | | | | |
| atg | aat | ccc | atg | tgc | att | tac | cgc | tcc | ccg | gag | aag | aag | gca | act | gag | 192 |
| Met | Asn | Pro | Met | Cys | Ile | Tyr | Arg | Ser | Pro | Glu | Lys | Lys | Ala | Thr | Glu | |
| 50 | | | | | 55 | | | | | 60 | | | | | | |
| gat | gag | ggc | tca | gaa | cag | aag | atc | ccg | gag | gcc | acc | aac | cgg | cgt | gtc | 240 |
| Asp | Glu | Gly | Ser | Glu | Gln | Lys | Ile | Pro | Glu | Ala | Thr | Asn | Arg | Arg | Val | |
| 65 | | | | 70 | | | | | 75 | | | | | 80 | | |
| tgg | gaa | ctg | tcc | aag | gcc | aat | tcc | cgc | ttt | gct | acc | act | ttc | tat | cag | 288 |
| Trp | Glu | Leu | Ser | Lys | Ala | Asn | Ser | Arg | Phe | Ala | Thr | Thr | Phe | Tyr | Gln | |
| | | | | 85 | | | | | 90 | | | | | 95 | | |
| cac | ctg | gca | gat | tcc | aag | aat | gac | aat | gat | aac | att | ttc | ctg | tca | ccc | 336 |
| His | Leu | Ala | Asp | Ser | Lys | Asn | Asp | Asn | Asp | Asn | Ile | Phe | Leu | Ser | Pro | |
| | | | 100 | | | | | 105 | | | | | 110 | | | |
| ctg | agt | atc | tcc | acg | gct | ttt | gct | atg | acc | aag | ctg | ggt | gcc | tgt | aat | 384 |
| Leu | Ser | Ile | Ser | Thr | Ala | Phe | Ala | Met | Thr | Lys | Leu | Gly | Ala | Cys | Asn | |
| | | 115 | | | | | 120 | | | | | 125 | | | | |
| gac | acc | ctc | cag | caa | ctg | atg | gag | gta | ttt | aag | ttt | gac | acc | ata | tct | 432 |
| Asp | Thr | Leu | Gln | Gln | Leu | Met | Glu | Val | Phe | Lys | Phe | Asp | Thr | Ile | Ser | |
| | 130 | | | | | 135 | | | | | 140 | | | | | |
| gag | aaa | aca | tct | gat | cag | atc | cac | ttc | ttc | ttt | gcc | aaa | ctg | aac | tgc | 480 |
| Glu | Lys | Thr | Ser | Asp | Gln | Ile | His | Phe | Phe | Phe | Ala | Lys | Leu | Asn | Cys | |
| 145 | | | | | 150 | | | | | 155 | | | | | 160 | |
| cga | ctc | tat | cga | aaa | gcc | aac | aaa | tcc | tcc | aag | tta | gta | tca | gcc | aat | 528 |
| Arg | Leu | Tyr | Arg | Lys | Ala | Asn | Lys | Ser | Ser | Lys | Leu | Val | Ser | Ala | Asn | |
| | | | | 165 | | | | | 170 | | | | | 175 | | |
| cgc | ctt | ttt | gga | gac | aaa | tcc | ctt | acc | ttc | aat | gag | acc | tac | cag | gac | 576 |
| Arg | Leu | Phe | Gly | Asp | Lys | Ser | Leu | Thr | Phe | Asn | Glu | Thr | Tyr | Gln | Asp | |
| | | | 180 | | | | | 185 | | | | | 190 | | | |
| atc | agt | gag | ttg | gta | tat | gga | gcc | aag | ctc | cag | ccc | ctg | gac | ttc | aag | 624 |
| Ile | Ser | Glu | Leu | Val | Tyr | Gly | Ala | Lys | Leu | Gln | Pro | Leu | Asp | Phe | Lys | |
| | | 195 | | | | | 200 | | | | | 205 | | | | |
| gaa | aat | gca | gag | caa | tcc | aga | gcg | gcc | atc | aac | aaa | tgg | gtg | tcc | aat | 672 |
| Glu | Asn | Ala | Glu | Gln | Ser | Arg | Ala | Ala | Ile | Asn | Lys | Trp | Val | Ser | Asn | |
| | 210 | | | | | 215 | | | | | 220 | | | | | |
| aag | acc | gaa | ggc | cga | atc | acc | gat | gtc | att | ccc | tcg | gaa | gcc | atc | aat | 720 |
| Lys | Thr | Glu | Gly | Arg | Ile | Thr | Asp | Val | Ile | Pro | Ser | Glu | Ala | Ile | Asn | |
| 225 | | | | | 230 | | | | | 235 | | | | | 240 | |
| gag | ctc | act | gtt | ctg | gtg | ctg | gtt | aac | acc | att | tac | ttc | aag | ggc | ctg | 768 |
| Glu | Leu | Thr | Val | Leu | Val | Leu | Val | Asn | Thr | Ile | Tyr | Phe | Lys | Gly | Leu | |
| | | | | 245 | | | | | 250 | | | | | 255 | | |
| tgg | aag | tca | aag | ttc | agc | cct | gag | aac | aca | agg | aag | gaa | ctg | ttc | tac | 816 |
| Trp | Lys | Ser | Lys | Phe | Ser | Pro | Glu | Asn | Thr | Arg | Lys | Glu | Leu | Phe | Tyr | |
| | | | 260 | | | | | 265 | | | | | 270 | | | |
| aag | gct | gat | gga | gag | tcg | tgt | tca | gca | tct | atg | atg | tac | cag | gaa | ggc | 864 |
| Lys | Ala | Asp | Gly | Glu | Ser | Cys | Ser | Ala | Ser | Met | Met | Tyr | Gln | Glu | Gly | |
| | | 275 | | | | | 280 | | | | | 285 | | | | |
| aag | ttc | cgt | tat | cgg | cgc | gtg | gct | gaa | ggc | acc | cag | gtg | ctt | gag | ttg | 912 |
| Lys | Phe | Arg | Tyr | Arg | Arg | Val | Ala | Glu | Gly | Thr | Gln | Val | Leu | Glu | Leu | |
| | 290 | | | | | 295 | | | | | 300 | | | | | |

-continued

| | | |
|---|---|---|
| ccc ttc aaa ggt gat gac atc acc atg gtc ctc atc ttg ccc aag cct<br>Pro Phe Lys Gly Asp Asp Ile Thr Met Val Leu Ile Leu Pro Lys Pro<br>305                310                315                320 | 960 |
| gag aag agc ctg gcc aag gta gag aag gaa ctc acc cca gag gtg ctg<br>Glu Lys Ser Leu Ala Lys Val Glu Lys Glu Leu Thr Pro Glu Val Leu<br>                325                330                335 | 1008 |
| caa gag tgg ctg gat gaa ttg gag gag atg atg ctg gtg gtc cac atg<br>Gln Glu Trp Leu Asp Glu Leu Glu Glu Met Met Leu Val Val His Met<br>           340                345                350 | 1056 |
| ccc cgc ttc cgc att gag gac ggc ttc agt ttg aag gag cag ctg caa<br>Pro Arg Phe Arg Ile Glu Asp Gly Phe Ser Leu Lys Glu Gln Leu Gln<br>                355                360                365 | 1104 |
| gac atg ggc ctt gtc gat ctg ttc agc cct gaa aag tcc aaa ctc cca<br>Asp Met Gly Leu Val Asp Leu Phe Ser Pro Glu Lys Ser Lys Leu Pro<br>370                375                380 | 1152 |
| ggt att gtt gca gaa ggc cga gat gac ctc tat gtc tca gat gca ttc<br>Gly Ile Val Ala Glu Gly Arg Asp Asp Leu Tyr Val Ser Asp Ala Phe<br>385                390                395                400 | 1200 |
| cat aag gca ttt ctt gag gta aat gaa gaa ggc agt gaa gca gct gca<br>His Lys Ala Phe Leu Glu Val Asn Glu Glu Gly Ser Glu Ala Ala Ala<br>           405                410                415 | 1248 |
| agt acc gct gtt gtg att gct ggc cgt cca tcg cta aac ccc aac agg<br>Ser Thr Ala Val Val Ile Ala Gly Arg Pro Ser Leu Asn Pro Asn Arg<br>        420                425                430 | 1296 |
| gtg act ttc aag gcc aac agg cct ttc ctg gtt ttt ata aga gaa gtt<br>Val Thr Phe Lys Ala Asn Arg Pro Phe Leu Val Phe Ile Arg Glu Val<br>435                440                445 | 1344 |
| cct ctg aac act att atc ttc atg ggc aga gta gcc aac cct tgt gtt<br>Pro Leu Asn Thr Ile Ile Phe Met Gly Arg Val Ala Asn Pro Cys Val<br>450                455                460 | 1392 |
| aag taaaatgttc ttattctttg cacctcttcc tattttggt ttgtgaacag<br>Lys<br>465 | 1445 |
| aagtaaaaat aaatacaaac tacttccatc tcacattaaa a | 1486 |

<210> SEQ ID NO 30
<211> LENGTH: 465
<212> TYPE: PRT
<213> ORGANISM: Homo sapiens

<400> SEQUENCE: 30

Met Tyr Ser Asn Val Ile Gly Thr Val Thr Ser Gly Lys Arg Lys Val
1                   5                      10                    15

Tyr Leu Leu Ser Leu Leu Leu Ile Gly Phe Trp Asp Cys Val Thr Cys
                20                      25                    30

His Gly Ser Pro Val Asp Ile Cys Thr Ala Lys Pro Arg Asp Ile Pro
            35                      40                    45

Met Asn Pro Met Cys Ile Tyr Arg Ser Pro Glu Lys Lys Ala Thr Glu
    50                      55                      60

Asp Glu Gly Ser Glu Gln Lys Ile Pro Glu Ala Thr Asn Arg Arg Val
65                    70                      75                    80

Trp Glu Leu Ser Lys Ala Asn Ser Arg Phe Ala Thr Thr Phe Tyr Gln
                85                      90                    95

His Leu Ala Asp Ser Lys Asn Asp Asn Asp Asn Ile Phe Leu Ser Pro
            100                  105                  110

Leu Ser Ile Ser Thr Ala Phe Ala Met Thr Lys Leu Gly Ala Cys Asn
        115                  120                  125

Asp Thr Leu Gln Gln Leu Met Glu Val Phe Lys Phe Asp Thr Ile Ser

```
                130                 135                 140
Glu Lys Thr Ser Asp Gln Ile His Phe Phe Ala Lys Leu Asn Cys
145                 150                 155                 160

Arg Leu Tyr Arg Lys Ala Asn Lys Ser Ser Lys Leu Val Ser Ala Asn
                165                 170                 175

Arg Leu Phe Gly Asp Lys Ser Leu Thr Phe Asn Glu Thr Tyr Gln Asp
                180                 185                 190

Ile Ser Glu Leu Val Tyr Gly Ala Lys Leu Gln Pro Leu Asp Phe Lys
                195                 200                 205

Glu Asn Ala Glu Gln Ser Arg Ala Ala Ile Asn Lys Trp Val Ser Asn
210                 215                 220

Lys Thr Glu Gly Arg Ile Thr Asp Val Ile Pro Ser Glu Ala Ile Asn
225                 230                 235                 240

Glu Leu Thr Val Leu Val Leu Val Asn Thr Ile Tyr Phe Lys Gly Leu
                245                 250                 255

Trp Lys Ser Lys Phe Ser Pro Glu Asn Thr Arg Lys Glu Leu Phe Tyr
                260                 265                 270

Lys Ala Asp Gly Glu Ser Cys Ser Ala Ser Met Met Tyr Gln Glu Gly
                275                 280                 285

Lys Phe Arg Tyr Arg Arg Val Ala Glu Gly Thr Gln Val Leu Glu Leu
                290                 295                 300

Pro Phe Lys Gly Asp Asp Ile Thr Met Val Leu Ile Leu Pro Lys Pro
305                 310                 315                 320

Glu Lys Ser Leu Ala Lys Val Glu Lys Glu Leu Thr Pro Glu Val Leu
                325                 330                 335

Gln Glu Trp Leu Asp Glu Leu Glu Glu Met Met Leu Val Val His Met
                340                 345                 350

Pro Arg Phe Arg Ile Glu Asp Gly Phe Ser Leu Lys Glu Gln Leu Gln
                355                 360                 365

Asp Met Gly Leu Val Asp Leu Phe Ser Pro Glu Lys Ser Lys Leu Pro
370                 375                 380

Gly Ile Val Ala Glu Gly Arg Asp Asp Leu Tyr Val Ser Asp Ala Phe
385                 390                 395                 400

His Lys Ala Phe Leu Glu Val Asn Glu Glu Gly Ser Glu Ala Ala Ala
                405                 410                 415

Ser Thr Ala Val Val Ile Ala Gly Arg Pro Ser Leu Asn Pro Asn Arg
                420                 425                 430

Val Thr Phe Lys Ala Asn Arg Pro Phe Leu Val Phe Ile Arg Glu Val
                435                 440                 445

Pro Leu Asn Thr Ile Ile Phe Met Gly Arg Val Ala Asn Pro Cys Val
                450                 455                 460

Lys
465

<210> SEQ ID NO 31
<211> LENGTH: 1480
<212> TYPE: DNA
<213> ORGANISM: Homo sapiens
<220> FEATURE:
<221> NAME/KEY: CDS
<222> LOCATION: (1)..(1389)

<400> SEQUENCE: 31 atg tat tcc aat gtg ata gga act gta acc tct gga aaa agg aag gtt    48
Met Tyr Ser Asn Val Ile Gly Thr Val Thr Ser Gly Lys Arg Lys Val
1               5                   10                  15
```

-continued

| | | |
|---|---|---|
| tat ctt ttg tcc ttg ctg ctc att ggc ttc tgg gac tgc gtg acc tgt<br>Tyr Leu Leu Ser Leu Leu Leu Ile Gly Phe Trp Asp Cys Val Thr Cys<br>              20                       25                  30 | 96 |
| cac ggg agc cct gtg gac atc tgc aca gcc aag ccg cgg gac att ccc<br>His Gly Ser Pro Val Asp Ile Cys Thr Ala Lys Pro Arg Asp Ile Pro<br>     35                      40                    45 | 144 |
| atg aat ccc atg tgc att tac cgc tcc ccg gag aag aag gca act gag<br>Met Asn Pro Met Cys Ile Tyr Arg Ser Pro Glu Lys Lys Ala Thr Glu<br>50                     55                    60 | 192 |
| gat gag ggc tca gaa cag aag atc ccg gag gcc acc aac cgg cgt gtc<br>Asp Glu Gly Ser Glu Gln Lys Ile Pro Glu Ala Thr Asn Arg Arg Val<br>65                     70                    75                  80 | 240 |
| tgg gaa ctg tcc aag gcc aat tcc cgc ttt gct acc act ttc tat cag<br>Trp Glu Leu Ser Lys Ala Asn Ser Arg Phe Ala Thr Thr Phe Tyr Gln<br>              85                       90                  95 | 288 |
| cac ctg gca gat tcc aag aat gac aat gat aac att ttc ctg tca ccc<br>His Leu Ala Asp Ser Lys Asn Asp Asn Asp Asn Ile Phe Leu Ser Pro<br>                    100                    105                110 | 336 |
| ctg agt atc tcc acg gct ttt gct atg acc aag ctg ggt gcc tgt aat<br>Leu Ser Ile Ser Thr Ala Phe Ala Met Thr Lys Leu Gly Ala Cys Asn<br>          115                    120                    125 | 384 |
| gac acc ctc cag caa ctg atg gag gta ttt aag ttt gac acc ata tct<br>Asp Thr Leu Gln Gln Leu Met Glu Val Phe Lys Phe Asp Thr Ile Ser<br>130                     135                    140 | 432 |
| gag aaa aca tct gat cag atc cac ttc ttc ttt gcc aaa ctg aac tgc<br>Glu Lys Thr Ser Asp Gln Ile His Phe Phe Phe Ala Lys Leu Asn Cys<br>145                     150                    155                160 | 480 |
| cga ctc tat cga aaa gcc aac aaa tcc tcc aag tta gta tca gcc aat<br>Arg Leu Tyr Arg Lys Ala Asn Lys Ser Ser Lys Leu Val Ser Ala Asn<br>                  165                    170                    175 | 528 |
| cgc ctt ttt gga gac aaa tcc ctt acc ttc aat gag acc tac cag gac<br>Arg Leu Phe Gly Asp Lys Ser Leu Thr Phe Asn Glu Thr Tyr Gln Asp<br>              180                    185                    190 | 576 |
| atc agt gag ttg gta tat gga gcc aag ctc cag ccc ctg gac ttc aag<br>Ile Ser Glu Leu Val Tyr Gly Ala Lys Leu Gln Pro Leu Asp Phe Lys<br>          195                    200                    205 | 624 |
| gaa aat gca gag caa tcc aga gcg gcc atc aac aaa tgg gtg tcc aat<br>Glu Asn Ala Glu Gln Ser Arg Ala Ala Ile Asn Lys Trp Val Ser Asn<br>210                     215                    220 | 672 |
| aag acc gaa ggc cga atc acc gat gtc att ccc tcg gaa gcc atc aat<br>Lys Thr Glu Gly Arg Ile Thr Asp Val Ile Pro Ser Glu Ala Ile Asn<br>225                     230                    235                240 | 720 |
| gag ctc act gtt ctg gtg ctg gtt aac acc att tac ttc aag ggc ctg<br>Glu Leu Thr Val Leu Val Leu Val Asn Thr Ile Tyr Phe Lys Gly Leu<br>              245                    250                    255 | 768 |
| tgg aag tca aag ttc agc cct gag aac aca agg aag gaa ctg ttc tac<br>Trp Lys Ser Lys Phe Ser Pro Glu Asn Thr Arg Lys Glu Leu Phe Tyr<br>          260                    265                    270 | 816 |
| aag gct gat gga gag tcg tgt tca gca tct atg atg tac cag gaa ggc<br>Lys Ala Asp Gly Glu Ser Cys Ser Ala Ser Met Met Tyr Gln Glu Gly<br>          275                    280                    285 | 864 |
| aag ttc cgt tat cgg cgc gtg gct gaa ggc acc cag gtg ctt gag ttg<br>Lys Phe Arg Tyr Arg Arg Val Ala Glu Gly Thr Gln Val Leu Glu Leu<br>          290                    295                    300 | 912 |
| ccc ttc aaa ggt gat gac atc acc atg gtc ctc atc ttg ccc aag cct<br>Pro Phe Lys Gly Asp Asp Ile Thr Met Val Leu Ile Leu Pro Lys Pro<br>305                     310                    315                320 | 960 |
| gag aag agc ctg gcc aag gta gag aag gaa ctc acc cca gag gtg ctg<br>Glu Lys Ser Leu Ala Lys Val Glu Lys Glu Leu Thr Pro Glu Val Leu | 1008 |

-continued

```
              325                 330                 335
caa gag tgg ctg gat gaa ttg gag gag atg atg ctg gtg gtc cac atg      1056
Gln Glu Trp Leu Asp Glu Leu Glu Glu Met Met Leu Val Val His Met
            340                 345                 350 ccc cgc ttc cgc att gag gac ggc ttc agt ttg aag gag cag ctg caa      1104
Pro Arg Phe Arg Ile Glu Asp Gly Phe Ser Leu Lys Glu Gln Leu Gln
        355                 360                 365 gac atg ggc ctt gtc gat ctg ttc agc cct gaa aag tcc aaa ctc cca      1152
Asp Met Gly Leu Val Asp Leu Phe Ser Pro Glu Lys Ser Lys Leu Pro
    370                 375                 380 ggt att gtt gca gaa ggc cga gat gac ctc tat gtc tca gat gca ttc      1200
Gly Ile Val Ala Glu Gly Arg Asp Asp Leu Tyr Val Ser Asp Ala Phe
385                 390                 395                 400 cat aag gca ttt ctt gag gta aat gaa gaa ggc agt gaa gca gct gca      1248
His Lys Ala Phe Leu Glu Val Asn Glu Glu Gly Ser Glu Ala Ala Ala
                405                 410                 415 agt acc gct gtt gtg att gct ggc tcg cta aac ccc aac agg gtg act      1296
Ser Thr Ala Val Val Ile Ala Gly Ser Leu Asn Pro Asn Arg Val Thr
            420                 425                 430 ttc aag gcc aac agg cct ttc ctg gtt ttt ata aga gaa gtt cct ctg      1344
Phe Lys Ala Asn Arg Pro Phe Leu Val Phe Ile Arg Glu Val Pro Leu
        435                 440                 445 aac act att atc ttc atg ggc aga gta gcc aac cct tgt gtt aag          1389
Asn Thr Ile Ile Phe Met Gly Arg Val Ala Asn Pro Cys Val Lys
    450                 455                 460 taaaatgttc ttattctttg cacctcttcc tatttttggt ttgtgaacag aagtaaaaat    1449
aaatacaaac tacttccatc tcacattaaa a                                   1480

<210> SEQ ID NO 32
<211> LENGTH: 463
<212> TYPE: PRT
<213> ORGANISM: Homo sapiens

<400> SEQUENCE: 32

Met Tyr Ser Asn Val Ile Gly Thr Val Thr Ser Gly Lys Arg Lys Val
1               5                   10                  15

Tyr Leu Leu Ser Leu Leu Leu Ile Gly Phe Trp Asp Cys Val Thr Cys
            20                  25                  30

His Gly Ser Pro Val Asp Ile Cys Thr Ala Lys Pro Arg Asp Ile Pro
        35                  40                  45

Met Asn Pro Met Cys Ile Tyr Arg Ser Pro Glu Lys Lys Ala Thr Glu
    50                  55                  60

Asp Glu Gly Ser Glu Gln Lys Ile Pro Glu Ala Thr Asn Arg Arg Val
65                  70                  75                  80

Trp Glu Leu Ser Lys Ala Asn Ser Arg Phe Ala Thr Thr Phe Tyr Gln
                85                  90                  95

His Leu Ala Asp Ser Lys Asn Asp Asn Asp Asn Ile Phe Leu Ser Pro
            100                 105                 110

Leu Ser Ile Ser Thr Ala Phe Ala Met Thr Lys Leu Gly Ala Cys Asn
        115                 120                 125

Asp Thr Leu Gln Gln Leu Met Glu Val Phe Lys Phe Asp Thr Ile Ser
    130                 135                 140

Glu Lys Thr Ser Asp Gln Ile His Phe Phe Phe Ala Lys Leu Asn Cys
145                 150                 155                 160

Arg Leu Tyr Arg Lys Ala Asn Lys Ser Ser Lys Leu Val Ser Ala Asn
                165                 170                 175
```

```
Arg Leu Phe Gly Asp Lys Ser Leu Thr Phe Asn Glu Thr Tyr Gln Asp
                180                 185                 190

Ile Ser Glu Leu Val Tyr Gly Ala Lys Leu Gln Pro Leu Asp Phe Lys
            195                 200                 205

Glu Asn Ala Glu Gln Ser Arg Ala Ala Ile Asn Lys Trp Val Ser Asn
        210                 215                 220

Lys Thr Glu Gly Arg Ile Thr Asp Val Ile Pro Ser Glu Ala Ile Asn
225                 230                 235                 240

Glu Leu Thr Val Leu Val Leu Asn Thr Ile Tyr Phe Lys Gly Leu
                245                 250                 255

Trp Lys Ser Lys Phe Ser Pro Glu Asn Thr Arg Lys Glu Leu Phe Tyr
            260                 265                 270

Lys Ala Asp Gly Glu Ser Cys Ser Ala Ser Met Met Tyr Gln Glu Gly
        275                 280                 285

Lys Phe Arg Tyr Arg Arg Val Ala Glu Gly Thr Gln Val Leu Glu Leu
        290                 295                 300

Pro Phe Lys Gly Asp Asp Ile Thr Met Val Leu Ile Leu Pro Lys Pro
305                 310                 315                 320

Glu Lys Ser Leu Ala Lys Val Glu Lys Glu Leu Thr Pro Glu Val Leu
                325                 330                 335

Gln Glu Trp Leu Asp Glu Leu Glu Glu Met Met Leu Val Val His Met
            340                 345                 350

Pro Arg Phe Arg Ile Glu Asp Gly Phe Ser Leu Lys Glu Gln Leu Gln
        355                 360                 365

Asp Met Gly Leu Val Asp Leu Phe Ser Pro Glu Lys Ser Lys Leu Pro
        370                 375                 380

Gly Ile Val Ala Glu Gly Arg Asp Asp Leu Tyr Val Ser Asp Ala Phe
385                 390                 395                 400

His Lys Ala Phe Leu Glu Val Asn Glu Glu Gly Ser Glu Ala Ala Ala
                405                 410                 415

Ser Thr Ala Val Val Ile Ala Gly Ser Leu Asn Pro Asn Arg Val Thr
            420                 425                 430

Phe Lys Ala Asn Arg Pro Phe Leu Val Phe Ile Arg Glu Val Pro Leu
        435                 440                 445

Asn Thr Ile Ile Phe Met Gly Arg Val Ala Asn Pro Cys Val Lys
        450                 455                 460

<210> SEQ ID NO 33
<211> LENGTH: 1480
<212> TYPE: DNA
<213> ORGANISM: Homo sapiens
<220> FEATURE:
<221> NAME/KEY: CDS
<222> LOCATION: (1)..(1389)

<400> SEQUENCE: 33 atg tat tcc aat gtg ata gga act gta acc tct gga aaa agg aag gtt      48
Met Tyr Ser Asn Val Ile Gly Thr Val Thr Ser Gly Lys Arg Lys Val
1               5                   10                  15 tat ctt ttg tcc ttg ctg ctc att ggc ttc tgg gac tgc gtg acc tgt      96
Tyr Leu Leu Ser Leu Leu Leu Ile Gly Phe Trp Asp Cys Val Thr Cys
                20                  25                  30 cac ggg agc cct gtg gac atc tgc aca gcc aag ccg cgg gac att ccc     144
His Gly Ser Pro Val Asp Ile Cys Thr Ala Lys Pro Arg Asp Ile Pro
            35                  40                  45 atg aat ccc atg tgc att tac cgc tcc ccg gag aag aag gca act gag     192
Met Asn Pro Met Cys Ile Tyr Arg Ser Pro Glu Lys Lys Ala Thr Glu
```

-continued

```
            50                  55                  60
gat gag ggc tca gaa cag aag atc ccg gag gcc acc aac cgg cgt gtc       240
Asp Glu Gly Ser Glu Gln Lys Ile Pro Glu Ala Thr Asn Arg Arg Val
 65                  70                  75                  80 tgg gaa ctg tcc aag gcc aat tcc cgc ttt gct acc act ttc tat cag       288
Trp Glu Leu Ser Lys Ala Asn Ser Arg Phe Ala Thr Thr Phe Tyr Gln
                 85                  90                  95 cac ctg gca gat tcc aag aat gac aat gat aac att ttc ctg tca ccc       336
His Leu Ala Asp Ser Lys Asn Asp Asn Asp Asn Ile Phe Leu Ser Pro
            100                 105                 110 ctg agt atc tcc acg gct ttt gct atg acc aag ctg ggt gcc tgt aat       384
Leu Ser Ile Ser Thr Ala Phe Ala Met Thr Lys Leu Gly Ala Cys Asn
        115                 120                 125 gac acc ctc cag caa ctg atg gag gta ttt aag ttt gac acc ata tct       432
Asp Thr Leu Gln Gln Leu Met Glu Val Phe Lys Phe Asp Thr Ile Ser
    130                 135                 140 gag aaa aca tct gat cag atc cac ttc ttc ttt gcc aaa ctg aac tgc       480
Glu Lys Thr Ser Asp Gln Ile His Phe Phe Phe Ala Lys Leu Asn Cys
145                 150                 155                 160 cga ctc tat cga aaa gcc aac aaa tcc tcc aag tta gta tca gcc aat       528
Arg Leu Tyr Arg Lys Ala Asn Lys Ser Ser Lys Leu Val Ser Ala Asn
                165                 170                 175 cgc ctt ttt gga gac aaa tcc ctt acc ttc aat gag acc tac cag gac       576
Arg Leu Phe Gly Asp Lys Ser Leu Thr Phe Asn Glu Thr Tyr Gln Asp
            180                 185                 190 atc agt gag ttg gta tat gga gcc aag ctc cag ccc ctg gac ttc aag       624
Ile Ser Glu Leu Val Tyr Gly Ala Lys Leu Gln Pro Leu Asp Phe Lys
        195                 200                 205 gaa aat gca gag caa tcc aga gcg gcc atc aac aaa tgg gtg tcc aat       672
Glu Asn Ala Glu Gln Ser Arg Ala Ala Ile Asn Lys Trp Val Ser Asn
    210                 215                 220 aag acc gaa ggc cga atc acc gat gtc att ccc tcg gaa gcc atc aat       720
Lys Thr Glu Gly Arg Ile Thr Asp Val Ile Pro Ser Glu Ala Ile Asn
225                 230                 235                 240 gag ctc act gtt ctg gtg ctg gtt aac acc att tac ttc aag ggc ctg       768
Glu Leu Thr Val Leu Val Leu Val Asn Thr Ile Tyr Phe Lys Gly Leu
                245                 250                 255 tgg aag tca aag ttc agc cct gag aac aca agg aag gaa ctg ttc tac       816
Trp Lys Ser Lys Phe Ser Pro Glu Asn Thr Arg Lys Glu Leu Phe Tyr
            260                 265                 270 aag gct gat gga gag tcg tgt tca gca tct atg atg tac cag gaa ggc       864
Lys Ala Asp Gly Glu Ser Cys Ser Ala Ser Met Met Tyr Gln Glu Gly
        275                 280                 285 aag ttc cgt tat cgg cgc gtg gct gaa ggc acc cag gtg ctt gag ttg       912
Lys Phe Arg Tyr Arg Arg Val Ala Glu Gly Thr Gln Val Leu Glu Leu
    290                 295                 300 ccc ttc aaa ggt gat gac atc acc atg gtc ctc atc ttg ccc aag cct       960
Pro Phe Lys Gly Asp Asp Ile Thr Met Val Leu Ile Leu Pro Lys Pro
305                 310                 315                 320 gag aag agc ctg gcc aag gta gag aag gaa ctc acc cca gag gtg ctg      1008
Glu Lys Ser Leu Ala Lys Val Glu Lys Glu Leu Thr Pro Glu Val Leu
                325                 330                 335 caa gag tgg ctg gat gaa ttg gag gag atg atg ctg gtg gtc cac atg      1056
Gln Glu Trp Leu Asp Glu Leu Glu Glu Met Met Leu Val Val His Met
            340                 345                 350 ccc cgc ttc cgc att gag gac ggc ttc agt ttg aag gag cag ctg caa      1104
Pro Arg Phe Arg Ile Glu Asp Gly Phe Ser Leu Lys Glu Gln Leu Gln
        355                 360                 365 gac atg ggc ctt gtc gat ctg ttc agc cct gaa aag tcc aaa ctc cca      1152
Asp Met Gly Leu Val Asp Leu Phe Ser Pro Glu Lys Ser Lys Leu Pro
```

```
              Asp Met Gly Leu Val Asp Leu Phe Ser Pro Glu Lys Ser Lys Leu Pro
                  370                 375                 380 ggt att gtt gca gaa ggc cga gat gac ctc tat gtc tca gat gca ttc          1200
Gly Ile Val Ala Glu Gly Arg Asp Asp Leu Tyr Val Ser Asp Ala Phe
385                 390                 395                 400 cat aag gca ttt ctt gag gta aat gaa gaa ggc agt gaa gca gct gca          1248
His Lys Ala Phe Leu Glu Val Asn Glu Glu Gly Ser Glu Ala Ala Ala
                405                 410                 415 agt acc gct gtt gtg att gct ggc cgt cta aac ccc aac agg gtg act          1296
Ser Thr Ala Val Val Ile Ala Gly Arg Leu Asn Pro Asn Arg Val Thr
            420                 425                 430 ttc aag gcc aac agg cct ttc ctg gtt ttt ata aga gaa gtt cct ctg          1344
Phe Lys Ala Asn Arg Pro Phe Leu Val Phe Ile Arg Glu Val Pro Leu
        435                 440                 445 aac act att atc ttc atg ggc aga gta gcc aac cct tgt gtt aag              1389
Asn Thr Ile Ile Phe Met Gly Arg Val Ala Asn Pro Cys Val Lys
    450                 455                 460 taaaatgttc ttattctttg cacctcttcc tattttggt ttgtgaacag aagtaaaaat         1449
aaatacaaac tacttccatc tcacattaaa a                                       1480

<210> SEQ ID NO 34
<211> LENGTH: 463
<212> TYPE: PRT
<213> ORGANISM: Homo sapiens

<400> SEQUENCE: 34

Met Tyr Ser Asn Val Ile Gly Thr Val Thr Ser Gly Lys Arg Lys Val
1               5                   10                  15

Tyr Leu Leu Ser Leu Leu Leu Ile Gly Phe Trp Asp Cys Val Thr Cys
                20                  25                  30

His Gly Ser Pro Val Asp Ile Cys Thr Ala Lys Pro Arg Asp Ile Pro
            35                  40                  45

Met Asn Pro Met Cys Ile Tyr Arg Ser Pro Glu Lys Lys Ala Thr Glu
        50                  55                  60

Asp Glu Gly Ser Glu Gln Lys Ile Pro Glu Ala Thr Asn Arg Arg Val
65                  70                  75                  80

Trp Glu Leu Ser Lys Ala Asn Ser Arg Phe Ala Thr Thr Phe Tyr Gln
                85                  90                  95

His Leu Ala Asp Ser Lys Asn Asp Asn Asp Asn Ile Phe Leu Ser Pro
            100                 105                 110

Leu Ser Ile Ser Thr Ala Phe Ala Met Thr Lys Leu Gly Ala Cys Asn
        115                 120                 125

Asp Thr Leu Gln Gln Leu Met Glu Val Phe Lys Phe Asp Thr Ile Ser
    130                 135                 140

Glu Lys Thr Ser Asp Gln Ile His Phe Phe Ala Lys Leu Asn Cys
145                 150                 155                 160

Arg Leu Tyr Arg Lys Ala Asn Lys Ser Ser Lys Leu Val Ser Ala Asn
                165                 170                 175

Arg Leu Phe Gly Asp Lys Ser Leu Thr Phe Asn Glu Thr Tyr Gln Asp
            180                 185                 190

Ile Ser Glu Leu Val Tyr Gly Ala Lys Leu Gln Pro Leu Asp Phe Lys
        195                 200                 205

Glu Asn Ala Glu Gln Ser Arg Ala Ala Ile Asn Lys Trp Val Ser Asn
    210                 215                 220

Lys Thr Glu Gly Arg Ile Thr Asp Val Ile Pro Ser Glu Ala Ile Asn
225                 230                 235                 240
```

```
Glu Leu Thr Val Leu Val Leu Val Asn Thr Ile Tyr Phe Lys Gly Leu
                245                 250                 255

Trp Lys Ser Lys Phe Ser Pro Glu Asn Thr Arg Lys Glu Leu Phe Tyr
            260                 265                 270

Lys Ala Asp Gly Glu Ser Cys Ser Ala Ser Met Met Tyr Gln Glu Gly
            275                 280                 285

Lys Phe Arg Tyr Arg Val Ala Glu Gly Thr Gln Val Leu Glu Leu
    290                 295                 300

Pro Phe Lys Gly Asp Asp Ile Thr Met Val Leu Ile Leu Pro Lys Pro
305                 310                 315                 320

Glu Lys Ser Leu Ala Lys Val Glu Lys Glu Leu Thr Pro Glu Val Leu
                325                 330                 335

Gln Glu Trp Leu Asp Glu Leu Glu Glu Met Met Leu Val Val His Met
                340                 345                 350

Pro Arg Phe Arg Ile Glu Asp Gly Phe Ser Leu Lys Glu Gln Leu Gln
                355                 360                 365

Asp Met Gly Leu Val Asp Leu Phe Ser Pro Glu Lys Ser Lys Leu Pro
    370                 375                 380

Gly Ile Val Ala Glu Gly Arg Asp Asp Leu Tyr Val Ser Asp Ala Phe
385                 390                 395                 400

His Lys Ala Phe Leu Glu Val Asn Glu Glu Gly Ser Glu Ala Ala Ala
                405                 410                 415

Ser Thr Ala Val Val Ile Ala Gly Arg Leu Asn Pro Asn Arg Val Thr
            420                 425                 430

Phe Lys Ala Asn Arg Pro Phe Leu Val Phe Ile Arg Glu Val Pro Leu
        435                 440                 445

Asn Thr Ile Ile Phe Met Gly Arg Val Ala Asn Pro Cys Val Lys
    450                 455                 460

<210> SEQ ID NO 35
<211> LENGTH: 1483
<212> TYPE: DNA
<213> ORGANISM: Homo sapiens
<220> FEATURE:
<221> NAME/KEY: CDS
<222> LOCATION: (1)..(1392)

<400> SEQUENCE: 35 atg tat tcc aat gtg ata gga act gta acc tct gga aaa agg aag gtt      48
Met Tyr Ser Asn Val Ile Gly Thr Val Thr Ser Gly Lys Arg Lys Val
1               5                   10                  15 tat ctt ttg tcc ttg ctg ctc att ggc ttc tgg gac tgc gtg acc tgt      96
Tyr Leu Leu Ser Leu Leu Leu Ile Gly Phe Trp Asp Cys Val Thr Cys
            20                  25                  30 cac ggg agc cct gtg gac atc tgc aca gcc aag ccg cgg gac att ccc     144
His Gly Ser Pro Val Asp Ile Cys Thr Ala Lys Pro Arg Asp Ile Pro
        35                  40                  45 atg aat ccc atg tgc att tac cgc tcc ccg gag aag aag gca act gag     192
Met Asn Pro Met Cys Ile Tyr Arg Ser Pro Glu Lys Lys Ala Thr Glu
    50                  55                  60 gat gag ggc tca gaa cag aag atc ccg gag gcc acc aac cgg gtg tc     240
Asp Glu Gly Ser Glu Gln Lys Ile Pro Glu Ala Thr Asn Arg Val
65                  70                  75                  80 tgg gaa ctg tcc aag gcc aat tcc cgc ttt gct acc act ttc tat cag     288
Trp Glu Leu Ser Lys Ala Asn Ser Arg Phe Ala Thr Thr Phe Tyr Gln
            85                  90                  95 cac ctg gca gat tcc aag aat gac aat gat aac att ttc ctg tca ccc     336
```

|     |     |     |     |     |     |     |     |     |     |     |     |     |     |
|---|---|---|---|---|---|---|---|---|---|---|---|---|---|
| His | Leu | Ala | Asp | Ser | Lys | Asn | Asp | Asn | Asp | Asn | Ile | Phe | Leu | Ser | Pro |
|     |     |     | 100 |     |     |     | 105 |     |     |     | 110 |     |     |

```
ctg agt atc tcc acg gct ttt gct atg acc aag ctg ggt gcc tgt aat    384
Leu Ser Ile Ser Thr Ala Phe Ala Met Thr Lys Leu Gly Ala Cys Asn
        115                 120                 125 gac acc ctc cag caa ctg atg gag gta ttt aag ttt gac acc ata tct    432
Asp Thr Leu Gln Gln Leu Met Glu Val Phe Lys Phe Asp Thr Ile Ser
130                 135                 140 gag aaa aca tct gat cag atc cac ttc ttc ttt gcc aaa ctg aac tgc    480
Glu Lys Thr Ser Asp Gln Ile His Phe Phe Phe Ala Lys Leu Asn Cys
145                 150                 155                 160 cga ctc tat cga aaa gcc cag aaa tcc tcc aag tta gta tca gcc aat    528
Arg Leu Tyr Arg Lys Ala Gln Lys Ser Ser Lys Leu Val Ser Ala Asn
        165                 170                 175 cgc ctt ttt gga gac aaa tcc ctt acc ttc aat gag acc tac cag gac    576
Arg Leu Phe Gly Asp Lys Ser Leu Thr Phe Asn Glu Thr Tyr Gln Asp
        180                 185                 190 atc agt gag ttg gta tat gga gcc aag ctc cag ccc ctg gac ttc aag    624
Ile Ser Glu Leu Val Tyr Gly Ala Lys Leu Gln Pro Leu Asp Phe Lys
        195                 200                 205 gaa aat gca gag caa tcc aga gcg gcc atc aac aaa tgg gtg tcc aat    672
Glu Asn Ala Glu Gln Ser Arg Ala Ala Ile Asn Lys Trp Val Ser Asn
210                 215                 220 aag acc gaa ggc cga atc acc gat gtc att ccc tcg gaa gcc atc aat    720
Lys Thr Glu Gly Arg Ile Thr Asp Val Ile Pro Ser Glu Ala Ile Asn
225                 230                 235                 240 gag ctc act gtt ctg gtg ctg gtt aac acc att tac ttc aag ggc ctg    768
Glu Leu Thr Val Leu Val Leu Val Asn Thr Ile Tyr Phe Lys Gly Leu
        245                 250                 255 tgg aag tca aag ttc agc cct gag aac aca agg aag gaa ctg ttc tac    816
Trp Lys Ser Lys Phe Ser Pro Glu Asn Thr Arg Lys Glu Leu Phe Tyr
        260                 265                 270 aag gct gat gga gag tcg tgt tca gca tct atg atg tac cag gaa ggc    864
Lys Ala Asp Gly Glu Ser Cys Ser Ala Ser Met Met Tyr Gln Glu Gly
        275                 280                 285 aag ttc cgt tat cgg cgc gtg gct gaa ggc acc cag gtg ctt gag ttg    912
Lys Phe Arg Tyr Arg Arg Val Ala Glu Gly Thr Gln Val Leu Glu Leu
        290                 295                 300 ccc ttc aaa ggt gat gac atc acc atg gtc ctc atc ttg ccc aag cct    960
Pro Phe Lys Gly Asp Asp Ile Thr Met Val Leu Ile Leu Pro Lys Pro
305                 310                 315                 320 gag aag agc ctg gcc aag gta gag aag gaa ctc acc cca gag gtg ctg   1008
Glu Lys Ser Leu Ala Lys Val Glu Lys Glu Leu Thr Pro Glu Val Leu
        325                 330                 335 caa gag tgg ctg gat gaa ttg gag gag atg atg ctg gtg gtc cac atg   1056
Gln Glu Trp Leu Asp Glu Leu Glu Glu Met Met Leu Val Val His Met
        340                 345                 350 ccc cgc ttc cgc att gag gac ggc ttc agt ttg aag gag cag ctg caa   1104
Pro Arg Phe Arg Ile Glu Asp Gly Phe Ser Leu Lys Glu Gln Leu Gln
        355                 360                 365 gac atg ggc ctt gtc gat ctg ttc agc cct gaa aag tcc aaa ctc cca   1152
Asp Met Gly Leu Val Asp Leu Phe Ser Pro Glu Lys Ser Lys Leu Pro
        370                 375                 380 ggt att gtt gca gaa ggc cga gat gac ctc tat gtc tca gat gca ttc   1200
Gly Ile Val Ala Glu Gly Arg Asp Asp Leu Tyr Val Ser Asp Ala Phe
385                 390                 395                 400 cat aag gca ttt ctt gag gta aat gaa gaa ggc agt gaa gca gct gca   1248
His Lys Ala Phe Leu Glu Val Asn Glu Glu Gly Ser Glu Ala Ala Ala
        405                 410                 415
```

-continued

```
agt acc gct gtt gtg att gct ggc cgt tcg cta aac ccc aac agg gtg      1296
Ser Thr Ala Val Val Ile Ala Gly Arg Ser Leu Asn Pro Asn Arg Val
            420                 425                 430 act ttc aag gcc aac agg cct ttc ctg gtt ttt ata aga gaa gtt cct      1344
Thr Phe Lys Ala Asn Arg Pro Phe Leu Val Phe Ile Arg Glu Val Pro
            435                 440                 445 ctg aac act att atc ttc atg ggc aga gta gcc aac cct tgt gtt aag      1392
Leu Asn Thr Ile Ile Phe Met Gly Arg Val Ala Asn Pro Cys Val Lys
            450                 455                 460 taaaatgttc ttattctttg cacctcttcc tattttggt ttgtgaacag aagtaaaaat      1452
aaatacaaac tacttccatc tcacattaaa a                                    1483

<210> SEQ ID NO 36
<211> LENGTH: 464
<212> TYPE: PRT
<213> ORGANISM: Homo sapiens

<400> SEQUENCE: 36

Met Tyr Ser Asn Val Ile Gly Thr Val Thr Ser Gly Lys Arg Lys Val
1               5                   10                  15

Tyr Leu Leu Ser Leu Leu Leu Ile Gly Phe Trp Asp Cys Val Thr Cys
            20                  25                  30

His Gly Ser Pro Val Asp Ile Cys Thr Ala Lys Pro Arg Asp Ile Pro
        35                  40                  45

Met Asn Pro Met Cys Ile Tyr Arg Ser Pro Glu Lys Lys Ala Thr Glu
    50                  55                  60

Asp Glu Gly Ser Glu Gln Lys Ile Pro Glu Ala Thr Asn Arg Arg Val
65                  70                  75                  80

Trp Glu Leu Ser Lys Ala Asn Ser Arg Phe Ala Thr Thr Phe Tyr Gln
                85                  90                  95

His Leu Ala Asp Ser Lys Asn Asp Asn Asp Asn Ile Phe Leu Ser Pro
            100                 105                 110

Leu Ser Ile Ser Thr Ala Phe Ala Met Thr Lys Leu Gly Ala Cys Asn
        115                 120                 125

Asp Thr Leu Gln Gln Leu Met Glu Val Phe Lys Phe Asp Thr Ile Ser
    130                 135                 140

Glu Lys Thr Ser Asp Gln Ile His Phe Phe Ala Lys Leu Asn Cys
145                 150                 155                 160

Arg Leu Tyr Arg Lys Ala Gln Lys Ser Ser Lys Leu Val Ser Ala Asn
                165                 170                 175

Arg Leu Phe Gly Asp Lys Ser Leu Thr Phe Asn Glu Thr Tyr Gln Asp
            180                 185                 190

Ile Ser Glu Leu Val Tyr Gly Ala Lys Leu Gln Pro Leu Asp Phe Lys
        195                 200                 205

Glu Asn Ala Glu Gln Ser Arg Ala Ala Ile Asn Lys Trp Val Ser Asn
    210                 215                 220

Lys Thr Glu Gly Arg Ile Thr Asp Val Ile Pro Ser Glu Ala Ile Asn
225                 230                 235                 240

Glu Leu Thr Val Leu Val Leu Val Asn Thr Ile Tyr Phe Lys Gly Leu
                245                 250                 255

Trp Lys Ser Lys Phe Ser Pro Glu Asn Thr Arg Lys Glu Leu Phe Tyr
            260                 265                 270

Lys Ala Asp Gly Glu Ser Cys Ser Ala Ser Met Met Tyr Gln Glu Gly
        275                 280                 285

Lys Phe Arg Tyr Arg Arg Val Ala Glu Gly Thr Gln Val Leu Glu Leu
```

```
                    290                 295                 300
Pro Phe Lys Gly Asp Asp Ile Thr Met Val Leu Ile Leu Pro Lys Pro
305                 310                 315                 320

Glu Lys Ser Leu Ala Lys Val Glu Lys Glu Leu Thr Pro Glu Val Leu
                325                 330                 335

Gln Glu Trp Leu Asp Glu Leu Glu Glu Met Met Leu Val Val His Met
                340                 345                 350

Pro Arg Phe Arg Ile Glu Asp Gly Phe Ser Leu Lys Glu Gln Leu Gln
                355                 360                 365

Asp Met Gly Leu Val Asp Leu Phe Ser Pro Glu Lys Ser Lys Leu Pro
            370                 375                 380

Gly Ile Val Ala Glu Gly Arg Asp Asp Leu Tyr Val Ser Asp Ala Phe
385                 390                 395                 400

His Lys Ala Phe Leu Glu Val Asn Glu Glu Gly Ser Glu Ala Ala Ala
                405                 410                 415

Ser Thr Ala Val Val Ile Ala Gly Arg Ser Leu Asn Pro Asn Arg Val
                420                 425                 430

Thr Phe Lys Ala Asn Arg Pro Phe Leu Val Phe Ile Arg Glu Val Pro
                435                 440                 445

Leu Asn Thr Ile Ile Phe Met Gly Arg Val Ala Asn Pro Cys Val Lys
            450                 455                 460

<210> SEQ ID NO 37
<211> LENGTH: 1483
<212> TYPE: DNA
<213> ORGANISM: Homo sapiens
<220> FEATURE:
<221> NAME/KEY: CDS
<222> LOCATION: (1)..(1392)

<400> SEQUENCE: 37 atg tat tcc aat gtg ata gga act gta acc tct gga aaa agg aag gtt     48
Met Tyr Ser Asn Val Ile Gly Thr Val Thr Ser Gly Lys Arg Lys Val
1               5                   10                  15 tat ctt ttg tcc ttg ctg ctc att ggc ttc tgg gac tgc gtg acc tgt     96
Tyr Leu Leu Ser Leu Leu Leu Ile Gly Phe Trp Asp Cys Val Thr Cys
                20                  25                  30 cac ggg agc cct gtg gac atc tgc aca gcc aag ccg cgg gac att ccc    144
His Gly Ser Pro Val Asp Ile Cys Thr Ala Lys Pro Arg Asp Ile Pro
            35                  40                  45 atg aat ccc atg tgc att tac cgc tcc ccg gag aag aag gca act gag    192
Met Asn Pro Met Cys Ile Tyr Arg Ser Pro Glu Lys Lys Ala Thr Glu
        50                  55                  60 gat gag ggc tca gaa cag aag atc ccg gag gcc acc aac cgg cgt gtc    240
Asp Glu Gly Ser Glu Gln Lys Ile Pro Glu Ala Thr Asn Arg Arg Val
65                  70                  75                  80 tgg gaa ctg tcc aag gcc aat tcc cgc ttt gct acc act ttc tat cag    288
Trp Glu Leu Ser Lys Ala Asn Ser Arg Phe Ala Thr Thr Phe Tyr Gln
                85                  90                  95 cac ctg gca gat tcc aag aat gac aat gat aac att ttc ctg tca ccc    336
His Leu Ala Asp Ser Lys Asn Asp Asn Asp Asn Ile Phe Leu Ser Pro
                100                 105                 110 ctg agt atc tcc acg gct ttt gct atg acc aag ctg ggt gcc tgt aat    384
Leu Ser Ile Ser Thr Ala Phe Ala Met Thr Lys Leu Gly Ala Cys Asn
            115                 120                 125 gac acc ctc cag caa ctg atg gag gta ttt aag ttt gac acc ata tct    432
Asp Thr Leu Gln Gln Leu Met Glu Val Phe Lys Phe Asp Thr Ile Ser
        130                 135                 140
```

```
gag aaa aca tct gat cag atc cac ttc ttc ttt gcc aaa ctg aac tgc     480
Glu Lys Thr Ser Asp Gln Ile His Phe Phe Phe Ala Lys Leu Asn Cys
145                 150                 155                 160 cga ctc tat cga aaa gcc cag aaa tcc tcc aag tta gta tca gcc aat     528
Arg Leu Tyr Arg Lys Ala Gln Lys Ser Ser Lys Leu Val Ser Ala Asn
                165                 170                 175 cgc ctt ttt gga gac aaa tcc ctt acc ttc aat gag acc tac cag gac     576
Arg Leu Phe Gly Asp Lys Ser Leu Thr Phe Asn Glu Thr Tyr Gln Asp
            180                 185                 190 atc agt gag ttg gta tat gga gcc aag ctc cag ccc ctg gac ttc aag     624
Ile Ser Glu Leu Val Tyr Gly Ala Lys Leu Gln Pro Leu Asp Phe Lys
        195                 200                 205 gaa aat gca gag caa tcc aga gcg gcc atc aac aaa tgg gtg tcc aat     672
Glu Asn Ala Glu Gln Ser Arg Ala Ala Ile Asn Lys Trp Val Ser Asn
    210                 215                 220 aag acc gaa ggc cga atc acc gat gtc att ccc tcg gaa gcc atc aat     720
Lys Thr Glu Gly Arg Ile Thr Asp Val Ile Pro Ser Glu Ala Ile Asn
225                 230                 235                 240 gag ctc act gtt ctg gtg ctg gtt aac acc att tac ttc aag ggc ctg     768
Glu Leu Thr Val Leu Val Leu Val Asn Thr Ile Tyr Phe Lys Gly Leu
                245                 250                 255 tgg aag tca aag ttc agc cct gag aac aca agg aag gaa ctg ttc tac     816
Trp Lys Ser Lys Phe Ser Pro Glu Asn Thr Arg Lys Glu Leu Phe Tyr
                260                 265                 270 aag gct gat gga gag tcg tgt tca gca tct atg atg tac cag gaa ggc     864
Lys Ala Asp Gly Glu Ser Cys Ser Ala Ser Met Met Tyr Gln Glu Gly
            275                 280                 285 aag ttc cgt tat cgg cgc gtg gct gaa ggc acc cag gtg ctt gag ttg     912
Lys Phe Arg Tyr Arg Arg Val Ala Glu Gly Thr Gln Val Leu Glu Leu
        290                 295                 300 ccc ttc aaa ggt gat gac atc acc atg gtc ctc atc ttg ccc aag cct     960
Pro Phe Lys Gly Asp Asp Ile Thr Met Val Leu Ile Leu Pro Lys Pro
305                 310                 315                 320 gag aag agc ctg gcc aag gta gag aag gaa ctc acc cca gag gtg ctg    1008
Glu Lys Ser Leu Ala Lys Val Glu Lys Glu Leu Thr Pro Glu Val Leu
                325                 330                 335 caa gag tgg ctg gat gaa ttg gag gag atg atg ctg gtg gtc cac atg    1056
Gln Glu Trp Leu Asp Glu Leu Glu Glu Met Met Leu Val Val His Met
                340                 345                 350 ccc cgc ttc cgc att gag gac ggc ttc agt ttg aag gag cag ctg caa    1104
Pro Arg Phe Arg Ile Glu Asp Gly Phe Ser Leu Lys Glu Gln Leu Gln
            355                 360                 365 gac atg ggc ctt gtc gat ctg ttc agc cct gaa aag tcc aaa ctc cca    1152
Asp Met Gly Leu Val Asp Leu Phe Ser Pro Glu Lys Ser Lys Leu Pro
        370                 375                 380 ggt att gtt gca gaa ggc cga gat gac ctc tat gtc tca gat gca ttc    1200
Gly Ile Val Ala Glu Gly Arg Asp Asp Leu Tyr Val Ser Asp Ala Phe
385                 390                 395                 400 cat aag gca ttt ctt gag gta aat gaa gaa ggc agt gaa gca gct gca    1248
His Lys Ala Phe Leu Glu Val Asn Glu Glu Gly Ser Glu Ala Ala Ala
                405                 410                 415 agt acc gct gtt gtg att gct ggc cat tcg cta aac ccc aac agg gtg    1296
Ser Thr Ala Val Val Ile Ala Gly His Ser Leu Asn Pro Asn Arg Val
                420                 425                 430 act ttc aag gcc aac agg cct ttc ctg gtt ttt ata aga gaa gtt cct    1344
Thr Phe Lys Ala Asn Arg Pro Phe Leu Val Phe Ile Arg Glu Val Pro
            435                 440                 445 ctg aac act att atc ttc atg ggc aga gta gcc aac cct tgt gtt aag    1392
Leu Asn Thr Ile Ile Phe Met Gly Arg Val Ala Asn Pro Cys Val Lys
        450                 455                 460
```

```
taaaatgttc ttattctttg cacctcttcc tattttttggt ttgtgaacag aagtaaaaat    1452
aaatacaaac tacttccatc tcacattaaa a                                    1483

<210> SEQ ID NO 38
<211> LENGTH: 464
<212> TYPE: PRT
<213> ORGANISM: Homo sapiens

<400> SEQUENCE: 38

Met Tyr Ser Asn Val Ile Gly Thr Val Thr Ser Gly Lys Arg Lys Val
1               5                   10                  15

Tyr Leu Leu Ser Leu Leu Leu Ile Gly Phe Trp Asp Cys Val Thr Cys
            20                  25                  30

His Gly Ser Pro Val Asp Ile Cys Thr Ala Lys Pro Arg Asp Ile Pro
        35                  40                  45

Met Asn Pro Met Cys Ile Tyr Arg Ser Pro Glu Lys Lys Ala Thr Glu
    50                  55                  60

Asp Glu Gly Ser Glu Gln Lys Ile Pro Glu Ala Thr Asn Arg Arg Val
65                  70                  75                  80

Trp Glu Leu Ser Lys Ala Asn Ser Arg Phe Ala Thr Thr Phe Tyr Gln
                85                  90                  95

His Leu Ala Asp Ser Lys Asn Asp Asn Asp Asn Ile Phe Leu Ser Pro
            100                 105                 110

Leu Ser Ile Ser Thr Ala Phe Ala Met Thr Lys Leu Gly Ala Cys Asn
        115                 120                 125

Asp Thr Leu Gln Gln Leu Met Glu Val Phe Lys Phe Asp Thr Ile Ser
    130                 135                 140

Glu Lys Thr Ser Asp Gln Ile His Phe Phe Phe Ala Lys Leu Asn Cys
145                 150                 155                 160

Arg Leu Tyr Arg Lys Ala Gln Lys Ser Lys Leu Val Ser Ala Asn
                165                 170                 175

Arg Leu Phe Gly Asp Lys Ser Leu Thr Phe Asn Glu Thr Tyr Gln Asp
            180                 185                 190

Ile Ser Glu Leu Val Tyr Gly Ala Lys Leu Gln Pro Leu Asp Phe Lys
        195                 200                 205

Glu Asn Ala Glu Gln Ser Arg Ala Ala Ile Asn Lys Trp Val Ser Asn
    210                 215                 220

Lys Thr Glu Gly Arg Ile Thr Asp Val Ile Pro Ser Glu Ala Ile Asn
225                 230                 235                 240

Glu Leu Thr Val Leu Val Leu Val Asn Thr Ile Tyr Phe Lys Gly Leu
                245                 250                 255

Trp Lys Ser Lys Phe Ser Pro Glu Asn Thr Arg Lys Glu Leu Phe Tyr
            260                 265                 270

Lys Ala Asp Gly Glu Ser Cys Ser Ala Ser Met Met Tyr Gln Glu Gly
        275                 280                 285

Lys Phe Arg Tyr Arg Arg Val Ala Glu Gly Thr Gln Val Leu Glu Leu
    290                 295                 300

Pro Phe Lys Gly Asp Asp Ile Thr Met Val Leu Ile Leu Pro Lys Pro
305                 310                 315                 320

Glu Lys Ser Leu Ala Lys Val Glu Lys Glu Leu Thr Pro Glu Val Leu
                325                 330                 335

Gln Glu Trp Leu Asp Glu Leu Glu Glu Met Met Leu Val Val His Met
            340                 345                 350
```

-continued

```
Pro Arg Phe Arg Ile Glu Asp Gly Phe Ser Leu Lys Glu Gln Leu Gln
        355                 360                 365

Asp Met Gly Leu Val Asp Leu Phe Ser Pro Glu Lys Ser Lys Leu Pro
370                 375                 380

Gly Ile Val Ala Glu Gly Arg Asp Asp Leu Tyr Val Ser Asp Ala Phe
385                 390                 395                 400

His Lys Ala Phe Leu Glu Val Asn Glu Glu Gly Ser Glu Ala Ala Ala
                405                 410                 415

Ser Thr Ala Val Val Ile Ala Gly His Ser Leu Asn Pro Asn Arg Val
                420                 425                 430

Thr Phe Lys Ala Asn Arg Pro Phe Leu Val Phe Ile Arg Glu Val Pro
            435                 440                 445

Leu Asn Thr Ile Ile Phe Met Gly Arg Val Ala Asn Pro Cys Val Lys
450                 455                 460

<210> SEQ ID NO 39
<211> LENGTH: 1486
<212> TYPE: DNA
<213> ORGANISM: Homo sapiens
<220> FEATURE:
<221> NAME/KEY: CDS
<222> LOCATION: (1)..(1395)

<400> SEQUENCE: 39 atg tat tcc aat gtg ata gga act gta acc tct gga aaa agg aag gtt      48
Met Tyr Ser Asn Val Ile Gly Thr Val Thr Ser Gly Lys Arg Lys Val
1               5                   10                  15 tat ctt ttg tcc ttg ctg ctc att ggc ttc tgg gac tgc gtg acc tgt      96
Tyr Leu Leu Ser Leu Leu Leu Ile Gly Phe Trp Asp Cys Val Thr Cys
                20                  25                  30 cac ggg agc cct gtg gac atc tgc aca gcc aag ccg cgg gac att ccc     144
His Gly Ser Pro Val Asp Ile Cys Thr Ala Lys Pro Arg Asp Ile Pro
            35                  40                  45 atg aat ccc atg tgc att tac cgc tcc ccg gag aag aag gca act gag     192
Met Asn Pro Met Cys Ile Tyr Arg Ser Pro Glu Lys Lys Ala Thr Glu
        50                  55                  60 gat gag ggc tca gaa cag aag atc ccg gag gcc acc aac cgg cgt gtc     240
Asp Glu Gly Ser Glu Gln Lys Ile Pro Glu Ala Thr Asn Arg Arg Val
65                  70                  75                  80 tgg gaa ctg tcc aag gcc aat tcc cgc ttt gct acc act ttc tat cag     288
Trp Glu Leu Ser Lys Ala Asn Ser Arg Phe Ala Thr Thr Phe Tyr Gln
                85                  90                  95 cac ctg gca gat tcc aag aat gac aat gat aac att ttc ctg tca ccc     336
His Leu Ala Asp Ser Lys Asn Asp Asn Asp Asn Ile Phe Leu Ser Pro
                100                 105                 110 ctg agt atc tcc acg gct ttt gct atg acc aag ctg ggt gcc tgt aat     384
Leu Ser Ile Ser Thr Ala Phe Ala Met Thr Lys Leu Gly Ala Cys Asn
            115                 120                 125 gac acc ctc cag caa ctg atg gag gta ttt aag ttt gac acc ata tct     432
Asp Thr Leu Gln Gln Leu Met Glu Val Phe Lys Phe Asp Thr Ile Ser
130                 135                 140 gag aaa aca tct gat cag atc cac ttc ttc ttt gcc aaa ctg aac tgc     480
Glu Lys Thr Ser Asp Gln Ile His Phe Phe Phe Ala Lys Leu Asn Cys
145                 150                 155                 160 cga ctc tat cga aaa gcc cag aaa tcc tcc aag tta gta tca gcc aat     528
Arg Leu Tyr Arg Lys Ala Gln Lys Ser Ser Lys Leu Val Ser Ala Asn
                165                 170                 175 cgc ctt ttt gga gac aaa tcc ctt acc ttc aat gag acc tac cag gac     576
Arg Leu Phe Gly Asp Lys Ser Leu Thr Phe Asn Glu Thr Tyr Gln Asp
            180                 185                 190
```

```
atc agt gag ttg gta tat gga gcc aag ctc cag ccc ctg gac ttc aag      624
Ile Ser Glu Leu Val Tyr Gly Ala Lys Leu Gln Pro Leu Asp Phe Lys
        195                 200                 205 gaa aat gca gag caa tcc aga gcg gcc atc aac aaa tgg gtg tcc aat      672
Glu Asn Ala Glu Gln Ser Arg Ala Ala Ile Asn Lys Trp Val Ser Asn
    210                 215                 220 aag acc gaa ggc cga atc acc gat gtc att ccc tcg gaa gcc atc aat      720
Lys Thr Glu Gly Arg Ile Thr Asp Val Ile Pro Ser Glu Ala Ile Asn
225                 230                 235                 240 gag ctc act gtt ctg gtg ctg gtt aac acc att tac ttc aag ggc ctg      768
Glu Leu Thr Val Leu Val Leu Val Asn Thr Ile Tyr Phe Lys Gly Leu
                245                 250                 255 tgg aag tca aag ttc agc cct gag aac aca agg aag gaa ctg ttc tac      816
Trp Lys Ser Lys Phe Ser Pro Glu Asn Thr Arg Lys Glu Leu Phe Tyr
            260                 265                 270 aag gct gat gga gag tcg tgt tca gca tct atg atg tac cag gaa ggc      864
Lys Ala Asp Gly Glu Ser Cys Ser Ala Ser Met Met Tyr Gln Glu Gly
        275                 280                 285 aag ttc cgt tat cgg cgc gtg gct gaa ggc acc cag gtg ctt gag ttg      912
Lys Phe Arg Tyr Arg Arg Val Ala Glu Gly Thr Gln Val Leu Glu Leu
    290                 295                 300 ccc ttc aaa ggt gat gac atc acc atg gtc ctc atc ttg ccc aag cct      960
Pro Phe Lys Gly Asp Asp Ile Thr Met Val Leu Ile Leu Pro Lys Pro
305                 310                 315                 320 gag aag agc ctg gcc aag gta gag aag gaa ctc acc cca gag gtg ctg     1008
Glu Lys Ser Leu Ala Lys Val Glu Lys Glu Leu Thr Pro Glu Val Leu
                325                 330                 335 caa gag tgg ctg gat gaa ttg gag gag atg atg ctg gtg gtc cac atg     1056
Gln Glu Trp Leu Asp Glu Leu Glu Glu Met Met Leu Val Val His Met
            340                 345                 350 ccc cgc ttc cgc att gag gac ggc ttc agt ttg aag gag cag ctg caa     1104
Pro Arg Phe Arg Ile Glu Asp Gly Phe Ser Leu Lys Glu Gln Leu Gln
        355                 360                 365 gac atg ggc ctt gtc gat ctg ttc agc cct gaa aag tcc aaa ctc cca     1152
Asp Met Gly Leu Val Asp Leu Phe Ser Pro Glu Lys Ser Lys Leu Pro
    370                 375                 380 ggt att gtt gca gaa ggc cga gat gac ctc tat gtc tca gat gca ttc     1200
Gly Ile Val Ala Glu Gly Arg Asp Asp Leu Tyr Val Ser Asp Ala Phe
385                 390                 395                 400 cat aag gca ttt ctt gag gta aat gaa gaa ggc agt gaa gca gct gca     1248
His Lys Ala Phe Leu Glu Val Asn Glu Glu Gly Ser Glu Ala Ala Ala
                405                 410                 415 agt acc gct gtt gtg att gct ggc cgt cca tcg cta aac ccc aac agg     1296
Ser Thr Ala Val Val Ile Ala Gly Arg Pro Ser Leu Asn Pro Asn Arg
            420                 425                 430 gtg act ttc aag gcc aac agg cct ttc ctg gtt ttt ata aga gaa gtt     1344
Val Thr Phe Lys Ala Asn Arg Pro Phe Leu Val Phe Ile Arg Glu Val
        435                 440                 445 cct ctg aac act att atc ttc atg gga aga gta gcc aac cct tgt gtt     1392
Pro Leu Asn Thr Ile Ile Phe Met Gly Arg Val Ala Asn Pro Cys Val
    450                 455                 460 aag taaaatgttc ttattctttg cacctcttcc tattttggt ttgtgaacag           1445
Lys
465 aagtaaaaat aaatacaaac tacttccatc tcacattaaa a                       1486
```

<210> SEQ ID NO 40
<211> LENGTH: 465
<212> TYPE: PRT

<213> ORGANISM: Homo sapiens

<400> SEQUENCE: 40

| | | | | | | | | | | | | | | |
|---|---|---|---|---|---|---|---|---|---|---|---|---|---|---|
| Met | Tyr | Ser | Asn | Val | Ile | Gly | Thr | Val | Thr | Ser | Gly | Lys | Arg | Lys | Val |
| 1 | | | | 5 | | | | | 10 | | | | | 15 | |
| Tyr | Leu | Leu | Ser | Leu | Leu | Leu | Ile | Gly | Phe | Trp | Asp | Cys | Val | Thr | Cys |
| | | | 20 | | | | | 25 | | | | | 30 | | |
| His | Gly | Ser | Pro | Val | Asp | Ile | Cys | Thr | Ala | Lys | Pro | Arg | Asp | Ile | Pro |
| | | 35 | | | | | 40 | | | | | 45 | | | |
| Met | Asn | Pro | Met | Cys | Ile | Tyr | Arg | Ser | Pro | Glu | Lys | Lys | Ala | Thr | Glu |
| | 50 | | | | | 55 | | | | | 60 | | | | |
| Asp | Glu | Gly | Ser | Glu | Gln | Lys | Ile | Pro | Glu | Ala | Thr | Asn | Arg | Arg | Val |
| 65 | | | | | 70 | | | | | 75 | | | | | 80 |
| Trp | Glu | Leu | Ser | Lys | Ala | Asn | Ser | Arg | Phe | Ala | Thr | Thr | Phe | Tyr | Gln |
| | | | | 85 | | | | | 90 | | | | | 95 | |
| His | Leu | Ala | Asp | Ser | Lys | Asn | Asp | Asn | Asp | Asn | Ile | Phe | Leu | Ser | Pro |
| | | | 100 | | | | | 105 | | | | | 110 | | |
| Leu | Ser | Ile | Ser | Thr | Ala | Phe | Ala | Met | Thr | Lys | Leu | Gly | Ala | Cys | Asn |
| | | 115 | | | | | 120 | | | | | 125 | | | |
| Asp | Thr | Leu | Gln | Gln | Leu | Met | Glu | Val | Phe | Lys | Phe | Asp | Thr | Ile | Ser |
| | 130 | | | | | 135 | | | | | 140 | | | | |
| Glu | Lys | Thr | Ser | Asp | Gln | Ile | His | Phe | Phe | Phe | Ala | Lys | Leu | Asn | Cys |
| 145 | | | | | 150 | | | | | 155 | | | | | 160 |
| Arg | Leu | Tyr | Arg | Lys | Ala | Gln | Lys | Ser | Ser | Lys | Leu | Val | Ser | Ala | Asn |
| | | | | 165 | | | | | 170 | | | | | 175 | |
| Arg | Leu | Phe | Gly | Asp | Lys | Ser | Leu | Thr | Phe | Asn | Glu | Thr | Tyr | Gln | Asp |
| | | | 180 | | | | | 185 | | | | | 190 | | |
| Ile | Ser | Glu | Leu | Val | Tyr | Gly | Ala | Lys | Leu | Gln | Pro | Leu | Asp | Phe | Lys |
| | | 195 | | | | | 200 | | | | | 205 | | | |
| Glu | Asn | Ala | Glu | Gln | Ser | Arg | Ala | Ala | Ile | Asn | Lys | Trp | Val | Ser | Asn |
| | 210 | | | | | 215 | | | | | 220 | | | | |
| Lys | Thr | Glu | Gly | Arg | Ile | Thr | Asp | Val | Ile | Pro | Ser | Glu | Ala | Ile | Asn |
| 225 | | | | | 230 | | | | | 235 | | | | | 240 |
| Glu | Leu | Thr | Val | Leu | Val | Leu | Val | Asn | Thr | Ile | Tyr | Phe | Lys | Gly | Leu |
| | | | | 245 | | | | | 250 | | | | | 255 | |
| Trp | Lys | Ser | Lys | Phe | Ser | Pro | Glu | Asn | Thr | Arg | Lys | Glu | Leu | Phe | Tyr |
| | | | 260 | | | | | 265 | | | | | 270 | | |
| Lys | Ala | Asp | Gly | Glu | Ser | Cys | Ser | Ala | Ser | Met | Met | Tyr | Gln | Glu | Gly |
| | | 275 | | | | | 280 | | | | | 285 | | | |
| Lys | Phe | Arg | Tyr | Arg | Arg | Val | Ala | Glu | Gly | Thr | Gln | Val | Leu | Glu | Leu |
| | 290 | | | | | 295 | | | | | 300 | | | | |
| Pro | Phe | Lys | Gly | Asp | Asp | Ile | Thr | Met | Val | Leu | Ile | Leu | Pro | Lys | Pro |
| 305 | | | | | 310 | | | | | 315 | | | | | 320 |
| Glu | Lys | Ser | Leu | Ala | Lys | Val | Glu | Lys | Glu | Leu | Thr | Pro | Glu | Val | Leu |
| | | | | 325 | | | | | 330 | | | | | 335 | |
| Gln | Glu | Trp | Leu | Asp | Glu | Leu | Glu | Glu | Met | Met | Leu | Val | Val | His | Met |
| | | | 340 | | | | | 345 | | | | | 350 | | |
| Pro | Arg | Phe | Arg | Ile | Glu | Asp | Gly | Phe | Ser | Leu | Lys | Glu | Gln | Leu | Gln |
| | | 355 | | | | | 360 | | | | | 365 | | | |
| Asp | Met | Gly | Leu | Val | Asp | Leu | Phe | Ser | Pro | Glu | Lys | Ser | Lys | Leu | Pro |
| | 370 | | | | | 375 | | | | | 380 | | | | |
| Gly | Ile | Val | Ala | Glu | Gly | Arg | Asp | Asp | Leu | Tyr | Val | Ser | Asp | Ala | Phe |
| 385 | | | | | 390 | | | | | 395 | | | | | 400 |

His Lys Ala Phe Leu Glu Val Asn Glu Glu Gly Ser Glu Ala Ala Ala
            405                 410                 415

Ser Thr Ala Val Val Ile Ala Gly Arg Pro Ser Leu Asn Pro Asn Arg
        420                 425                 430

Val Thr Phe Lys Ala Asn Arg Pro Phe Leu Val Phe Ile Arg Glu Val
        435                 440                 445

Pro Leu Asn Thr Ile Ile Phe Met Gly Arg Val Ala Asn Pro Cys Val
    450                 455                 460

Lys
465

<210> SEQ ID NO 41
<211> LENGTH: 1477
<212> TYPE: DNA
<213> ORGANISM: Homo sapiens
<220> FEATURE:
<221> NAME/KEY: CDS
<222> LOCATION: (1)..(1386)

<400> SEQUENCE: 41

| | | |
|---|---|---|
| atg tat tcc aat gtg ata gga act gta acc tct gga aaa agg aag gtt | 48 |
| Met Tyr Ser Asn Val Ile Gly Thr Val Thr Ser Gly Lys Arg Lys Val | |
| 1               5                   10                  15 | |
| tat ctt ttg tcc ttg ctc att ggc ttc tgg gac tgc gtg acc tgt | 96 |
| Tyr Leu Leu Ser Leu Leu Ile Gly Phe Trp Asp Cys Val Thr Cys | |
|             20                  25                  30 | |
| cac ggg agc cct gtg gac atc tgc aca gcc aag ccg cgg gac att ccc | 144 |
| His Gly Ser Pro Val Asp Ile Cys Thr Ala Lys Pro Arg Asp Ile Pro | |
|         35                  40                  45 | |
| atg aat ccc atg tgc att tac cgc tcc ccg gag aag aag gca act gag | 192 |
| Met Asn Pro Met Cys Ile Tyr Arg Ser Pro Glu Lys Lys Ala Thr Glu | |
| 50                  55                  60 | |
| gat gag ggc tca gaa cag aag atc ccg gag gcc acc aac cgg cgt gtc | 240 |
| Asp Glu Gly Ser Glu Gln Lys Ile Pro Glu Ala Thr Asn Arg Arg Val | |
| 65                  70                  75                  80 | |
| tgg gaa ctg tcc aag gcc aat tcc cgc ttt gct acc act ttc tat cag | 288 |
| Trp Glu Leu Ser Lys Ala Asn Ser Arg Phe Ala Thr Thr Phe Tyr Gln | |
|                 85                  90                  95 | |
| cac ctg gca gat tcc aag aat gac aat gat aac att ttc ctg tca ccc | 336 |
| His Leu Ala Asp Ser Lys Asn Asp Asn Asp Asn Ile Phe Leu Ser Pro | |
|             100                 105                 110 | |
| ctg agt atc tcc acg gct ttt gct atg acc aag ctg ggt gcc tgt aat | 384 |
| Leu Ser Ile Ser Thr Ala Phe Ala Met Thr Lys Leu Gly Ala Cys Asn | |
|         115                 120                 125 | |
| gac acc ctc cag caa ctg atg gag gta ttt aag ttt gac acc ata tct | 432 |
| Asp Thr Leu Gln Gln Leu Met Glu Val Phe Lys Phe Asp Thr Ile Ser | |
| 130                 135                 140 | |
| gag aaa aca tct gat cag atc cac ttc ttc ttt gcc aaa ctg aac tgc | 480 |
| Glu Lys Thr Ser Asp Gln Ile His Phe Phe Phe Ala Lys Leu Asn Cys | |
| 145                 150                 155                 160 | |
| cga ctc tat cga aaa gcc aac aaa tcc tcc aag tta gta tca gcc aat | 528 |
| Arg Leu Tyr Arg Lys Ala Asn Lys Ser Ser Lys Leu Val Ser Ala Asn | |
|                 165                 170                 175 | |
| cgc ctt ttt gga gac aaa tcc ctt acc ttc aat gag acc tac cag gac | 576 |
| Arg Leu Phe Gly Asp Lys Ser Leu Thr Phe Asn Glu Thr Tyr Gln Asp | |
|             180                 185                 190 | |
| atc agt gag ttg gta tat gga gcc aag ctc cag ccc ctg gac ttc aag | 624 |
| Ile Ser Glu Leu Val Tyr Gly Ala Lys Leu Gln Pro Leu Asp Phe Lys | |
|         195                 200                 205 | |
| gaa aat gca gag caa tcc aga gcg gcc atc aac aaa tgg gtg tcc aat | 672 |

```
                    Glu Asn Ala Glu Gln Ser Arg Ala Ala Ile Asn Lys Trp Val Ser Asn
                        210                 215                 220 aag acc gaa ggc cga atc acc gat gtc att ccc tcg gaa gcc atc aat        720
Lys Thr Glu Gly Arg Ile Thr Asp Val Ile Pro Ser Glu Ala Ile Asn
225                 230                 235                 240 gag ctc act gtt ctg gtg ctg gtt aac acc att tac ttc aag ggc ctg        768
Glu Leu Thr Val Leu Val Leu Val Asn Thr Ile Tyr Phe Lys Gly Leu
                245                 250                 255 tgg aag tca aag ttc agc cct gag aac aca agg aag gaa ctg ttc tac        816
Trp Lys Ser Lys Phe Ser Pro Glu Asn Thr Arg Lys Glu Leu Phe Tyr
            260                 265                 270 aag gct gat gga gag tcg tgt tca gca tct atg atg tac cag gaa ggc        864
Lys Ala Asp Gly Glu Ser Cys Ser Ala Ser Met Met Tyr Gln Glu Gly
        275                 280                 285 aag ttc cgt tat cgg cgc gtg gct gaa ggc acc cag gtg ctt gag ttg        912
Lys Phe Arg Tyr Arg Arg Val Ala Glu Gly Thr Gln Val Leu Glu Leu
    290                 295                 300 ccc ttc aaa ggt gat gac atc acc atg gtc ctc atc ttg ccc aag cct        960
Pro Phe Lys Gly Asp Asp Ile Thr Met Val Leu Ile Leu Pro Lys Pro
305                 310                 315                 320 gag aag agc ctg gcc aag gta gag aag gaa ctc acc cca gag gtg ctg       1008
Glu Lys Ser Leu Ala Lys Val Glu Lys Glu Leu Thr Pro Glu Val Leu
                325                 330                 335 caa gag tgg ctg gat gaa ttg gag gag atg atg ctg gtg gtc cac atg       1056
Gln Glu Trp Leu Asp Glu Leu Glu Glu Met Met Leu Val Val His Met
            340                 345                 350 ccc cgc ttc cgc att gag gac ggc ttc agt ttg aag gag cag ctg caa       1104
Pro Arg Phe Arg Ile Glu Asp Gly Phe Ser Leu Lys Glu Gln Leu Gln
        355                 360                 365 gac atg ggc ctt gtc gat ctg ttc agc cct gaa aag tcc aaa ctc cca       1152
Asp Met Gly Leu Val Asp Leu Phe Ser Pro Glu Lys Ser Lys Leu Pro
    370                 375                 380 ggt att gtt gca gaa ggc cga gat gac ctc tat gtc tca gat gca ttc       1200
Gly Ile Val Ala Glu Gly Arg Asp Asp Leu Tyr Val Ser Asp Ala Phe
385                 390                 395                 400 cat aag gca ttt ctt gag gta aat gaa gaa ggc agt gaa gca gct gca       1248
His Lys Ala Phe Leu Glu Val Asn Glu Glu Gly Ser Glu Ala Ala Ala
                405                 410                 415 agt acc gct gtt gtg att gct ggc cta aac ccc aac agg gtg act ttc       1296
Ser Thr Ala Val Val Ile Ala Gly Leu Asn Pro Asn Arg Val Thr Phe
            420                 425                 430 aag gcc aac agg cct ttc ctg gtt ttt ata aga gaa gtt cct ctg aac       1344
Lys Ala Asn Arg Pro Phe Leu Val Phe Ile Arg Glu Val Pro Leu Asn
        435                 440                 445 act att atc ttc atg ggc aga gta gcc aac cct tgt gtt aag                1386
Thr Ile Ile Phe Met Gly Arg Val Ala Asn Pro Cys Val Lys
    450                 455                 460 taaaatgttc ttattctttg cacctcttcc tattttggt ttgtgaacag aagtaaaaat      1446
aaatacaaac tacttccatc tcacattaaa a                                    1477

<210> SEQ ID NO 42
<211> LENGTH: 462
<212> TYPE: PRT
<213> ORGANISM: Homo sapiens

<400> SEQUENCE: 42

Met Tyr Ser Asn Val Ile Gly Thr Val Thr Ser Gly Lys Arg Lys Val
1               5                   10                  15

Tyr Leu Leu Ser Leu Leu Leu Ile Gly Phe Trp Asp Cys Val Thr Cys
```

-continued

```
            20                  25                  30
His Gly Ser Pro Val Asp Ile Cys Thr Ala Lys Pro Arg Asp Ile Pro
        35                  40                  45
Met Asn Pro Met Cys Ile Tyr Arg Ser Pro Glu Lys Lys Ala Thr Glu
    50                  55                  60
Asp Glu Gly Ser Glu Gln Lys Ile Pro Glu Ala Thr Asn Arg Arg Val
65                  70                  75                  80
Trp Glu Leu Ser Lys Ala Asn Ser Arg Phe Ala Thr Thr Phe Tyr Gln
                85                  90                  95
His Leu Ala Asp Ser Lys Asn Asp Asn Asp Asn Ile Phe Leu Ser Pro
            100                 105                 110
Leu Ser Ile Ser Thr Ala Phe Ala Met Thr Lys Leu Gly Ala Cys Asn
        115                 120                 125
Asp Thr Leu Gln Gln Leu Met Glu Val Phe Lys Phe Asp Thr Ile Ser
    130                 135                 140
Glu Lys Thr Ser Asp Gln Ile His Phe Phe Ala Lys Leu Asn Cys
145                 150                 155                 160
Arg Leu Tyr Arg Lys Ala Asn Lys Ser Ser Lys Leu Val Ser Ala Asn
                165                 170                 175
Arg Leu Phe Gly Asp Lys Ser Leu Thr Phe Asn Glu Thr Tyr Gln Asp
            180                 185                 190
Ile Ser Glu Leu Val Tyr Gly Ala Lys Leu Gln Pro Leu Asp Phe Lys
        195                 200                 205
Glu Asn Ala Glu Gln Ser Arg Ala Ala Ile Asn Lys Trp Val Ser Asn
    210                 215                 220
Lys Thr Glu Gly Arg Ile Thr Asp Val Ile Pro Ser Glu Ala Ile Asn
225                 230                 235                 240
Glu Leu Thr Val Leu Val Leu Val Asn Thr Ile Tyr Phe Lys Gly Leu
                245                 250                 255
Trp Lys Ser Lys Phe Ser Pro Glu Asn Thr Arg Lys Glu Leu Phe Tyr
            260                 265                 270
Lys Ala Asp Gly Glu Ser Cys Ser Ala Ser Met Met Tyr Gln Glu Gly
        275                 280                 285
Lys Phe Arg Tyr Arg Arg Val Ala Glu Gly Thr Gln Val Leu Glu Leu
    290                 295                 300
Pro Phe Lys Gly Asp Asp Ile Thr Met Val Leu Ile Leu Pro Lys Pro
305                 310                 315                 320
Glu Lys Ser Leu Ala Lys Val Glu Lys Glu Leu Thr Pro Glu Val Leu
                325                 330                 335
Gln Glu Trp Leu Asp Glu Leu Glu Glu Met Met Leu Val Val His Met
            340                 345                 350
Pro Arg Phe Arg Ile Glu Asp Gly Phe Ser Leu Lys Glu Gln Leu Gln
        355                 360                 365
Asp Met Gly Leu Val Asp Leu Phe Ser Pro Lys Ser Lys Leu Pro
    370                 375                 380
Gly Ile Val Ala Glu Gly Arg Asp Asp Leu Tyr Val Ser Asp Ala Phe
385                 390                 395                 400
His Lys Ala Phe Leu Glu Val Asn Glu Glu Gly Ser Glu Ala Ala Ala
                405                 410                 415
Ser Thr Ala Val Val Ile Ala Gly Leu Asn Pro Asn Arg Val Thr Phe
            420                 425                 430
Lys Ala Asn Arg Pro Phe Leu Val Phe Ile Arg Glu Val Pro Leu Asn
        435                 440                 445
```

```
Thr Ile Ile Phe Met Gly Arg Val Ala Asn Pro Cys Val Lys
    450             455                 460
```

<210> SEQ ID NO 43
<211> LENGTH: 1480
<212> TYPE: DNA
<213> ORGANISM: Homo sapiens
<220> FEATURE:
<221> NAME/KEY: CDS
<222> LOCATION: (1)..(1389)

<400> SEQUENCE: 43

```
atg tat tcc aat gtg ata gga act gta acc tct gga aaa agg aag gtt      48
Met Tyr Ser Asn Val Ile Gly Thr Val Thr Ser Gly Lys Arg Lys Val
1               5                   10                  15 tat ctt ttg tcc ttg ctg ctc att ggc ttc tgg gac tgc gtg acc tgt      96
Tyr Leu Leu Ser Leu Leu Leu Ile Gly Phe Trp Asp Cys Val Thr Cys
                20                  25                  30 cac ggg agc cct gtg gac atc tgc aca gcc aag ccg cgg gac att ccc     144
His Gly Ser Pro Val Asp Ile Cys Thr Ala Lys Pro Arg Asp Ile Pro
            35                  40                  45 atg aat ccc atg tgc att tac cgc tcc ccg gag aag aag gca act gag     192
Met Asn Pro Met Cys Ile Tyr Arg Ser Pro Glu Lys Lys Ala Thr Glu
        50                  55                  60 gat gag ggc tca gaa cag aag atc ccg gag gcc acc aac cgg cgt gtc     240
Asp Glu Gly Ser Glu Gln Lys Ile Pro Glu Ala Thr Asn Arg Arg Val
65                  70                  75                  80 tgg gaa ctg tcc aag gcc aat tcc cgc ttt gct acc act ttc tat cag     288
Trp Glu Leu Ser Lys Ala Asn Ser Arg Phe Ala Thr Thr Phe Tyr Gln
                85                  90                  95 cac ctg gca gat tcc aag aat gac aat gat aac att ttc ctg tca ccc     336
His Leu Ala Asp Ser Lys Asn Asp Asn Asp Asn Ile Phe Leu Ser Pro
            100                 105                 110 ctg agt atc tcc acg gct ttt gct atg acc aag ctg ggt gcc tgt aat     384
Leu Ser Ile Ser Thr Ala Phe Ala Met Thr Lys Leu Gly Ala Cys Asn
        115                 120                 125 gac acc ctc cag caa ctg atg gag gta ttt aag ttt gac acc ata tct     432
Asp Thr Leu Gln Gln Leu Met Glu Val Phe Lys Phe Asp Thr Ile Ser
    130                 135                 140 gag aaa aca tct gat cag atc cac ttc ttc ttt gcc aaa ctg aac tgc     480
Glu Lys Thr Ser Asp Gln Ile His Phe Phe Phe Ala Lys Leu Asn Cys
145                 150                 155                 160 cga ctc tat cga aaa gcc cag aaa tcc tcc aag tta gta tca gcc aat     528
Arg Leu Tyr Arg Lys Ala Gln Lys Ser Ser Lys Leu Val Ser Ala Asn
                165                 170                 175 cgc ctt ttt gga gac aaa tcc ctt acc ttc aat gag acc tac cag gac     576
Arg Leu Phe Gly Asp Lys Ser Leu Thr Phe Asn Glu Thr Tyr Gln Asp
            180                 185                 190 atc agt gag ttg gta tat gga gcc aag ctc cag ccc ctg gac ttc aag     624
Ile Ser Glu Leu Val Tyr Gly Ala Lys Leu Gln Pro Leu Asp Phe Lys
        195                 200                 205 gaa aat gca gag caa tcc aga gcg gcc atc aac aaa tgg gtg tcc aat     672
Glu Asn Ala Glu Gln Ser Arg Ala Ala Ile Asn Lys Trp Val Ser Asn
    210                 215                 220 aag acc gaa ggc cga atc acc gat gtc att ccc tcg gaa gcc atc aat     720
Lys Thr Glu Gly Arg Ile Thr Asp Val Ile Pro Ser Glu Ala Ile Asn
225                 230                 235                 240 gag ctc act gtt ctg gtg ctg gtt aac acc att tac ttc aag ggc ctg     768
Glu Leu Thr Val Leu Val Leu Val Asn Thr Ile Tyr Phe Lys Gly Leu
                245                 250                 255
```

-continued

| | | |
|---|---|---|
| tgg aag tca aag ttc agc cct gag aac aca agg aag gaa ctg ttc tac<br>Trp Lys Ser Lys Phe Ser Pro Glu Asn Thr Arg Lys Glu Leu Phe Tyr<br>         260                     265                    270 | | 816 |
| aag gct gat gga gag tcg tgt tca gca tct atg atg tac cag gaa ggc<br>Lys Ala Asp Gly Glu Ser Cys Ser Ala Ser Met Met Tyr Gln Glu Gly<br>         275                      280                    285 | | 864 |
| aag ttc cgt tat cgg cgc gtg gct gaa ggc acc cag gtg ctt gag ttg<br>Lys Phe Arg Tyr Arg Arg Val Ala Glu Gly Thr Gln Val Leu Glu Leu<br>     290                      295                    300 | | 912 |
| ccc ttc aaa ggt gat gac atc acc atg gtc ctc atc ttg ccc aag cct<br>Pro Phe Lys Gly Asp Asp Ile Thr Met Val Leu Ile Leu Pro Lys Pro<br>305                   310                    315                    320 | | 960 |
| gag aag agc ctg gcc aag gta gag aag gaa ctc acc cca gag gtg ctg<br>Glu Lys Ser Leu Ala Lys Val Glu Lys Glu Leu Thr Pro Glu Val Leu<br>                   325                      330                    335 | | 1008 |
| caa gag tgg ctg gat gaa ttg gag gag atg atg ctg gtg gtc cac atg<br>Gln Glu Trp Leu Asp Glu Leu Glu Glu Met Met Leu Val Val His Met<br>         340                      345                    350 | | 1056 |
| ccc cgc ttc cgc att gag gac ggc ttc agt ttg aag gag cag ctg caa<br>Pro Arg Phe Arg Ile Glu Asp Gly Phe Ser Leu Lys Glu Gln Leu Gln<br>     355                      360                    365 | | 1104 |
| gac atg ggc ctt gtc gat ctg ttc agc cct gaa aag tcc aaa ctc cca<br>Asp Met Gly Leu Val Asp Leu Phe Ser Pro Glu Lys Ser Lys Leu Pro<br>370                   375                    380 | | 1152 |
| ggt att gtt gca gaa ggc cga gat gac ctc tat gtc tca gat gca ttc<br>Gly Ile Val Ala Glu Gly Arg Asp Asp Leu Tyr Val Ser Asp Ala Phe<br>385                   390                    395                    400 | | 1200 |
| cat aag gca ttt ctt gag gta aat gaa gaa ggc agt gaa gca gct gca<br>His Lys Ala Phe Leu Glu Val Asn Glu Glu Gly Ser Glu Ala Ala Ala<br>                   405                      410                    415 | | 1248 |
| agt acc gct gtt gtg att gct ggc tcg cta aac ccc aac agg gtg act<br>Ser Thr Ala Val Val Ile Ala Gly Ser Leu Asn Pro Asn Arg Val Thr<br>         420                      425                    430 | | 1296 |
| ttc aag gcc aac agg cct ttc ctg gtt ttt ata aga gaa gtt cct ctg<br>Phe Lys Ala Asn Arg Pro Phe Leu Val Phe Ile Arg Glu Val Pro Leu<br>     435                      440                    445 | | 1344 |
| aac act att atc ttc atg ggc aga gta gcc aac cct tgt gtt aag<br>Asn Thr Ile Ile Phe Met Gly Arg Val Ala Asn Pro Cys Val Lys<br>450                   455                    460 | | 1389 |
| taaaatgttc ttattctttg cacctcttcc tattttggt ttgtgaacag aagtaaaaat | | 1449 |
| aaatacaaac tacttccatc tcacattaaa a | | 1480 |

<210> SEQ ID NO 44
<211> LENGTH: 463
<212> TYPE: PRT
<213> ORGANISM: Homo sapiens

<400> SEQUENCE: 44

Met Tyr Ser Asn Val Ile Gly Thr Val Thr Ser Gly Lys Arg Lys Val
1                 5                     10                   15

Tyr Leu Leu Ser Leu Leu Leu Ile Gly Phe Trp Asp Cys Val Thr Cys
                  20                     25                   30

His Gly Ser Pro Val Asp Ile Cys Thr Ala Lys Pro Arg Asp Ile Pro
              35                     40                   45

Met Asn Pro Met Cys Ile Tyr Arg Ser Pro Glu Lys Lys Ala Thr Glu
    50                      55                      60

Asp Glu Gly Ser Glu Gln Lys Ile Pro Glu Ala Thr Asn Arg Arg Val
65                  70                     75                   80

```
Trp Glu Leu Ser Lys Ala Asn Ser Arg Phe Ala Thr Thr Phe Tyr Gln
             85                  90                  95
His Leu Ala Asp Ser Lys Asn Asp Asn Ile Phe Leu Ser Pro
        100                 105                 110
Leu Ser Ile Ser Thr Ala Phe Ala Met Thr Lys Leu Gly Ala Cys Asn
            115                 120                 125
Asp Thr Leu Gln Gln Leu Met Glu Val Phe Lys Phe Asp Thr Ile Ser
    130                 135                 140
Glu Lys Thr Ser Asp Gln Ile His Phe Phe Ala Lys Leu Asn Cys
145                 150                 155                 160
Arg Leu Tyr Arg Lys Ala Gln Lys Ser Ser Lys Leu Val Ser Ala Asn
                165                 170                 175
Arg Leu Phe Gly Asp Lys Ser Leu Thr Phe Asn Glu Thr Tyr Gln Asp
            180                 185                 190
Ile Ser Glu Leu Val Tyr Gly Ala Lys Leu Gln Pro Leu Asp Phe Lys
                195                 200                 205
Glu Asn Ala Glu Gln Ser Arg Ala Ala Ile Asn Lys Trp Val Ser Asn
        210                 215                 220
Lys Thr Glu Gly Arg Ile Thr Asp Val Ile Pro Ser Glu Ala Ile Asn
225                 230                 235                 240
Glu Leu Thr Val Leu Val Leu Val Asn Thr Ile Tyr Phe Lys Gly Leu
                245                 250                 255
Trp Lys Ser Lys Phe Ser Pro Glu Asn Thr Arg Lys Glu Leu Phe Tyr
            260                 265                 270
Lys Ala Asp Gly Glu Ser Cys Ser Ala Ser Met Met Tyr Gln Glu Gly
        275                 280                 285
Lys Phe Arg Tyr Arg Arg Val Ala Glu Gly Thr Gln Val Leu Glu Leu
    290                 295                 300
Pro Phe Lys Gly Asp Asp Ile Thr Met Val Leu Ile Leu Pro Lys Pro
305                 310                 315                 320
Glu Lys Ser Leu Ala Lys Val Glu Lys Glu Leu Thr Pro Glu Val Leu
                325                 330                 335
Gln Glu Trp Leu Asp Glu Leu Glu Glu Met Met Leu Val Val His Met
            340                 345                 350
Pro Arg Phe Arg Ile Glu Asp Gly Phe Ser Leu Lys Glu Gln Leu Gln
        355                 360                 365
Asp Met Gly Leu Val Asp Leu Phe Ser Pro Glu Lys Ser Lys Leu Pro
    370                 375                 380
Gly Ile Val Ala Glu Gly Arg Asp Asp Leu Tyr Val Ser Asp Ala Phe
385                 390                 395                 400
His Lys Ala Phe Leu Glu Val Asn Glu Glu Gly Ser Glu Ala Ala Ala
                405                 410                 415
Ser Thr Ala Val Val Ile Ala Gly Ser Leu Asn Pro Asn Arg Val Thr
            420                 425                 430
Phe Lys Ala Asn Arg Pro Phe Leu Val Phe Ile Arg Glu Val Pro Leu
        435                 440                 445
Asn Thr Ile Ile Phe Met Gly Arg Val Ala Asn Pro Cys Val Lys
    450                 455                 460

<210> SEQ ID NO 45
<211> LENGTH: 1480
<212> TYPE: DNA
<213> ORGANISM: Homo sapiens
<220> FEATURE:
<221> NAME/KEY: CDS
```

<222> LOCATION: (1)..(1389)

<400> SEQUENCE: 45

| | | | | | | | | | | | | | | | | |
|---|---|---|---|---|---|---|---|---|---|---|---|---|---|---|---|---|
| atg | tat | tcc | aat | gtg | ata | gga | act | gta | acc | tct | gga | aaa | agg | aag | gtt | 48 |
| Met | Tyr | Ser | Asn | Val | Ile | Gly | Thr | Val | Thr | Ser | Gly | Lys | Arg | Lys | Val | |
| 1 | | | | 5 | | | | | 10 | | | | | 15 | | |

| tat | ctt | ttg | tcc | ttg | ctg | ctc | att | ggc | ttc | tgg | gac | tgc | gtg | acc | tgt | 96 |
|---|---|---|---|---|---|---|---|---|---|---|---|---|---|---|---|---|
| Tyr | Leu | Leu | Ser | Leu | Leu | Leu | Ile | Gly | Phe | Trp | Asp | Cys | Val | Thr | Cys | |
| | | | 20 | | | | | 25 | | | | | 30 | | | |

| cac | ggg | agc | cct | gtg | gac | atc | tgc | aca | gcc | aag | ccg | cgg | gac | att | ccc | 144 |
|---|---|---|---|---|---|---|---|---|---|---|---|---|---|---|---|---|
| His | Gly | Ser | Pro | Val | Asp | Ile | Cys | Thr | Ala | Lys | Pro | Arg | Asp | Ile | Pro | |
| | | 35 | | | | | 40 | | | | | 45 | | | | |

| atg | aat | ccc | atg | tgc | att | tac | cgc | tcc | ccg | gag | aag | aag | gca | act | gag | 192 |
|---|---|---|---|---|---|---|---|---|---|---|---|---|---|---|---|---|
| Met | Asn | Pro | Met | Cys | Ile | Tyr | Arg | Ser | Pro | Glu | Lys | Lys | Ala | Thr | Glu | |
| | 50 | | | | | 55 | | | | | 60 | | | | | |

| gat | gag | ggc | tca | gaa | cag | aag | atc | ccg | gag | gcc | acc | aac | cgg | cgt | gtc | 240 |
|---|---|---|---|---|---|---|---|---|---|---|---|---|---|---|---|---|
| Asp | Glu | Gly | Ser | Glu | Gln | Lys | Ile | Pro | Glu | Ala | Thr | Asn | Arg | Arg | Val | |
| 65 | | | | | 70 | | | | | 75 | | | | | 80 | |

| tgg | gaa | ctg | tcc | aag | gcc | aat | tcc | cgc | ttt | gct | acc | act | ttc | tat | cag | 288 |
|---|---|---|---|---|---|---|---|---|---|---|---|---|---|---|---|---|
| Trp | Glu | Leu | Ser | Lys | Ala | Asn | Ser | Arg | Phe | Ala | Thr | Thr | Phe | Tyr | Gln | |
| | | | | 85 | | | | | 90 | | | | | 95 | | |

| cac | ctg | gca | gat | tcc | aag | aat | gac | aat | gat | aac | att | ttc | ctg | tca | ccc | 336 |
|---|---|---|---|---|---|---|---|---|---|---|---|---|---|---|---|---|
| His | Leu | Ala | Asp | Ser | Lys | Asn | Asp | Asn | Asp | Asn | Ile | Phe | Leu | Ser | Pro | |
| | | | 100 | | | | | 105 | | | | | 110 | | | |

| ctg | agt | atc | tcc | acg | gct | ttt | gct | atg | acc | aag | ctg | ggt | gcc | tgt | aat | 384 |
|---|---|---|---|---|---|---|---|---|---|---|---|---|---|---|---|---|
| Leu | Ser | Ile | Ser | Thr | Ala | Phe | Ala | Met | Thr | Lys | Leu | Gly | Ala | Cys | Asn | |
| | | 115 | | | | | 120 | | | | | 125 | | | | |

| gac | acc | ctc | cag | caa | ctg | atg | gag | gta | ttt | aag | ttt | gac | acc | ata | tct | 432 |
|---|---|---|---|---|---|---|---|---|---|---|---|---|---|---|---|---|
| Asp | Thr | Leu | Gln | Gln | Leu | Met | Glu | Val | Phe | Lys | Phe | Asp | Thr | Ile | Ser | |
| | 130 | | | | | 135 | | | | | 140 | | | | | |

| gag | aaa | aca | tct | gat | cag | atc | cac | ttc | ttc | ttt | gcc | aaa | ctg | aac | tgc | 480 |
|---|---|---|---|---|---|---|---|---|---|---|---|---|---|---|---|---|
| Glu | Lys | Thr | Ser | Asp | Gln | Ile | His | Phe | Phe | Phe | Ala | Lys | Leu | Asn | Cys | |
| 145 | | | | | 150 | | | | | 155 | | | | | 160 | |

| cga | ctc | tat | cga | aaa | gcc | cag | aaa | tcc | tcc | aag | tta | gta | tca | gcc | aat | 528 |
|---|---|---|---|---|---|---|---|---|---|---|---|---|---|---|---|---|
| Arg | Leu | Tyr | Arg | Lys | Ala | Gln | Lys | Ser | Ser | Lys | Leu | Val | Ser | Ala | Asn | |
| | | | | 165 | | | | | 170 | | | | | 175 | | |

| cgc | ctt | ttt | gga | gac | aaa | tcc | ctt | acc | ttc | aat | gag | acc | tac | cag | gac | 576 |
|---|---|---|---|---|---|---|---|---|---|---|---|---|---|---|---|---|
| Arg | Leu | Phe | Gly | Asp | Lys | Ser | Leu | Thr | Phe | Asn | Glu | Thr | Tyr | Gln | Asp | |
| | | | 180 | | | | | 185 | | | | | 190 | | | |

| atc | agt | gag | ttg | gta | tat | gga | gcc | aag | ctc | cag | ccc | ctg | gac | ttc | aag | 624 |
|---|---|---|---|---|---|---|---|---|---|---|---|---|---|---|---|---|
| Ile | Ser | Glu | Leu | Val | Tyr | Gly | Ala | Lys | Leu | Gln | Pro | Leu | Asp | Phe | Lys | |
| | | 195 | | | | | 200 | | | | | 205 | | | | |

| gaa | aat | gca | gag | caa | tcc | aga | gcg | gcc | atc | aac | aaa | tgg | gtg | tcc | aat | 672 |
|---|---|---|---|---|---|---|---|---|---|---|---|---|---|---|---|---|
| Glu | Asn | Ala | Glu | Gln | Ser | Arg | Ala | Ala | Ile | Asn | Lys | Trp | Val | Ser | Asn | |
| | 210 | | | | | 215 | | | | | 220 | | | | | |

| aag | acc | gaa | ggc | cga | atc | acc | gat | gtc | att | ccc | tcg | gaa | gcc | atc | aat | 720 |
|---|---|---|---|---|---|---|---|---|---|---|---|---|---|---|---|---|
| Lys | Thr | Glu | Gly | Arg | Ile | Thr | Asp | Val | Ile | Pro | Ser | Glu | Ala | Ile | Asn | |
| 225 | | | | | 230 | | | | | 235 | | | | | 240 | |

| gag | ctc | act | gtt | ctg | gtg | ctg | gtt | aac | acc | att | tac | ttc | aag | ggc | ctg | 768 |
|---|---|---|---|---|---|---|---|---|---|---|---|---|---|---|---|---|
| Glu | Leu | Thr | Val | Leu | Val | Leu | Val | Asn | Thr | Ile | Tyr | Phe | Lys | Gly | Leu | |
| | | | 245 | | | | | 250 | | | | | 255 | | | |

| tgg | aag | tca | aag | ttc | agc | cct | gag | aac | aca | agg | aag | gaa | ctg | ttc | tac | 816 |
|---|---|---|---|---|---|---|---|---|---|---|---|---|---|---|---|---|
| Trp | Lys | Ser | Lys | Phe | Ser | Pro | Glu | Asn | Thr | Arg | Lys | Glu | Leu | Phe | Tyr | |
| | | | 260 | | | | | 265 | | | | | 270 | | | |

| aag | gct | gat | gga | gag | tcg | tgt | tca | gca | tct | atg | atg | tac | cag | gaa | ggc | 864 |
|---|---|---|---|---|---|---|---|---|---|---|---|---|---|---|---|---|
| Lys | Ala | Asp | Gly | Glu | Ser | Cys | Ser | Ala | Ser | Met | Met | Tyr | Gln | Glu | Gly | |
| | | 275 | | | | | 280 | | | | | 285 | | | | |

| aag | ttc | cgt | tat | cgg | cgc | gtg | gct | gaa | ggc | acc | cag | gtg | ctt | gag | ttg | 912 |
|---|---|---|---|---|---|---|---|---|---|---|---|---|---|---|---|---|
| Lys | Phe | Arg | Tyr | Arg | Arg | Val | Ala | Glu | Gly | Thr | Gln | Val | Leu | Glu | Leu | |
| | 290 | | | | | 295 | | | | | 300 | | | | | |

```
ccc ttc aaa ggt gat gac atc acc atg gtc ctc atc ttg ccc aag cct      960
Pro Phe Lys Gly Asp Asp Ile Thr Met Val Leu Ile Leu Pro Lys Pro
305                 310                 315                 320 gag aag agc ctg gcc aag gta gag aag gaa ctc acc cca gag gtg ctg     1008
Glu Lys Ser Leu Ala Lys Val Glu Lys Glu Leu Thr Pro Glu Val Leu
            325                 330                 335 caa gag tgg ctg gat gaa ttg gag gag atg atg ctg gtg gtc cac atg     1056
Gln Glu Trp Leu Asp Glu Leu Glu Glu Met Met Leu Val Val His Met
        340                 345                 350 ccc cgc ttc cgc att gag gac ggc ttc agt ttg aag gag cag ctg caa     1104
Pro Arg Phe Arg Ile Glu Asp Gly Phe Ser Leu Lys Glu Gln Leu Gln
    355                 360                 365 gac atg ggc ctt gtc gat ctg ttc agc cct gaa aag tcc aaa ctc cca     1152
Asp Met Gly Leu Val Asp Leu Phe Ser Pro Glu Lys Ser Lys Leu Pro
370                 375                 380 ggt att gtt gca gaa ggc cga gat gac ctc tat gtc tca gat gca ttc     1200
Gly Ile Val Ala Glu Gly Arg Asp Asp Leu Tyr Val Ser Asp Ala Phe
385                 390                 395                 400 cat aag gca ttt ctt gag gta aat gaa gaa ggc agt gaa gca gct gca     1248
His Lys Ala Phe Leu Glu Val Asn Glu Glu Gly Ser Glu Ala Ala Ala
            405                 410                 415 agt acc gct gtt gtg att gct ggc cgt cta aac ccc aac agg gtg act     1296
Ser Thr Ala Val Val Ile Ala Gly Arg Leu Asn Pro Asn Arg Val Thr
        420                 425                 430 ttc aag gcc aac agg cct ttc ctg gtt ttt ata aga gaa gtt cct ctg     1344
Phe Lys Ala Asn Arg Pro Phe Leu Val Phe Ile Arg Glu Val Pro Leu
    435                 440                 445 aac act att atc ttc atg ggc aga gta gcc aac cct tgt gtt aag         1389
Asn Thr Ile Ile Phe Met Gly Arg Val Ala Asn Pro Cys Val Lys
450                 455                 460 taaaatgttc ttattctttg cacctcttcc tattttggt ttgtgaacag aagtaaaaat    1449
aaatacaaac tacttccatc tcacattaaa a                                  1480

<210> SEQ ID NO 46
<211> LENGTH: 463
<212> TYPE: PRT
<213> ORGANISM: Homo sapiens

<400> SEQUENCE: 46

Met Tyr Ser Asn Val Ile Gly Thr Val Thr Ser Gly Lys Arg Lys Val
1               5                   10                  15

Tyr Leu Leu Ser Leu Leu Leu Ile Gly Phe Trp Asp Cys Val Thr Cys
            20                  25                  30

His Gly Ser Pro Val Asp Ile Cys Thr Ala Lys Pro Arg Asp Ile Pro
        35                  40                  45

Met Asn Pro Met Cys Ile Tyr Arg Ser Pro Glu Lys Lys Ala Thr Glu
    50                  55                  60

Asp Glu Gly Ser Glu Gln Lys Ile Pro Glu Ala Thr Asn Arg Arg Val
65                  70                  75                  80

Trp Glu Leu Ser Lys Ala Asn Ser Arg Phe Ala Thr Thr Phe Tyr Gln
                85                  90                  95

His Leu Ala Asp Ser Lys Asn Asp Asn Asp Asn Ile Phe Leu Ser Pro
            100                 105                 110

Leu Ser Ile Ser Thr Ala Phe Ala Met Thr Lys Leu Gly Ala Cys Asn
        115                 120                 125

Asp Thr Leu Gln Gln Leu Met Glu Val Phe Lys Phe Asp Thr Ile Ser
    130                 135                 140
```

| | | | | | | | | | | | | | | |
|---|---|---|---|---|---|---|---|---|---|---|---|---|---|---|
| Glu | Lys | Thr | Ser | Asp | Gln | Ile | His | Phe | Phe | Ala | Lys | Leu | Asn | Cys |
| 145 | | | | 150 | | | | 155 | | | | | | 160 |

| | | | | | | | | | | | | | | |
|---|---|---|---|---|---|---|---|---|---|---|---|---|---|---|
| Arg | Leu | Tyr | Arg | Lys | Ala | Gln | Lys | Ser | Ser | Lys | Leu | Val | Ser | Ala | Asn |
| | | | | 165 | | | | | 170 | | | | | 175 | |

Arg Leu Phe Gly Asp Lys Ser Leu Thr Phe Asn Glu Thr Tyr Gln Asp
                180                 185                 190

Ile Ser Glu Leu Val Tyr Gly Ala Lys Leu Gln Pro Leu Asp Phe Lys
        195                 200                 205

Glu Asn Ala Glu Gln Ser Arg Ala Ala Ile Asn Lys Trp Val Ser Asn
    210                 215                 220

Lys Thr Glu Gly Arg Ile Thr Asp Val Ile Pro Ser Glu Ala Ile Asn
225                 230                 235                 240

Glu Leu Thr Val Leu Val Leu Asn Thr Ile Tyr Phe Lys Gly Leu
                245                 250                 255

Trp Lys Ser Lys Phe Ser Pro Glu Asn Thr Arg Lys Glu Leu Phe Tyr
                260                 265                 270

Lys Ala Asp Gly Glu Ser Cys Ser Ala Ser Met Met Tyr Gln Glu Gly
        275                 280                 285

Lys Phe Arg Tyr Arg Arg Val Ala Glu Gly Thr Gln Val Leu Glu Leu
    290                 295                 300

Pro Phe Lys Gly Asp Asp Ile Thr Met Val Leu Ile Leu Pro Lys Pro
305                 310                 315                 320

Glu Lys Ser Leu Ala Lys Val Glu Lys Glu Leu Thr Pro Glu Val Leu
                325                 330                 335

Gln Glu Trp Leu Asp Glu Leu Glu Glu Met Met Leu Val Val His Met
                340                 345                 350

Pro Arg Phe Arg Ile Glu Asp Gly Phe Ser Leu Lys Glu Gln Leu Gln
        355                 360                 365

Asp Met Gly Leu Val Asp Leu Phe Ser Pro Glu Lys Ser Lys Leu Pro
    370                 375                 380

Gly Ile Val Ala Glu Gly Arg Asp Asp Leu Tyr Val Ser Asp Ala Phe
385                 390                 395                 400

His Lys Ala Phe Leu Glu Val Asn Glu Glu Gly Ser Glu Ala Ala Ala
                405                 410                 415

Ser Thr Ala Val Val Ile Ala Gly Arg Leu Asn Pro Asn Arg Val Thr
                420                 425                 430

Phe Lys Ala Asn Arg Pro Phe Leu Val Phe Ile Arg Glu Val Pro Leu
        435                 440                 445

Asn Thr Ile Ile Phe Met Gly Arg Val Ala Asn Pro Cys Val Lys
    450                 455                 460

```
<210> SEQ ID NO 47
<211> LENGTH: 1477
<212> TYPE: DNA
<213> ORGANISM: Homo sapiens
<220> FEATURE:
<221> NAME/KEY: CDS
<222> LOCATION: (1)..(1386)

<400> SEQUENCE: 47
``` atg tat tcc aat gtg ata gga act gta acc tct gga aaa agg aag gtt         48
Met Tyr Ser Asn Val Ile Gly Thr Val Thr Ser Gly Lys Arg Lys Val
1               5                   10                  15 tat ctt ttg tcc ttg ctg ctc att ggc ttc tgg gac tgc gtg acc tgt         96
Tyr Leu Leu Ser Leu Leu Leu Ile Gly Phe Trp Asp Cys Val Thr Cys
            20                  25                  30

```
cac ggg agc cct gtg gac atc tgc aca gcc aag ccg cgg gac att ccc        144
His Gly Ser Pro Val Asp Ile Cys Thr Ala Lys Pro Arg Asp Ile Pro
        35                  40                  45 atg aat ccc atg tgc att tac cgc tcc ccg gag aag aag gca act gag        192
Met Asn Pro Met Cys Ile Tyr Arg Ser Pro Glu Lys Lys Ala Thr Glu
 50                  55                  60 gat gag ggc tca gaa cag aag atc ccg gag gcc acc aac cgg cgt gtc        240
Asp Glu Gly Ser Glu Gln Lys Ile Pro Glu Ala Thr Asn Arg Arg Val
 65                  70                  75                  80 tgg gaa ctg tcc aag gcc aat tcc cgc ttt gct acc act ttc tat cag        288
Trp Glu Leu Ser Lys Ala Asn Ser Arg Phe Ala Thr Thr Phe Tyr Gln
                 85                  90                  95 cac ctg gca gat tcc aag aat gac aat gat aac att ttc ctg tca ccc        336
His Leu Ala Asp Ser Lys Asn Asp Asn Asp Asn Ile Phe Leu Ser Pro
                100                 105                 110 ctg agt atc tcc acg gct ttt gct atg acc aag ctg ggt gcc tgt aat        384
Leu Ser Ile Ser Thr Ala Phe Ala Met Thr Lys Leu Gly Ala Cys Asn
                115                 120                 125 gac acc ctc cag caa ctg atg gag gta ttt aag ttt gac acc ata tct        432
Asp Thr Leu Gln Gln Leu Met Glu Val Phe Lys Phe Asp Thr Ile Ser
130                 135                 140 gag aaa aca tct gat cag atc cac ttc ttc ttt gcc aaa ctg aac tgc        480
Glu Lys Thr Ser Asp Gln Ile His Phe Phe Phe Ala Lys Leu Asn Cys
145                 150                 155                 160 cga ctc tat cga aaa gcc cag aaa tcc tcc aag tta gta tca gcc aat        528
Arg Leu Tyr Arg Lys Ala Gln Lys Ser Ser Lys Leu Val Ser Ala Asn
                165                 170                 175 cgc ctt ttt gga gac aaa tcc ctt acc ttc aat gag acc tac cag gac        576
Arg Leu Phe Gly Asp Lys Ser Leu Thr Phe Asn Glu Thr Tyr Gln Asp
                180                 185                 190 atc agt gag ttg gta tat gga gcc aag ctc cag ccc ctg gac ttc aag        624
Ile Ser Glu Leu Val Tyr Gly Ala Lys Leu Gln Pro Leu Asp Phe Lys
                195                 200                 205 gaa aat gca gag caa tcc aga gcg gcc atc aac aaa tgg gtg tcc aat        672
Glu Asn Ala Glu Gln Ser Arg Ala Ala Ile Asn Lys Trp Val Ser Asn
210                 215                 220 aag acc gaa ggc cga atc acc gat gtc att ccc tcg gaa gcc atc aat        720
Lys Thr Glu Gly Arg Ile Thr Asp Val Ile Pro Ser Glu Ala Ile Asn
225                 230                 235                 240 gag ctc act gtt ctg gtg ctg gtt aac acc att tac ttc aag ggc ctg        768
Glu Leu Thr Val Leu Val Leu Val Asn Thr Ile Tyr Phe Lys Gly Leu
                245                 250                 255 tgg aag tca aag ttc agc cct gag aac aca agg aag gaa ctg ttc tac        816
Trp Lys Ser Lys Phe Ser Pro Glu Asn Thr Arg Lys Glu Leu Phe Tyr
                260                 265                 270 aag gct gat gga gag tcg tgt tca gca tct atg atg tac cag gaa ggc        864
Lys Ala Asp Gly Glu Ser Cys Ser Ala Ser Met Met Tyr Gln Glu Gly
                275                 280                 285 aag ttc cgt tat cgg cgc gtg gct gaa ggc acc cag gtg ctt gag ttg        912
Lys Phe Arg Tyr Arg Arg Val Ala Glu Gly Thr Gln Val Leu Glu Leu
                290                 295                 300 ccc ttc aaa ggt gat gac atc acc atg gtc ctc atc ttg ccc aag cct        960
Pro Phe Lys Gly Asp Asp Ile Thr Met Val Leu Ile Leu Pro Lys Pro
305                 310                 315                 320 gag aag agc ctg gcc aag gta gag aag gaa ctc acc cca gag gtg ctg       1008
Glu Lys Ser Leu Ala Lys Val Glu Lys Glu Leu Thr Pro Glu Val Leu
                325                 330                 335 caa gag tgg ctg gat gaa ttg gag gag atg atg ctg gtg gtc cac atg       1056
Gln Glu Trp Leu Asp Glu Leu Glu Glu Met Met Leu Val Val His Met
```

```
                    340                 345                 350
ccc cgc ttc cgc att gag gac ggc ttc agt ttg aag gag cag ctg caa    1104
Pro Arg Phe Arg Ile Glu Asp Gly Phe Ser Leu Lys Glu Gln Leu Gln
            355                 360                 365 gac atg ggc ctt gtc gat ctg ttc agc cct gaa aag tcc aaa ctc cca    1152
Asp Met Gly Leu Val Asp Leu Phe Ser Pro Glu Lys Ser Lys Leu Pro
370                 375                 380 ggt att gtt gca gaa ggc cga gat gac ctc tat gtc tca gat gca ttc    1200
Gly Ile Val Ala Glu Gly Arg Asp Asp Leu Tyr Val Ser Asp Ala Phe
385                 390                 395                 400 cat aag gca ttt ctt gag gta aat gaa gaa ggc agt gaa gca gct gca    1248
His Lys Ala Phe Leu Glu Val Asn Glu Glu Gly Ser Glu Ala Ala Ala
            405                 410                 415 agt acc gct gtt gtg att gct ggc cta aac ccc aac agg gtg act ttc    1296
Ser Thr Ala Val Val Ile Ala Gly Leu Asn Pro Asn Arg Val Thr Phe
            420                 425                 430 aag gcc aac agg cct ttc ctg gtt ttt ata aga gaa gtt cct ctg aac    1344
Lys Ala Asn Arg Pro Phe Leu Val Phe Ile Arg Glu Val Pro Leu Asn
            435                 440                 445 act att atc ttc atg ggc aga gta gcc aac cct tgt gtt aag            1386
Thr Ile Ile Phe Met Gly Arg Val Ala Asn Pro Cys Val Lys
450                 455                 460 taaaatgttc ttattctttg cacctcttcc tattttggt ttgtgaacag aagtaaaaat   1446
aaatacaaac tacttccatc tcacattaaa a                                 1477

<210> SEQ ID NO 48
<211> LENGTH: 462
<212> TYPE: PRT
<213> ORGANISM: Homo sapiens

<400> SEQUENCE: 48

Met Tyr Ser Asn Val Ile Gly Thr Val Thr Ser Gly Lys Arg Lys Val
1               5                   10                  15

Tyr Leu Leu Ser Leu Leu Leu Ile Gly Phe Trp Asp Cys Val Thr Cys
            20                  25                  30

His Gly Ser Pro Val Asp Ile Cys Thr Ala Lys Pro Arg Asp Ile Pro
        35                  40                  45

Met Asn Pro Met Cys Ile Tyr Arg Ser Pro Glu Lys Lys Ala Thr Glu
    50                  55                  60

Asp Glu Gly Ser Glu Gln Lys Ile Pro Glu Ala Thr Asn Arg Arg Val
65                  70                  75                  80

Trp Glu Leu Ser Lys Ala Asn Ser Arg Phe Ala Thr Thr Phe Tyr Gln
                85                  90                  95

His Leu Ala Asp Ser Lys Asn Asp Asn Asp Asn Ile Phe Leu Ser Pro
            100                 105                 110

Leu Ser Ile Ser Thr Ala Phe Ala Met Thr Lys Leu Gly Ala Cys Asn
        115                 120                 125

Asp Thr Leu Gln Gln Leu Met Glu Val Phe Lys Phe Asp Thr Ile Ser
    130                 135                 140

Glu Lys Thr Ser Asp Gln Ile His Phe Phe Ala Lys Leu Asn Cys
145                 150                 155                 160

Arg Leu Tyr Arg Lys Ala Gln Lys Ser Lys Leu Val Ser Ala Asn
                165                 170                 175

Arg Leu Phe Gly Asp Lys Ser Leu Thr Phe Asn Glu Thr Tyr Gln Asp
            180                 185                 190

Ile Ser Glu Leu Val Tyr Gly Ala Lys Leu Gln Pro Leu Asp Phe Lys
```

```
                195                 200                 205
Glu Asn Ala Glu Gln Ser Arg Ala Ala Ile Asn Lys Trp Val Ser Asn
    210                 215                 220

Lys Thr Glu Gly Arg Ile Thr Asp Val Ile Pro Ser Glu Ala Ile Asn
225                 230                 235                 240

Glu Leu Thr Val Leu Val Leu Val Asn Thr Ile Tyr Phe Lys Gly Leu
                245                 250                 255

Trp Lys Ser Lys Phe Ser Pro Glu Asn Thr Arg Lys Glu Leu Phe Tyr
            260                 265                 270

Lys Ala Asp Gly Glu Ser Cys Ser Ala Ser Met Met Tyr Gln Glu Gly
        275                 280                 285

Lys Phe Arg Tyr Arg Arg Val Ala Glu Gly Thr Gln Val Leu Glu Leu
    290                 295                 300

Pro Phe Lys Gly Asp Asp Ile Thr Met Val Leu Ile Leu Pro Lys Pro
305                 310                 315                 320

Glu Lys Ser Leu Ala Lys Val Glu Lys Glu Leu Thr Pro Glu Val Leu
                325                 330                 335

Gln Glu Trp Leu Asp Glu Leu Glu Glu Met Met Leu Val Val His Met
            340                 345                 350

Pro Arg Phe Arg Ile Glu Asp Gly Phe Ser Leu Lys Glu Gln Leu Gln
        355                 360                 365

Asp Met Gly Leu Val Asp Leu Phe Ser Pro Glu Lys Ser Lys Leu Pro
    370                 375                 380

Gly Ile Val Ala Glu Gly Arg Asp Asp Leu Tyr Val Ser Asp Ala Phe
385                 390                 395                 400

His Lys Ala Phe Leu Glu Val Asn Glu Glu Gly Ser Glu Ala Ala Ala
                405                 410                 415

Ser Thr Ala Val Val Ile Ala Gly Leu Asn Pro Asn Arg Val Thr Phe
            420                 425                 430

Lys Ala Asn Arg Pro Phe Leu Val Phe Ile Arg Glu Val Pro Leu Asn
        435                 440                 445

Thr Ile Ile Phe Met Gly Arg Val Ala Asn Pro Cys Val Lys
    450                 455                 460

<210> SEQ ID NO 49
<211> LENGTH: 41
<212> TYPE: DNA
<213> ORGANISM: Artificial
<220> FEATURE:
<223> OTHER INFORMATION: Forward primer

<400> SEQUENCE: 49
gccgactcta tcgaaaagcc cagaaatcct ccaagttagt g                          41

<210> SEQ ID NO 50
<211> LENGTH: 41
<212> TYPE: DNA
<213> ORGANISM: Artificial
<220> FEATURE:
<223> OTHER INFORMATION: Reverse primer

<400> SEQUENCE: 50
cactaacttg gaggatttct gggcttttcg atagagtcgg c                          41

<210> SEQ ID NO 51
<211> LENGTH: 33
<212> TYPE: DNA
<213> ORGANISM: Artificial
```

```
<220> FEATURE:
<223> OTHER INFORMATION: Forward primer

<400> SEQUENCE: 51
gttgtgattg ctggccattc gctaaacccc aac                              33

<210> SEQ ID NO 52
<211> LENGTH: 33
<212> TYPE: DNA
<213> ORGANISM: Artificial
<220> FEATURE:
<223> OTHER INFORMATION: Reverse primer

<400> SEQUENCE: 52
gttggggttt agcgaatggc cagcaatcac aac                              33

<210> SEQ ID NO 53
<211> LENGTH: 36
<212> TYPE: DNA
<213> ORGANISM: Artificial
<220> FEATURE:
<223> OTHER INFORMATION: Forward primer

<400> SEQUENCE: 53
gttgtgattg ctggccgtcc atcgctaaac cccaac                           36

<210> SEQ ID NO 54
<211> LENGTH: 36
<212> TYPE: DNA
<213> ORGANISM: Artificial
<220> FEATURE:
<223> OTHER INFORMATION: Reverse primer

<400> SEQUENCE: 54
gttggggttt agcgatggac ggccagcaat cacaac                           36

<210> SEQ ID NO 55
<211> LENGTH: 36
<212> TYPE: DNA
<213> ORGANISM: Artificial
<220> FEATURE:
<223> OTHER INFORMATION: Forward primer

<400> SEQUENCE: 55
gctgttgtga ttgctggcct aaaccccaac agggtg                           36

<210> SEQ ID NO 56
<211> LENGTH: 36
<212> TYPE: DNA
<213> ORGANISM: Artificial
<220> FEATURE:
<223> OTHER INFORMATION: Reverse primer

<400> SEQUENCE: 56
caccctgttg ggtttaggc cagcaatcac aacagc                            36

<210> SEQ ID NO 57
<211> LENGTH: 34
<212> TYPE: DNA
<213> ORGANISM: Artificial
<220> FEATURE:
<223> OTHER INFORMATION: Forward primer

<400> SEQUENCE: 57
ctgttgtgat tgctggctcg ctaaacccca acag                             34
```

<210> SEQ ID NO 58
<211> LENGTH: 34
<212> TYPE: DNA
<213> ORGANISM: Artificial
<220> FEATURE:
<223> OTHER INFORMATION: Reverse primer

<400> SEQUENCE: 58
ctgttggggt ttagcgagcc agcaatcaca acag                                34

<210> SEQ ID NO 59
<211> LENGTH: 32
<212> TYPE: DNA
<213> ORGANISM: Artificial
<220> FEATURE:
<223> OTHER INFORMATION: Forward primer

<400> SEQUENCE: 59
tgtgattgct ggccgtctaa accccaacag gg                                  32

<210> SEQ ID NO 60
<211> LENGTH: 32
<212> TYPE: DNA
<213> ORGANISM: Artificial
<220> FEATURE:
<223> OTHER INFORMATION: Reverse primer

<400> SEQUENCE: 60
ccctgttggg gtttagacgg ccagcaatca ca                                  32

<210> SEQ ID NO 61
<211> LENGTH: 1299
<212> TYPE: DNA
<213> ORGANISM: Homo sapiens
<220> FEATURE:
<221> NAME/KEY: CDS
<222> LOCATION: (1)..(1299)

<400> SEQUENCE: 61

```
cac ggg agc cct gtg gac atc tgc aca gcc aag ccg cgg gac att ccc        48
His Gly Ser Pro Val Asp Ile Cys Thr Ala Lys Pro Arg Asp Ile Pro
1               5                   10                  15 atg aat ccc atg tgc att tac cgc tcc ccg gag aag aag gca act gag        96
Met Asn Pro Met Cys Ile Tyr Arg Ser Pro Glu Lys Lys Ala Thr Glu
            20                  25                  30 gat gag ggc tca gaa cag aag atc ccg gag gcc acc aac cgg cgt gtc       144
Asp Glu Gly Ser Glu Gln Lys Ile Pro Glu Ala Thr Asn Arg Arg Val
        35                  40                  45 tgg gaa ctg tcc aag gcc aat tcc cgc ttt gct acc act ttc tat cag       192
Trp Glu Leu Ser Lys Ala Asn Ser Arg Phe Ala Thr Thr Phe Tyr Gln
    50                  55                  60 cac ctg gca gat tcc aag aat gac aat gat aac att ttc ctg tca ccc       240
His Leu Ala Asp Ser Lys Asn Asp Asn Asp Asn Ile Phe Leu Ser Pro
65                  70                  75                  80 ctg agt atc tcc acg gct ttt gct atg acc aag ctg ggt gcc tgt aat       288
Leu Ser Ile Ser Thr Ala Phe Ala Met Thr Lys Leu Gly Ala Cys Asn
                85                  90                  95 gac acc ctc cag caa ctg atg gag gta ttt aag ttt gac acc ata tct       336
Asp Thr Leu Gln Gln Leu Met Glu Val Phe Lys Phe Asp Thr Ile Ser
            100                 105                 110 gag aaa aca tct gat cag atc cac ttc ttc ttt gcc aaa ctg aac tgc       384
Glu Lys Thr Ser Asp Gln Ile His Phe Phe Phe Ala Lys Leu Asn Cys
        115                 120                 125
```

```
cga ctc tat cga aaa gcc aac aaa tcc tcc aag tta gta tca gcc aat       432
Arg Leu Tyr Arg Lys Ala Asn Lys Ser Ser Lys Leu Val Ser Ala Asn
130                 135                 140 cgc ctt ttt gga gac aaa tcc ctt acc ttc aat gag acc tac cag gac       480
Arg Leu Phe Gly Asp Lys Ser Leu Thr Phe Asn Glu Thr Tyr Gln Asp
145                 150                 155                 160 atc agt gag ttg gta tat gga gcc aag ctc cag ccc ctg gac ttc aag       528
Ile Ser Glu Leu Val Tyr Gly Ala Lys Leu Gln Pro Leu Asp Phe Lys
                165                 170                 175 gaa aat gca gag caa tcc aga gcg gcc atc aac aaa tgg gtg tcc aat       576
Glu Asn Ala Glu Gln Ser Arg Ala Ala Ile Asn Lys Trp Val Ser Asn
            180                 185                 190 aag acc gaa ggc cga atc acc gat gtc att ccc tcg gaa gcc atc aat       624
Lys Thr Glu Gly Arg Ile Thr Asp Val Ile Pro Ser Glu Ala Ile Asn
        195                 200                 205 gag ctc act gtt ctg gtg ctg gtt aac acc att tac ttc aag ggc ctg       672
Glu Leu Thr Val Leu Val Leu Val Asn Thr Ile Tyr Phe Lys Gly Leu
    210                 215                 220 tgg aag tca aag ttc agc cct gag aac aca agg aag gaa ctg ttc tac       720
Trp Lys Ser Lys Phe Ser Pro Glu Asn Thr Arg Lys Glu Leu Phe Tyr
225                 230                 235                 240 aag gct gat gga gag tcg tgt tca gca tct atg atg tac cag gaa ggc       768
Lys Ala Asp Gly Glu Ser Cys Ser Ala Ser Met Met Tyr Gln Glu Gly
                245                 250                 255 aag ttc cgt tat cgg cgc gtg gct gaa ggc acc cag gtg ctt gag ttg       816
Lys Phe Arg Tyr Arg Arg Val Ala Glu Gly Thr Gln Val Leu Glu Leu
            260                 265                 270 ccc ttc aaa ggt gat gac atc acc atg gtc ctc atc ttg ccc aag cct       864
Pro Phe Lys Gly Asp Asp Ile Thr Met Val Leu Ile Leu Pro Lys Pro
        275                 280                 285 gag aag agc ctg gcc aag gtg gag aag gaa ctc acc cca gag gtg ctg       912
Glu Lys Ser Leu Ala Lys Val Glu Lys Glu Leu Thr Pro Glu Val Leu
    290                 295                 300 cag gag tgg ctg gat gaa ttg gag gag atg atg ctg gtg gtc cac atg       960
Gln Glu Trp Leu Asp Glu Leu Glu Glu Met Met Leu Val Val His Met
305                 310                 315                 320 ccc cgc ttc cgc att gag gac ggc ttc agt ttg aag gag cag ctg caa      1008
Pro Arg Phe Arg Ile Glu Asp Gly Phe Ser Leu Lys Glu Gln Leu Gln
                325                 330                 335 gac atg ggc ctt gtc gat ctg ttc agc cct gaa aag tcc aaa ctc cca      1056
Asp Met Gly Leu Val Asp Leu Phe Ser Pro Glu Lys Ser Lys Leu Pro
            340                 345                 350 ggt att gtt gca gaa ggc cga gat gac ctc tat gtc tca gat gca ttc      1104
Gly Ile Val Ala Glu Gly Arg Asp Asp Leu Tyr Val Ser Asp Ala Phe
        355                 360                 365 cat aag gca ttt ctt gag gta aat gaa gaa ggc agt gaa gca gct gca      1152
His Lys Ala Phe Leu Glu Val Asn Glu Glu Gly Ser Glu Ala Ala Ala
    370                 375                 380 agt acc gct gtt gtg att gct ggc cgt cag cta aac ccc aac agg gtg      1200
Ser Thr Ala Val Val Ile Ala Gly Arg Gln Leu Asn Pro Asn Arg Val
385                 390                 395                 400 act ttc aag gcc aac agg cct ttc ctg gtt ttt ata aga gaa gtt cct      1248
Thr Phe Lys Ala Asn Arg Pro Phe Leu Val Phe Ile Arg Glu Val Pro
                405                 410                 415 ctg aac act att atc ttc atg ggc aga gta gcc aac cct tgt gtt aag      1296
Leu Asn Thr Ile Ile Phe Met Gly Arg Val Ala Asn Pro Cys Val Lys
            420                 425                 430 tag                                                                   1299
```

-continued

```
<210> SEQ ID NO 62
<211> LENGTH: 432
<212> TYPE: PRT
<213> ORGANISM: Homo sapiens

<400> SEQUENCE: 62
```

| | | | | | | | | | | | | | | | |
|---|---|---|---|---|---|---|---|---|---|---|---|---|---|---|---|
| His | Gly | Ser | Pro | Val | Asp | Ile | Cys | Thr | Ala | Lys | Pro | Arg | Asp | Ile | Pro |
| 1 | | | | 5 | | | | | 10 | | | | | 15 | |
| Met | Asn | Pro | Met | Cys | Ile | Tyr | Arg | Ser | Pro | Glu | Lys | Lys | Ala | Thr | Glu |
| | | | 20 | | | | | 25 | | | | | 30 | | |
| Asp | Glu | Gly | Ser | Glu | Gln | Lys | Ile | Pro | Glu | Ala | Thr | Asn | Arg | Arg | Val |
| | | | 35 | | | | | 40 | | | | | 45 | | |
| Trp | Glu | Leu | Ser | Lys | Ala | Asn | Ser | Arg | Phe | Ala | Thr | Thr | Phe | Tyr | Gln |
| | 50 | | | | | 55 | | | | | 60 | | | | |
| His | Leu | Ala | Asp | Ser | Lys | Asn | Asp | Asn | Asp | Asn | Ile | Phe | Leu | Ser | Pro |
| 65 | | | | | 70 | | | | | 75 | | | | | 80 |
| Leu | Ser | Ile | Ser | Thr | Ala | Phe | Ala | Met | Thr | Lys | Leu | Gly | Ala | Cys | Asn |
| | | | | 85 | | | | | 90 | | | | | 95 | |
| Asp | Thr | Leu | Gln | Gln | Leu | Met | Glu | Val | Phe | Lys | Phe | Asp | Thr | Ile | Ser |
| | | | | 100 | | | | | 105 | | | | | 110 | |
| Glu | Lys | Thr | Ser | Asp | Gln | Ile | His | Phe | Phe | Phe | Ala | Lys | Leu | Asn | Cys |
| | | | 115 | | | | | 120 | | | | | 125 | | |
| Arg | Leu | Tyr | Arg | Lys | Ala | Asn | Lys | Ser | Ser | Lys | Leu | Val | Ser | Ala | Asn |
| | 130 | | | | | 135 | | | | | 140 | | | | |
| Arg | Leu | Phe | Gly | Asp | Lys | Ser | Leu | Thr | Phe | Asn | Glu | Thr | Tyr | Gln | Asp |
| 145 | | | | | 150 | | | | | 155 | | | | | 160 |
| Ile | Ser | Glu | Leu | Val | Tyr | Gly | Ala | Lys | Leu | Gln | Pro | Leu | Asp | Phe | Lys |
| | | | | 165 | | | | | 170 | | | | | 175 | |
| Glu | Asn | Ala | Glu | Gln | Ser | Arg | Ala | Ala | Ile | Asn | Lys | Trp | Val | Ser | Asn |
| | | | 180 | | | | | 185 | | | | | 190 | | |
| Lys | Thr | Glu | Gly | Arg | Ile | Thr | Asp | Val | Ile | Pro | Ser | Glu | Ala | Ile | Asn |
| | | | 195 | | | | | 200 | | | | | 205 | | |
| Glu | Leu | Thr | Val | Leu | Val | Leu | Val | Asn | Thr | Ile | Tyr | Phe | Lys | Gly | Leu |
| | 210 | | | | | 215 | | | | | 220 | | | | |
| Trp | Lys | Ser | Lys | Phe | Ser | Pro | Glu | Asn | Thr | Arg | Lys | Glu | Leu | Phe | Tyr |
| 225 | | | | | 230 | | | | | 235 | | | | | 240 |
| Lys | Ala | Asp | Gly | Glu | Ser | Cys | Ser | Ala | Ser | Met | Met | Tyr | Gln | Glu | Gly |
| | | | | 245 | | | | | 250 | | | | | 255 | |
| Lys | Phe | Arg | Tyr | Arg | Arg | Val | Ala | Glu | Gly | Thr | Gln | Val | Leu | Glu | Leu |
| | | | 260 | | | | | 265 | | | | | 270 | | |
| Pro | Phe | Lys | Gly | Asp | Asp | Ile | Thr | Met | Val | Leu | Ile | Leu | Pro | Lys | Pro |
| | | | 275 | | | | | 280 | | | | | 285 | | |
| Glu | Lys | Ser | Leu | Ala | Lys | Val | Glu | Lys | Glu | Leu | Thr | Pro | Glu | Val | Leu |
| | 290 | | | | | 295 | | | | | 300 | | | | |
| Gln | Glu | Trp | Leu | Asp | Glu | Leu | Glu | Met | Met | Leu | Val | Val | His | Met | |
| 305 | | | | | 310 | | | | | 315 | | | | | 320 |
| Pro | Arg | Phe | Arg | Ile | Glu | Asp | Gly | Phe | Ser | Leu | Lys | Glu | Gln | Leu | Gln |
| | | | | 325 | | | | | 330 | | | | | 335 | |
| Asp | Met | Gly | Leu | Val | Asp | Leu | Phe | Ser | Pro | Glu | Lys | Ser | Lys | Leu | Pro |
| | | | 340 | | | | | 345 | | | | | 350 | | |
| Gly | Ile | Val | Ala | Glu | Gly | Arg | Asp | Asp | Leu | Tyr | Val | Ser | Asp | Ala | Phe |
| | | | 355 | | | | | 360 | | | | | 365 | | |
| His | Lys | Ala | Phe | Leu | Glu | Val | Asn | Glu | Glu | Gly | Ser | Glu | Ala | Ala | Ala |
| | 370 | | | | | 375 | | | | | 380 | | | | |

```
Ser Thr Ala Val Val Ile Ala Gly Arg Gln Leu Asn Pro Asn Arg Val
385                 390                 395                 400

Thr Phe Lys Ala Asn Arg Pro Phe Leu Val Phe Ile Arg Glu Val Pro
            405                 410                 415

Leu Asn Thr Ile Ile Phe Met Gly Arg Val Ala Asn Pro Cys Val Lys
        420                 425                 430

<210> SEQ ID NO 63
<211> LENGTH: 1299
<212> TYPE: DNA
<213> ORGANISM: Homo sapiens
<220> FEATURE:
<221> NAME/KEY: CDS
<222> LOCATION: (1)..(1299)

<400> SEQUENCE: 63 cac ggg agc cct gtg gac atc tgc aca gcc aag ccg cgg gac att ccc      48
His Gly Ser Pro Val Asp Ile Cys Thr Ala Lys Pro Arg Asp Ile Pro
1               5                   10                  15 atg aat ccc atg tgc att tac cgc tcc ccg gag aag aag gca act gag      96
Met Asn Pro Met Cys Ile Tyr Arg Ser Pro Glu Lys Lys Ala Thr Glu
            20                  25                  30 gat gag ggc tca gaa cag aag atc ccg gag gcc acc aac cgg cgt gtc     144
Asp Glu Gly Ser Glu Gln Lys Ile Pro Glu Ala Thr Asn Arg Arg Val
        35                  40                  45 tgg gaa ctg tcc aag gcc aat tcc cgc ttt gct acc act ttc tat cag     192
Trp Glu Leu Ser Lys Ala Asn Ser Arg Phe Ala Thr Thr Phe Tyr Gln
    50                  55                  60 cac ctg gca gat tcc aag aat gac aat gat aac att ttc ctg tca ccc     240
His Leu Ala Asp Ser Lys Asn Asp Asn Asp Asn Ile Phe Leu Ser Pro
65                  70                  75                  80 ctg agt atc tcc acg gct ttt gct atg acc aag ctg ggt gcc tgt aat     288
Leu Ser Ile Ser Thr Ala Phe Ala Met Thr Lys Leu Gly Ala Cys Asn
                85                  90                  95 gac acc ctc cag caa ctg atg gag gta ttt aag ttt gac acc ata tct     336
Asp Thr Leu Gln Gln Leu Met Glu Val Phe Lys Phe Asp Thr Ile Ser
            100                 105                 110 gag aaa aca tct gat cag atc cac ttc ttc ttt gcc aaa ctg aac tgc     384
Glu Lys Thr Ser Asp Gln Ile His Phe Phe Phe Ala Lys Leu Asn Cys
        115                 120                 125 cga ctc tat cga aaa gcc aac aaa tcc tcc aag tta gta tca gcc aat     432
Arg Leu Tyr Arg Lys Ala Asn Lys Ser Ser Lys Leu Val Ser Ala Asn
    130                 135                 140 cgc ctt ttt gga gac aaa tcc ctt acc ttc aat gag acc tac cag gac     480
Arg Leu Phe Gly Asp Lys Ser Leu Thr Phe Asn Glu Thr Tyr Gln Asp
145                 150                 155                 160 atc agt gag ttg gta tat gga gcc aag ctc cag ccc ctg gac ttc aag     528
Ile Ser Glu Leu Val Tyr Gly Ala Lys Leu Gln Pro Leu Asp Phe Lys
                165                 170                 175 gaa aat gca gag caa tcc aga gcg gcc atc aac aaa tgg gtg tcc aat     576
Glu Asn Ala Glu Gln Ser Arg Ala Ala Ile Asn Lys Trp Val Ser Asn
            180                 185                 190 aag acc gaa ggc cga atc acc gat gtc att ccc tcg gaa gcc atc aat     624
Lys Thr Glu Gly Arg Ile Thr Asp Val Ile Pro Ser Glu Ala Ile Asn
        195                 200                 205 gag ctc act gtt ctg gtg ctg gtt aac acc att tac ttc aag ggc ctg     672
Glu Leu Thr Val Leu Val Leu Val Asn Thr Ile Tyr Phe Lys Gly Leu
    210                 215                 220 tgg aag tca aag ttc agc cct gag aac aca agg aag gaa ctg ttc tac     720
Trp Lys Ser Lys Phe Ser Pro Glu Asn Thr Arg Lys Glu Leu Phe Tyr
225                 230                 235                 240
```

```
aag gct gat gga gag tcg tgt tca gca tct atg atg tac cag gaa ggc        768
Lys Ala Asp Gly Glu Ser Cys Ser Ala Ser Met Met Tyr Gln Glu Gly
                245                 250                 255 aag ttc cgt tat cgg cgc gtg gct gaa ggc acc cag gtg ctt gag ttg        816
Lys Phe Arg Tyr Arg Arg Val Ala Glu Gly Thr Gln Val Leu Glu Leu
            260                 265                 270 ccc ttc aaa ggt gat gac atc acc atg gtc ctc atc ttg ccc aag cct        864
Pro Phe Lys Gly Asp Asp Ile Thr Met Val Leu Ile Leu Pro Lys Pro
        275                 280                 285 gag aag agc ctg gcc aag gtg gag aag gaa ctc acc cca gag gtg ctg        912
Glu Lys Ser Leu Ala Lys Val Glu Lys Glu Leu Thr Pro Glu Val Leu
    290                 295                 300 cag gag tgg ctg gat gaa ttg gag gag atg atg ctg gtg gtc cac atg        960
Gln Glu Trp Leu Asp Glu Leu Glu Glu Met Met Leu Val Val His Met
305                 310                 315                 320 ccc cgc ttc cgc att gag gac ggc ttc agt ttg aag gag cag ctg caa       1008
Pro Arg Phe Arg Ile Glu Asp Gly Phe Ser Leu Lys Glu Gln Leu Gln
                325                 330                 335 gac atg ggc ctt gtc gat ctg ttc agc cct gaa aag tcc aaa ctc cca       1056
Asp Met Gly Leu Val Asp Leu Phe Ser Pro Glu Lys Ser Lys Leu Pro
            340                 345                 350 ggt att gtt gca gaa ggc cga gat gac ctc tat gtc tca gat gca ttc       1104
Gly Ile Val Ala Glu Gly Arg Asp Asp Leu Tyr Val Ser Asp Ala Phe
        355                 360                 365 cat aag gca ttt ctt gag gta aat gaa gaa ggc agt gaa gca gct gca       1152
His Lys Ala Phe Leu Glu Val Asn Glu Glu Gly Ser Glu Ala Ala Ala
    370                 375                 380 agt acc gct gtt gtg att gct ggc cgt gag cta aac ccc aac agg gtg       1200
Ser Thr Ala Val Val Ile Ala Gly Arg Glu Leu Asn Pro Asn Arg Val
385                 390                 395                 400 act ttc aag gcc aac agg cct ttc ctg gtt ttt ata aga gaa gtt cct       1248
Thr Phe Lys Ala Asn Arg Pro Phe Leu Val Phe Ile Arg Glu Val Pro
                405                 410                 415 ctg aac act att atc ttc atg ggc aga gta gcc aac cct tgt gtt aag       1296
Leu Asn Thr Ile Ile Phe Met Gly Arg Val Ala Asn Pro Cys Val Lys
            420                 425                 430 tag                                                                   1299

<210> SEQ ID NO 64
<211> LENGTH: 432
<212> TYPE: PRT
<213> ORGANISM: Homo sapiens

<400> SEQUENCE: 64

His Gly Ser Pro Val Asp Ile Cys Thr Ala Lys Pro Arg Asp Ile Pro
1               5                   10                  15

Met Asn Pro Met Cys Ile Tyr Arg Ser Pro Glu Lys Lys Ala Thr Glu
            20                  25                  30

Asp Glu Gly Ser Glu Gln Lys Ile Pro Glu Ala Thr Asn Arg Arg Val
        35                  40                  45

Trp Glu Leu Ser Lys Ala Asn Ser Arg Phe Ala Thr Thr Phe Tyr Gln
    50                  55                  60

His Leu Ala Asp Ser Lys Asn Asp Asn Asp Asn Ile Phe Leu Ser Pro
65                  70                  75                  80

Leu Ser Ile Ser Thr Ala Phe Ala Met Thr Lys Leu Gly Ala Cys Asn
                85                  90                  95

Asp Thr Leu Gln Gln Leu Met Glu Val Phe Lys Phe Asp Thr Ile Ser
            100                 105                 110
```

```
Glu Lys Thr Ser Asp Gln Ile His Phe Phe Ala Lys Leu Asn Cys
        115                 120                 125
Arg Leu Tyr Arg Lys Ala Asn Lys Ser Ser Lys Leu Val Ser Ala Asn
130                 135                 140
Arg Leu Phe Gly Asp Lys Ser Leu Thr Phe Asn Glu Thr Tyr Gln Asp
145                 150                 155                 160
Ile Ser Glu Leu Val Tyr Gly Ala Lys Leu Gln Pro Leu Asp Phe Lys
                165                 170                 175
Glu Asn Ala Glu Gln Ser Arg Ala Ala Ile Asn Lys Trp Val Ser Asn
            180                 185                 190
Lys Thr Glu Gly Arg Ile Thr Asp Val Ile Pro Ser Glu Ala Ile Asn
        195                 200                 205
Glu Leu Thr Val Leu Val Leu Val Asn Thr Ile Tyr Phe Lys Gly Leu
210                 215                 220
Trp Lys Ser Lys Phe Ser Pro Glu Asn Thr Arg Lys Glu Leu Phe Tyr
225                 230                 235                 240
Lys Ala Asp Gly Glu Ser Cys Ser Ala Ser Met Met Tyr Gln Glu Gly
                245                 250                 255
Lys Phe Arg Tyr Arg Arg Val Ala Glu Gly Thr Gln Val Leu Glu Leu
            260                 265                 270
Pro Phe Lys Gly Asp Asp Ile Thr Met Val Leu Ile Leu Pro Lys Pro
        275                 280                 285
Glu Lys Ser Leu Ala Lys Val Glu Lys Glu Leu Thr Pro Glu Val Leu
290                 295                 300
Gln Glu Trp Leu Asp Glu Leu Glu Met Met Leu Val Val His Met
305                 310                 315                 320
Pro Arg Phe Arg Ile Glu Asp Gly Phe Ser Leu Lys Glu Gln Leu Gln
                325                 330                 335
Asp Met Gly Leu Val Asp Leu Phe Ser Pro Glu Lys Ser Lys Leu Pro
            340                 345                 350
Gly Ile Val Ala Glu Gly Arg Asp Asp Leu Tyr Val Ser Asp Ala Phe
        355                 360                 365
His Lys Ala Phe Leu Glu Val Asn Glu Glu Gly Ser Glu Ala Ala Ala
370                 375                 380
Ser Thr Ala Val Val Ile Ala Gly Arg Glu Leu Asn Pro Asn Arg Val
385                 390                 395                 400
Thr Phe Lys Ala Asn Arg Pro Phe Leu Val Phe Ile Arg Glu Val Pro
                405                 410                 415
Leu Asn Thr Ile Ile Phe Met Gly Arg Val Ala Asn Pro Cys Val Lys
            420                 425                 430

<210> SEQ ID NO 65
<211> LENGTH: 1299
<212> TYPE: DNA
<213> ORGANISM: Homo sapiens
<220> FEATURE:
<221> NAME/KEY: CDS
<222> LOCATION: (1)..(1299)

<400> SEQUENCE: 65 cac ggg agc cct gtg gac atc tgc aca gcc aag ccg cgg gac att ccc      48
His Gly Ser Pro Val Asp Ile Cys Thr Ala Lys Pro Arg Asp Ile Pro
1               5                   10                  15 atg aat ccc atg tgc att tac cgc tcc ccg gag aag aag gca act gag      96
Met Asn Pro Met Cys Ile Tyr Arg Ser Pro Glu Lys Lys Ala Thr Glu
            20                  25                  30
```

-continued

| | | |
|---|---|---|
| gat gag ggc tca gaa cag aag atc ccg gag gcc acc aac cgg cgt gtc<br>Asp Glu Gly Ser Glu Gln Lys Ile Pro Glu Ala Thr Asn Arg Arg Val<br>35                      40                     45 | 144 |
| tgg gaa ctg tcc aag gcc aat tcc cgc ttt gct acc act ttc tat cag<br>Trp Glu Leu Ser Lys Ala Asn Ser Arg Phe Ala Thr Thr Phe Tyr Gln<br>50                      55                     60 | 192 |
| cac ctg gca gat tcc aag aat gac aat gat aac att ttc ctg tca ccc<br>His Leu Ala Asp Ser Lys Asn Asp Asn Asp Asn Ile Phe Leu Ser Pro<br>65                      70                     75                     80 | 240 |
| ctg agt atc tcc acg gct ttt gct atg acc aag ctg ggt gcc tgt aat<br>Leu Ser Ile Ser Thr Ala Phe Ala Met Thr Lys Leu Gly Ala Cys Asn<br>                  85                     90                     95 | 288 |
| gac acc ctc cag caa ctg atg gag gta ttt aag ttt gac acc ata tct<br>Asp Thr Leu Gln Gln Leu Met Glu Val Phe Lys Phe Asp Thr Ile Ser<br>                    100                  105                  110 | 336 |
| gag aaa aca tct gat cag atc cac ttc ttc ttt gcc aaa ctg aac tgc<br>Glu Lys Thr Ser Asp Gln Ile His Phe Phe Phe Ala Lys Leu Asn Cys<br>                    115                  120                  125 | 384 |
| cga ctc tat cga aaa gcc cag aaa tcc tcc aag tta gta tca gcc aat<br>Arg Leu Tyr Arg Lys Ala Gln Lys Ser Ser Lys Leu Val Ser Ala Asn<br>130                     135                    140 | 432 |
| cgc ctt ttt gga gac aaa tcc ctt acc ttc aat gag acc tac cag gac<br>Arg Leu Phe Gly Asp Lys Ser Leu Thr Phe Asn Glu Thr Tyr Gln Asp<br>145                     150                  155                  160 | 480 |
| atc agt gag ttg gta tat gga gcc aag ctc cag ccc ctg gac ttc aag<br>Ile Ser Glu Leu Val Tyr Gly Ala Lys Leu Gln Pro Leu Asp Phe Lys<br>                    165                  170                  175 | 528 |
| gaa aat gca gag caa tcc aga gcg gcc atc aac aaa tgg gtg tcc aat<br>Glu Asn Ala Glu Gln Ser Arg Ala Ala Ile Asn Lys Trp Val Ser Asn<br>                    180                  185                  190 | 576 |
| aag acc gaa ggc cga atc acc gat gtc att ccc tcg gaa gcc atc aat<br>Lys Thr Glu Gly Arg Ile Thr Asp Val Ile Pro Ser Glu Ala Ile Asn<br>               195                  200                  205 | 624 |
| gag ctc act gtt ctg gtg ctg gtt aac acc att tac ttc aag ggc ctg<br>Glu Leu Thr Val Leu Val Leu Val Asn Thr Ile Tyr Phe Lys Gly Leu<br>210                     215                    220 | 672 |
| tgg aag tca aag ttc agc cct gag aac aca agg aag gaa ctg ttc tac<br>Trp Lys Ser Lys Phe Ser Pro Glu Asn Thr Arg Lys Glu Leu Phe Tyr<br>225                     230                  235                  240 | 720 |
| aag gct gat gga gag tcg tgt tca gca tct atg atg tac cag gaa ggc<br>Lys Ala Asp Gly Glu Ser Cys Ser Ala Ser Met Met Tyr Gln Glu Gly<br>                    245                  250                  255 | 768 |
| aag ttc cgt tat cgg cgc gtg gct gaa ggc acc cag gtg ctt gag ttg<br>Lys Phe Arg Tyr Arg Arg Val Ala Glu Gly Thr Gln Val Leu Glu Leu<br>                    260                  265                  270 | 816 |
| ccc ttc aaa ggt gat gac atc acc atg gtc ctc atc ttg ccc aag cct<br>Pro Phe Lys Gly Asp Asp Ile Thr Met Val Leu Ile Leu Pro Lys Pro<br>                    275                  280                  285 | 864 |
| gag aag agc ctg gcc aag gtg gag aag gaa ctc acc cca gag gtg ctg<br>Glu Lys Ser Leu Ala Lys Val Glu Lys Glu Leu Thr Pro Glu Val Leu<br>290                     295                    300 | 912 |
| cag gag tgg ctg gat gaa ttg gag gag atg atg ctg gtg gtc cac atg<br>Gln Glu Trp Leu Asp Glu Leu Glu Glu Met Met Leu Val Val His Met<br>305                     310                  315                  320 | 960 |
| ccc cgc ttc cgc att gag gac ggc ttc agt ttg aag gag cag ctg caa<br>Pro Arg Phe Arg Ile Glu Asp Gly Phe Ser Leu Lys Glu Gln Leu Gln<br>                    325                  330                  335 | 1008 |
| gac atg ggc ctt gtc gat ctg ttc agc cct gaa aag tcc aaa ctc cca<br>Asp Met Gly Leu Val Asp Leu Phe Ser Pro Glu Lys Ser Lys Leu Pro | 1056 |

```
                340             345             350
ggt att gtt gca gaa ggc cga gat gac ctc tat gtc tca gat gca ttc      1104
Gly Ile Val Ala Glu Gly Arg Asp Asp Leu Tyr Val Ser Asp Ala Phe
        355             360             365 cat aag gca ttt ctt gag gta aat gaa gaa ggc agt gaa gca gct gca      1152
His Lys Ala Phe Leu Glu Val Asn Glu Glu Gly Ser Glu Ala Ala Ala
370             375             380 agt acc gct gtt gtg att gct ggc cgt cag cta aac ccc aac agg gtg      1200
Ser Thr Ala Val Val Ile Ala Gly Arg Gln Leu Asn Pro Asn Arg Val
385             390             395             400 act ttc aag gcc aac agg cct ttc ctg gtt ttt ata aga gaa gtt cct      1248
Thr Phe Lys Ala Asn Arg Pro Phe Leu Val Phe Ile Arg Glu Val Pro
            405             410             415 ctg aac act att atc ttc atg ggc aga gta gcc aac cct tgt gtt aag      1296
Leu Asn Thr Ile Ile Phe Met Gly Arg Val Ala Asn Pro Cys Val Lys
            420             425             430 tag                                                                   1299

<210> SEQ ID NO 66
<211> LENGTH: 432
<212> TYPE: PRT
<213> ORGANISM: Homo sapiens

<400> SEQUENCE: 66

His Gly Ser Pro Val Asp Ile Cys Thr Ala Lys Pro Arg Asp Ile Pro
1               5                   10                  15

Met Asn Pro Met Cys Ile Tyr Arg Ser Pro Glu Lys Lys Ala Thr Glu
            20                  25                  30

Asp Glu Gly Ser Glu Gln Lys Ile Pro Glu Ala Thr Asn Arg Arg Val
        35                  40                  45

Trp Glu Leu Ser Lys Ala Asn Ser Arg Phe Ala Thr Thr Phe Tyr Gln
    50                  55                  60

His Leu Ala Asp Ser Lys Asn Asp Asn Asp Asn Ile Phe Leu Ser Pro
65                  70                  75                  80

Leu Ser Ile Ser Thr Ala Phe Ala Met Thr Lys Leu Gly Ala Cys Asn
                85                  90                  95

Asp Thr Leu Gln Gln Leu Met Glu Val Phe Lys Phe Asp Thr Ile Ser
            100                 105                 110

Glu Lys Thr Ser Asp Gln Ile His Phe Phe Phe Ala Lys Leu Asn Cys
        115                 120                 125

Arg Leu Tyr Arg Lys Ala Gln Lys Ser Ser Lys Leu Val Ser Ala Asn
    130                 135                 140

Arg Leu Phe Gly Asp Lys Ser Leu Thr Phe Asn Glu Thr Tyr Gln Asp
145                 150                 155                 160

Ile Ser Glu Leu Val Tyr Gly Ala Lys Leu Gln Pro Leu Asp Phe Lys
                165                 170                 175

Glu Asn Ala Glu Gln Ser Arg Ala Ala Ile Asn Lys Trp Val Ser Asn
            180                 185                 190

Lys Thr Glu Gly Arg Ile Thr Asp Val Ile Pro Ser Glu Ala Ile Asn
        195                 200                 205

Glu Leu Thr Val Leu Val Leu Val Asn Thr Ile Tyr Phe Lys Gly Leu
    210                 215                 220

Trp Lys Ser Lys Phe Ser Pro Glu Asn Thr Arg Lys Glu Leu Phe Tyr
225                 230                 235                 240

Lys Ala Asp Gly Glu Ser Cys Ser Ala Ser Met Met Tyr Gln Glu Gly
                245                 250                 255
```

```
Lys Phe Arg Tyr Arg Val Ala Glu Gly Thr Gln Val Leu Glu Leu
            260                 265                 270

Pro Phe Lys Gly Asp Asp Ile Thr Met Val Leu Ile Leu Pro Lys Pro
        275                 280                 285

Glu Lys Ser Leu Ala Lys Val Glu Lys Glu Leu Thr Pro Glu Val Leu
    290                 295                 300

Gln Glu Trp Leu Asp Glu Leu Glu Glu Met Met Leu Val Val His Met
305                 310                 315                 320

Pro Arg Phe Arg Ile Glu Asp Gly Phe Ser Leu Lys Glu Gln Leu Gln
                325                 330                 335

Asp Met Gly Leu Val Asp Leu Phe Ser Pro Lys Ser Lys Leu Pro
            340                 345                 350

Gly Ile Val Ala Glu Gly Arg Asp Asp Leu Tyr Val Ser Asp Ala Phe
        355                 360                 365

His Lys Ala Phe Leu Glu Val Asn Glu Glu Gly Ser Glu Ala Ala Ala
    370                 375                 380

Ser Thr Ala Val Val Ile Ala Gly Arg Gln Leu Asn Pro Asn Arg Val
385                 390                 395                 400

Thr Phe Lys Ala Asn Arg Pro Phe Leu Val Phe Ile Arg Glu Val Pro
                405                 410                 415

Leu Asn Thr Ile Ile Phe Met Gly Arg Val Ala Asn Pro Cys Val Lys
            420                 425                 430

<210> SEQ ID NO 67
<211> LENGTH: 1299
<212> TYPE: DNA
<213> ORGANISM: Homo sapiens
<220> FEATURE:
<221> NAME/KEY: CDS
<222> LOCATION: (1)..(1299)

<400> SEQUENCE: 67 cac ggg agc cct gtg gac atc tgc aca gcc aag ccg cgg gac att ccc      48
His Gly Ser Pro Val Asp Ile Cys Thr Ala Lys Pro Arg Asp Ile Pro
1               5                   10                  15 atg aat ccc atg tgc att tac cgc tcc ccg gag aag aag gca act gag      96
Met Asn Pro Met Cys Ile Tyr Arg Ser Pro Glu Lys Lys Ala Thr Glu
            20                  25                  30 gat gag ggc tca gaa cag aag atc ccg gag gcc acc aac cgg cgt gtc     144
Asp Glu Gly Ser Glu Gln Lys Ile Pro Glu Ala Thr Asn Arg Arg Val
        35                  40                  45 tgg gaa ctg tcc aag gcc aat tcc cgc ttt gct acc act ttc tat cag     192
Trp Glu Leu Ser Lys Ala Asn Ser Arg Phe Ala Thr Thr Phe Tyr Gln
    50                  55                  60 cac ctg gca gat tcc aag aat gac aat gat aac att ttc ctg tca ccc     240
His Leu Ala Asp Ser Lys Asn Asp Asn Asp Asn Ile Phe Leu Ser Pro
65                  70                  75                  80 ctg agt atc tcc acg gct ttt gct atg acc aag ctg ggt gcc tgt aat     288
Leu Ser Ile Ser Thr Ala Phe Ala Met Thr Lys Leu Gly Ala Cys Asn
                85                  90                  95 gac acc ctc cag caa ctg atg gag gta ttt aag ttt gac acc ata tct     336
Asp Thr Leu Gln Gln Leu Met Glu Val Phe Lys Phe Asp Thr Ile Ser
            100                 105                 110 gag aaa aca tct gat cag atc cac ttc ttc ttt gcc aaa ctg aac tgc     384
Glu Lys Thr Ser Asp Gln Ile His Phe Phe Phe Ala Lys Leu Asn Cys
        115                 120                 125 cga ctc tat cga aaa gcc cag aaa tcc tcc aag tta gta tca gcc aat     432
Arg Leu Tyr Arg Lys Ala Gln Lys Ser Ser Lys Leu Val Ser Ala Asn
```

```
                      130                 135                 140
cgc ctt ttt gga gac aaa tcc ctt acc ttc aat gag acc tac cag gac      480
Arg Leu Phe Gly Asp Lys Ser Leu Thr Phe Asn Glu Thr Tyr Gln Asp
145                 150                 155                 160 atc agt gag ttg gta tat gga gcc aag ctc cag ccc ctg gac ttc aag      528
Ile Ser Glu Leu Val Tyr Gly Ala Lys Leu Gln Pro Leu Asp Phe Lys
                165                 170                 175 gaa aat gca gag caa tcc aga gcg gcc atc aac aaa tgg gtg tcc aat      576
Glu Asn Ala Glu Gln Ser Arg Ala Ala Ile Asn Lys Trp Val Ser Asn
            180                 185                 190 aag acc gaa ggc cga atc acc gat gtc att ccc tcg gaa gcc atc aat      624
Lys Thr Glu Gly Arg Ile Thr Asp Val Ile Pro Ser Glu Ala Ile Asn
        195                 200                 205 gag ctc act gtt ctg gtg ctg gtt aac acc att tac ttc aag ggc ctg      672
Glu Leu Thr Val Leu Val Leu Val Asn Thr Ile Tyr Phe Lys Gly Leu
    210                 215                 220 tgg aag tca aag ttc agc cct gag aac aca agg aag gaa ctg ttc tac      720
Trp Lys Ser Lys Phe Ser Pro Glu Asn Thr Arg Lys Glu Leu Phe Tyr
225                 230                 235                 240 aag gct gat gga gag tcg tgt tca gca tct atg atg tac cag gaa ggc      768
Lys Ala Asp Gly Glu Ser Cys Ser Ala Ser Met Met Tyr Gln Glu Gly
                245                 250                 255 aag ttc cgt tat cgg cgc gtg gct gaa ggc acc cag gtg ctt gag ttg      816
Lys Phe Arg Tyr Arg Arg Val Ala Glu Gly Thr Gln Val Leu Glu Leu
            260                 265                 270 ccc ttc aaa ggt gat gac atc acc atg gtc ctc atc ttg ccc aag cct      864
Pro Phe Lys Gly Asp Asp Ile Thr Met Val Leu Ile Leu Pro Lys Pro
        275                 280                 285 gag aag agc ctg gcc aag gtg gag aag gaa ctc acc cca gag gtg ctg      912
Glu Lys Ser Leu Ala Lys Val Glu Lys Glu Leu Thr Pro Glu Val Leu
    290                 295                 300 cag gag tgg ctg gat gaa ttg gag gag atg atg ctg gtg gtc cac atg      960
Gln Glu Trp Leu Asp Glu Leu Glu Glu Met Met Leu Val Val His Met
305                 310                 315                 320 ccc cgc ttc cgc att gag gac ggc ttc agt ttg aag gag cag ctg caa     1008
Pro Arg Phe Arg Ile Glu Asp Gly Phe Ser Leu Lys Glu Gln Leu Gln
                325                 330                 335 gac atg ggc ctt gtc gat ctg ttc agc cct gaa aag tcc aaa ctc cca     1056
Asp Met Gly Leu Val Asp Leu Phe Ser Pro Glu Lys Ser Lys Leu Pro
            340                 345                 350 ggt att gtt gca gaa ggc cga gat gac ctc tat gtc tca gat gca ttc     1104
Gly Ile Val Ala Glu Gly Arg Asp Asp Leu Tyr Val Ser Asp Ala Phe
        355                 360                 365 cat aag gca ttt ctt gag gta aat gaa gaa ggc agt gaa gca gct gca     1152
His Lys Ala Phe Leu Glu Val Asn Glu Glu Gly Ser Glu Ala Ala Ala
    370                 375                 380 agt acc gct gtt gtg att gct ggc cgt gag cta aac ccc aac agg gtg     1200
Ser Thr Ala Val Val Ile Ala Gly Arg Glu Leu Asn Pro Asn Arg Val
385                 390                 395                 400 act ttc aag gcc aac agg cct ttc ctg gtt ttt ata aga gaa gtt cct     1248
Thr Phe Lys Ala Asn Arg Pro Phe Leu Val Phe Ile Arg Glu Val Pro
                405                 410                 415 ctg aac act att atc ttc atg ggc aga gta gcc aac cct tgt gtt aag     1296
Leu Asn Thr Ile Ile Phe Met Gly Arg Val Ala Asn Pro Cys Val Lys
            420                 425                 430 tag                                                                 1299

<210> SEQ ID NO 68
<211> LENGTH: 432
```

<212> TYPE: PRT
<213> ORGANISM: Homo sapiens

<400> SEQUENCE: 68

```
His Gly Ser Pro Val Asp Ile Cys Thr Ala Lys Pro Arg Asp Ile Pro
1               5                   10                  15

Met Asn Pro Met Cys Ile Tyr Arg Ser Pro Glu Lys Lys Ala Thr Glu
            20                  25                  30

Asp Glu Gly Ser Glu Gln Lys Ile Pro Glu Ala Thr Asn Arg Arg Val
        35                  40                  45

Trp Glu Leu Ser Lys Ala Asn Ser Arg Phe Ala Thr Thr Phe Tyr Gln
    50                  55                  60

His Leu Ala Asp Ser Lys Asn Asp Asn Asp Asn Ile Phe Leu Ser Pro
65                  70                  75                  80

Leu Ser Ile Ser Thr Ala Phe Ala Met Thr Lys Leu Gly Ala Cys Asn
                85                  90                  95

Asp Thr Leu Gln Gln Leu Met Glu Val Phe Lys Phe Asp Thr Ile Ser
            100                 105                 110

Glu Lys Thr Ser Asp Gln Ile His Phe Phe Phe Ala Lys Leu Asn Cys
        115                 120                 125

Arg Leu Tyr Arg Lys Ala Gln Lys Ser Ser Lys Leu Val Ser Ala Asn
    130                 135                 140

Arg Leu Phe Gly Asp Lys Ser Leu Thr Phe Asn Glu Thr Tyr Gln Asp
145                 150                 155                 160

Ile Ser Glu Leu Val Tyr Gly Ala Lys Leu Gln Pro Leu Asp Phe Lys
                165                 170                 175

Glu Asn Ala Glu Gln Ser Arg Ala Ala Ile Asn Lys Trp Val Ser Asn
            180                 185                 190

Lys Thr Glu Gly Arg Ile Thr Asp Val Ile Pro Ser Glu Ala Ile Asn
        195                 200                 205

Glu Leu Thr Val Leu Val Leu Val Asn Thr Ile Tyr Phe Lys Gly Leu
    210                 215                 220

Trp Lys Ser Lys Phe Ser Pro Glu Asn Thr Arg Lys Glu Leu Phe Tyr
225                 230                 235                 240

Lys Ala Asp Gly Glu Ser Cys Ser Ala Ser Met Met Tyr Gln Glu Gly
                245                 250                 255

Lys Phe Arg Tyr Arg Arg Val Ala Glu Gly Thr Gln Val Leu Glu Leu
            260                 265                 270

Pro Phe Lys Gly Asp Asp Ile Thr Met Val Leu Ile Leu Pro Lys Pro
        275                 280                 285

Glu Lys Ser Leu Ala Lys Val Glu Lys Glu Leu Thr Pro Glu Val Leu
    290                 295                 300

Gln Glu Trp Leu Asp Glu Leu Glu Glu Met Met Leu Val Val His Met
305                 310                 315                 320

Pro Arg Phe Arg Ile Glu Asp Gly Phe Ser Leu Lys Glu Gln Leu Gln
                325                 330                 335

Asp Met Gly Leu Val Asp Leu Phe Ser Pro Glu Lys Ser Lys Leu Pro
            340                 345                 350

Gly Ile Val Ala Glu Gly Arg Asp Asp Leu Tyr Val Ser Asp Ala Phe
        355                 360                 365

His Lys Ala Phe Leu Glu Val Asn Glu Glu Gly Ser Glu Ala Ala Ala
    370                 375                 380

Ser Thr Ala Val Val Ile Ala Gly Arg Glu Leu Asn Pro Asn Arg Val
385                 390                 395                 400
```

```
Thr Phe Lys Ala Asn Arg Pro Phe Leu Val Phe Ile Arg Glu Val Pro
                405                 410                 415

Leu Asn Thr Ile Ile Phe Met Gly Arg Val Ala Asn Pro Cys Val Lys
            420                 425                 430

<210> SEQ ID NO 69
<211> LENGTH: 1395
<212> TYPE: DNA
<213> ORGANISM: Homo sapiens
<220> FEATURE:
<221> NAME/KEY: CDS
<222> LOCATION: (1)..(1395)

<400> SEQUENCE: 69 atg tat tcc aat gtg ata gga act gta acc tct gga aaa agg aag gtt     48
Met Tyr Ser Asn Val Ile Gly Thr Val Thr Ser Gly Lys Arg Lys Val
1               5                   10                  15 tat ctt ttg tcc ttg ctc att ggc ttc tgg gac tgc gtg acc tgt         96
Tyr Leu Leu Ser Leu Leu Ile Gly Phe Trp Asp Cys Val Thr Cys
            20                  25                  30 cac ggg agc cct gtg gac atc tgc aca gcc aag ccg cgg gac att ccc    144
His Gly Ser Pro Val Asp Ile Cys Thr Ala Lys Pro Arg Asp Ile Pro
            35                  40                  45 atg aat ccc atg tgc att tac cgc tcc ccg gag aag aag gca act gag    192
Met Asn Pro Met Cys Ile Tyr Arg Ser Pro Glu Lys Lys Ala Thr Glu
50                  55                  60 gat gag ggc tca gaa cag aag atc ccg gag gcc acc aac cgg cgt gtc    240
Asp Glu Gly Ser Glu Gln Lys Ile Pro Glu Ala Thr Asn Arg Arg Val
65                  70                  75                  80 tgg gaa ctg tcc aag gcc aat tcc cgc ttt gct acc act ttc tat cag    288
Trp Glu Leu Ser Lys Ala Asn Ser Arg Phe Ala Thr Thr Phe Tyr Gln
                85                  90                  95 cac ctg gca gat tcc aag aat gac aat gat aac att ttc ctg tca ccc    336
His Leu Ala Asp Ser Lys Asn Asp Asn Asp Asn Ile Phe Leu Ser Pro
            100                 105                 110 ctg agt atc tcc acg gct ttt gct atg acc aag ctg ggt gcc tgt aat    384
Leu Ser Ile Ser Thr Ala Phe Ala Met Thr Lys Leu Gly Ala Cys Asn
            115                 120                 125 gac acc ctc cag caa ctg atg gag gta ttt aag ttt gac acc ata tct    432
Asp Thr Leu Gln Gln Leu Met Glu Val Phe Lys Phe Asp Thr Ile Ser
130                 135                 140 gag aaa aca tct gat cag atc cac ttc ttc ttt gcc aaa ctg aac tgc    480
Glu Lys Thr Ser Asp Gln Ile His Phe Phe Phe Ala Lys Leu Asn Cys
145                 150                 155                 160 cga ctc tat cga aaa gcc aac aaa tcc tcc aag tta gta tca gcc aat    528
Arg Leu Tyr Arg Lys Ala Asn Lys Ser Ser Lys Leu Val Ser Ala Asn
                165                 170                 175 cgc ctt ttt gga gac aaa tcc ctt acc ttc aat gag acc tac cag gac    576
Arg Leu Phe Gly Asp Lys Ser Leu Thr Phe Asn Glu Thr Tyr Gln Asp
            180                 185                 190 atc agt gag ttg gta tat gga gcc aag ctc cag ccc ctg gac ttc aag    624
Ile Ser Glu Leu Val Tyr Gly Ala Lys Leu Gln Pro Leu Asp Phe Lys
            195                 200                 205 gaa aat gca gag caa tcc aga gcg gcc atc aac aaa tgg gtg tcc aat    672
Glu Asn Ala Glu Gln Ser Arg Ala Ala Ile Asn Lys Trp Val Ser Asn
        210                 215                 220 aag acc gaa ggc cga atc acc gat gtc att ccc tcg gaa gcc atc aat    720
Lys Thr Glu Gly Arg Ile Thr Asp Val Ile Pro Ser Glu Ala Ile Asn
225                 230                 235                 240 gag ctc act gtt ctg gtg ctg gtt aac acc att tac ttc aag ggc ctg    768
```

| | | | | | | | | | | | | |
|---|---|---|---|---|---|---|---|---|---|---|---|---|
| Glu | Leu | Thr | Val | Leu | Val | Leu | Val | Asn | Thr | Ile | Tyr | Phe | Lys | Gly | Leu |
|  |  |  | 245 |  |  |  | 250 |  |  |  | 255 |  |

```
tgg aag tca aag ttc agc cct gag aac aca agg aag gaa ctg ttc tac       816
Trp Lys Ser Lys Phe Ser Pro Glu Asn Thr Arg Lys Glu Leu Phe Tyr
        260                 265                 270 aag gct gat gga gag tcg tgt tca gca tct atg atg tac cag gaa ggc       864
Lys Ala Asp Gly Glu Ser Cys Ser Ala Ser Met Met Tyr Gln Glu Gly
            275                 280                 285 aag ttc cgt tat cgg cgc gtg gct gaa ggc acc cag gtg ctt gag ttg       912
Lys Phe Arg Tyr Arg Arg Val Ala Glu Gly Thr Gln Val Leu Glu Leu
        290                 295                 300 ccc ttc aaa ggt gat gac atc acc atg gtc ctc atc ttg ccc aag cct       960
Pro Phe Lys Gly Asp Asp Ile Thr Met Val Leu Ile Leu Pro Lys Pro
305                 310                 315                 320 gag aag agc ctg gcc aag gtg gag aag gaa ctc acc cca gag gtg ctg      1008
Glu Lys Ser Leu Ala Lys Val Glu Lys Glu Leu Thr Pro Glu Val Leu
                325                 330                 335 cag gag tgg ctg gat gaa ttg gag gag atg atg ctg gtg gtc cac atg      1056
Gln Glu Trp Leu Asp Glu Leu Glu Glu Met Met Leu Val Val His Met
            340                 345                 350 ccc cgc ttc cgc att gag gac ggc ttc agt ttg aag gag cag ctg caa      1104
Pro Arg Phe Arg Ile Glu Asp Gly Phe Ser Leu Lys Glu Gln Leu Gln
        355                 360                 365 gac atg ggc ctt gtc gat ctg ttc agc cct gaa aag tcc aaa ctc cca      1152
Asp Met Gly Leu Val Asp Leu Phe Ser Pro Glu Lys Ser Lys Leu Pro
370                 375                 380 ggt att gtt gca gaa ggc cga gat gac ctc tat gtc tca gat gca ttc      1200
Gly Ile Val Ala Glu Gly Arg Asp Asp Leu Tyr Val Ser Asp Ala Phe
385                 390                 395                 400 cat aag gca ttt ctt gag gta aat gaa gaa ggc agt gaa gca gct gca      1248
His Lys Ala Phe Leu Glu Val Asn Glu Glu Gly Ser Glu Ala Ala Ala
                405                 410                 415 agt acc gct gtt gtg att gct ggc cgt cag cta aac ccc aac agg gtg      1296
Ser Thr Ala Val Val Ile Ala Gly Arg Gln Leu Asn Pro Asn Arg Val
            420                 425                 430 act ttc aag gcc aac agg cct ttc ctg gtt ttt ata aga gaa gtt cct      1344
Thr Phe Lys Ala Asn Arg Pro Phe Leu Val Phe Ile Arg Glu Val Pro
        435                 440                 445 ctg aac act att atc ttc atg ggc aga gta gcc aac cct tgt gtt aag      1392
Leu Asn Thr Ile Ile Phe Met Gly Arg Val Ala Asn Pro Cys Val Lys
450                 455                 460 tag                                                                  1395
```

<210> SEQ ID NO 70
<211> LENGTH: 464
<212> TYPE: PRT
<213> ORGANISM: Homo sapiens

<400> SEQUENCE: 70

| | | | | | | | | | | | | | | | |
|---|---|---|---|---|---|---|---|---|---|---|---|---|---|---|---|
| Met | Tyr | Ser | Asn | Val | Ile | Gly | Thr | Val | Thr | Ser | Gly | Lys | Arg | Lys | Val |
| 1 |  |  |  | 5 |  |  |  |  | 10 |  |  |  |  | 15 |  |

| | | | | | | | | | | | | | | | |
|---|---|---|---|---|---|---|---|---|---|---|---|---|---|---|---|
| Tyr | Leu | Leu | Ser | Leu | Leu | Leu | Ile | Gly | Phe | Trp | Asp | Cys | Val | Thr | Cys |
|  |  |  | 20 |  |  |  |  | 25 |  |  |  |  | 30 |  |  |

| | | | | | | | | | | | | | | | |
|---|---|---|---|---|---|---|---|---|---|---|---|---|---|---|---|
| His | Gly | Ser | Pro | Val | Asp | Ile | Cys | Thr | Ala | Lys | Pro | Arg | Asp | Ile | Pro |
|  |  | 35 |  |  |  |  | 40 |  |  |  |  | 45 |  |  |  |

| | | | | | | | | | | | | | | | |
|---|---|---|---|---|---|---|---|---|---|---|---|---|---|---|---|
| Met | Asn | Pro | Met | Cys | Ile | Tyr | Arg | Ser | Pro | Glu | Lys | Lys | Ala | Thr | Glu |
|  | 50 |  |  |  |  | 55 |  |  |  |  | 60 |  |  |  |  |

| | | | | | | | | | | | | | | | |
|---|---|---|---|---|---|---|---|---|---|---|---|---|---|---|---|
| Asp | Glu | Gly | Ser | Glu | Gln | Lys | Ile | Pro | Glu | Ala | Thr | Asn | Arg | Arg | Val |
| 65 |  |  |  |  | 70 |  |  |  |  | 75 |  |  |  |  | 80 |

Trp Glu Leu Ser Lys Ala Asn Ser Arg Phe Ala Thr Thr Phe Tyr Gln
                85                  90                  95

His Leu Ala Asp Ser Lys Asn Asp Asp Asn Ile Phe Leu Ser Pro
            100                 105                 110

Leu Ser Ile Ser Thr Ala Phe Ala Met Thr Lys Leu Gly Ala Cys Asn
        115                 120                 125

Asp Thr Leu Gln Gln Leu Met Glu Val Phe Lys Phe Asp Thr Ile Ser
    130                 135                 140

Glu Lys Thr Ser Asp Gln Ile His Phe Phe Phe Ala Lys Leu Asn Cys
145                 150                 155                 160

Arg Leu Tyr Arg Lys Ala Asn Lys Ser Ser Lys Leu Val Ser Ala Asn
                165                 170                 175

Arg Leu Phe Gly Asp Lys Ser Leu Thr Phe Asn Glu Thr Tyr Gln Asp
            180                 185                 190

Ile Ser Glu Leu Val Tyr Gly Ala Lys Leu Gln Pro Leu Asp Phe Lys
        195                 200                 205

Glu Asn Ala Glu Gln Ser Arg Ala Ala Ile Asn Lys Trp Val Ser Asn
    210                 215                 220

Lys Thr Glu Gly Arg Ile Thr Asp Val Ile Pro Ser Glu Ala Ile Asn
225                 230                 235                 240

Glu Leu Thr Val Leu Val Leu Val Asn Thr Ile Tyr Phe Lys Gly Leu
                245                 250                 255

Trp Lys Ser Lys Phe Ser Pro Glu Asn Thr Arg Lys Glu Leu Phe Tyr
            260                 265                 270

Lys Ala Asp Gly Glu Ser Cys Ser Ala Ser Met Met Tyr Gln Glu Gly
        275                 280                 285

Lys Phe Arg Tyr Arg Arg Val Ala Glu Gly Thr Gln Val Leu Glu Leu
    290                 295                 300

Pro Phe Lys Gly Asp Asp Ile Thr Met Val Leu Ile Leu Pro Lys Pro
305                 310                 315                 320

Glu Lys Ser Leu Ala Lys Val Glu Lys Glu Leu Thr Pro Glu Val Leu
                325                 330                 335

Gln Glu Trp Leu Asp Glu Leu Glu Met Met Leu Val Val His Met
            340                 345                 350

Pro Arg Phe Arg Ile Glu Asp Gly Phe Ser Leu Lys Glu Gln Leu Gln
        355                 360                 365

Asp Met Gly Leu Val Asp Leu Phe Ser Pro Glu Lys Ser Lys Leu Pro
    370                 375                 380

Gly Ile Val Ala Glu Gly Arg Asp Asp Leu Tyr Val Ser Asp Ala Phe
385                 390                 395                 400

His Lys Ala Phe Leu Glu Val Asn Glu Glu Gly Ser Glu Ala Ala Ala
                405                 410                 415

Ser Thr Ala Val Val Ile Ala Gly Arg Gln Leu Asn Pro Asn Arg Val
            420                 425                 430

Thr Phe Lys Ala Asn Arg Pro Phe Leu Val Phe Ile Arg Glu Val Pro
        435                 440                 445

Leu Asn Thr Ile Ile Phe Met Gly Arg Val Ala Asn Pro Cys Val Lys
    450                 455                 460

<210> SEQ ID NO 71
<211> LENGTH: 1395
<212> TYPE: DNA
<213> ORGANISM: Homo sapiens
<220> FEATURE:

<221> NAME/KEY: CDS
<222> LOCATION: (1)..(1395)

<400> SEQUENCE: 71

```
atg tat tcc aat gtg ata gga act gta acc tct gga aaa agg aag gtt      48
Met Tyr Ser Asn Val Ile Gly Thr Val Thr Ser Gly Lys Arg Lys Val
1               5                   10                  15 tat ctt ttg tcc ttg ctg ctc att ggc ttc tgg gac tgc gtg acc tgt      96
Tyr Leu Leu Ser Leu Leu Leu Ile Gly Phe Trp Asp Cys Val Thr Cys
            20                  25                  30 cac ggg agc cct gtg gac atc tgc aca gcc aag ccg cgg gac att ccc     144
His Gly Ser Pro Val Asp Ile Cys Thr Ala Lys Pro Arg Asp Ile Pro
        35                  40                  45 atg aat ccc atg tgc att tac cgc tcc ccg gag aag aag gca act gag     192
Met Asn Pro Met Cys Ile Tyr Arg Ser Pro Glu Lys Lys Ala Thr Glu
    50                  55                  60 gat gag ggc tca gaa cag aag atc ccg gag gcc acc aac cgg gtc gtc     240
Asp Glu Gly Ser Glu Gln Lys Ile Pro Glu Ala Thr Asn Arg Arg Val
65                  70                  75                  80 tgg gaa ctg tcc aag gcc aat tcc cgc ttt gct acc act ttc tat cag     288
Trp Glu Leu Ser Lys Ala Asn Ser Arg Phe Ala Thr Thr Phe Tyr Gln
                85                  90                  95 cac ctg gca gat tcc aag aat gac aat gat aac att ttc ctg tca ccc     336
His Leu Ala Asp Ser Lys Asn Asp Asn Asp Asn Ile Phe Leu Ser Pro
            100                 105                 110 ctg agt atc tcc acg gct ttt gct atg acc aag ctg ggt gcc tgt aat     384
Leu Ser Ile Ser Thr Ala Phe Ala Met Thr Lys Leu Gly Ala Cys Asn
        115                 120                 125 gac acc ctc cag caa ctg atg gag gta ttt aag ttt gac acc ata tct     432
Asp Thr Leu Gln Gln Leu Met Glu Val Phe Lys Phe Asp Thr Ile Ser
    130                 135                 140 gag aaa aca tct gat cag atc cac ttc ttc ttt gcc aaa ctg aac tgc     480
Glu Lys Thr Ser Asp Gln Ile His Phe Phe Phe Ala Lys Leu Asn Cys
145                 150                 155                 160 cga ctc tat cga aaa gcc aac aaa tcc tcc aag tta gta tca gcc aat     528
Arg Leu Tyr Arg Lys Ala Asn Lys Ser Ser Lys Leu Val Ser Ala Asn
                165                 170                 175 cgc ctt ttt gga gac aaa tcc ctt acc ttc aat gag acc tac cag gac     576
Arg Leu Phe Gly Asp Lys Ser Leu Thr Phe Asn Glu Thr Tyr Gln Asp
            180                 185                 190 atc agt gag ttg gta tat gga gcc aag ctc cag ccc ctg gac ttc aag     624
Ile Ser Glu Leu Val Tyr Gly Ala Lys Leu Gln Pro Leu Asp Phe Lys
        195                 200                 205 gaa aat gca gag caa tcc aga gcg gcc atc aac aaa tgg gtg tcc aat     672
Glu Asn Ala Glu Gln Ser Arg Ala Ala Ile Asn Lys Trp Val Ser Asn
    210                 215                 220 aag acc gaa ggc cga atc acc gat gtc att ccc tcg gaa gcc atc aat     720
Lys Thr Glu Gly Arg Ile Thr Asp Val Ile Pro Ser Glu Ala Ile Asn
225                 230                 235                 240 gag ctc act gtt ctg gtg ctg gtt aac acc att tac ttc aag ggc ctg     768
Glu Leu Thr Val Leu Val Leu Val Asn Thr Ile Tyr Phe Lys Gly Leu
                245                 250                 255 tgg aag tca aag ttc agc cct gag aac aca agg aag gaa ctg ttc tac     816
Trp Lys Ser Lys Phe Ser Pro Glu Asn Thr Arg Lys Glu Leu Phe Tyr
            260                 265                 270 aag gct gat gga gag tcg tgt tca gca tct atg atg tac cag gaa ggc     864
Lys Ala Asp Gly Glu Ser Cys Ser Ala Ser Met Met Tyr Gln Glu Gly
        275                 280                 285 aag ttc cgt tat cgg cgc gtg gct gaa ggc acc cag gtg ctt gag ttg     912
Lys Phe Arg Tyr Arg Arg Val Ala Glu Gly Thr Gln Val Leu Glu Leu
```

```
ccc ttc aaa ggt gat gac atc acc atg gtc ctc atc ttg ccc aag cct    960
Pro Phe Lys Gly Asp Asp Ile Thr Met Val Leu Ile Leu Pro Lys Pro
305             310                 315                 320 gag aag agc ctg gcc aag gtg gag aag gaa ctc acc cca gag gtg ctg   1008
Glu Lys Ser Leu Ala Lys Val Glu Lys Glu Leu Thr Pro Glu Val Leu
            325                 330                 335 cag gag tgg ctg gat gaa ttg gag gag atg atg ctg gtg gtc cac atg   1056
Gln Glu Trp Leu Asp Glu Leu Glu Glu Met Met Leu Val Val His Met
        340                 345                 350 ccc cgc ttc cgc att gag gac ggc ttc agt ttg aag gag cag ctg caa   1104
Pro Arg Phe Arg Ile Glu Asp Gly Phe Ser Leu Lys Glu Gln Leu Gln
    355                 360                 365 gac atg ggc ctt gtc gat ctg ttc agc cct gaa aag tcc aaa ctc cca   1152
Asp Met Gly Leu Val Asp Leu Phe Ser Pro Glu Lys Ser Lys Leu Pro
370                 375                 380 ggt att gtt gca gaa ggc cga gat gac ctc tat gtc tca gat gca ttc   1200
Gly Ile Val Ala Glu Gly Arg Asp Asp Leu Tyr Val Ser Asp Ala Phe
385                 390                 395                 400 cat aag gca ttt ctt gag gta aat gaa gaa ggc agt gaa gca gct gca   1248
His Lys Ala Phe Leu Glu Val Asn Glu Glu Gly Ser Glu Ala Ala Ala
            405                 410                 415 agt acc gct gtt gtg att gct ggc cgt gag cta aac ccc aac agg gtg   1296
Ser Thr Ala Val Val Ile Ala Gly Arg Glu Leu Asn Pro Asn Arg Val
        420                 425                 430 act ttc aag gcc aac agg cct ttc ctg gtt ttt ata aga gaa gtt cct   1344
Thr Phe Lys Ala Asn Arg Pro Phe Leu Val Phe Ile Arg Glu Val Pro
    435                 440                 445 ctg aac act att atc ttc atg ggc aga gta gcc aac cct tgt gtt aag   1392
Leu Asn Thr Ile Ile Phe Met Gly Arg Val Ala Asn Pro Cys Val Lys
450                 455                 460 tag                                                               1395

<210> SEQ ID NO 72
<211> LENGTH: 464
<212> TYPE: PRT
<213> ORGANISM: Homo sapiens

<400> SEQUENCE: 72

Met Tyr Ser Asn Val Ile Gly Thr Val Thr Ser Gly Lys Arg Lys Val
1               5                   10                  15

Tyr Leu Leu Ser Leu Leu Ile Gly Phe Trp Asp Cys Val Thr Cys
            20                  25                  30

His Gly Ser Pro Val Asp Ile Cys Thr Ala Lys Pro Arg Asp Ile Pro
        35                  40                  45

Met Asn Pro Met Cys Ile Tyr Arg Ser Pro Glu Lys Lys Ala Thr Glu
    50                  55                  60

Asp Glu Gly Ser Glu Gln Lys Ile Pro Glu Ala Thr Asn Arg Arg Val
65                  70                  75                  80

Trp Glu Leu Ser Lys Ala Asn Ser Arg Phe Ala Thr Thr Phe Tyr Gln
                85                  90                  95

His Leu Ala Asp Ser Lys Asn Asp Asn Asp Asn Ile Phe Leu Ser Pro
            100                 105                 110

Leu Ser Ile Ser Thr Ala Phe Ala Met Thr Lys Leu Gly Ala Cys Asn
        115                 120                 125

Asp Thr Leu Gln Gln Leu Met Glu Val Phe Lys Phe Asp Thr Ile Ser
    130                 135                 140
```

```
Glu Lys Thr Ser Asp Gln Ile His Phe Phe Ala Lys Leu Asn Cys
145                 150                 155                 160

Arg Leu Tyr Arg Lys Ala Asn Lys Ser Ser Lys Leu Val Ser Ala Asn
                165                 170                 175

Arg Leu Phe Gly Asp Lys Ser Leu Thr Phe Asn Glu Thr Tyr Gln Asp
            180                 185                 190

Ile Ser Glu Leu Val Tyr Gly Ala Lys Leu Gln Pro Leu Asp Phe Lys
        195                 200                 205

Glu Asn Ala Glu Gln Ser Arg Ala Ala Ile Asn Lys Trp Val Ser Asn
    210                 215                 220

Lys Thr Glu Gly Arg Ile Thr Asp Val Ile Pro Ser Glu Ala Ile Asn
225                 230                 235                 240

Glu Leu Thr Val Leu Val Leu Val Asn Thr Ile Tyr Phe Lys Gly Leu
                245                 250                 255

Trp Lys Ser Lys Phe Ser Pro Glu Asn Thr Arg Lys Glu Leu Phe Tyr
                260                 265                 270

Lys Ala Asp Gly Glu Ser Cys Ser Ala Ser Met Met Tyr Gln Glu Gly
            275                 280                 285

Lys Phe Arg Tyr Arg Arg Val Ala Glu Gly Thr Gln Val Leu Glu Leu
        290                 295                 300

Pro Phe Lys Gly Asp Asp Ile Thr Met Val Leu Ile Leu Pro Lys Pro
305                 310                 315                 320

Glu Lys Ser Leu Ala Lys Val Glu Lys Glu Leu Thr Pro Glu Val Leu
                325                 330                 335

Gln Glu Trp Leu Asp Glu Leu Glu Glu Met Met Leu Val Val His Met
                340                 345                 350

Pro Arg Phe Arg Ile Glu Asp Gly Phe Ser Leu Lys Glu Gln Leu Gln
            355                 360                 365

Asp Met Gly Leu Val Asp Leu Phe Ser Pro Glu Lys Ser Lys Leu Pro
        370                 375                 380

Gly Ile Val Ala Glu Gly Arg Asp Asp Leu Tyr Val Ser Asp Ala Phe
385                 390                 395                 400

His Lys Ala Phe Leu Glu Val Asn Glu Glu Gly Ser Glu Ala Ala Ala
                405                 410                 415

Ser Thr Ala Val Val Ile Ala Gly Arg Glu Leu Asn Pro Asn Arg Val
                420                 425                 430

Thr Phe Lys Ala Asn Arg Pro Phe Leu Val Phe Ile Arg Glu Val Pro
            435                 440                 445

Leu Asn Thr Ile Ile Phe Met Gly Arg Val Ala Asn Pro Cys Val Lys
        450                 455                 460

<210> SEQ ID NO 73
<211> LENGTH: 1395
<212> TYPE: DNA
<213> ORGANISM: Homo sapiens
<220> FEATURE:
<221> NAME/KEY: CDS
<222> LOCATION: (1)..(1395)

<400> SEQUENCE: 73 atg tat tcc aat gtg ata gga act gta acc tct gga aaa agg aag gtt     48
Met Tyr Ser Asn Val Ile Gly Thr Val Thr Ser Gly Lys Arg Lys Val
1               5                   10                  15 tat ctt ttg tcc ttg ctg ctc att ggc ttc tgg gac tgc gtg acc tgt     96
Tyr Leu Leu Ser Leu Leu Leu Ile Gly Phe Trp Asp Cys Val Thr Cys
            20                  25                  30
```

```
cac ggg agc cct gtg gac atc tgc aca gcc aag ccg cgg gac att ccc      144
His Gly Ser Pro Val Asp Ile Cys Thr Ala Lys Pro Arg Asp Ile Pro
    35                  40                  45 atg aat ccc atg tgc att tac cgc tcc ccg gag aag aag gca act gag      192
Met Asn Pro Met Cys Ile Tyr Arg Ser Pro Glu Lys Lys Ala Thr Glu
 50                  55                  60 gat gag ggc tca gaa cag aag atc ccg gag gcc acc aac cgg cgt gtc      240
Asp Glu Gly Ser Glu Gln Lys Ile Pro Glu Ala Thr Asn Arg Arg Val
 65                  70                  75                  80 tgg gaa ctg tcc aag gcc aat tcc cgc ttt gct acc act ttc tat cag      288
Trp Glu Leu Ser Lys Ala Asn Ser Arg Phe Ala Thr Thr Phe Tyr Gln
                 85                  90                  95 cac ctg gca gat tcc aag aat gac aat gat aac att ttc ctg tca ccc      336
His Leu Ala Asp Ser Lys Asn Asp Asn Asp Asn Ile Phe Leu Ser Pro
            100                 105                 110 ctg agt atc tcc acg gct ttt gct atg acc aag ctg ggt gcc tgt aat      384
Leu Ser Ile Ser Thr Ala Phe Ala Met Thr Lys Leu Gly Ala Cys Asn
            115                 120                 125 gac acc ctc cag caa ctg atg gag gta ttt aag ttt gac acc ata tct      432
Asp Thr Leu Gln Gln Leu Met Glu Val Phe Lys Phe Asp Thr Ile Ser
130                 135                 140 gag aaa aca tct gat cag atc cac ttc ttc ttt gcc aaa ctg aac tgc      480
Glu Lys Thr Ser Asp Gln Ile His Phe Phe Phe Ala Lys Leu Asn Cys
145                 150                 155                 160 cga ctc tat cga aaa gcc cag aaa tcc tcc aag tta gta tca gcc aat      528
Arg Leu Tyr Arg Lys Ala Gln Lys Ser Ser Lys Leu Val Ser Ala Asn
                165                 170                 175 cgc ctt ttt gga gac aaa tcc ctt acc ttc aat gag acc tac cag gac      576
Arg Leu Phe Gly Asp Lys Ser Leu Thr Phe Asn Glu Thr Tyr Gln Asp
            180                 185                 190 atc agt gag ttg gta tat gga gcc aag ctc cag ccc ctg gac ttc aag      624
Ile Ser Glu Leu Val Tyr Gly Ala Lys Leu Gln Pro Leu Asp Phe Lys
            195                 200                 205 gaa aat gca gag caa tcc aga gcg gcc atc aac aaa tgg gtg tcc aat      672
Glu Asn Ala Glu Gln Ser Arg Ala Ala Ile Asn Lys Trp Val Ser Asn
210                 215                 220 aag acc gaa ggc cga atc acc gat gtc att ccc tcg gaa gcc atc aat      720
Lys Thr Glu Gly Arg Ile Thr Asp Val Ile Pro Ser Glu Ala Ile Asn
225                 230                 235                 240 gag ctc act gtt ctg gtg ctg gtt aac acc att tac ttc aag ggc ctg      768
Glu Leu Thr Val Leu Val Leu Val Asn Thr Ile Tyr Phe Lys Gly Leu
                245                 250                 255 tgg aag tca aag ttc agc cct gag aac aca agg aag gaa ctg ttc tac      816
Trp Lys Ser Lys Phe Ser Pro Glu Asn Thr Arg Lys Glu Leu Phe Tyr
            260                 265                 270 aag gct gat gga gag tcg tgt tca gca tct atg atg tac cag gaa ggc      864
Lys Ala Asp Gly Glu Ser Cys Ser Ala Ser Met Met Tyr Gln Glu Gly
            275                 280                 285 aag ttc cgt tat cgg cgc gtg gct gaa ggc acc cag gtg ctt gag ttg      912
Lys Phe Arg Tyr Arg Arg Val Ala Glu Gly Thr Gln Val Leu Glu Leu
            290                 295                 300 ccc ttc aaa ggt gat gac atc acc atg gtc ctc atc ttg ccc aag cct      960
Pro Phe Lys Gly Asp Asp Ile Thr Met Val Leu Ile Leu Pro Lys Pro
305                 310                 315                 320 gag aag agc ctg gcc aag gtg gag aag gaa ctc acc cca gag gtg ctg     1008
Glu Lys Ser Leu Ala Lys Val Glu Lys Glu Leu Thr Pro Glu Val Leu
                325                 330                 335 cag gag tgg ctg gat gaa ttg gag gag atg atg ctg gtg gtc cac atg     1056
Gln Glu Trp Leu Asp Glu Leu Glu Glu Met Met Leu Val Val His Met
            340                 345                 350
```

```
ccc cgc ttc cgc att gag gac ggc ttc agt ttg aag gag cag ctg caa    1104
Pro Arg Phe Arg Ile Glu Asp Gly Phe Ser Leu Lys Glu Gln Leu Gln
        355                 360                 365 gac atg ggc ctt gtc gat ctg ttc agc cct gaa aag tcc aaa ctc cca    1152
Asp Met Gly Leu Val Asp Leu Phe Ser Pro Glu Lys Ser Lys Leu Pro
370                 375                 380 ggt att gtt gca gaa ggc cga gat gac ctc tat gtc tca gat gca ttc    1200
Gly Ile Val Ala Glu Gly Arg Asp Asp Leu Tyr Val Ser Asp Ala Phe
385                 390                 395                 400 cat aag gca ttt ctt gag gta aat gaa gaa ggc agt gaa gca gct gca    1248
His Lys Ala Phe Leu Glu Val Asn Glu Glu Gly Ser Glu Ala Ala Ala
                405                 410                 415 agt acc gct gtt gtg att gct ggc cgt cag cta aac ccc aac agg gtg    1296
Ser Thr Ala Val Val Ile Ala Gly Arg Gln Leu Asn Pro Asn Arg Val
        420                 425                 430 act ttc aag gcc aac agg cct ttc ctg gtt ttt ata aga gaa gtt cct    1344
Thr Phe Lys Ala Asn Arg Pro Phe Leu Val Phe Ile Arg Glu Val Pro
    435                 440                 445 ctg aac act att atc ttc atg ggc aga gta gcc aac cct tgt gtt aag    1392
Leu Asn Thr Ile Ile Phe Met Gly Arg Val Ala Asn Pro Cys Val Lys
450                 455                 460 tag                                                                 1395

<210> SEQ ID NO 74
<211> LENGTH: 464
<212> TYPE: PRT
<213> ORGANISM: Homo sapiens

<400> SEQUENCE: 74

Met Tyr Ser Asn Val Ile Gly Thr Val Thr Ser Gly Lys Arg Lys Val
1               5                   10                  15

Tyr Leu Leu Ser Leu Leu Leu Ile Gly Phe Trp Asp Cys Val Thr Cys
            20                  25                  30

His Gly Ser Pro Val Asp Ile Cys Thr Ala Lys Pro Arg Asp Ile Pro
        35                  40                  45

Met Asn Pro Met Cys Ile Tyr Arg Ser Pro Glu Lys Lys Ala Thr Glu
    50                  55                  60

Asp Glu Gly Ser Glu Gln Lys Ile Pro Glu Ala Thr Asn Arg Arg Val
65                  70                  75                  80

Trp Glu Leu Ser Lys Ala Asn Ser Arg Phe Ala Thr Thr Phe Tyr Gln
                85                  90                  95

His Leu Ala Asp Ser Lys Asn Asp Asn Asp Asn Ile Phe Leu Ser Pro
            100                 105                 110

Leu Ser Ile Ser Thr Ala Phe Ala Met Thr Lys Leu Gly Ala Cys Asn
        115                 120                 125

Asp Thr Leu Gln Gln Leu Met Glu Val Phe Lys Phe Asp Thr Ile Ser
    130                 135                 140

Glu Lys Thr Ser Asp Gln Ile His Phe Phe Ala Lys Leu Asn Cys
145                 150                 155                 160

Arg Leu Tyr Arg Lys Ala Gln Lys Ser Ser Lys Leu Val Ser Ala Asn
                165                 170                 175

Arg Leu Phe Gly Asp Lys Ser Leu Thr Phe Asn Glu Thr Tyr Gln Asp
            180                 185                 190

Ile Ser Glu Leu Val Tyr Gly Ala Lys Leu Gln Pro Leu Asp Phe Lys
        195                 200                 205

Glu Asn Ala Glu Gln Ser Arg Ala Ala Ile Asn Lys Trp Val Ser Asn
```

```
                210             215             220
Lys Thr Glu Gly Arg Ile Thr Asp Val Ile Pro Ser Glu Ala Ile Asn
225                 230                 235                 240

Glu Leu Thr Val Leu Val Leu Val Asn Thr Ile Tyr Phe Lys Gly Leu
                245                 250                 255

Trp Lys Ser Lys Phe Ser Pro Glu Asn Thr Arg Lys Glu Leu Phe Tyr
                260                 265                 270

Lys Ala Asp Gly Glu Ser Cys Ser Ala Ser Met Met Tyr Gln Glu Gly
            275                 280                 285

Lys Phe Arg Tyr Arg Arg Val Ala Glu Gly Thr Gln Val Leu Glu Leu
        290                 295                 300

Pro Phe Lys Gly Asp Asp Ile Thr Met Val Leu Ile Leu Pro Lys Pro
305                 310                 315                 320

Glu Lys Ser Leu Ala Lys Val Glu Lys Glu Leu Thr Pro Glu Val Leu
                325                 330                 335

Gln Glu Trp Leu Asp Glu Leu Glu Glu Met Met Leu Val Val His Met
                340                 345                 350

Pro Arg Phe Arg Ile Glu Asp Gly Phe Ser Leu Lys Glu Gln Leu Gln
                355                 360                 365

Asp Met Gly Leu Val Asp Leu Phe Ser Pro Glu Lys Ser Lys Leu Pro
            370                 375                 380

Gly Ile Val Ala Glu Gly Arg Asp Asp Leu Tyr Val Ser Asp Ala Phe
385                 390                 395                 400

His Lys Ala Phe Leu Glu Val Asn Glu Glu Gly Ser Glu Ala Ala Ala
                405                 410                 415

Ser Thr Ala Val Val Ile Ala Gly Arg Gln Leu Asn Pro Asn Arg Val
            420                 425                 430

Thr Phe Lys Ala Asn Arg Pro Phe Leu Val Phe Ile Arg Glu Val Pro
        435                 440                 445

Leu Asn Thr Ile Ile Phe Met Gly Arg Val Ala Asn Pro Cys Val Lys
        450                 455                 460

<210> SEQ ID NO 75
<211> LENGTH: 1395
<212> TYPE: DNA
<213> ORGANISM: Homo sapiens
<220> FEATURE:
<221> NAME/KEY: CDS
<222> LOCATION: (1)..(1395)

<400> SEQUENCE: 75 atg tat tcc aat gtg ata gga act gta acc tct gga aaa agg aag gtt    48
Met Tyr Ser Asn Val Ile Gly Thr Val Thr Ser Gly Lys Arg Lys Val
1               5                   10                  15 tat ctt ttg tcc ttg ctg ctc att ggc ttc tgg gac tgc gtg acc tgt    96
Tyr Leu Leu Ser Leu Leu Leu Ile Gly Phe Trp Asp Cys Val Thr Cys
            20                  25                  30 cac ggg agc cct gtg gac atc tgc aca gcc aag ccg cgg gac att ccc   144
His Gly Ser Pro Val Asp Ile Cys Thr Ala Lys Pro Arg Asp Ile Pro
        35                  40                  45 atg aat ccc atg tgc att tac cgc tcc ccg gag aag aag gca act gag   192
Met Asn Pro Met Cys Ile Tyr Arg Ser Pro Glu Lys Lys Ala Thr Glu
50                  55                  60 gat gag ggc tca gaa cag aag atc ccg gag gcc acc aac cgg gtc gtc   240
Asp Glu Gly Ser Glu Gln Lys Ile Pro Glu Ala Thr Asn Arg Val Val
65                  70                  75                  80 tgg gaa ctg tcc aag gcc aat tcc cgc ttt gct acc act ttc tat cag   288
```

```
              Trp Glu Leu Ser Lys Ala Asn Ser Arg Phe Ala Thr Thr Phe Tyr Gln
                              85                  90                  95 cac ctg gca gat tcc aag aat gac aat gat aac att ttc ctg tca ccc             336
His Leu Ala Asp Ser Lys Asn Asp Asn Asp Asn Ile Phe Leu Ser Pro
                100                 105                 110 ctg agt atc tcc acg gct ttt gct atg acc aag ctg ggt gcc tgt aat             384
Leu Ser Ile Ser Thr Ala Phe Ala Met Thr Lys Leu Gly Ala Cys Asn
                115                 120                 125 gac acc ctc cag caa ctg atg gag gta ttt aag ttt gac acc ata tct             432
Asp Thr Leu Gln Gln Leu Met Glu Val Phe Lys Phe Asp Thr Ile Ser
    130                 135                 140 gag aaa aca tct gat cag atc cac ttc ttc ttt gcc aaa ctg aac tgc             480
Glu Lys Thr Ser Asp Gln Ile His Phe Phe Phe Ala Lys Leu Asn Cys
145                 150                 155                 160 cga ctc tat cga aaa gcc cag aaa tcc tcc aag tta gta tca gcc aat             528
Arg Leu Tyr Arg Lys Ala Gln Lys Ser Ser Lys Leu Val Ser Ala Asn
                    165                 170                 175 cgc ctt ttt gga gac aaa tcc ctt acc ttc aat gag acc tac cag gac             576
Arg Leu Phe Gly Asp Lys Ser Leu Thr Phe Asn Glu Thr Tyr Gln Asp
                180                 185                 190 atc agt gag ttg gta tat gga gcc aag ctc cag ccc ctg gac ttc aag             624
Ile Ser Glu Leu Val Tyr Gly Ala Lys Leu Gln Pro Leu Asp Phe Lys
            195                 200                 205 gaa aat gca gag caa tcc aga gcg gcc atc aac aaa tgg gtg tcc aat             672
Glu Asn Ala Glu Gln Ser Arg Ala Ala Ile Asn Lys Trp Val Ser Asn
        210                 215                 220 aag acc gaa ggc cga atc acc gat gtc att ccc tcg gaa gcc atc aat             720
Lys Thr Glu Gly Arg Ile Thr Asp Val Ile Pro Ser Glu Ala Ile Asn
225                 230                 235                 240 gag ctc act gtt ctg gtg ctg gtt aac acc att tac ttc aag ggc ctg             768
Glu Leu Thr Val Leu Val Leu Val Asn Thr Ile Tyr Phe Lys Gly Leu
                    245                 250                 255 tgg aag tca aag ttc agc cct gag aac aca agg aag gaa ctg ttc tac             816
Trp Lys Ser Lys Phe Ser Pro Glu Asn Thr Arg Lys Glu Leu Phe Tyr
                260                 265                 270 aag gct gat gga gag tcg tgt tca gca tct atg atg tac cag gaa ggc             864
Lys Ala Asp Gly Glu Ser Cys Ser Ala Ser Met Met Tyr Gln Glu Gly
            275                 280                 285 aag ttc cgt tat cgg cgc gtg gct gaa ggc acc cag gtg ctt gag ttg             912
Lys Phe Arg Tyr Arg Arg Val Ala Glu Gly Thr Gln Val Leu Glu Leu
        290                 295                 300 ccc ttc aaa ggt gat gac atc acc atg gtc ctc atc ttg ccc aag cct             960
Pro Phe Lys Gly Asp Asp Ile Thr Met Val Leu Ile Leu Pro Lys Pro
305                 310                 315                 320 gag aag agc ctg gcc aag gtg gag aag gaa ctc acc cca gag gtg ctg            1008
Glu Lys Ser Leu Ala Lys Val Glu Lys Glu Leu Thr Pro Glu Val Leu
                    325                 330                 335 cag gag tgg ctg gat gaa ttg gag gag atg atg ctg gtg gtc cac atg            1056
Gln Glu Trp Leu Asp Glu Leu Glu Glu Met Met Leu Val Val His Met
                340                 345                 350 ccc cgc ttc cgc att gag gac ggc ttc agt ttg aag gag cag ctg caa            1104
Pro Arg Phe Arg Ile Glu Asp Gly Phe Ser Leu Lys Glu Gln Leu Gln
            355                 360                 365 gac atg ggc ctt gtc gat ctg ttc agc cct gaa aag tcc aaa ctc cca            1152
Asp Met Gly Leu Val Asp Leu Phe Ser Pro Glu Lys Ser Lys Leu Pro
        370                 375                 380 ggt att gtt gca gaa ggc cga gat gac ctc tat gtc tca gat gca ttc            1200
Gly Ile Val Ala Glu Gly Arg Asp Asp Leu Tyr Val Ser Asp Ala Phe
385                 390                 395                 400
```

| | | | | | | | | | | | | | | | | |
|---|---|---|---|---|---|---|---|---|---|---|---|---|---|---|---|---|
| cat | aag | gca | ttt | ctt | gag | gta | aat | gaa | gaa | ggc | agt | gaa | gca | gct | gca | 1248 |
| His | Lys | Ala | Phe | Leu | Glu | Val | Asn | Glu | Glu | Gly | Ser | Glu | Ala | Ala | Ala | |
| | | | 405 | | | | | 410 | | | | | 415 | | | |
| agt | acc | gct | gtt | gtg | att | gct | ggc | cgt | gag | cta | aac | ccc | aac | agg | gtg | 1296 |
| Ser | Thr | Ala | Val | Val | Ile | Ala | Gly | Arg | Glu | Leu | Asn | Pro | Asn | Arg | Val | |
| | | 420 | | | | | 425 | | | | | 430 | | | | |
| act | ttc | aag | gcc | aac | agg | cct | ttc | ctg | gtt | ttt | ata | aga | gaa | gtt | cct | 1344 |
| Thr | Phe | Lys | Ala | Asn | Arg | Pro | Phe | Leu | Val | Phe | Ile | Arg | Glu | Val | Pro | |
| | | 435 | | | | | 440 | | | | | 445 | | | | |
| ctg | aac | act | att | atc | ttc | atg | ggc | aga | gta | gcc | aac | cct | tgt | gtt | aag | 1392 |
| Leu | Asn | Thr | Ile | Ile | Phe | Met | Gly | Arg | Val | Ala | Asn | Pro | Cys | Val | Lys | |
| | 450 | | | | | 455 | | | | | 460 | | | | | |
| tag | | | | | | | | | | | | | | | | 1395 |

<210> SEQ ID NO 76
<211> LENGTH: 464
<212> TYPE: PRT
<213> ORGANISM: Homo sapiens

<400> SEQUENCE: 76

Met Tyr Ser Asn Val Ile Gly Thr Val Thr Ser Gly Lys Arg Lys Val
1               5                   10                  15

Tyr Leu Leu Ser Leu Leu Leu Ile Gly Phe Trp Asp Cys Val Thr Cys
                20                  25                  30

His Gly Ser Pro Val Asp Ile Cys Thr Ala Lys Pro Arg Asp Ile Pro
            35                  40                  45

Met Asn Pro Met Cys Ile Tyr Arg Ser Pro Glu Lys Lys Ala Thr Glu
        50                  55                  60

Asp Glu Gly Ser Glu Gln Lys Ile Pro Glu Ala Thr Asn Arg Arg Val
65                  70                  75                  80

Trp Glu Leu Ser Lys Ala Asn Ser Arg Phe Ala Thr Thr Phe Tyr Gln
                85                  90                  95

His Leu Ala Asp Ser Lys Asn Asp Asn Asp Asn Ile Phe Leu Ser Pro
            100                 105                 110

Leu Ser Ile Ser Thr Ala Phe Ala Met Thr Lys Leu Gly Ala Cys Asn
        115                 120                 125

Asp Thr Leu Gln Gln Leu Met Glu Val Phe Lys Phe Asp Thr Ile Ser
130                 135                 140

Glu Lys Thr Ser Asp Gln Ile His Phe Phe Phe Ala Lys Leu Asn Cys
145                 150                 155                 160

Arg Leu Tyr Arg Lys Ala Gln Lys Ser Ser Lys Leu Val Ser Ala Asn
                165                 170                 175

Arg Leu Phe Gly Asp Lys Ser Leu Thr Phe Asn Glu Thr Tyr Gln Asp
            180                 185                 190

Ile Ser Glu Leu Val Tyr Gly Ala Lys Leu Gln Pro Leu Asp Phe Lys
        195                 200                 205

Glu Asn Ala Glu Gln Ser Arg Ala Ala Ile Asn Lys Trp Val Ser Asn
    210                 215                 220

Lys Thr Glu Gly Arg Ile Thr Asp Val Ile Pro Ser Glu Ala Ile Asn
225                 230                 235                 240

Glu Leu Thr Val Leu Val Leu Val Asn Thr Ile Tyr Phe Lys Gly Leu
                245                 250                 255

Trp Lys Ser Lys Phe Ser Pro Glu Asn Thr Arg Lys Glu Leu Phe Tyr
            260                 265                 270

Lys Ala Asp Gly Glu Ser Cys Ser Ala Ser Met Met Tyr Gln Glu Gly
        275                 280                 285

```
Lys Phe Arg Tyr Arg Arg Val Ala Glu Gly Thr Gln Val Leu Glu Leu
            290                 295                 300

Pro Phe Lys Gly Asp Asp Ile Thr Met Val Leu Ile Leu Pro Lys Pro
305                 310                 315                 320

Glu Lys Ser Leu Ala Lys Val Glu Lys Glu Leu Thr Pro Glu Val Leu
                325                 330                 335

Gln Glu Trp Leu Asp Glu Leu Glu Met Met Leu Val Val His Met
            340                 345                 350

Pro Arg Phe Arg Ile Glu Asp Gly Phe Ser Leu Lys Glu Gln Leu Gln
                355                 360                 365

Asp Met Gly Leu Val Asp Leu Phe Ser Pro Glu Lys Ser Lys Leu Pro
370                 375                 380

Gly Ile Val Ala Glu Gly Arg Asp Asp Leu Tyr Val Ser Asp Ala Phe
385                 390                 395                 400

His Lys Ala Phe Leu Glu Val Asn Glu Gly Ser Glu Ala Ala Ala
                405                 410                 415

Ser Thr Ala Val Val Ile Ala Gly Arg Glu Leu Asn Pro Asn Arg Val
                420                 425                 430

Thr Phe Lys Ala Asn Arg Pro Phe Leu Val Phe Ile Arg Glu Val Pro
            435                 440                 445

Leu Asn Thr Ile Ile Phe Met Gly Arg Val Ala Asn Pro Cys Val Lys
450                 455                 460

<210> SEQ ID NO 77
<211> LENGTH: 1299
<212> TYPE: DNA
<213> ORGANISM: Homo sapiens
<220> FEATURE:
<221> NAME/KEY: CDS
<222> LOCATION: (1)..(1299)

<400> SEQUENCE: 77 cac ggg agc cct gtg gac atc tgc aca gcc aag ccg cgg gac att ccc      48
His Gly Ser Pro Val Asp Ile Cys Thr Ala Lys Pro Arg Asp Ile Pro
1               5                   10                  15 atg aat ccc atg tgc att tac cgc tcc ccg gag aag aag gca act gag      96
Met Asn Pro Met Cys Ile Tyr Arg Ser Pro Glu Lys Lys Ala Thr Glu
            20                  25                  30 gat gag ggc tca gaa cag aag atc ccg gag gcc acc aac cgg cgt gtc     144
Asp Glu Gly Ser Glu Gln Lys Ile Pro Glu Ala Thr Asn Arg Arg Val
        35                  40                  45 tgg gaa ctg tcc aag gcc aat tcc cgc ttt gct acc act ttc tat cag     192
Trp Glu Leu Ser Lys Ala Asn Ser Arg Phe Ala Thr Thr Phe Tyr Gln
50                  55                  60 cac ctg gca gat tcc aag aat gac aat gat aac att ttc ctg tca ccc     240
His Leu Ala Asp Ser Lys Asn Asp Asn Asp Asn Ile Phe Leu Ser Pro
65                  70                  75                  80 ctg agt atc tcc acg gct ttt gct atg acc aag ctg ggt gcc tgt aat     288
Leu Ser Ile Ser Thr Ala Phe Ala Met Thr Lys Leu Gly Ala Cys Asn
                85                  90                  95 gac acc ctc cag caa ctg atg gag gta ttt aag ttt gac acc ata tct     336
Asp Thr Leu Gln Gln Leu Met Glu Val Phe Lys Phe Asp Thr Ile Ser
            100                 105                 110 gag aaa aca tct gat cag atc cac ttc ttc ttt gcc aaa ctg aac tgc     384
Glu Lys Thr Ser Asp Gln Ile His Phe Phe Phe Ala Lys Leu Asn Cys
        115                 120                 125 cga ctc tat cga aaa gcc cag aaa tcc tcc aag tta gta tca gcc aat     432
Arg Leu Tyr Arg Lys Ala Gln Lys Ser Ser Lys Leu Val Ser Ala Asn
```

```
                130                 135                 140
cgc ctt ttt gga gac aaa tcc ctt acc ttc aat gag acc tac cag gac      480
Arg Leu Phe Gly Asp Lys Ser Leu Thr Phe Asn Glu Thr Tyr Gln Asp
145                 150                 155                 160 atc agt gag ttg gta tat gga gcc aag ctc cag ccc ctg gac ttc aag      528
Ile Ser Glu Leu Val Tyr Gly Ala Lys Leu Gln Pro Leu Asp Phe Lys
                165                 170                 175 gaa aat gca gag caa tcc aga gcg gcc atc aac aaa tgg gtg tcc aat      576
Glu Asn Ala Glu Gln Ser Arg Ala Ala Ile Asn Lys Trp Val Ser Asn
            180                 185                 190 aag acc gaa ggc cga atc acc gat gtc att ccc tcg gaa gcc atc aat      624
Lys Thr Glu Gly Arg Ile Thr Asp Val Ile Pro Ser Glu Ala Ile Asn
        195                 200                 205 gag ctc act gtt ctg gtg ctg gtt aac acc att tac ttc aag ggc ctg      672
Glu Leu Thr Val Leu Val Leu Val Asn Thr Ile Tyr Phe Lys Gly Leu
    210                 215                 220 tgg aag tca aag ttc agc cct gag aac aca agg aag gaa ctg ttc tac      720
Trp Lys Ser Lys Phe Ser Pro Glu Asn Thr Arg Lys Glu Leu Phe Tyr
225                 230                 235                 240 aag gct gat gga gag tcg tgt tca gca tct atg atg tac cag gaa ggc      768
Lys Ala Asp Gly Glu Ser Cys Ser Ala Ser Met Met Tyr Gln Glu Gly
                245                 250                 255 aag ttc cgt tat cgg cgc gtg gct gaa ggc acc cag gtg ctt gag ttg      816
Lys Phe Arg Tyr Arg Arg Val Ala Glu Gly Thr Gln Val Leu Glu Leu
            260                 265                 270 ccc ttc aaa ggt gat gac atc acc atg gtc ctc atc ttg ccc aag cct      864
Pro Phe Lys Gly Asp Asp Ile Thr Met Val Leu Ile Leu Pro Lys Pro
        275                 280                 285 gag aag agc ctg gcc aag gtg gag aag gaa ctc acc cca gag gtg ctg      912
Glu Lys Ser Leu Ala Lys Val Glu Lys Glu Leu Thr Pro Glu Val Leu
    290                 295                 300 cag gag tgg ctg gat gaa ttg gag gag atg atg ctg gtg gtc cac atg      960
Gln Glu Trp Leu Asp Glu Leu Glu Glu Met Met Leu Val Val His Met
305                 310                 315                 320 ccc cgc ttc cgc att gag gac ggc ttc agt ttg aag gag cag ctg caa     1008
Pro Arg Phe Arg Ile Glu Asp Gly Phe Ser Leu Lys Glu Gln Leu Gln
                325                 330                 335 gac atg ggc ctt gtc gat ctg ttc agc cct gaa aag tcc aaa ctc cca     1056
Asp Met Gly Leu Val Asp Leu Phe Ser Pro Glu Lys Ser Lys Leu Pro
            340                 345                 350 ggt att gtt gca gaa ggc cga gat gac ctc tat gtc tca gat gca ttc     1104
Gly Ile Val Ala Glu Gly Arg Asp Asp Leu Tyr Val Ser Asp Ala Phe
        355                 360                 365 cat aag gca ttt ctt gag gta aat gaa gaa ggc agt gaa gca gct gca     1152
His Lys Ala Phe Leu Glu Val Asn Glu Glu Gly Ser Glu Ala Ala Ala
    370                 375                 380 agt acc gct gtt gtg att gct ggc cgt tcg cta aac ccc aac agg gtg     1200
Ser Thr Ala Val Val Ile Ala Gly Arg Ser Leu Asn Pro Asn Arg Val
385                 390                 395                 400 act ttc aag gcc aac agg cct ttc ctg gtt ttt ata aga gaa gtt cct     1248
Thr Phe Lys Ala Asn Arg Pro Phe Leu Val Phe Ile Arg Glu Val Pro
                405                 410                 415 ctg aac act att atc ttc atg ggc aga gta gcc aac cct tgt gtt aag     1296
Leu Asn Thr Ile Ile Phe Met Gly Arg Val Ala Asn Pro Cys Val Lys
            420                 425                 430 tag                                                                  1299
```

<210> SEQ ID NO 78
<211> LENGTH: 432

```
<212> TYPE: PRT
<213> ORGANISM: Homo sapiens

<400> SEQUENCE: 78

His Gly Ser Pro Val Asp Ile Cys Thr Ala Lys Pro Arg Asp Ile Pro
1               5                   10                  15

Met Asn Pro Met Cys Ile Tyr Arg Ser Pro Glu Lys Lys Ala Thr Glu
            20                  25                  30

Asp Glu Gly Ser Glu Gln Lys Ile Pro Glu Ala Thr Asn Arg Arg Val
        35                  40                  45

Trp Glu Leu Ser Lys Ala Asn Ser Arg Phe Ala Thr Thr Phe Tyr Gln
    50                  55                  60

His Leu Ala Asp Ser Lys Asn Asp Asn Asp Asn Ile Phe Leu Ser Pro
65                  70                  75                  80

Leu Ser Ile Ser Thr Ala Phe Ala Met Thr Lys Leu Gly Ala Cys Asn
                85                  90                  95

Asp Thr Leu Gln Gln Leu Met Glu Val Phe Lys Phe Asp Thr Ile Ser
            100                 105                 110

Glu Lys Thr Ser Asp Gln Ile His Phe Phe Phe Ala Lys Leu Asn Cys
        115                 120                 125

Arg Leu Tyr Arg Lys Ala Gln Lys Ser Ser Lys Leu Val Ser Ala Asn
130                 135                 140

Arg Leu Phe Gly Asp Lys Ser Leu Thr Phe Asn Glu Thr Tyr Gln Asp
145                 150                 155                 160

Ile Ser Glu Leu Val Tyr Gly Ala Lys Leu Gln Pro Leu Asp Phe Lys
                165                 170                 175

Glu Asn Ala Glu Gln Ser Arg Ala Ala Ile Asn Lys Trp Val Ser Asn
            180                 185                 190

Lys Thr Glu Gly Arg Ile Thr Asp Val Ile Pro Ser Glu Ala Ile Asn
        195                 200                 205

Glu Leu Thr Val Leu Val Leu Val Asn Thr Ile Tyr Phe Lys Gly Leu
    210                 215                 220

Trp Lys Ser Lys Phe Ser Pro Glu Asn Thr Arg Lys Glu Leu Phe Tyr
225                 230                 235                 240

Lys Ala Asp Gly Glu Ser Cys Ser Ala Ser Met Met Tyr Gln Glu Gly
                245                 250                 255

Lys Phe Arg Tyr Arg Arg Val Ala Glu Gly Thr Gln Val Leu Glu Leu
            260                 265                 270

Pro Phe Lys Gly Asp Asp Ile Thr Met Val Leu Ile Leu Pro Lys Pro
        275                 280                 285

Glu Lys Ser Leu Ala Lys Val Glu Lys Glu Leu Thr Pro Glu Val Leu
    290                 295                 300

Gln Glu Trp Leu Asp Glu Leu Glu Glu Met Met Leu Val Val His Met
305                 310                 315                 320

Pro Arg Phe Arg Ile Glu Asp Gly Phe Ser Leu Lys Glu Gln Leu Gln
                325                 330                 335

Asp Met Gly Leu Val Asp Leu Phe Ser Pro Glu Lys Ser Lys Leu Pro
            340                 345                 350

Gly Ile Val Ala Glu Gly Arg Asp Asp Leu Tyr Val Ser Asp Ala Phe
        355                 360                 365

His Lys Ala Phe Leu Glu Val Asn Glu Glu Gly Ser Glu Ala Ala Ala
    370                 375                 380

Ser Thr Ala Val Val Ile Ala Gly Arg Ser Leu Asn Pro Asn Arg Val
385                 390                 395                 400
```

```
Thr Phe Lys Ala Asn Arg Pro Phe Leu Val Phe Ile Arg Glu Val Pro
                405                 410                 415

Leu Asn Thr Ile Ile Phe Met Gly Arg Val Ala Asn Pro Cys Val Lys
            420                 425                 430

<210> SEQ ID NO 79
<211> LENGTH: 1395
<212> TYPE: DNA
<213> ORGANISM: Homo sapiens
<220> FEATURE:
<221> NAME/KEY: CDS
<222> LOCATION: (1)..(1395)

<400> SEQUENCE: 79 atg tat tcc aat gtg ata gga act gta acc tct gga aaa agg aag gtt        48
Met Tyr Ser Asn Val Ile Gly Thr Val Thr Ser Gly Lys Arg Lys Val
1               5                   10                  15 tat ctt ttg tcc ttg ctc att ggc ttc tgg gac tgc gtg acc tgt            96
Tyr Leu Leu Ser Leu Leu Ile Gly Phe Trp Asp Cys Val Thr Cys
            20                  25                  30 cac ggg agc cct gtg gac atc tgc aca gcc aag ccg cgg gac att ccc       144
His Gly Ser Pro Val Asp Ile Cys Thr Ala Lys Pro Arg Asp Ile Pro
        35                  40                  45 atg aat ccc atg tgc att tac cgc tcc ccg gag aag aag gca act gag       192
Met Asn Pro Met Cys Ile Tyr Arg Ser Pro Glu Lys Lys Ala Thr Glu
    50                  55                  60 gat gag ggc tca gaa cag aag atc ccg gag gcc acc aac cgg cgt gtc       240
Asp Glu Gly Ser Glu Gln Lys Ile Pro Glu Ala Thr Asn Arg Arg Val
65                  70                  75                  80 tgg gaa ctg tcc aag gcc aat tcc cgc ttt gct acc act ttc tat cag       288
Trp Glu Leu Ser Lys Ala Asn Ser Arg Phe Ala Thr Thr Phe Tyr Gln
                85                  90                  95 cac ctg gca gat tcc aag aat gac aat gat aac att ttc ctg tca ccc       336
His Leu Ala Asp Ser Lys Asn Asp Asn Asp Asn Ile Phe Leu Ser Pro
            100                 105                 110 ctg agt atc tcc acg gct ttt gct atg acc aag ctg ggt gcc tgt aat       384
Leu Ser Ile Ser Thr Ala Phe Ala Met Thr Lys Leu Gly Ala Cys Asn
        115                 120                 125 gac acc ctc cag caa ctg atg gag gta ttt aag ttt gac acc ata tct       432
Asp Thr Leu Gln Gln Leu Met Glu Val Phe Lys Phe Asp Thr Ile Ser
    130                 135                 140 gag aaa aca tct gat cag atc cac ttc ttc ttt gcc aaa ctg aac tgc       480
Glu Lys Thr Ser Asp Gln Ile His Phe Phe Phe Ala Lys Leu Asn Cys
145                 150                 155                 160 cga ctc tat cga aaa gcc cag aaa tcc tcc aag tta gta tca gcc aat       528
Arg Leu Tyr Arg Lys Ala Gln Lys Ser Ser Lys Leu Val Ser Ala Asn
                165                 170                 175 cgc ctt ttt gga gac aaa tcc ctt acc ttc aat gag acc tac cag gac       576
Arg Leu Phe Gly Asp Lys Ser Leu Thr Phe Asn Glu Thr Tyr Gln Asp
            180                 185                 190 atc agt gag ttg gta tat gga gcc aag ctc cag ccc ctg gac ttc aag       624
Ile Ser Glu Leu Val Tyr Gly Ala Lys Leu Gln Pro Leu Asp Phe Lys
        195                 200                 205 gaa aat gca gag caa tcc aga gcg gcc atc aac aaa tgg gtg tcc aat       672
Glu Asn Ala Glu Gln Ser Arg Ala Ala Ile Asn Lys Trp Val Ser Asn
    210                 215                 220 aag acc gaa ggc cga atc acc gat gtc att ccc tcg gaa gcc atc aat       720
Lys Thr Glu Gly Arg Ile Thr Asp Val Ile Pro Ser Glu Ala Ile Asn
225                 230                 235                 240 gag ctc act gtt ctg gtg ctg gtt aac acc att tac ttc aag ggc ctg       768
```

```

Glu Leu Thr Val Leu Val Leu Val Asn Thr Ile Tyr Phe Lys Gly Leu
                       245                 250                 255 tgg aag tca aag ttc agc cct gag aac aca agg aag gaa ctg ttc tac              816
Trp Lys Ser Lys Phe Ser Pro Glu Asn Thr Arg Lys Glu Leu Phe Tyr
            260                 265                 270 aag gct gat gga gag tcg tgt tca gca tct atg atg tac cag gaa ggc              864
Lys Ala Asp Gly Glu Ser Cys Ser Ala Ser Met Met Tyr Gln Glu Gly
275                 280                 285 aag ttc cgt tat cgg cgc gtg gct gaa ggc acc cag gtg ctt gag ttg              912
Lys Phe Arg Tyr Arg Arg Val Ala Glu Gly Thr Gln Val Leu Glu Leu
        290                 295                 300 ccc ttc aaa ggt gat gac atc acc atg gtc ctc atc ttg ccc aag cct              960
Pro Phe Lys Gly Asp Asp Ile Thr Met Val Leu Ile Leu Pro Lys Pro
305                 310                 315                 320 gag aag agc ctg gcc aag gtg gag aag gaa ctc acc cca gag gtg ctg             1008
Glu Lys Ser Leu Ala Lys Val Glu Lys Glu Leu Thr Pro Glu Val Leu
                325                 330                 335 cag gag tgg ctg gat gaa ttg gag gag atg atg ctg gtg gtc cac atg             1056
Gln Glu Trp Leu Asp Glu Leu Glu Glu Met Met Leu Val Val His Met
            340                 345                 350 ccc cgc ttc cgc att gag gac ggc ttc agt ttg aag gag cag ctg caa             1104
Pro Arg Phe Arg Ile Glu Asp Gly Phe Ser Leu Lys Glu Gln Leu Gln
        355                 360                 365 gac atg ggc ctt gtc gat ctg ttc agc cct gaa aag tcc aaa ctc cca             1152
Asp Met Gly Leu Val Asp Leu Phe Ser Pro Glu Lys Ser Lys Leu Pro
370                 375                 380 ggt att gtt gca gaa ggc cga gat gac ctc tat gtc tca gat gca ttc             1200
Gly Ile Val Ala Glu Gly Arg Asp Asp Leu Tyr Val Ser Asp Ala Phe
                385                 390                 395                 400 cat aag gca ttt ctt gag gta aat gaa gaa ggc agt gaa gca gct gca             1248
His Lys Ala Phe Leu Glu Val Asn Glu Glu Gly Ser Glu Ala Ala Ala
                405                 410                 415 agt acc gct gtt gtg att gct ggc cgt tcg cta aac ccc aac agg gtg             1296
Ser Thr Ala Val Val Ile Ala Gly Arg Ser Leu Asn Pro Asn Arg Val
        420                 425                 430 act ttc aag gcc aac agg cct ttc ctg gtt ttt ata aga gaa gtt cct             1344
Thr Phe Lys Ala Asn Arg Pro Phe Leu Val Phe Ile Arg Glu Val Pro
    435                 440                 445 ctg aac act att atc ttc atg ggc aga gta gcc aac cct tgt gtt aag             1392
Leu Asn Thr Ile Ile Phe Met Gly Arg Val Ala Asn Pro Cys Val Lys
450                 455                 460 tag                                                                         1395

<210> SEQ ID NO 80
<211> LENGTH: 464
<212> TYPE: PRT
<213> ORGANISM: Homo sapiens

<400> SEQUENCE: 80

Met Tyr Ser Asn Val Ile Gly Thr Val Thr Ser Gly Lys Arg Lys Val
1               5                   10                  15

Tyr Leu Leu Ser Leu Leu Leu Ile Gly Phe Trp Asp Cys Val Thr Cys
            20                  25                  30

His Gly Ser Pro Val Asp Ile Cys Thr Ala Lys Pro Arg Asp Ile Pro
        35                  40                  45

Met Asn Pro Met Cys Ile Tyr Arg Ser Pro Glu Lys Lys Ala Thr Glu
    50                  55                  60

Asp Glu Gly Ser Glu Gln Lys Ile Pro Glu Ala Thr Asn Arg Arg Val
65                  70                  75                  80
```

Trp Glu Leu Ser Lys Ala Asn Ser Arg Phe Ala Thr Thr Phe Tyr Gln
            85                  90                  95

His Leu Ala Asp Ser Lys Asn Asp Asp Asn Ile Phe Leu Ser Pro
                100                 105                 110

Leu Ser Ile Ser Thr Ala Phe Ala Met Thr Lys Leu Gly Ala Cys Asn
            115                 120                 125

Asp Thr Leu Gln Gln Leu Met Glu Val Phe Lys Phe Asp Thr Ile Ser
    130                 135                 140

Glu Lys Thr Ser Asp Gln Ile His Phe Phe Phe Ala Lys Leu Asn Cys
145                 150                 155                 160

Arg Leu Tyr Arg Lys Ala Gln Lys Ser Ser Lys Leu Val Ser Ala Asn
            165                 170                 175

Arg Leu Phe Gly Asp Lys Ser Leu Thr Phe Asn Glu Thr Tyr Gln Asp
            180                 185                 190

Ile Ser Glu Leu Val Tyr Gly Ala Lys Leu Gln Pro Leu Asp Phe Lys
            195                 200                 205

Glu Asn Ala Glu Gln Ser Arg Ala Ala Ile Asn Lys Trp Val Ser Asn
    210                 215                 220

Lys Thr Glu Gly Arg Ile Thr Asp Val Ile Pro Ser Glu Ala Ile Asn
225                 230                 235                 240

Glu Leu Thr Val Leu Val Leu Val Asn Thr Ile Tyr Phe Lys Gly Leu
            245                 250                 255

Trp Lys Ser Lys Phe Ser Pro Glu Asn Thr Arg Lys Glu Leu Phe Tyr
            260                 265                 270

Lys Ala Asp Gly Glu Ser Cys Ser Ala Ser Met Met Tyr Gln Glu Gly
            275                 280                 285

Lys Phe Arg Tyr Arg Arg Val Ala Glu Gly Thr Gln Val Leu Glu Leu
            290                 295                 300

Pro Phe Lys Gly Asp Asp Ile Thr Met Val Leu Ile Leu Pro Lys Pro
305                 310                 315                 320

Glu Lys Ser Leu Ala Lys Val Glu Lys Glu Leu Thr Pro Glu Val Leu
            325                 330                 335

Gln Glu Trp Leu Asp Glu Leu Glu Met Met Leu Val Val His Met
            340                 345                 350

Pro Arg Phe Arg Ile Glu Asp Gly Phe Ser Leu Lys Glu Gln Leu Gln
            355                 360                 365

Asp Met Gly Leu Val Asp Leu Phe Ser Pro Glu Lys Ser Lys Leu Pro
    370                 375                 380

Gly Ile Val Ala Glu Gly Arg Asp Asp Leu Tyr Val Ser Asp Ala Phe
385                 390                 395                 400

His Lys Ala Phe Leu Glu Val Asn Glu Glu Gly Ser Glu Ala Ala Ala
            405                 410                 415

Ser Thr Ala Val Val Ile Ala Gly Arg Ser Leu Asn Pro Asn Arg Val
            420                 425                 430

Thr Phe Lys Ala Asn Arg Pro Phe Leu Val Phe Ile Arg Glu Val Pro
            435                 440                 445

Leu Asn Thr Ile Ile Phe Met Gly Arg Val Ala Asn Pro Cys Val Lys
450                 455                 460

<210> SEQ ID NO 81
<211> LENGTH: 33
<212> TYPE: DNA
<213> ORGANISM: Artificial sequence
<220> FEATURE:

```
<223> OTHER INFORMATION: mutated oligonucleotide

<400> SEQUENCE: 81
gtgattgctg gccgtcagct aaaccccaac agg                                33

<210> SEQ ID NO 82
<211> LENGTH: 33
<212> TYPE: DNA
<213> ORGANISM: Artificial Sequence
<220> FEATURE:
<223> OTHER INFORMATION: mutated oligonucleotide

<400> SEQUENCE: 82
cctgttgggg tttagctgac ggccagcaat cac                                33

<210> SEQ ID NO 83
<211> LENGTH: 33
<212> TYPE: DNA
<213> ORGANISM: Artificial sequence
<220> FEATURE:
<223> OTHER INFORMATION: mutated oligonucleotide

<400> SEQUENCE: 83
gtgattgctg gccgtgagct aaaccccaac agg                                33

<210> SEQ ID NO 84
<211> LENGTH: 33
<212> TYPE: DNA
<213> ORGANISM: Artificial sequence
<220> FEATURE:
<223> OTHER INFORMATION: mutated oligonucleotide

<400> SEQUENCE: 84
cctgttgggg tttagctcac ggccagcaat cac                                33
```